US012641998B2

(12) United States Patent
Zhai

(10) Patent No.: US 12,641,998 B2
(45) Date of Patent: May 26, 2026

(54) COMPOUND, DISPLAY PANEL AND DISPLAY DEVICE

(71) Applicants: Wuhan Tianma Microelectronics Co., Ltd., Wuhan (CN); Wuhan Tianma Microelectronics Co., Ltd. Shanghai Branch, Shanghai (CN)

(72) Inventor: Lu Zhai, Wuhan (CN)

(73) Assignees: Wuhan Tianma Microelectronics Co., Ltd., Wuhan (CN); Wuhan Tianma Microelectronics Co., Ltd. Shanghai Branch, Shanghai (CN)

( * ) Notice: Subject to any disclaimer, the term of this patent is extended or adjusted under 35 U.S.C. 154(b) by 874 days.

(21) Appl. No.: 17/980,565

(22) Filed: Nov. 4, 2022

(65) Prior Publication Data

US 2023/0422605 A1 Dec. 28, 2023

(30) Foreign Application Priority Data

Jun. 24, 2022 (CN) ......................... 202210727167.2

(51) Int. Cl.
*H10K 85/60* (2023.01)
*C07D 285/14* (2006.01)
(Continued)

(52) U.S. Cl.
CPC ......... *H10K 85/636* (2023.02); *C07D 285/14* (2013.01); *C07D 417/14* (2013.01);
(Continued)

(58) Field of Classification Search
CPC .. H10K 85/636; H10K 85/633; H10K 85/657; H10K 85/6572; H10K 85/654;
(Continued)

(56) References Cited

U.S. PATENT DOCUMENTS

2011/0187294 A1 8/2011 Bergmann et al.

FOREIGN PATENT DOCUMENTS

CN 101492428 A 7/2009
CN 103555318 B 3/2016
(Continued)

OTHER PUBLICATIONS

Machine Translation of CN109824659A (Year: 2019).*
The First Office Action for Chinese Application No. 202210727167.2, dated Mar. 24, 2023, 8 pages.

*Primary Examiner* — Jenna N Chandhok
(74) *Attorney, Agent, or Firm* — East IP P.C.

(57) ABSTRACT

The present application discloses a compound, a display panel and a display device. The compound has the structure shown in Formula 1. The compound of the present application can improve the light extraction efficiency and luminous efficiency, especially the external quantum efficiency of a device, and can also effectively reduce the color shift of the device at multi-angle display.
(Continued)

Formula 1

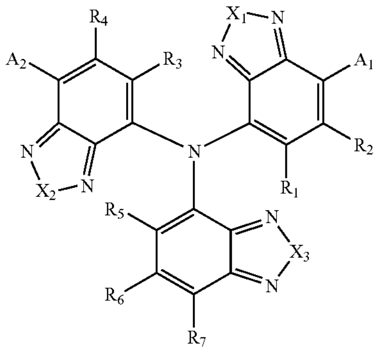

14 Claims, 2 Drawing Sheets

(51) Int. Cl.
*C07D 417/14* (2006.01)
*C09K 11/06* (2006.01)
*H10K 50/844* (2023.01)

(52) U.S. Cl.
CPC ............ *C09K 11/06* (2013.01); *H10K 50/844* (2023.02); *H10K 50/8445* (2023.02); *H10K 85/633* (2023.02); *C09K 2211/1018* (2013.01); *H10K 85/626* (2023.02); *H10K 85/657* (2023.02); *H10K 85/6572* (2023.02); *H10K 85/6574* (2023.02)

(58) Field of Classification Search
CPC .. C07D 285/14; C07D 417/14; C07D 235/08; C07D 249/18; C07D 271/12; C07D 403/14; C07D 413/14; C09K 2211/1018; C07F 7/10
See application file for complete search history.

(56) References Cited

FOREIGN PATENT DOCUMENTS

| | | | | |
|---|---|---|---|---|
| CN | 109824659 | A | * | 5/2019 |
| JP | 2018189715 | A | | 11/2018 |

* cited by examiner

COMPOUND, DISPLAY PANEL AND DISPLAY DEVICE

CROSS-REFERENCE TO RELATED APPLICATIONS

This application claims priority to Chinese Patent Application No. 202210727167.2, filed on Jun. 24, 2022, which is hereby incorporated by reference in its entirety.

TECHNICAL FIELD

The present application belongs to the technical field of organic electroluminescence, and specifically relates to a compound, a display panel and a display device.

BACKGROUND

According to the directions of light emitted by organic luminescent layers, organic electroluminescent devices (or organic light emitting diode, OLED) devices can be divided into bottom emitting devices and top emitting devices. In a bottom emitting device, light is emitted toward a substrate, a reflective electrode is formed on the organic luminescent layer, and a transparent (or semi-transparent) electrode is formed under the organic luminescent layer. In a top emitting device, a transparent (or semi-transparent) electrode is formed on the organic luminescent layer, and a reflective electrode is formed under the organic luminescent layer, so light is emitted in a direction opposite to the substrate, thereby increasing the light transmission area and improving the brightness. After decades of development, a great progress has been made for OLED devices and their internal quantum efficiency is close to 100%, but their external quantum efficiency is only about 20%. Most of the light emitted from OLED devices is confined inside the devices due to the factors such as substrate mode loss, surface plasmon loss and waveguide effects, resulting in the loss of a large amount of energy.

In view of the current situation of low light extraction efficiency of OLED devices, an organic capping layer (CPL) needs to be evaporated and deposited on the transparent (or semi-transparent) electrode in the top emitting device to adjust the optical interference distance, suppress external light reflection, and suppress extinction caused by the movement of surface plasmon energy, so as to improve the extraction efficiency of light and the luminous efficiency of the device. At present, CPL materials have many problems, such as low refractive index, not good enough light extraction effect, and incapability of obtaining high light extraction efficiency for all light in blue, green and red light emitting devices at the same time.

Therefore, there is an urgent need to develop more kinds of CPL materials with higher performance in this art.

SUMMARY

An objective of the present application is to provide a compound, a display panel and a display device, which can improve the light extraction efficiency and luminous efficiency, especially the external quantum efficiency of a device, and can also effectively reduce the color shift of the device at multi-angle display.

A first aspect of the present application provides a compound having the structure shown in Formula 1, Formula 1

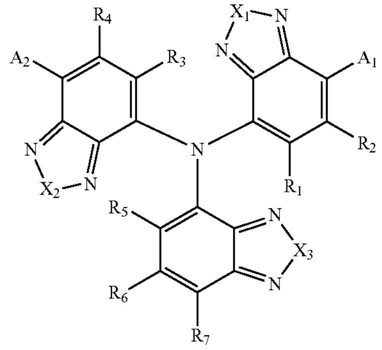

$A_1$ and $A_2$ each independently represent $-(L)_n-R$, where L each independently represents 6-membered to 60-membered divalent aryl unsubstituted or substituted by $R^a$ or 5-membered to 60-membered divalent heteroaryl unsubstituted or substituted by $R^a$, R represents 6-membered to 60-membered monovalent aryl unsubstituted or substituted by $R^a$ or 5-membered to 60-membered monovalent heteroaryl unsubstituted or substituted by $R^a$, and n represents 0, 1 or 2;

$R_1$, $R_2$, $R_3$, $R_4$, $R_5$, $R_6$, and $R_7$ each independently represent hydrogen, deuterium, tritium, a halogen atom or the following group unsubstituted or substituted by $R^a$:

C1-C20 monovalent alkyl, C1-C20 monovalent alkoxy, C1-C20 monovalent alkylthio, C2-C20 monovalent alkenyl, C2-C20 monovalent alkynyl, 3-membered to 20-membered monovalent alcyl, 3-membered to 20-membered monovalent heteroalcyl, 6-membered to 40-membered monovalent aryl, or 5-membered to 40-membered monovalent heteroaryl;

$X_1$, $X_2$, and $X_3$ each independently represent S, O, $N(Y_1)$, $C(Y_2)_2$ or $Si(Y_3)_2$, and $Y_1$, $Y_2$, and $Y_3$ each independently represent hydrogen, deuterium, tritium, or the following group unsubstituted or substituted by $R^a$:

C1-C20 monovalent alkyl, C1-C20 monovalent alkoxy, C1-C20 monovalent alkylthio, C2-C20 monovalent alkenyl, C2-C20 monovalent alkynyl, 3-membered to 20-membered monovalent alcyl, 3-membered to 20-membered monovalent heteroalcyl, 6-membered to 40-membered monovalent aryl, or 5-membered to 40-membered monovalent heteroaryl; and $R^a$ represents deuterium, tritium, a halogen atom, cyano, nitro, carboxyl, carbonyl, amino, C1-C20 monovalent alkyl, C1-C20 monovalent alkoxy, C1-C20 monovalent alkylthio, C2-C20 monovalent alkenyl, C2-C20 monovalent alkynyl, 3-membered to 20-membered monovalent alcyl, 3-membered to 20-membered monovalent heteroalcyl, 6-membered to 40-membered monovalent aryl, or 5-membered to 40-membered monovalent heteroaryl, wherein one or more hydrogens of C1-C20 monovalent alkyl, C1-C20 monovalent alkoxy, C1-C20 monovalent alkylthio, C2-C20 monovalent alkenyl, C2-C20 monovalent alkynyl, 3-membered to 20-membered monovalent alcyl, 3-membered to 20-membered monovalent heteroalcyl, 6-membered to 40-membered monovalent aryl, or 5-membered to 40-membered monovalent heteroaryl each are independently substituted by deuterium, tritium, a halogen atom, cyano, nitro, carboxyl, carbonyl, or amino.

A second aspect of the present application provides a display panel, including an organic electroluminescent device, the organic electroluminescent device including a cathode, an anode arranged opposite to the cathode, a capping layer located on the side of the cathode away from the anode, and an organic film layer located between the cathode and the anode, wherein at least one of the capping layer and the organic film layer includes the compound according to the first aspect of the present application.

A third aspect of the present application provides a display device, including the display panel according to the second aspect of the present application.

DESCRIPTION OF THE DRAWINGS

In order to explain the technical solutions of the embodiments of the present application more clearly, the following will briefly introduce the drawings that need to be used in the embodiments of the present application. Apparently, the drawings described below are only some embodiments of the present application. A person of ordinary skill in the art can obtain other drawings based on the drawings without creative work.

Figure 1:
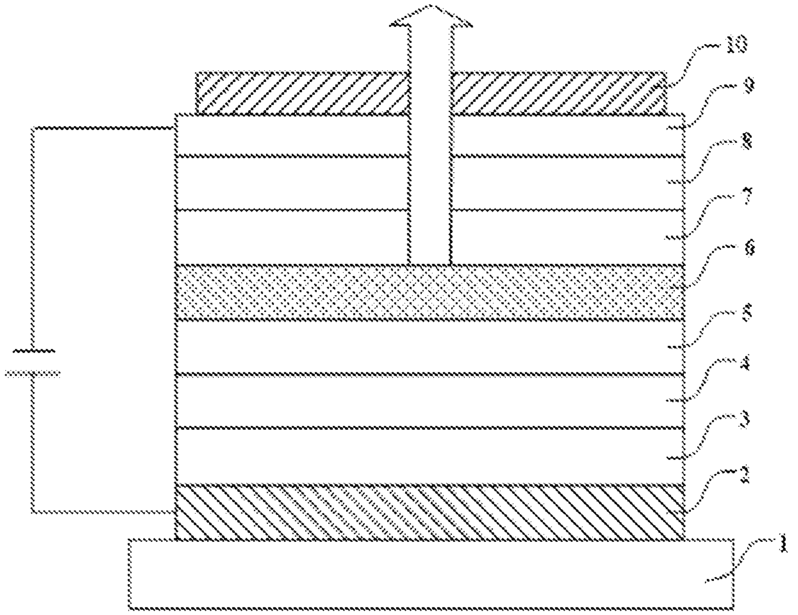
FIG. 1 is a schematic structural diagram of an organic electroluminescent device according to an embodiment of the present application.

Reference numerals are explained as follows: 1 substrate, 2 anode, 3 hole injection layer, 4 first hole transport layer, 5 second hole transport layer, 6 luminescent layer, 7 first electron transport layer, 8 second electron transport layer, 9 cathode, 10 first capping layer, 11 second capping layer, 100 mobile phone.

DETAILED DESCRIPTION

In order to make the objectives, technical solutions and beneficial technical effects of the present application clearer, the present application will be further described in detail below in conjunction with embodiments. It should be understood that the embodiments described in this specification are only for explaining the application, not intending to limit the application.

The above summary of the present application is not intended to describe each disclosed embodiment or every implementation in the present application. The following description illustrates exemplary embodiments more specifically. In many places throughout the application, guidance is provided through a series of examples, which can be used in various combinations. In each instance, the enumerated examples is only a representative group and should not be interpreted as exhaustive.

In the description herein, unless otherwise specified, a numeric range described with the term "above" or "below" includes the lower or upper limit itself.

In the description herein, unless otherwise specified, "multiple", "more", and "plurality" mean two or more.

The terms "a", "an" and "the" refer to one or more molecules of the compound and are not limited to a single molecule of the compound. Furthermore, one or more molecules may or may not be the same, as long as they fall within the scope of the chemical compound.

The terms "include", "comprise" and variations thereof in the specification and claims have a non-limiting meaning.

The terms "optional" and "optionally" refer to embodiments of the present application that may provide certain benefits under certain circumstances. However, other embodiments may also be used under the same or other circumstances. Furthermore, the description of one or more optional embodiments does not imply that other embodiments are unavailable, and is not intended to exclude other embodiments from the scope of the present disclosure.

The grouping of alternative elements or embodiments disclosed herein should not be construed as limiting. Each group member may be employed and claimed individually or in any combination with other members of the group or other elements found herein. It is anticipated that one or more members of a group may be included in or deleted from the group for reasons of convenience and/or patentability. When any such inclusion or deletion occurs, the specification is hereby deemed to contain the group as modified, thus satisfying the written description of all Markush groups used in the claims.

Unless otherwise specified, when a compound or chemical structure feature (e.g., aryl) is referred to as being "substituted", the compound or chemical structure feature may have one or more substituents, and when a plurality of substituents exist, the substituents may be the same or different. The term "substituent" has the broadest meaning known to those of ordinary skill in the art, and includes a moiety that occupies the locations normally occupied by one or more hydrogen atoms attached to the parent compound or chemical structural feature.

The term "aryl" refers to a closed aromatic ring or ring system. When not explicitly indicated, an "aryl" structure may be monocyclic, polycyclic or fused. Examples of the aryl include, but are not limited to, phenyl, naphthyl, anthryl, phenanthryl, biphenyl, terphenyl, tetraphenyl, triphenylenyl, pyrenyl, chrysenyl, perylenyl, indenyl, triphenylenyl, fluorenyl, 9,9-dimethylfluorenyl, and spirobifluorenyl. In various embodiments, a 6-membered to 60-membered aryl group refers to an aryl group that may contain 6 to 60 carbon atoms for ring formation.

The term "heteroaryl" indicates that one or more atoms in the ring of the aryl group are elements other than carbon. Examples of the heteroaryl include, but are not limited to, pyrrolyl, furanyl, thienyl, indolyl, benzofuranyl, benzothienyl, dibenzofuran, dibenzothiophene, carbazolyl, indenocarbazolyl, indolocarbazolyl, pyridyl, pyrimidinyl, pyrazinyl, pyridazinyl, triazinyl, oxazolyl, isooxazolyl, thiazolyl, isothiazolyl, benzoxazolyl, benzoisoxazolyl, benzothiazolyl, and benzoisothiazolyl. In various embodiments, a 5-membered to 60-membered heteroaryl group refers to a heteroaryl group that may contain 5 to 60 atoms (including carbon atoms and heteroatoms) for ring formation. In some embodiments, a whole 5-membered to 60-membered heteroaryl group may include 1 to 10, 1 to 6 or 1 to 3 ring heteroatoms (e.g., N, O, S, Si, Se, etc.).

The term "alkyl" refers to a saturated hydrocarbon, including both linear and branched structures. Examples of the alkyl include, but are not limited to, methyl, ethyl, propyl (e.g., n-propyl and isopropyl), butyl (e.g., n-butyl, isobutyl, sec-butyl, and tert-butyl), and pentyl (e.g., n-pentyl, isopentyl, and neopentyl). In various embodiments, a C1-C20 alkyl group refers to an alkyl group that may contain 1 to 20 carbon atoms.

The term "alkoxy" refers to an alkyl group containing an oxygen atom (—O—). Examples of the alkoxy include, but are not limited to, methoxy, ethoxy, and propoxy. In various embodiments, a C1-C20 alkoxy group refers to an alkoxy group that may contain 1 to 20 carbon atoms.

The term "alkylthio" refers to an alkyl group containing a sulfur atom (—S—). Examples of the alkylthio include, but are not limited to, methylthio, ethylthio, and propylthio. In various embodiments, a C1-C20 alkylthio group refers to an alkylthio group that may contain 1 to 20 carbon atoms.

The term "alkenyl" refers to an unsaturated hydrocarbon group containing carbon-carbon double bonds, including both linear and branched structures, and the number of carbon-carbon double bonds may be one or more. Examples of the alkenyl include, but are not limited to, vinyl, propenyl, allyl, and butadienyl. In various embodiments, a C2-C20 alkenyl group refers to an alkenyl group that may contain 2 to 20 carbon atoms.

The term "alkynyl" refers to an unsaturated hydrocarbon group containing carbon-carbon triple bonds, including both linear and branched structures, and the number of carbon-carbon triple bonds may be one or more. Examples of the alkynyl include, but are not limited to, ethynyl, propynyl, butynyl, and butadiynyl. In various embodiments, a C2-C20 alkynyl group refers to an alkynyl group that may contain 2 to 20 carbon atoms.

The term "alcyl" refers to a carbocyclic system with aliphatic nature, including cyclized alkyl, alkenyl and alkynyl, which may be monocyclic, fused, bridged or spirocyclic. Examples of the alcyl include, but are not limited to, cyclopropyl, cyclobutyl, cyclopentyl, cyclohexyl, cycloheptyl, cyclopentenyl, cyclohexenyl, and cyclohexynyl. In various embodiments, a 3-membered to 20-membered alcyl group refers to an alcyl group that may contain 3 to 20 carbon atoms for ring formation.

The term "heteroalcyl" indicates that one or more atoms in an alcyl ring are elements (e.g., N, O, S, Si, Se, etc.) other than carbon. Examples of the heteroalcyl include, but are not limited to, oxiranyl, aziridyl, propiolactonyl, tetrahydrofuranyl, and tetrahydrothienyl. In various embodiments, a 3-membered to 20-membered heteroalcyl group refers to a heteroalcyl group that may contain 3 to 20 atoms (including carbon atoms and heteroatoms) for ring formation.

The term "hydrogen" refers to $^{1}H(H)$.

The term "deuterium" refers to $^{2}H(D)$.

The term "tritium" refers to $^{3}H(T)$.

When a substituent is "monovalent", it refers to a group formed by removing one H atom from the molecule. When a substituent is "divalent", it refers to a group formed by removing two H atoms from the molecule.

At various places of this specification, substituents of compounds are disclosed in form of groups or ranges. This description is expressly anticipated to include each individual sub-combination of members in these groups and ranges. For example, the term "C1-C8 alkyl" is expressly anticipated to individually disclose C1, C2, C3, C4, C5, C6, C7, C8, C1-C8, C1-C7, C1-C6, C1-05, C1-C4, C1-C3, C1-C2, C2-C8, C2-C7, C2-C6, C2-05, C2-C4, C2-C3, C3-C8, C3-C7, C3-C6, C3-05, C3-C4, C4-C8, C4-C7, C4-C6, C4-05, C5-C8, C5-C7, C5-C6, C6-C8, C6-C7 and C7-C8 alkyl. As other examples, integers ranging from 1 to 20 are expressly anticipated to individually disclose 1, 2, 3, 4, 5, 6, 7, 8, 9, 10, 11, 12, 13, 14, 15, 16, 17, 18, 19 and 20. Accordingly, other groups or ranges are expressly anticipated.

Herein, the representation of a single bond passing through a ring or ring system indicates that the single bond can be attached to any accessible position of the ring or ring system. "#" appears to indicate an attachment position.

Compound

An embodiment of a first aspect of the present application provides a compound having the structure shown in Formula 1.

Formula 1

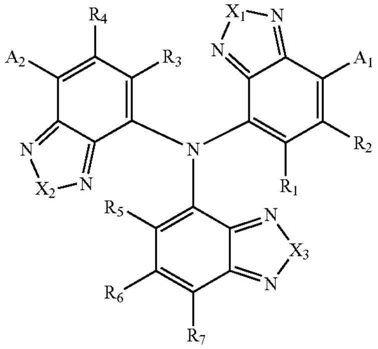

$A_1$ and $A_2$ each independently represent $-(L)_n-R$, where L each independently represents 6-membered to 60-membered divalent aryl unsubstituted or substituted by $R^a$ or to 60-membered divalent heteroaryl unsubstituted or substituted by $R^a$, R represents 6-membered to 60-membered monovalent aryl unsubstituted or substituted by $R^a$ or 5-membered to 60-membered monovalent heteroaryl unsubstituted or substituted by $R^a$, and n represents 0, 1 or 2.

$R_1$, $R_2$, $R_3$, $R_4$, $R_5$, $R_6$, and $R_7$ each independently represent hydrogen, deuterium, tritium, a halogen atom or the following group unsubstituted or substituted by $R^a$:

C1-C20 monovalent alkyl, C1-C20 monovalent alkoxy, C1-C20 monovalent alkylthio, C2-C20 monovalent alkenyl, C2-C20 monovalent alkynyl, 3-membered to 20-membered monovalent alcyl, 3-membered to 20-membered monovalent heteroalcyl, 6-membered to monovalent aryl, or 5-membered to 40-membered monovalent heteroaryl.

$X_1$, $X_2$, and $X_3$ each independently represent S, O, $N(Y_1)$, $C(Y_2)_2$ or $Si(Y_3)_2$, and $Y_1$, $Y_2$, and $Y_3$ each independently represent hydrogen, deuterium, tritium, or the following group unsubstituted or substituted by $R^a$:

C1-C20 monovalent alkyl, C1-C20 monovalent alkoxy, C1-C20 monovalent alkylthio, C2-C20 monovalent alkenyl, C2-C20 monovalent alkynyl, 3-membered to 20-membered monovalent alcyl, 3-membered to 20-membered monovalent heteroalcyl, 6-membered to monovalent aryl, or 5-membered to 40-membered monovalent heteroaryl.

$R^a$ represents deuterium, tritium, a halogen atom, cyano, nitro, carboxyl, carbonyl, amino, C1-C20 monovalent alkyl, C1-C20 monovalent alkoxy, C1-C20 monovalent alkylthio, C2-C20 monovalent alkenyl, C2-C20 monovalent alkynyl, 3-membered to monovalent alcyl, 3-membered to 20-membered monovalent heteroalcyl, 6-membered to 40-membered monovalent aryl, or 5-membered to 40-membered monovalent heteroaryl, wherein one or more hydrogens of C1-C20 monovalent alkyl, C1-C20 monovalent alkoxy, C1-C20 monovalent alkylthio, C2-C20 monovalent alkenyl, C2-C20 monovalent alkynyl, 3-membered to 20-membered monovalent alcyl, 3-membered to 20-membered monovalent heteroalcyl, 6-membered to 40-membered monovalent aryl, or 5-membered to 40-membered monovalent heteroaryl each are independently replaced by deuterium, tritium, a halogen atom, cyano, nitro, carboxyl, carbonyl, or amino.

Optionally, $R^a$ represents deuterium, tritium, a halogen atom, methyl, ethyl, propyl, butyl, methoxy, ethoxy, propoxy, cyclopropyl, cyclobutyl, cyclopentyl, cyclohexyl, tetrahydrofuranyl, tetrahydrothienyl, or phenyl.

In the present application, heteroatoms include at least one of N, O, S, Si, and Se.

In the present application, the compound has a refractive index $n \geq 2.1$ at a wavelength of 460 nm.

The compound provided in the present application has a difference between the refractive index at a wavelength of 460 nm and the refractive index at a wavelength of 530 nm being less than or equal to 0.17, optionally 0.09-0.17, and more optionally 0.09-0.15.

The compound provided in the present application has a difference between the refractive index at a wavelength of 530 nm and the refractive index at a wavelength of 620 nm being less than or equal to 0.11, optionally 0.03-0.11, and more optionally 0.05-0.11.

The compound provided in the present application has a difference between the refractive index at a wavelength of 460 nm and the refractive index at a wavelength of 620 nm being less than or equal to 0.24, optionally 0.15-0.24, and more optionally 0.18-0.24.

Existing CPL materials mostly use aromatic amine derivatives, phosphoroxy derivatives and quinolinone derivatives having both hole transport function and electron transport function, which improves the light extraction efficiency to a certain extent. However, the existing CPL materials have relatively low refractive indexes, generally less than 1.9, which cannot meet the requirements of high refractive index; or the CPL materials such as aromatic amine derivatives having specific structures with high refractive indexes improve the light extraction efficiency, but do not have good luminous efficiency and color purity at the same time, especially for blue light emitting elements; or when the refractive indexes of the CPL materials meet the requirements, the CPL materials have relatively strong absorption or relatively large extinction coefficients in visible light regions. In addition, in order to increase the density of molecules and achieve high thermal stability of the existing CPL materials, the designed molecular structures are usually large and loose, and the molecules cannot be tightly packed, resulting in too many molecular gel holes that cannot be covered completely during evaporation and deposition.

The compound provided by the present application has a simple molecular structure and has a high refractive index in visible light region, thereby helping to improve the light extraction efficiency and luminous efficiency, especially the external quantum efficiency of a device.

The compound provided by the present application has a small extinction coefficient in blue light region, and hardly absorbs blue light, which is beneficial to improving the luminous efficiency and alleviates the dependence of the device on the light emitting angle.

The compound provided by the present application has small differences in refractive indexes in respective wavelength regions of blue, green and red light, so that all light in the blue, green and red light emitting devices can simultaneously have high light extraction efficiency.

The compound provided by the present application almost does not have absorbance in the respective wavelength regions of blue, green and red light, so that the color purity does not decrease.

Therefore, the compound provided by the present application can improve the light extraction efficiency and luminous efficiency, especially the external quantum efficiency of a device, and can also effectively reduce the color shift of the device at multi-angle display.

In addition, the compound provided by the present application has relatively high glass transition temperature and decomposition temperature and relatively high molecular thermal stability, can be evaporated and deposited without thermal decomposition, has high film-forming stability and excellent durability, and can block water and oxygen in the external environment, protect a device from water and oxygen erosion, and prolong the life of the device.

The compound provided by the present application has a relatively large extinction coefficient in an ultraviolet light region (less than 400 nm), which is beneficial to absorbing harmful light and protecting eyesight.

In some embodiments, n represents 0 or 1.

In some embodiments, L each independently represents phenyl, naphthyl, anthryl, phenanthryl, biphenyl, terphenyl, tetraphenyl, triphenylenyl, pyrenyl, chrysenyl, perylenyl, indenyl, triphenylenyl, fluorenyl, 9,9-dimethylfluorenyl, spirobifluorenyl, pyrrolyl, furanyl, thienyl, indolyl, benzofuranyl, benzothienyl, dibenzofuran, dibenzothiophene, carbazolyl, indenocarbazolyl, indolocarbazolyl, pyridyl, pyrimidinyl, pyrazinyl, pyridazinyl, triazinyl, oxazolyl, isooxazolyl, thiazolyl, isothiazolyl, benzoxazolyl, benzoisoxazolyl, benzothiazolyl, or benzoisothiazolyl unsubstituted or substituted by $R^a$.

Optionally, L each independently represents phenyl, naphthyl, biphenyl, terphenyl, or tetraphenyl. Further, L each independently represents phenyl.

In some embodiments, R represents phenyl, naphthyl, anthryl, phenanthryl, biphenyl, terphenyl, tetraphenyl, triphenylenyl, pyrenyl, chrysenyl, perylenyl, indenyl, triphenylenyl, fluorenyl, 9,9-dimethylfluorenyl, spirobifluorenyl, pyrrolyl, furanyl, thienyl, indolyl, benzofuranyl, benzothienyl, dibenzofuran, dibenzothiophene, carbazolyl, indenocarbazolyl, indolocarbazolyl, pyridyl, pyrimidinyl, pyrazinyl, pyridazinyl, triazinyl, oxazolyl, isooxazolyl, thiazolyl, isothiazolyl, benzoxazolyl, benzoisoxazolyl, benzothiazolyl, benzoisothiazolyl unsubstituted or substituted by $R^a$.

Optionally, R represents phenyl, naphthyl, anthryl, phenanthryl, 9,9-dimethylfluorenyl, dibenzofuran, dibenzothiophene, carbazolyl, benzoxazolyl, or benzothiazolyl unsubstituted or substituted by $R^a$.

In some embodiments, n represents 0 or 1, and R represents phenyl, naphthyl, anthryl, phenanthryl, 9,9-dimethylfluorenyl, dibenzofuran, dibenzothiophene, carbazolyl, benzoxazolyl, or benzothiazolyl unsubstituted or substituted by $R^a$.

In some embodiments, $A_1$ and $A_2$ each independently represent any one of the following groups,

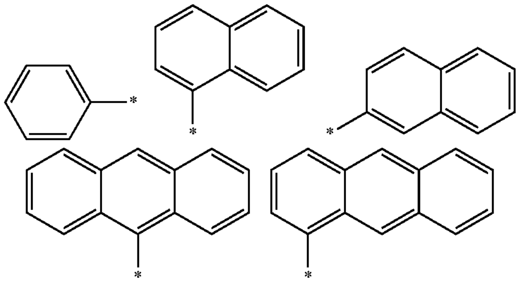

-continued
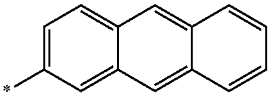
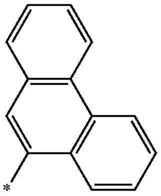
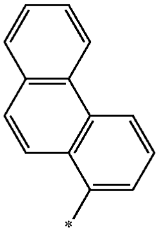
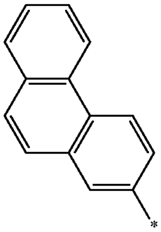
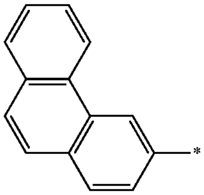
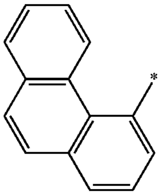
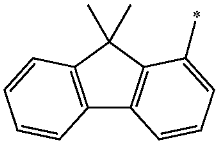
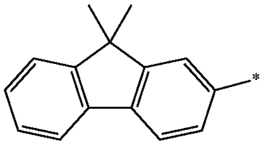
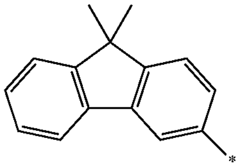
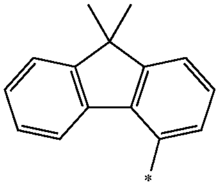
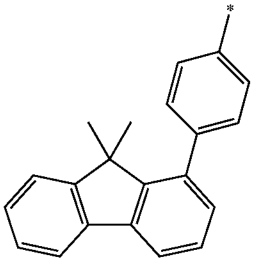
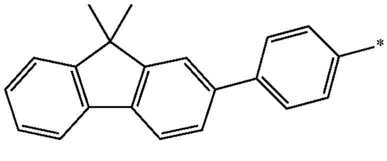
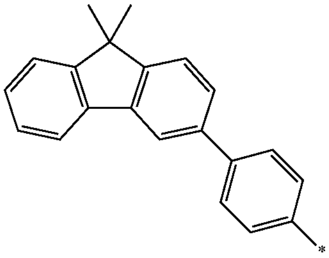
-continued
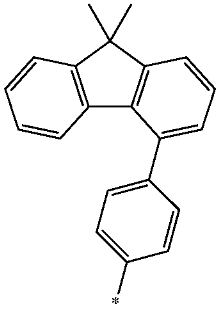
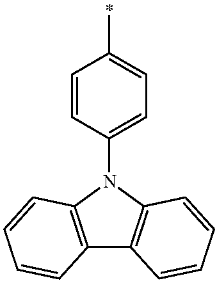
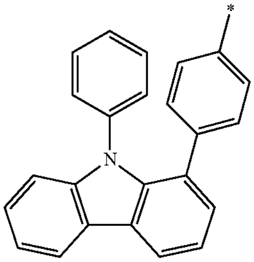
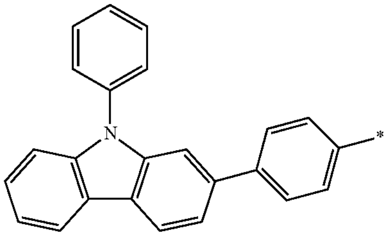
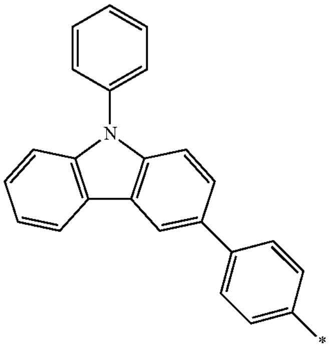
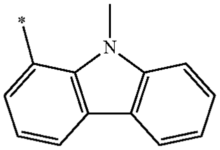
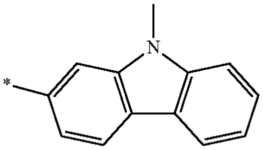
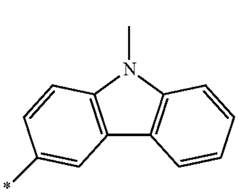
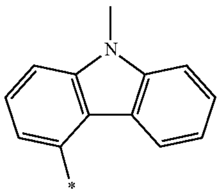
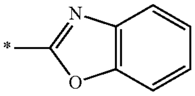
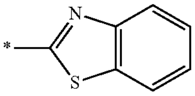
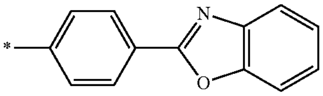

-continued

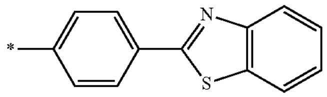

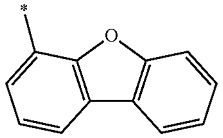

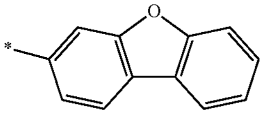

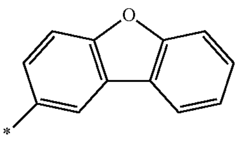

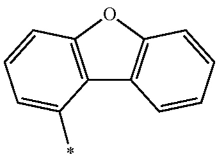

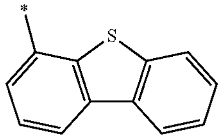

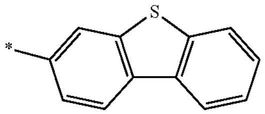

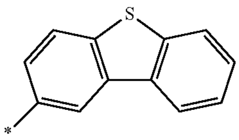

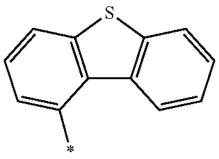

# represents an attachment position.

In some embodiments, $A_1$ and $A_2$ are the same.

In some embodiments, $R_1$, $R_2$, $R_3$, $R_4$, $R_5$, $R_6$, and $R_7$ each independently represent hydrogen, deuterium, tritium, a halogen atom or the following group unsubstituted or substituted by $R^a$:

methyl, ethyl, propyl, butyl, methoxy, ethoxy, propoxy, cyclopropyl, cyclobutyl, cyclopentyl, cyclohexyl, tetrahydrofuranyl, tetrahydrothienyl, phenyl, naphthyl, anthryl, phenanthryl, biphenyl, terphenyl, tetraphenyl, triphenylenyl, pyrenyl, chrysenyl, perylenyl, indenyl, triphenylenyl, fluorenyl, 9,9-dimethylfluorenyl, spirobifluorenyl, pyrrolyl, furanyl, thienyl, indolyl, benzofuranyl, benzothienyl, dibenzofuran, dibenzothiophene, carbazolyl, indenocarbazolyl, indolocarbazolyl, pyridyl, pyrimidinyl, pyrazinyl, pyridazinyl, triazinyl, oxazolyl, isooxazolyl, thiazolyl, isothiazolyl, benzoxazolyl, benzoisoxazolyl, benzothiazolyl, or benzoisothiazolyl.

Optionally, $R_1$, $R_2$, $R_3$, $R_4$, $R_5$, $R_6$, and $R_7$ each independently represent hydrogen, deuterium, tritium, a halogen atom or the following group unsubstituted or substituted by $R^a$:

methyl, ethyl, propyl, butyl, methoxy, ethoxy, propoxy, cyclopropyl, cyclobutyl, cyclopentyl, cyclohexyl, tetrahydrofuranyl, tetrahydrothienyl, or phenyl.

In some embodiments, $X_1$, $X_2$, and $X_3$ are the same.

In some embodiments, $X_1$, $X_2$, and $X_3$ all represent S or O. As an example, the compound is selected from any of the following,

H01

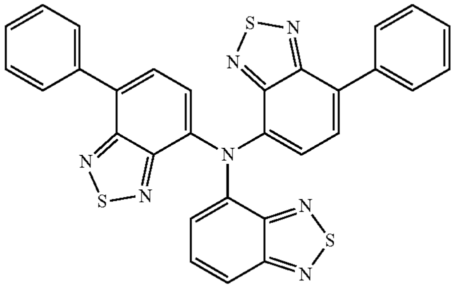

H02

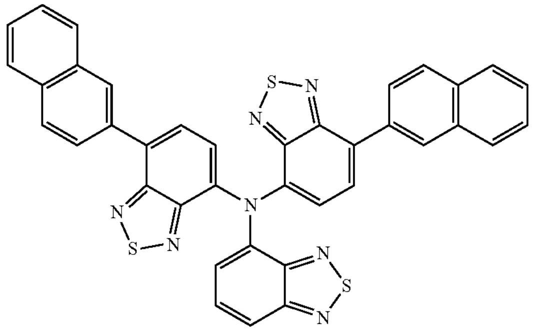

H03

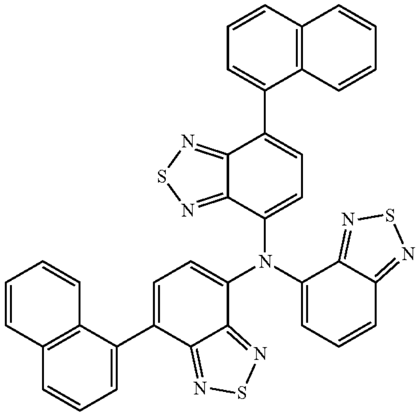

H04

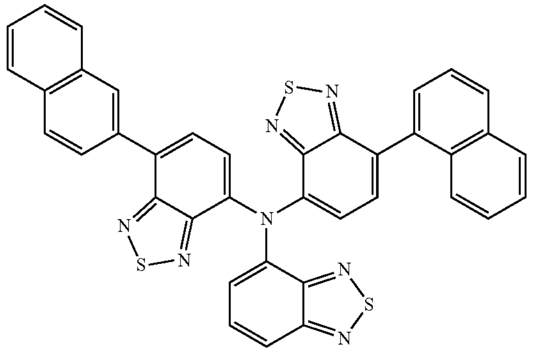

-continued
H05
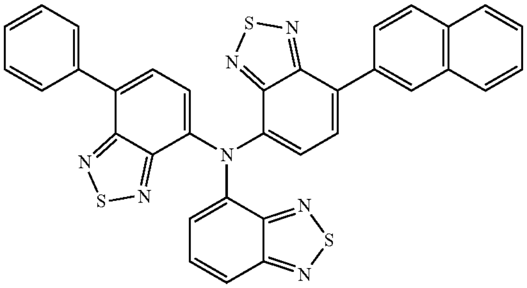
H06
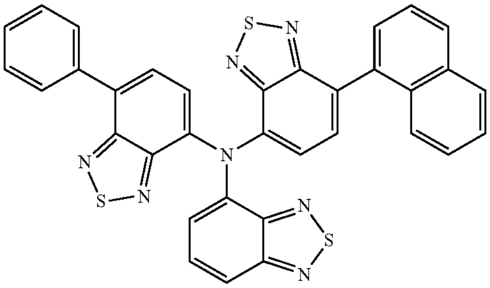
H07
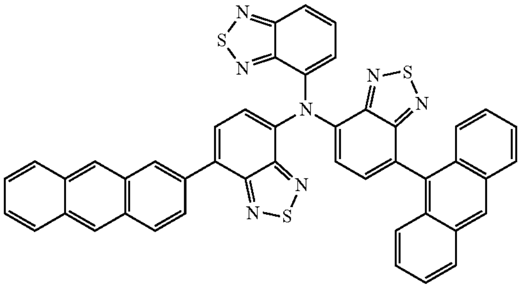
H08
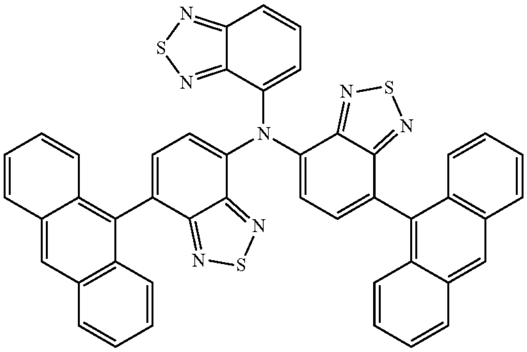
H09
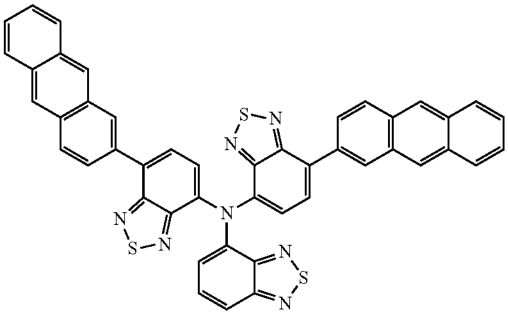
H10
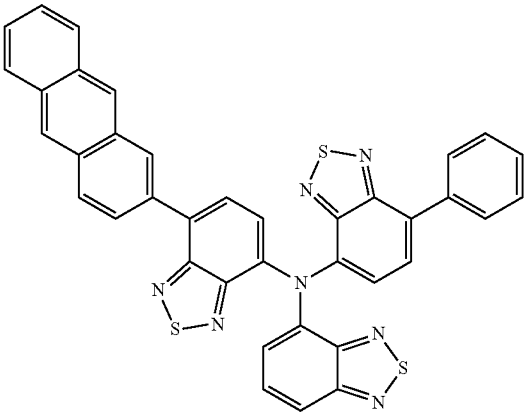
H11
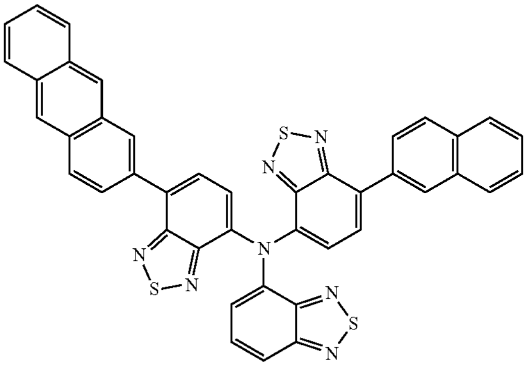
H12
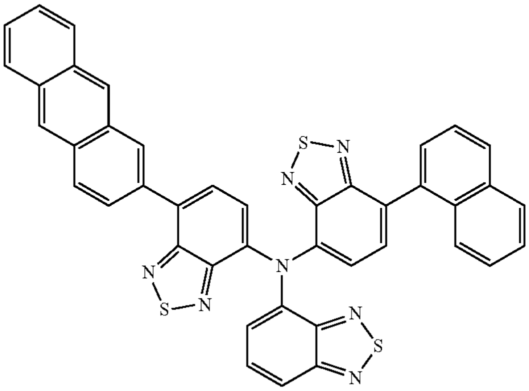

-continued
H13
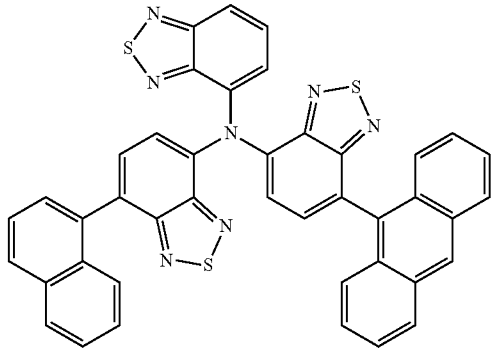
H14
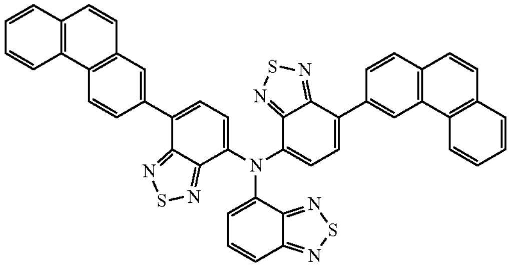
H15
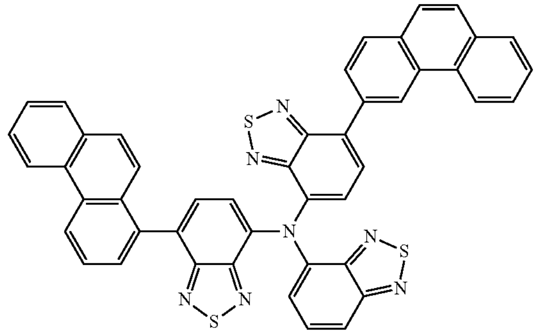
H16
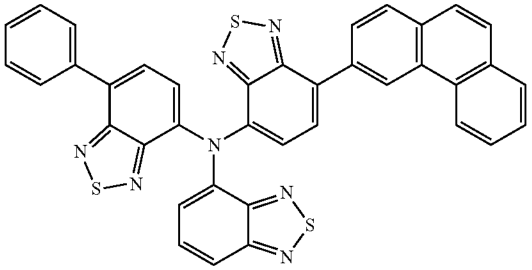
H17
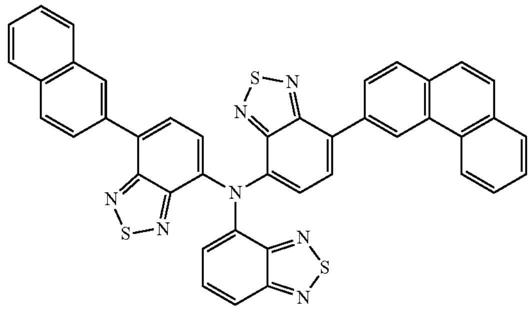
H18
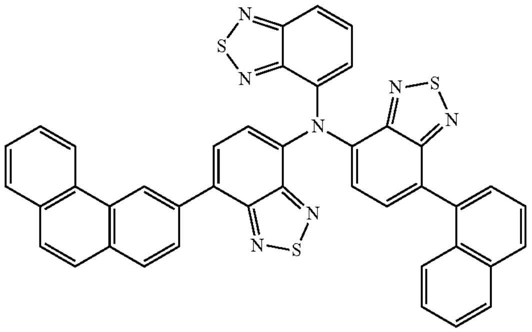
H19
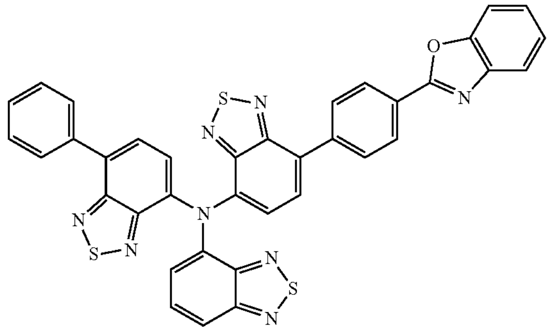
H20
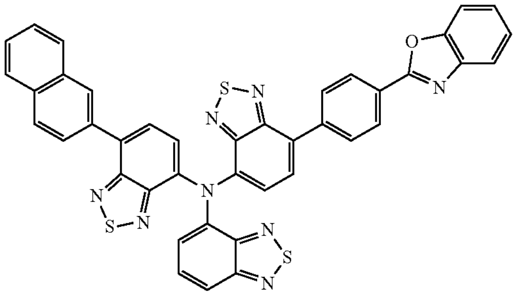

-continued
H21
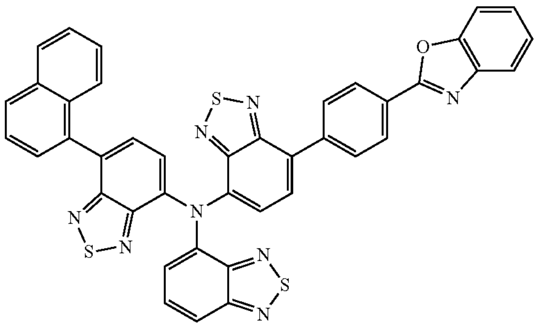
H22
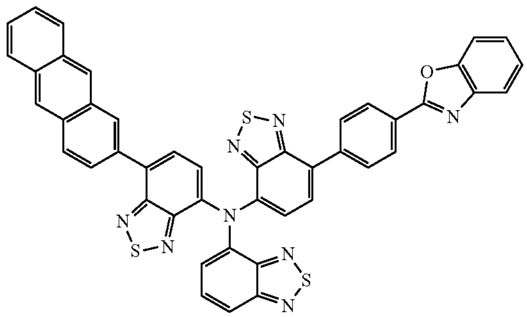
H23
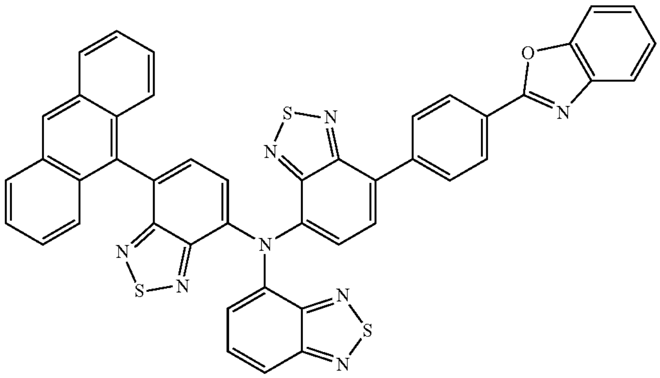
H24
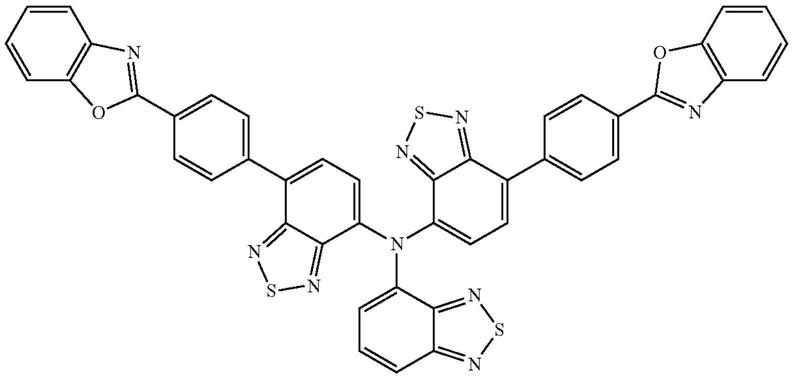
H25
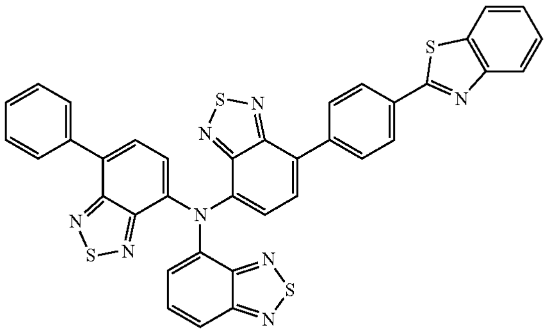
H26
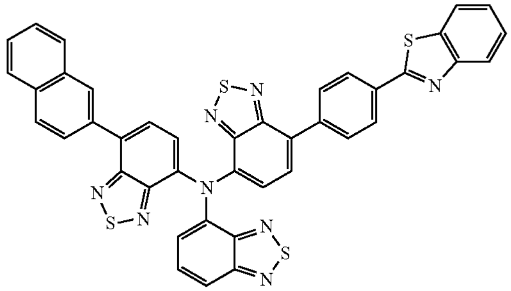

-continued
H27
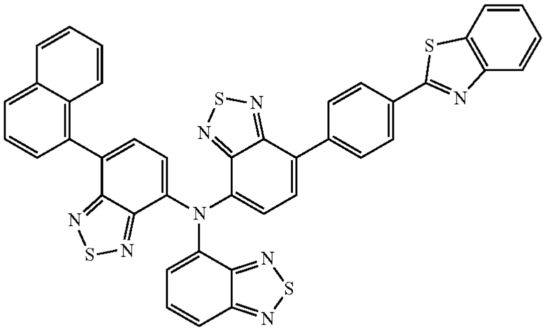
H28
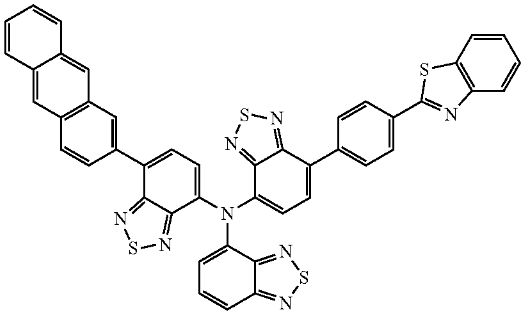
H29
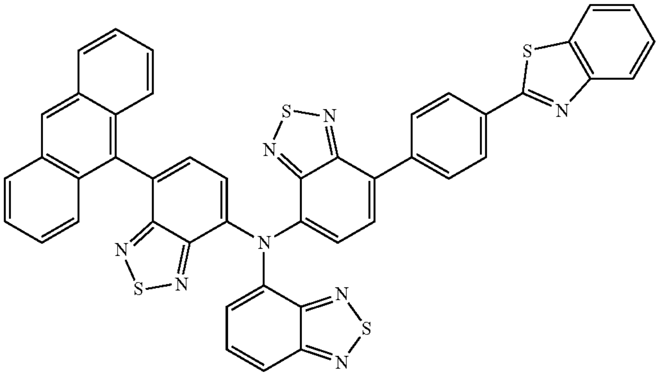
H30
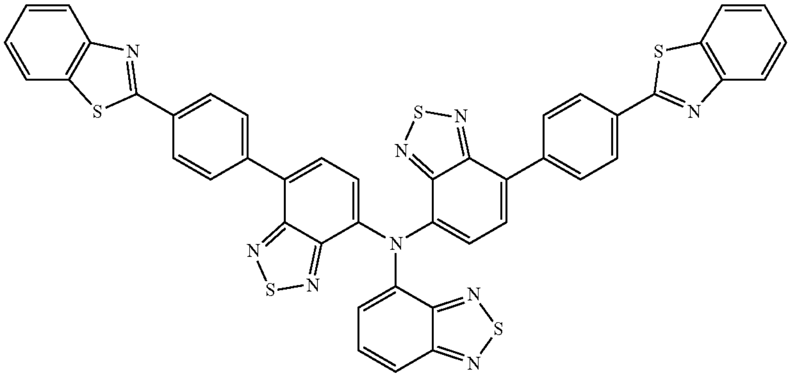
H31
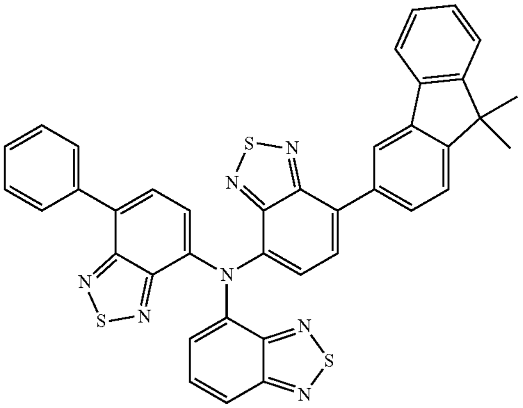
H32
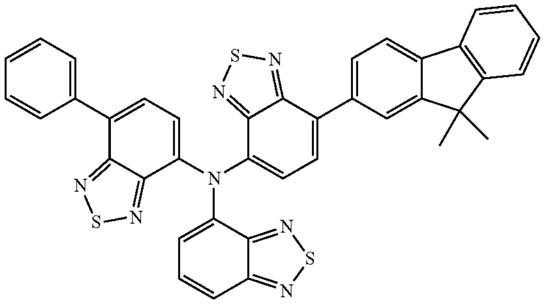

-continued
H33
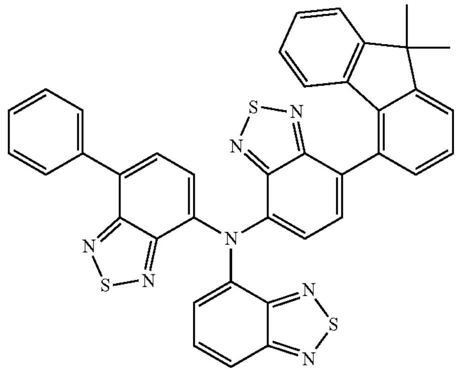
H34
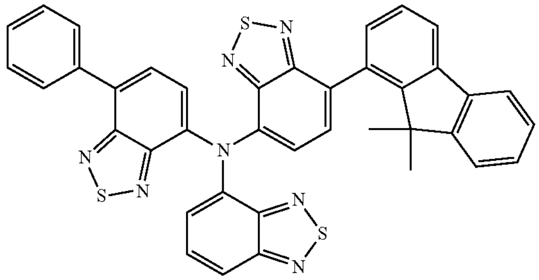
H35
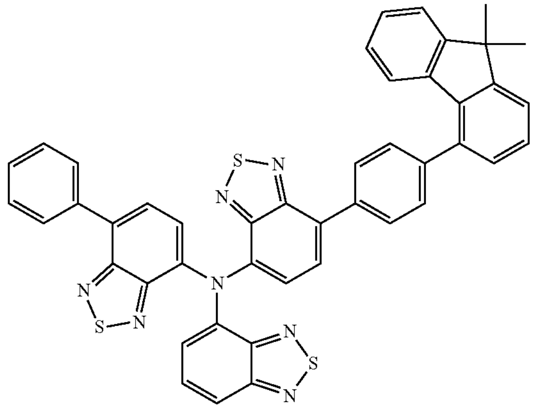
H36
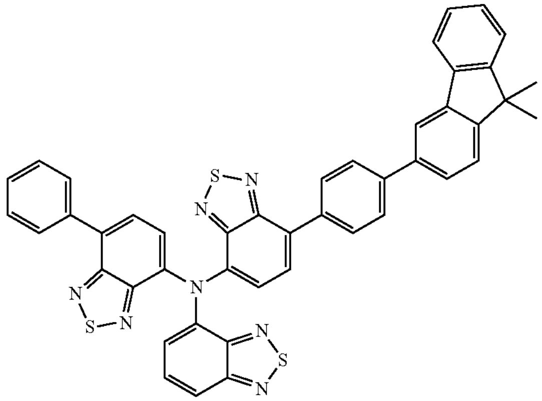
H37
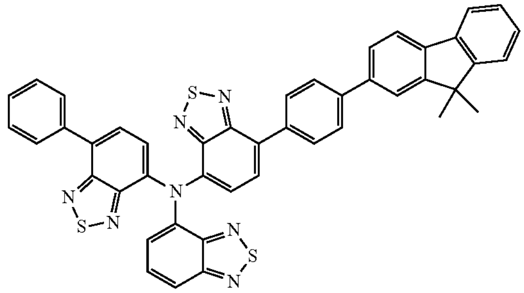
H38
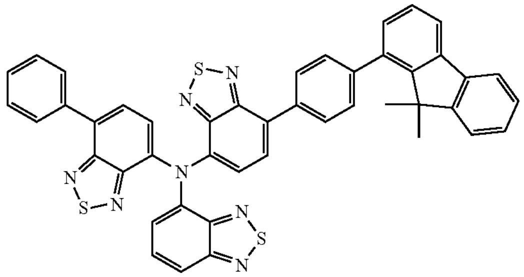
H39
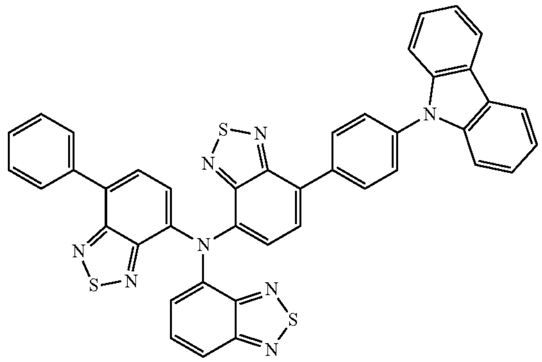
H40
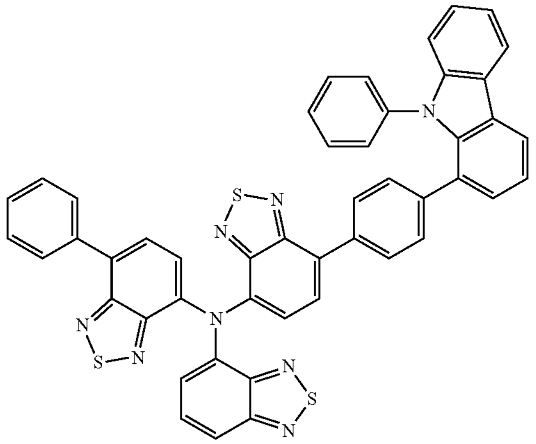

-continued
H41
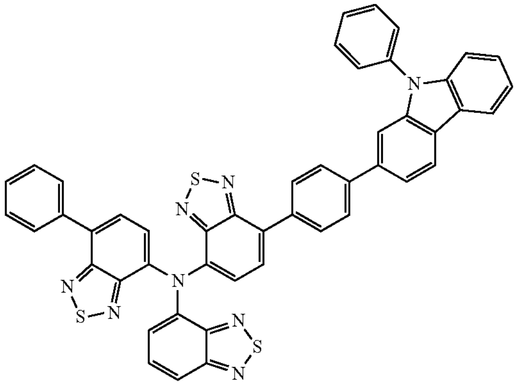
H42
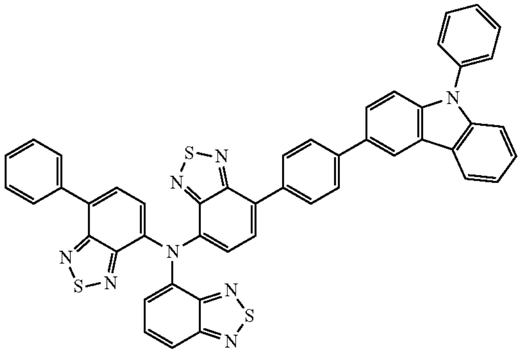
H43
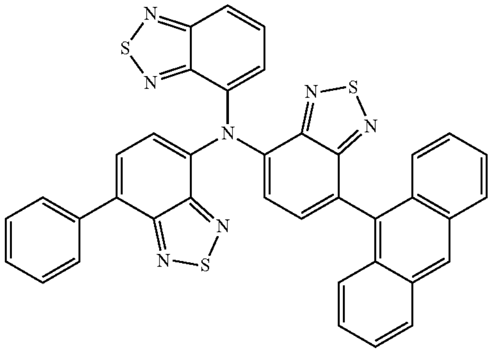
H44
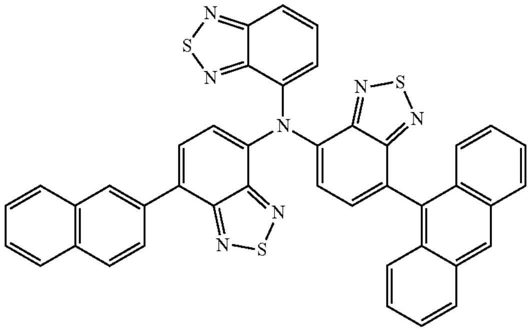
H45
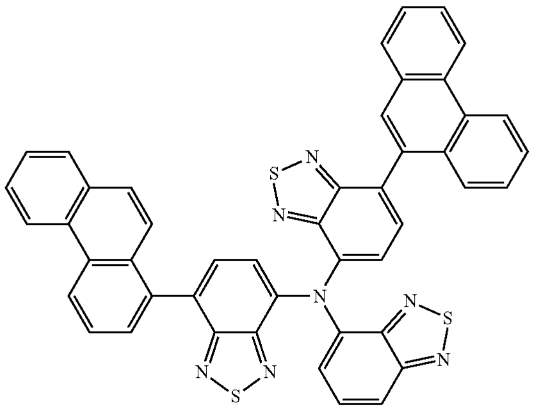
H46
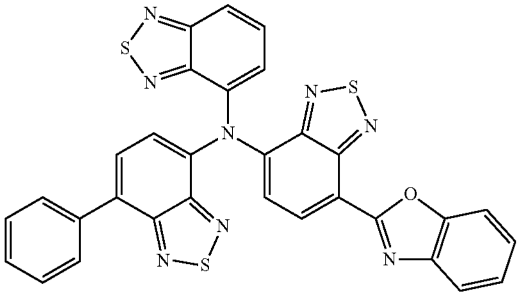
H47
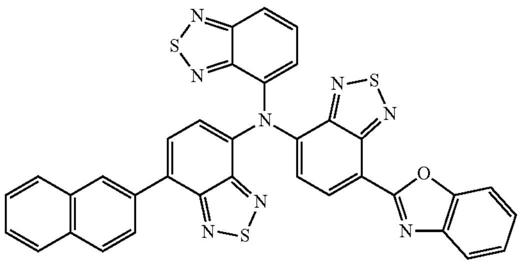
H48
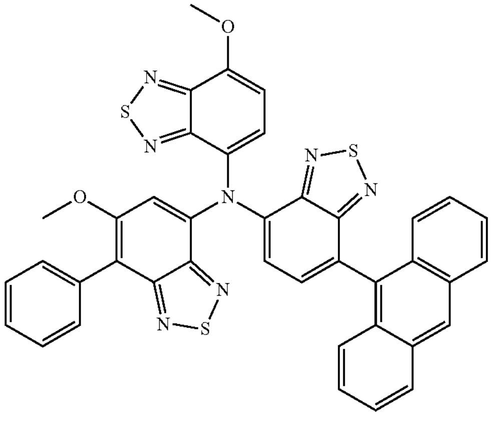

-continued
H49
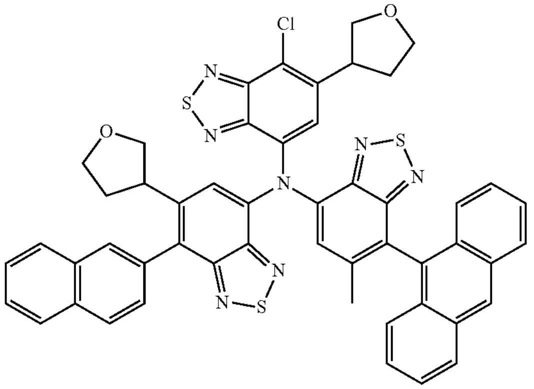
H50
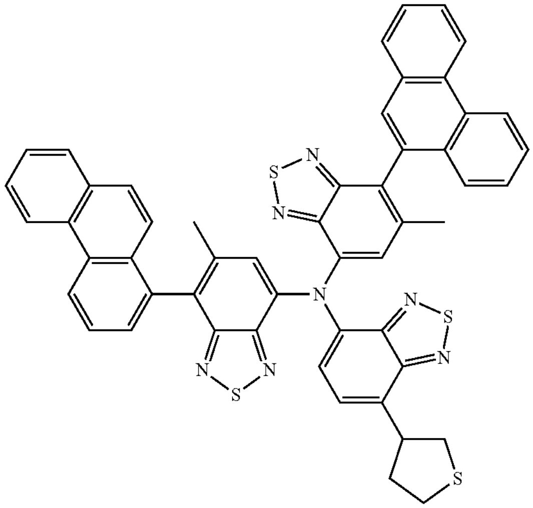
H51
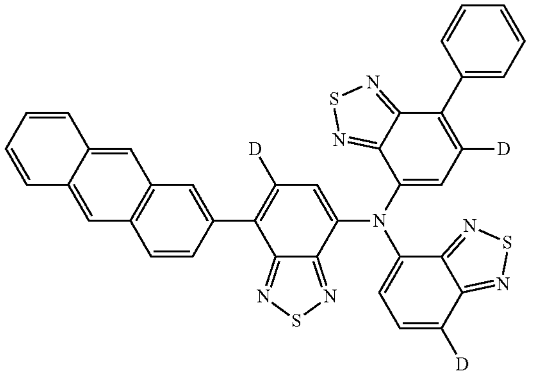
H52
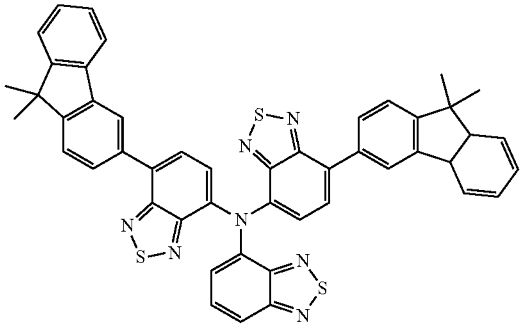
H53
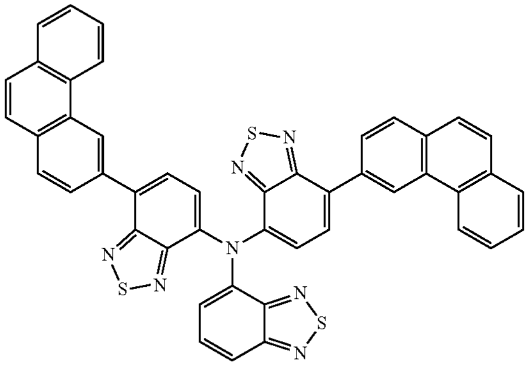
H54
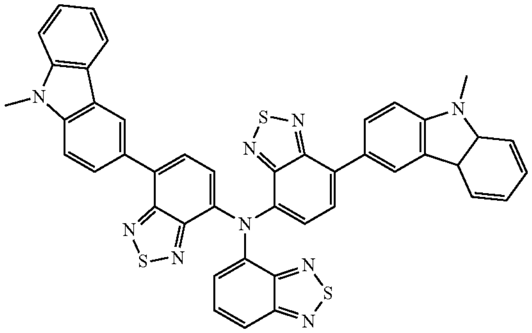
H55
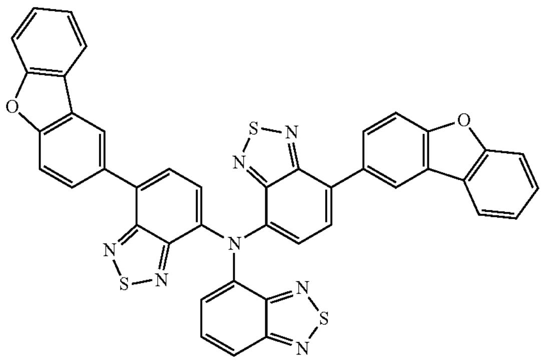
H56
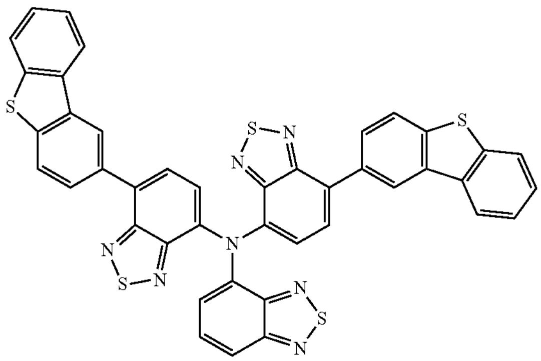

-continued
H57
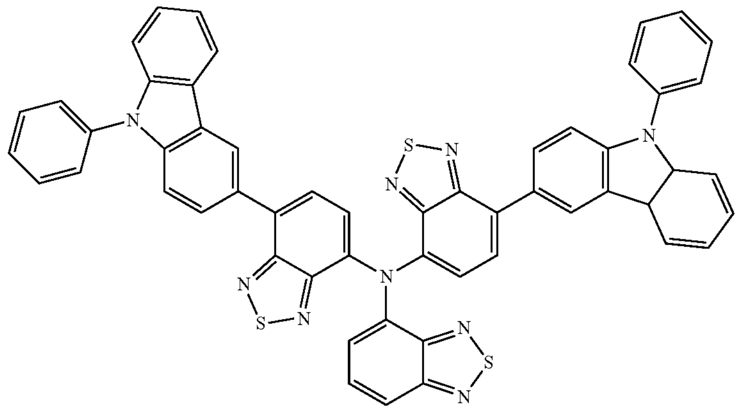
H58
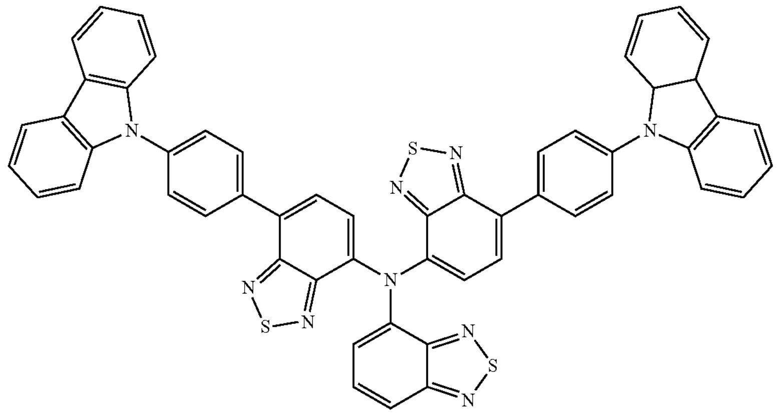
H59
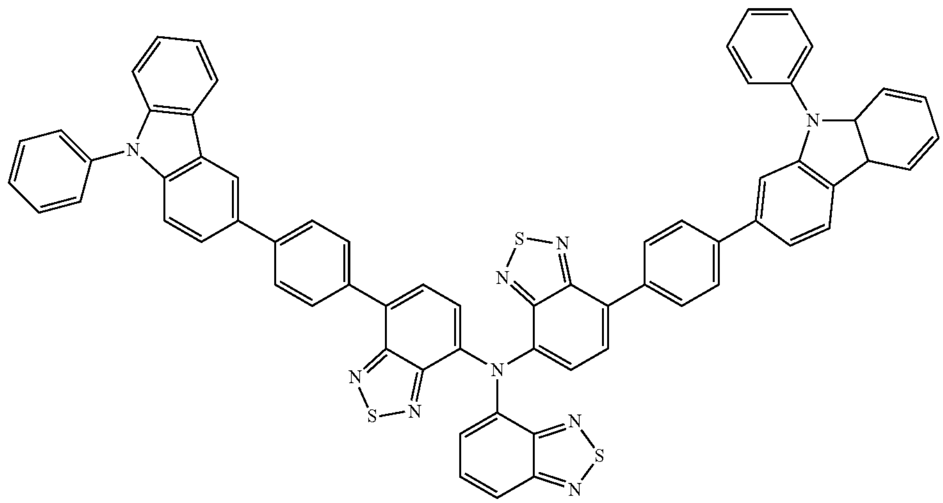
H60
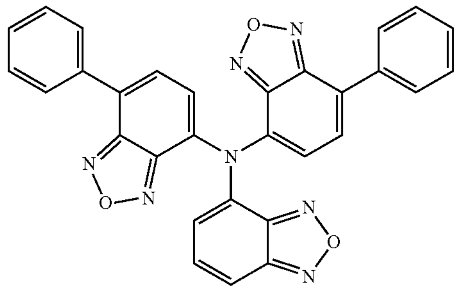
H61
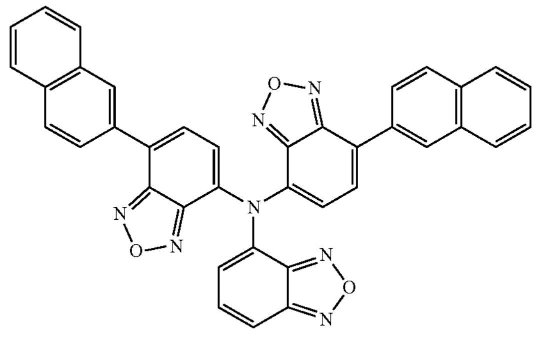

-continued
H62
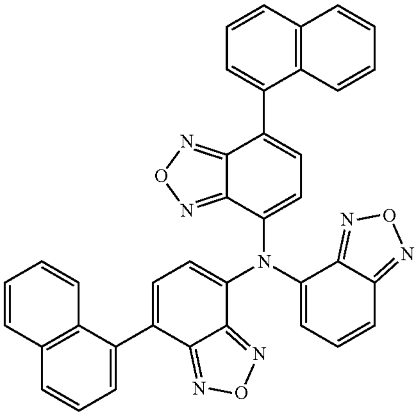
H63
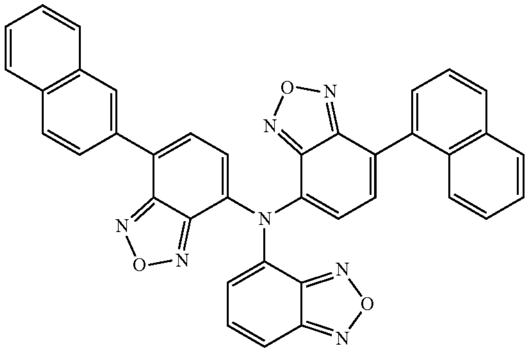
H64
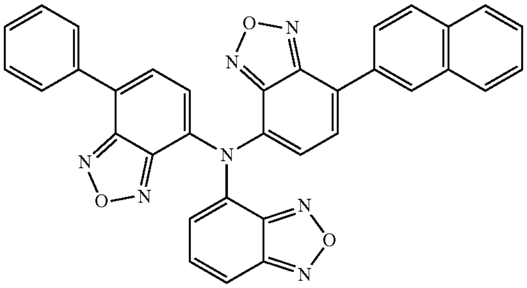
H65
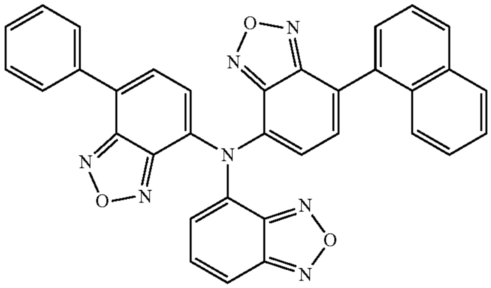
H66
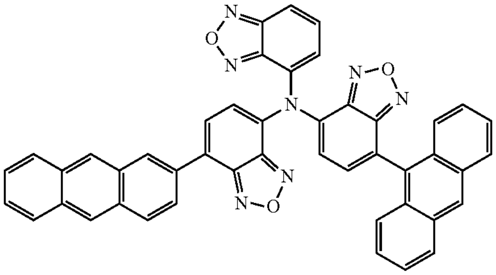
H67
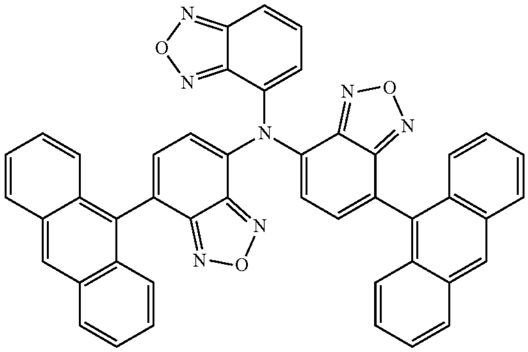
H68
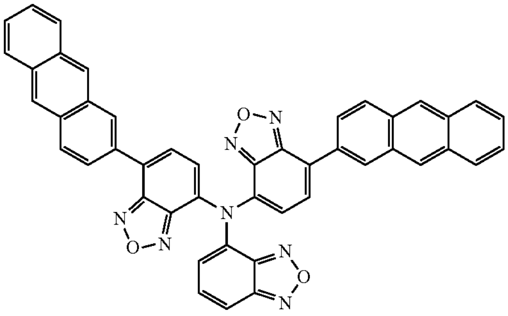
H69
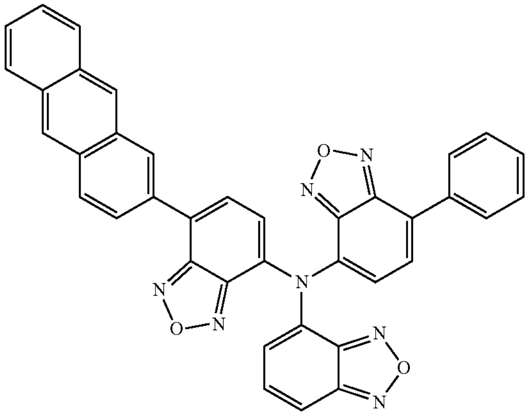

-continued
H70
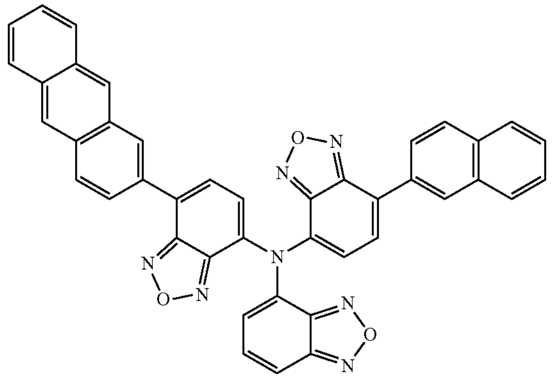
H71
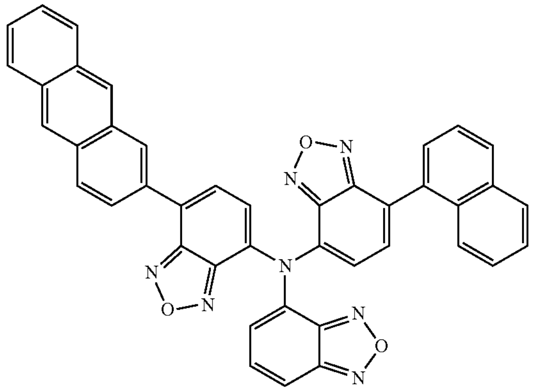
H72
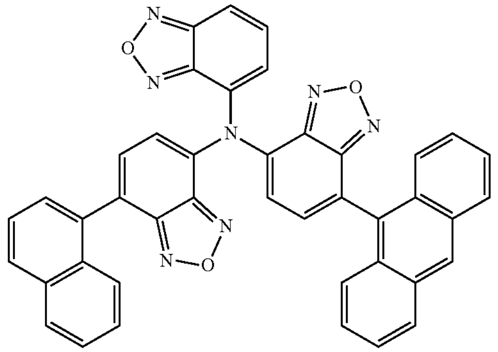
H73
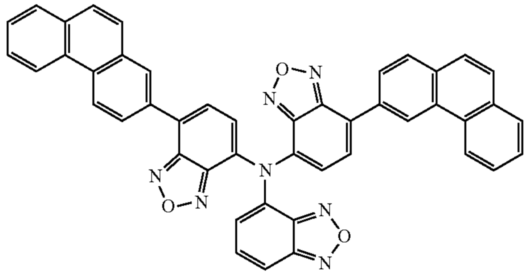
H74
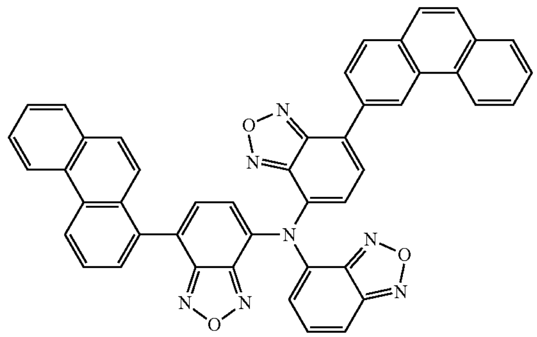
H75
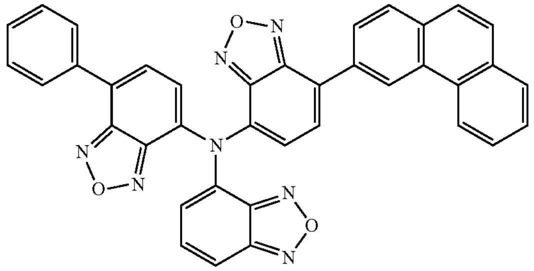
H76
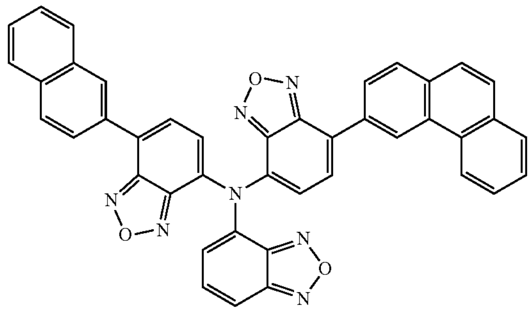
H77
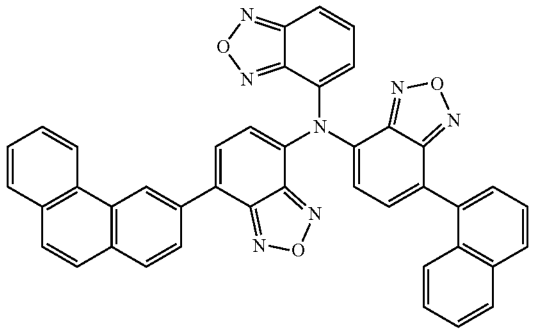

-continued
H78
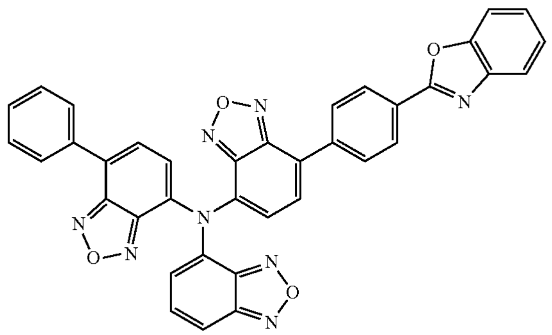
H79
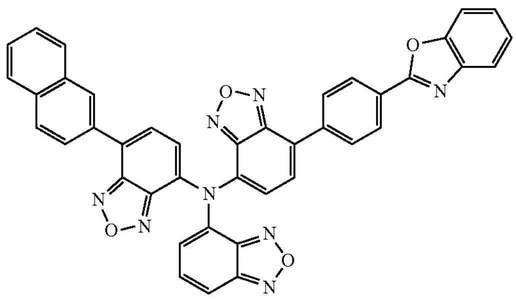
H80
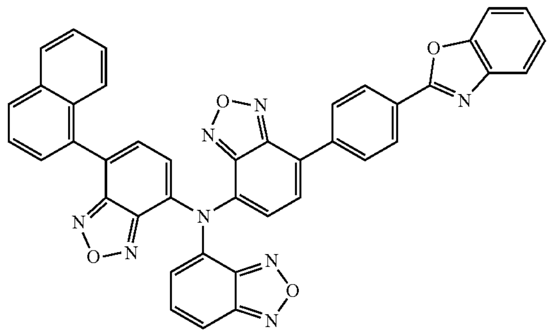
H81
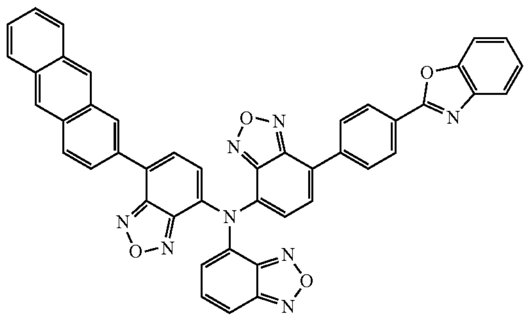
H82
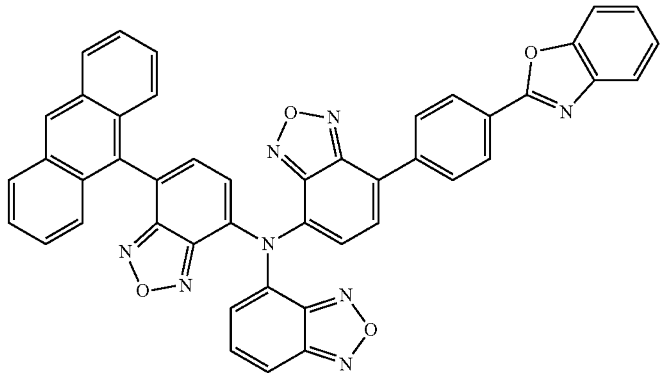
H83
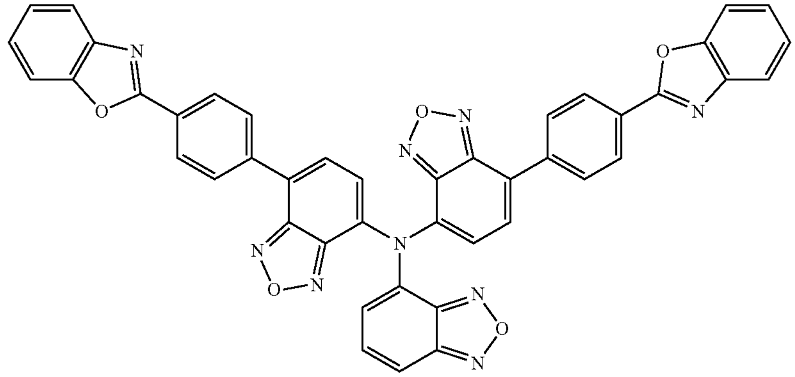

-continued
H84
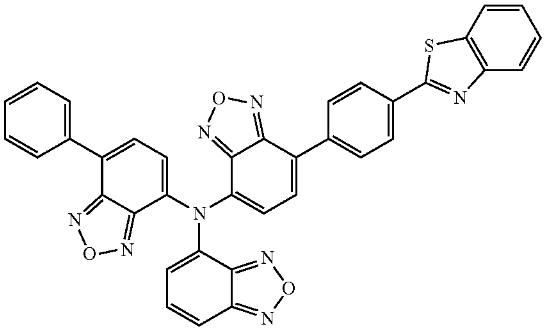
H85
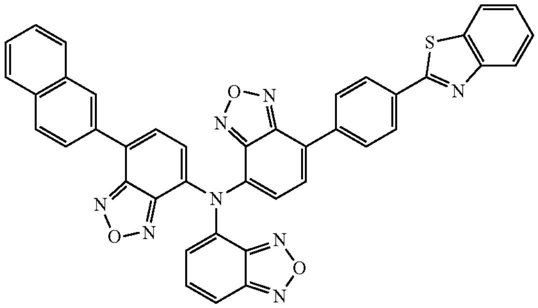
H86
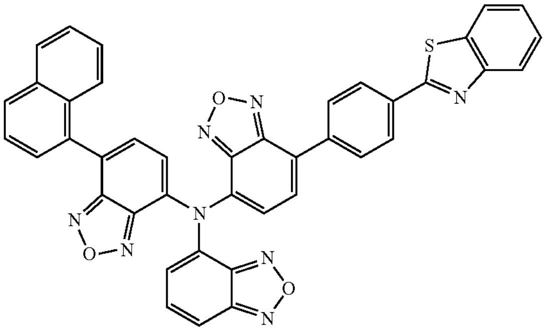
H87
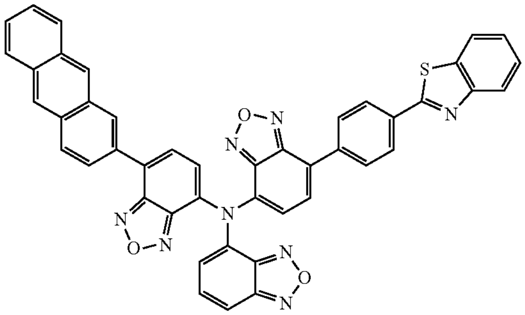
H88
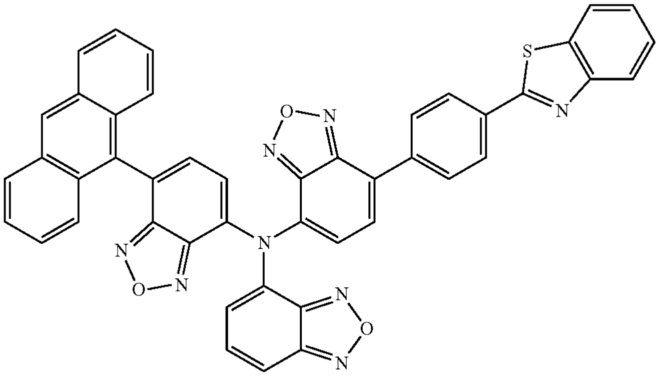
H89
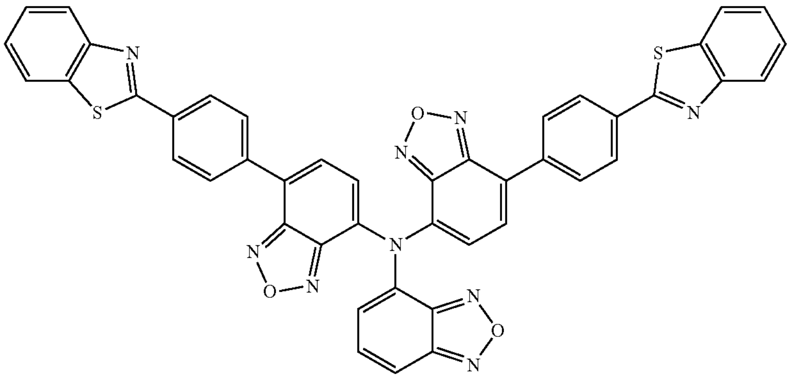

-continued
H90
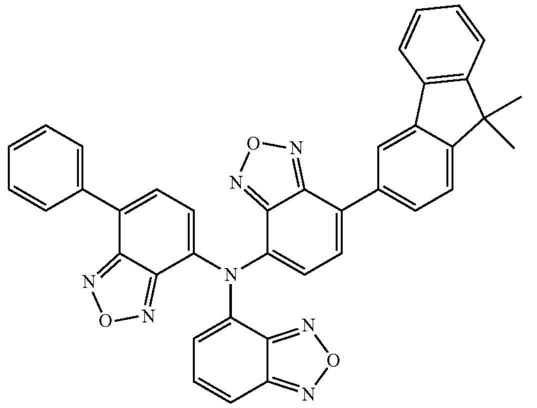
H91
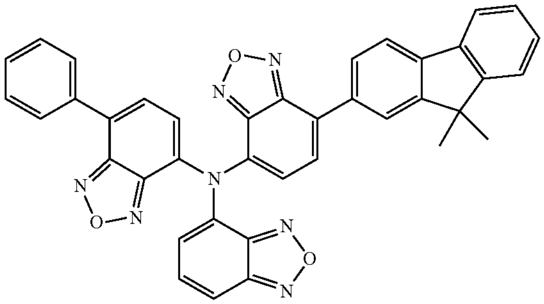
H92
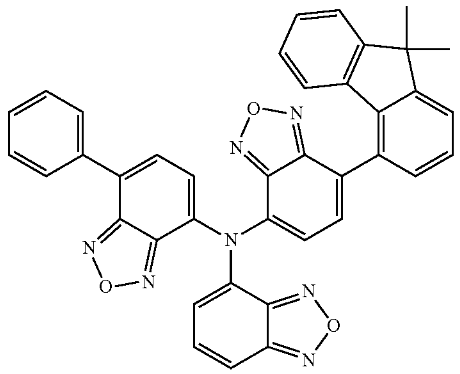
H93
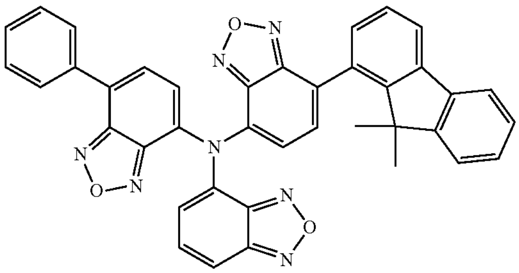
H94
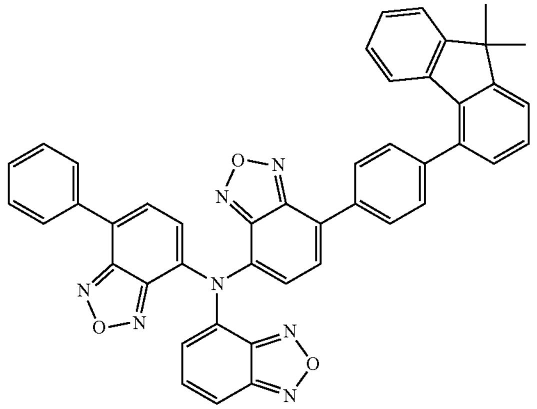
H95
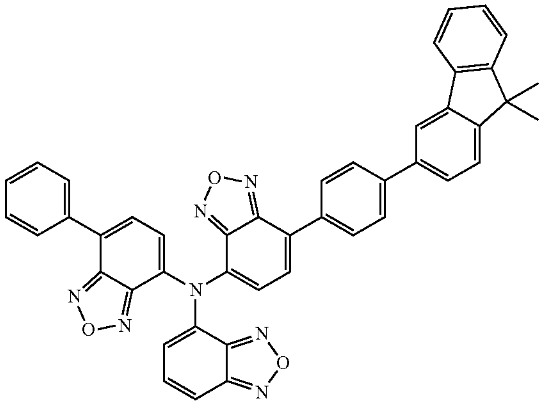
H96
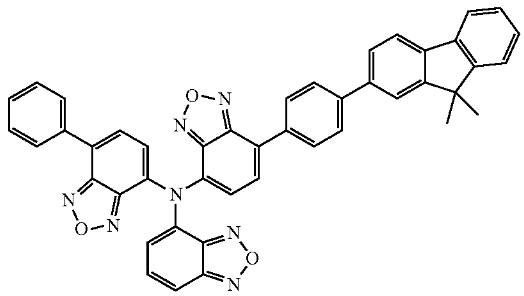
H97
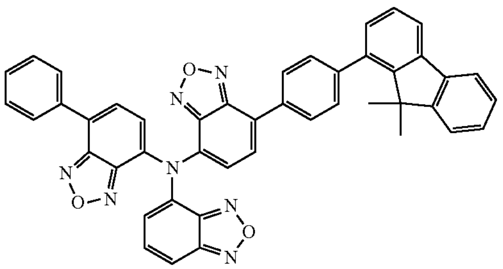

-continued
H98
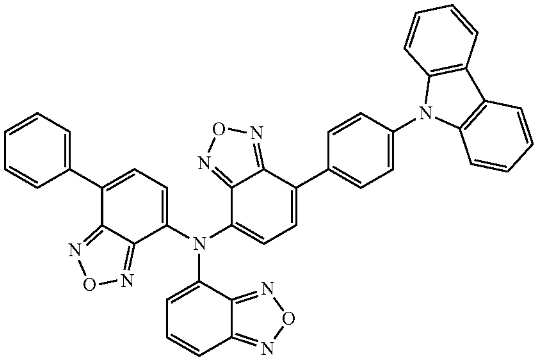
H99
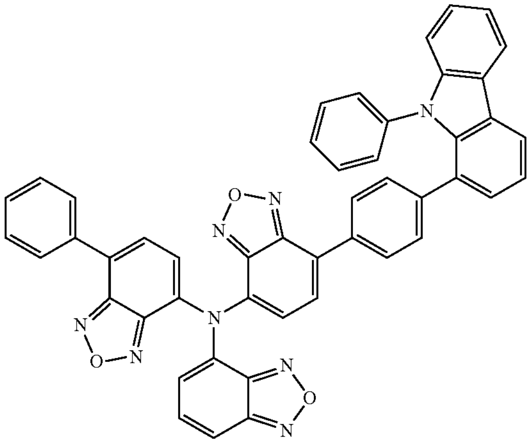
H100
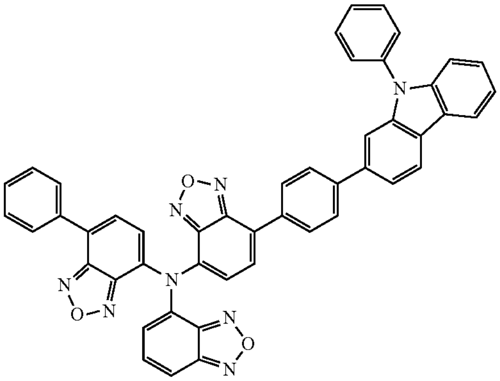
H101
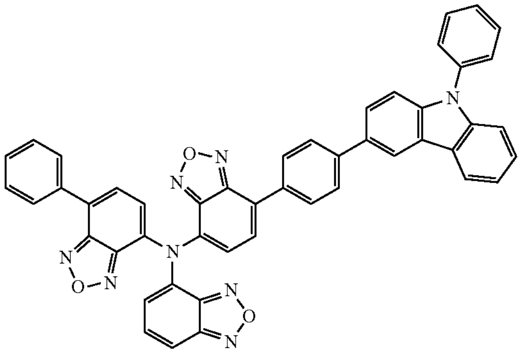
H102
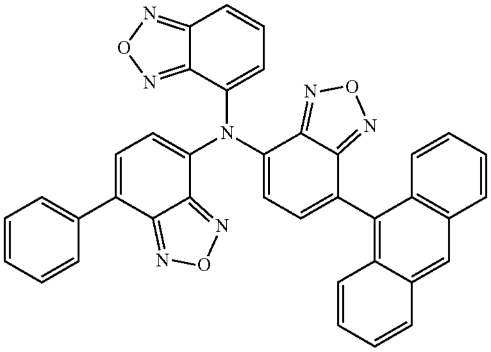
H103
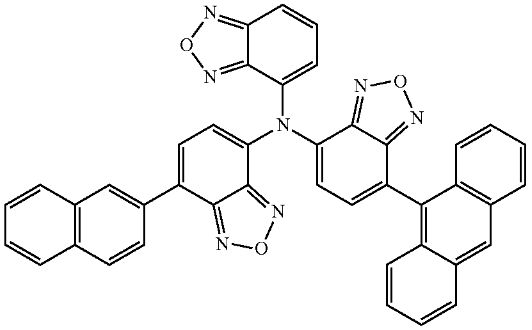
H104
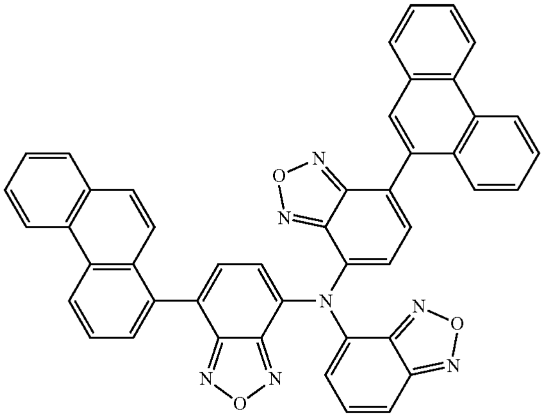
H105
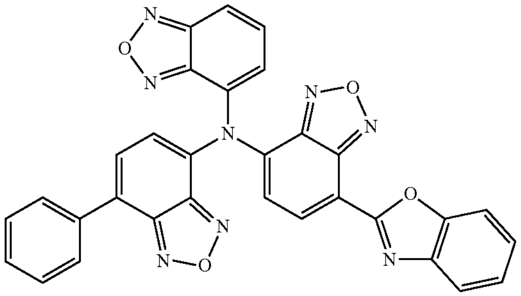

-continued
H106
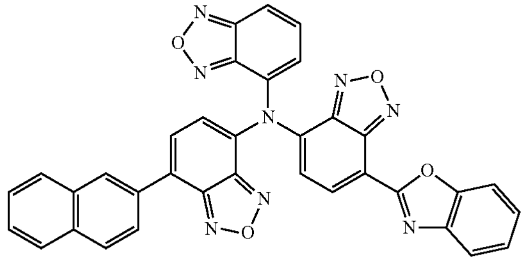
H107
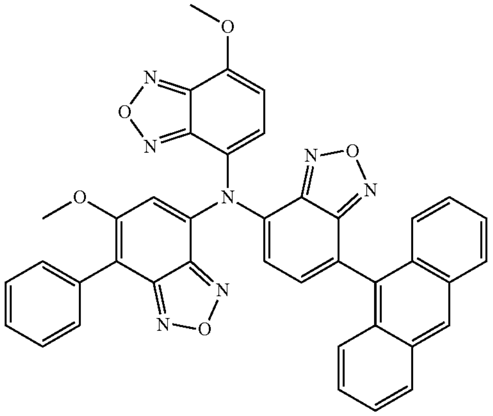
H108
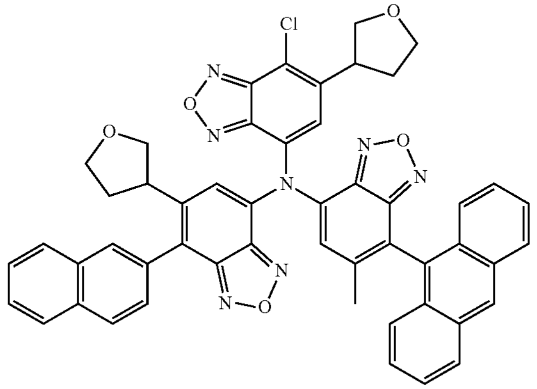
H109
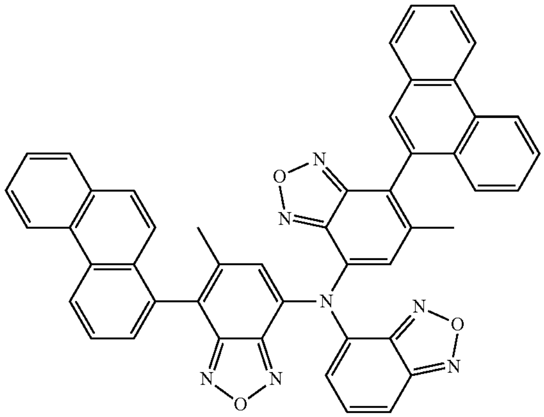
H110
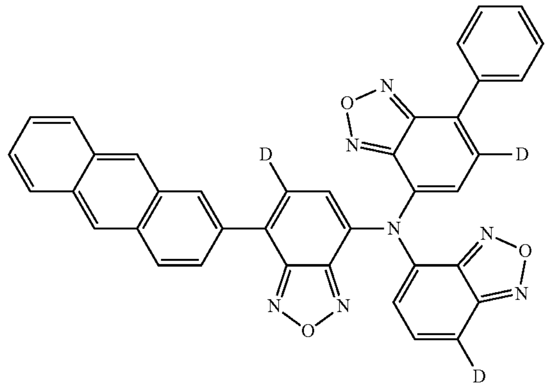
H111
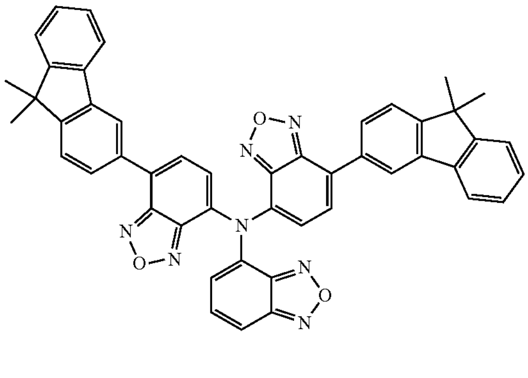
H112
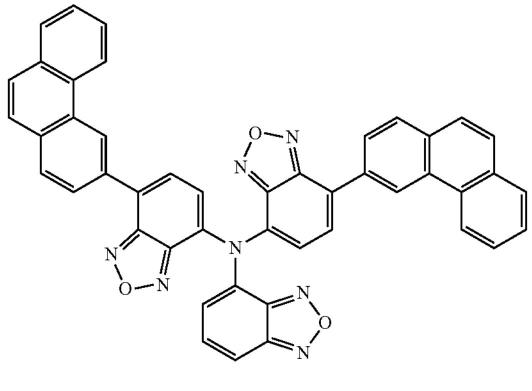
H113
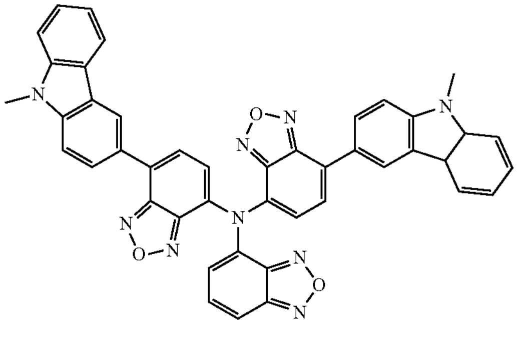

-continued
H114
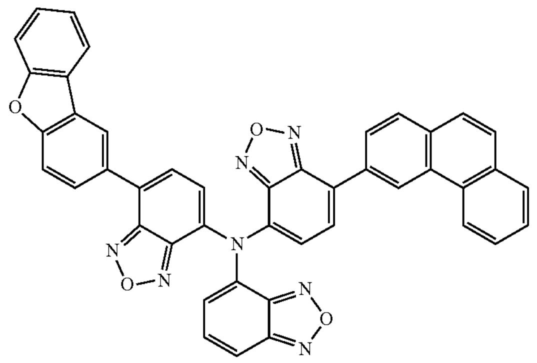
H115
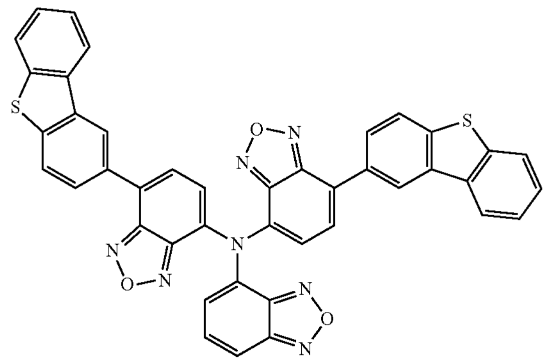
H116
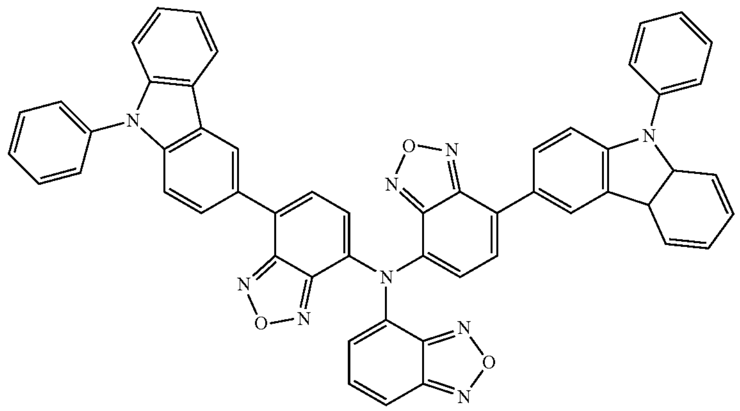
H117
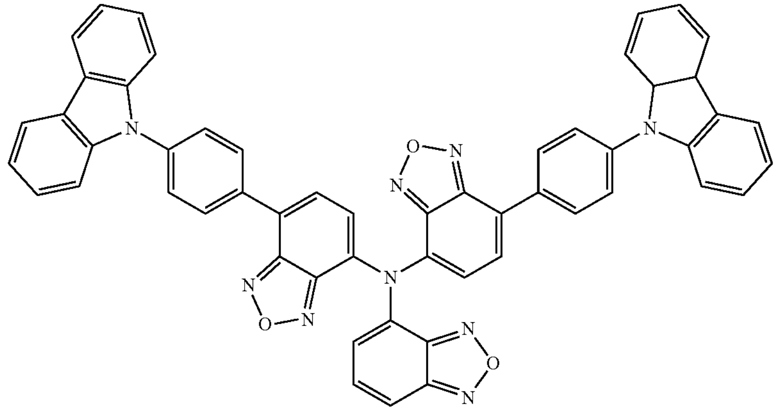

-continued

H118

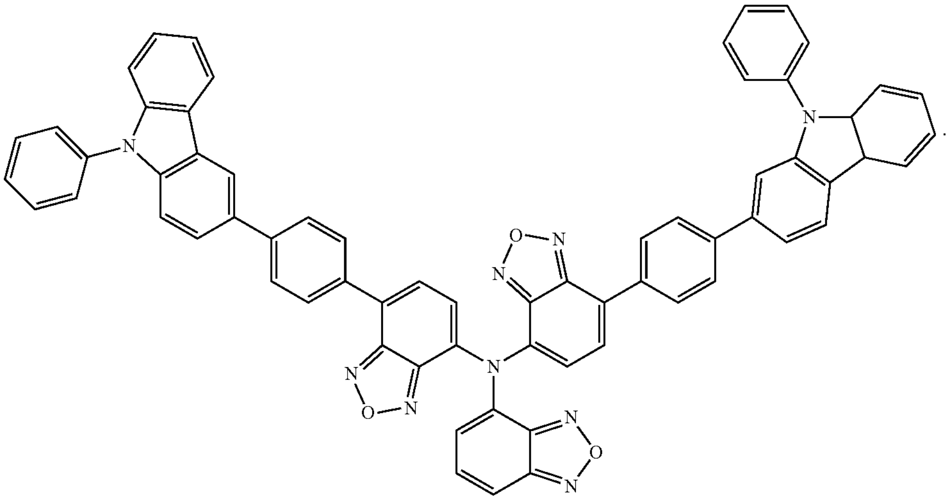

In some embodiments, $X_1$, $X_2$, and $X_3$ all represent $N(Y_1)$, and $Y_1$ represents hydrogen, deuterium, tritium or the following group unsubstituted or substituted by $R^a$: methyl, ethyl, propyl, butyl, methoxy, ethoxy, propoxy, cyclopropyl, cyclobutyl, cyclopentyl, cyclohexyl, tetrahydrofuranyl, tetrahydrothienyl, phenyl, naphthyl, anthryl, phenanthryl, biphenyl, terphenyl, tetraphenyl, triphenylenyl, pyrenyl, chrysenyl, perylenyl, indenyl, triphenylenyl, fluorenyl, 9,9-dimethylfluorenyl, spirobifluorenyl, pyrrolyl, furanyl, thienyl, indolyl, benzofuranyl, benzothienyl, dibenzofuran, dibenzothiophene, carbazolyl, indenocarbazolyl, indolocarbazolyl, pyridyl, pyrimidinyl, pyrazinyl, pyridazinyl, triazinyl, oxazolyl, isooxazolyl, thiazolyl, isothiazolyl, benzoxazolyl, benzoisoxazolyl, benzothiazolyl, or benzoisothiazolyl.

Optionally, $Y_1$ represents hydrogen, deuterium, tritium or the following group unsubstituted or substituted by $R^a$:

methyl, ethyl, propyl, butyl, methoxy, ethoxy, propoxy, cyclopropyl, cyclobutyl, cyclopentyl, cyclohexyl, tetrahydrofuranyl, tetrahydrothienyl, or phenyl.

As an example, the compound is selected from any of the following,

H119

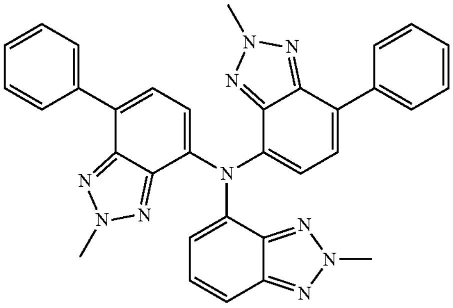

H120

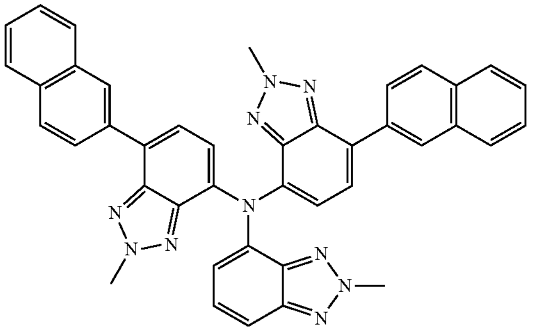

H121

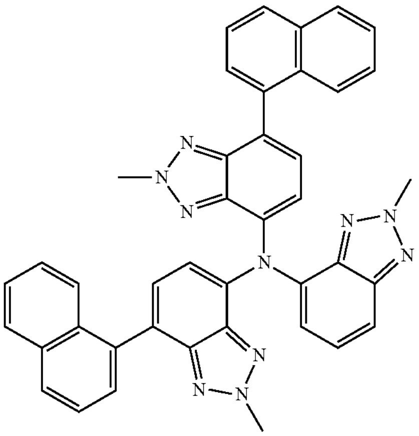

H122

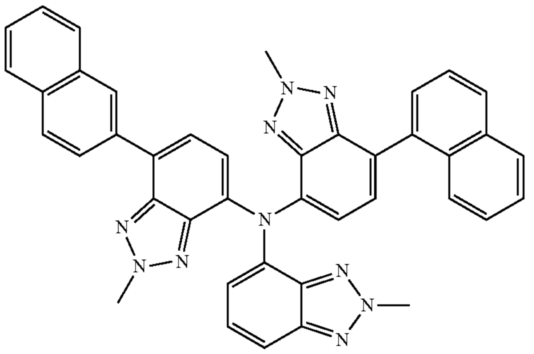

-continued
H123
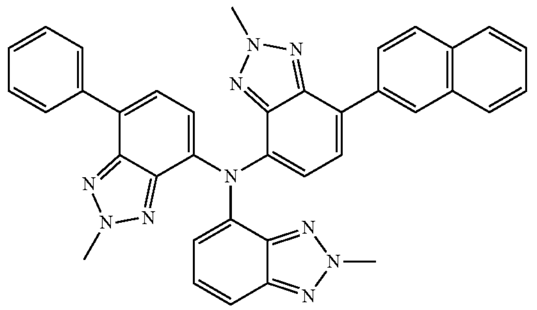
H124
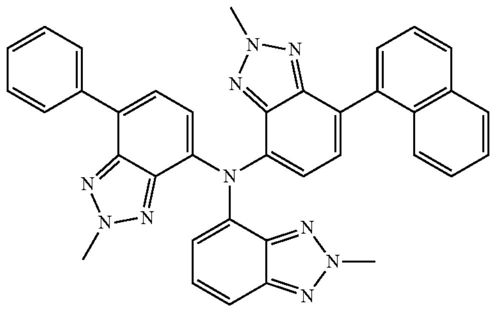
H125
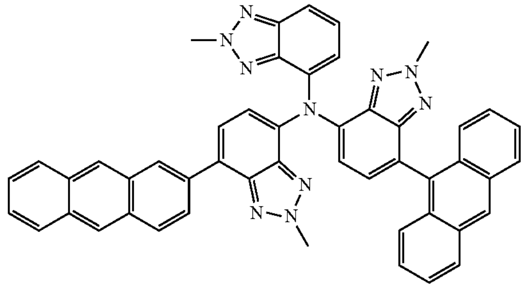
H126
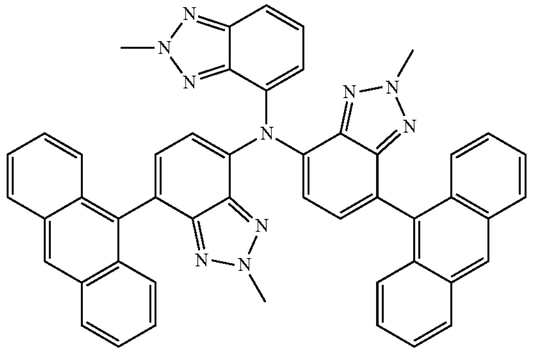
H127
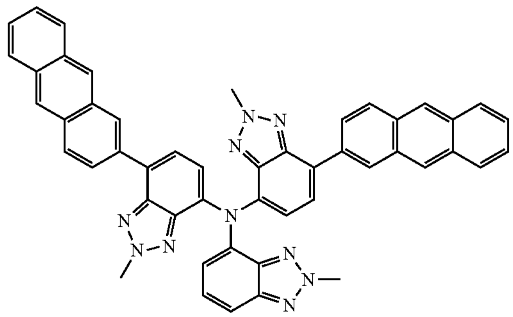
H128
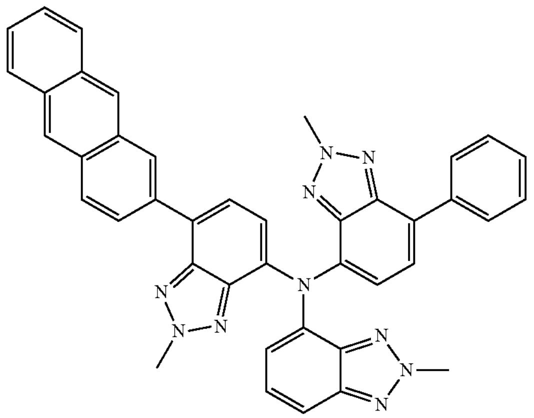
H129
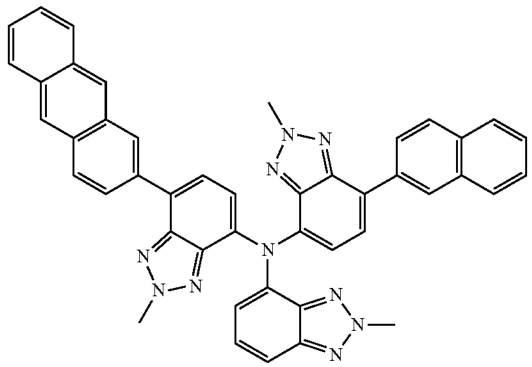
H130
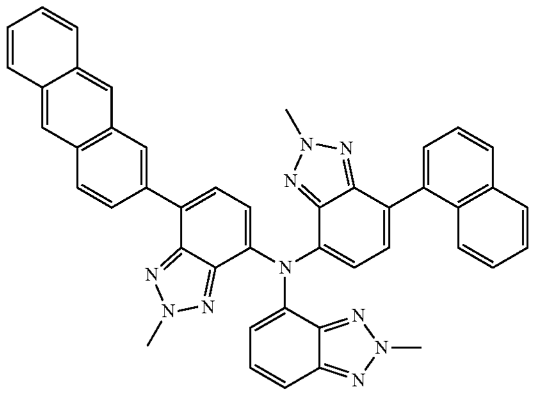

-continued
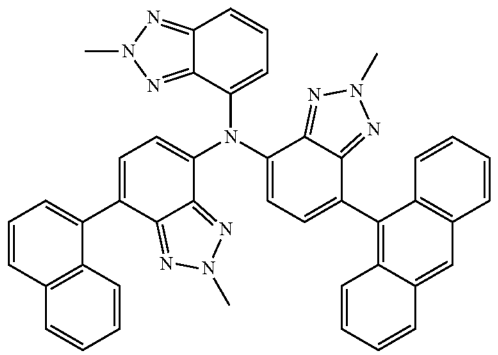
H131
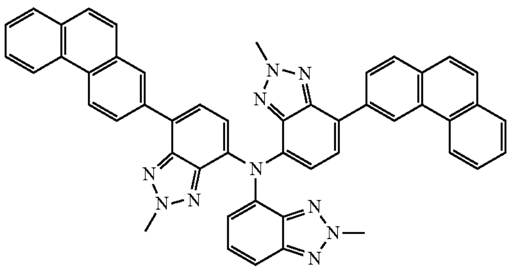
H132
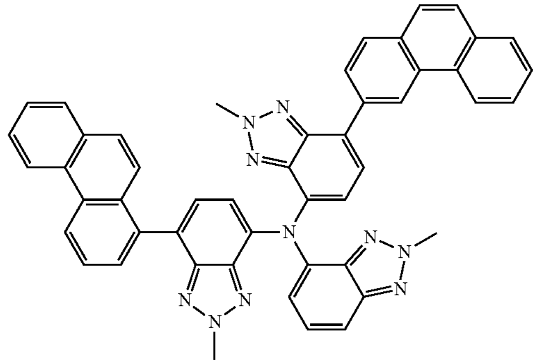
H133
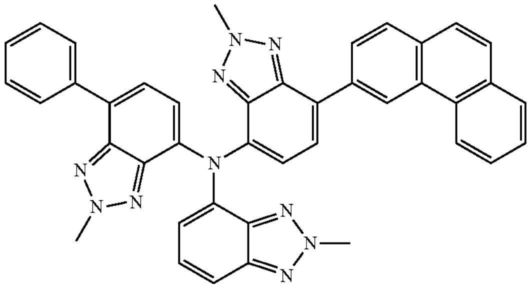
H134
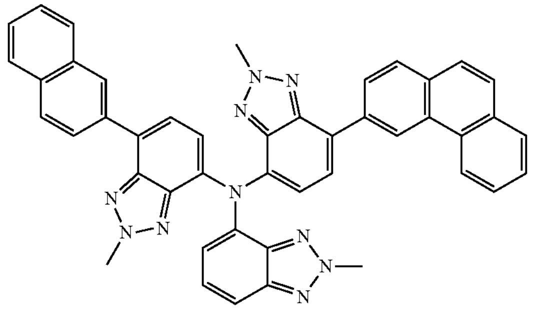
H135
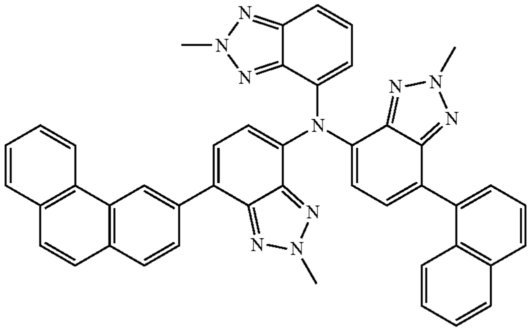
H136
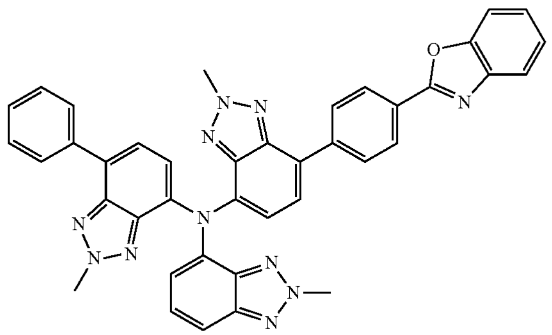
H137
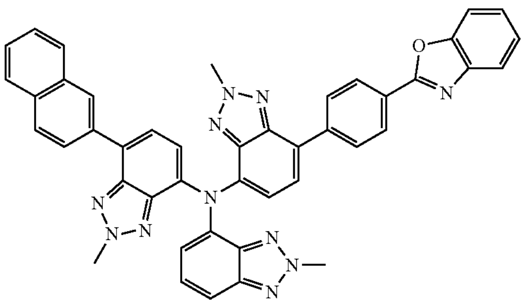
H138

-continued
H139
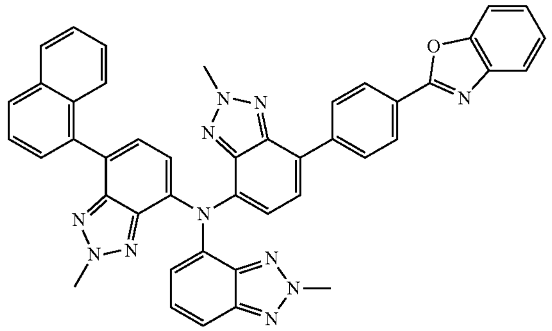
H140
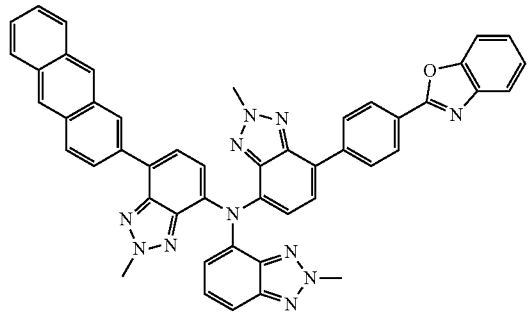
H141
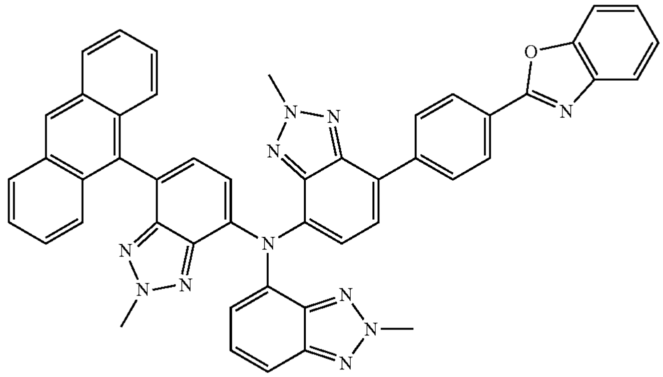
H142
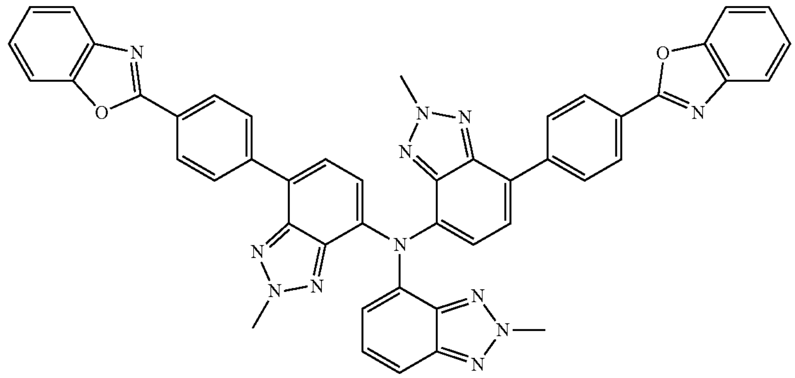
H143
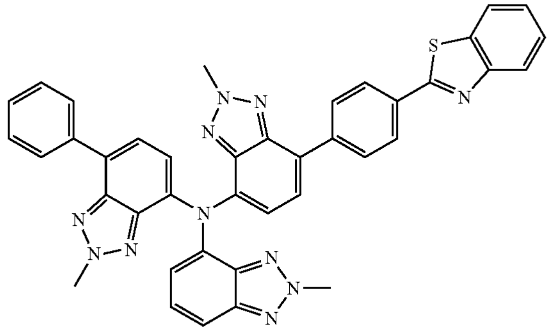
H144
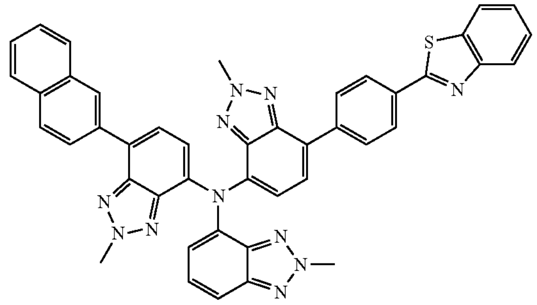

-continued
H145
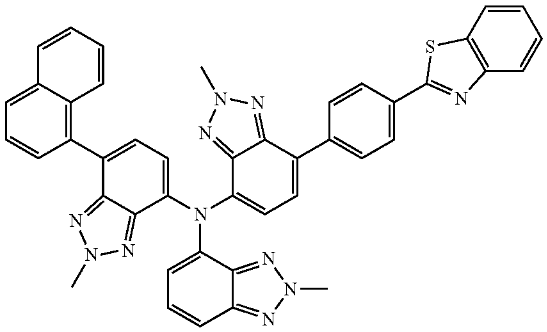
H146
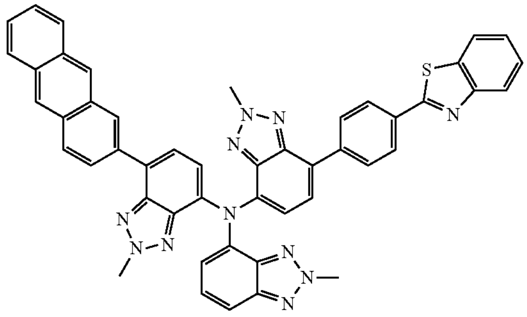
H147
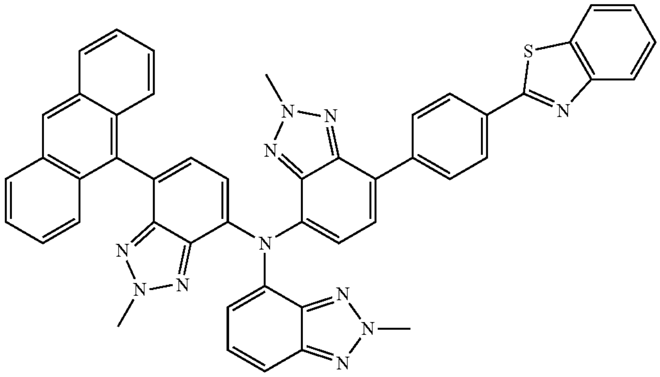
H148
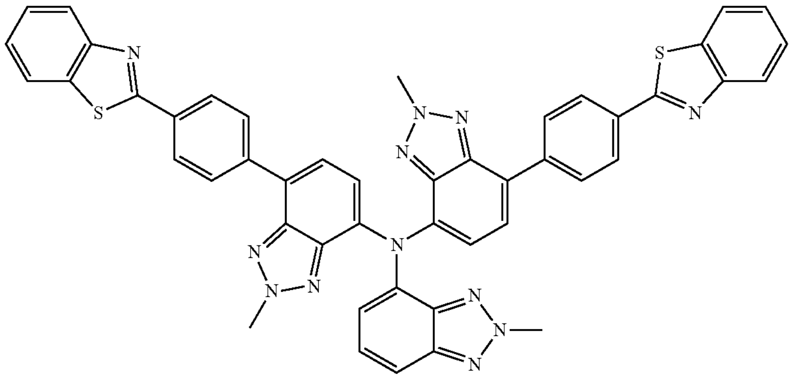
H149
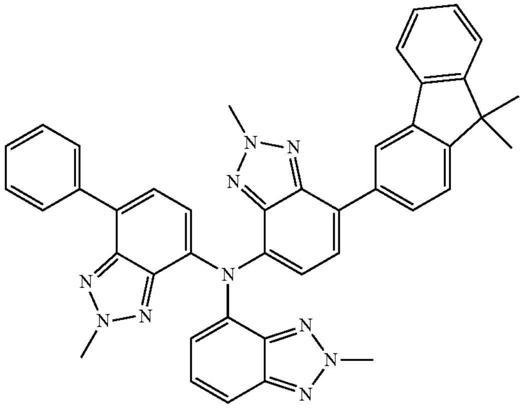
H150
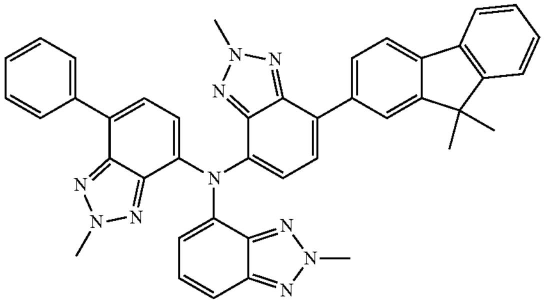

-continued
H151
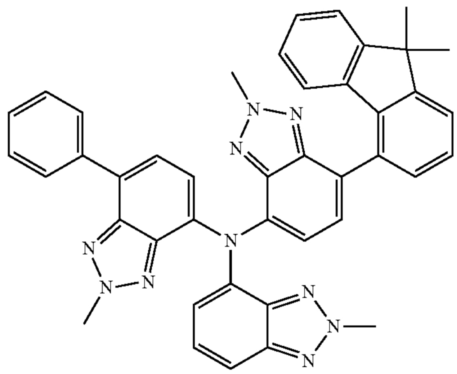
H152
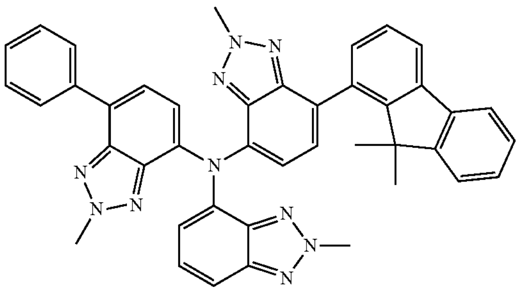
H153
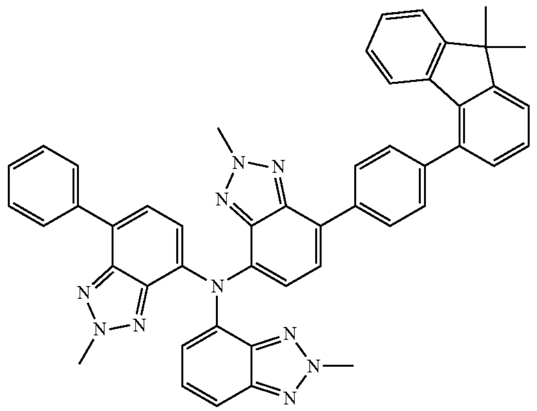
H154
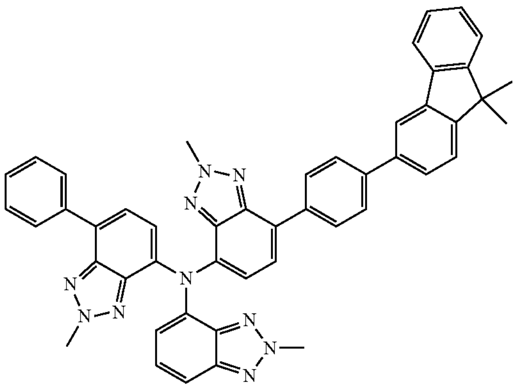
H155
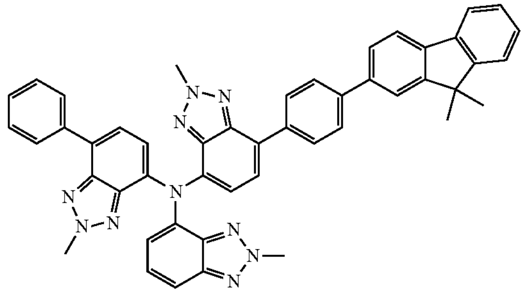
H156
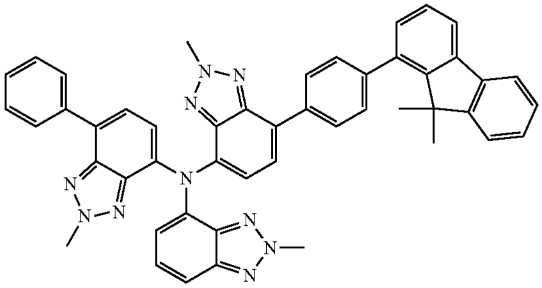
H157
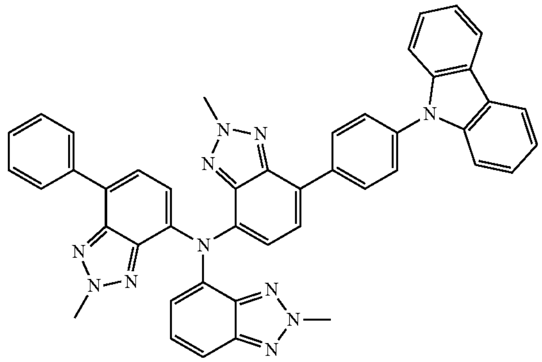
H158
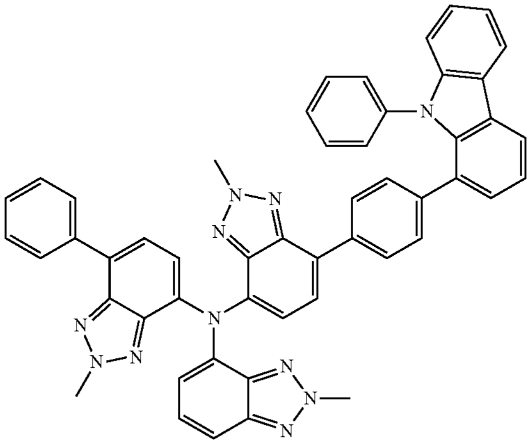

-continued
H159
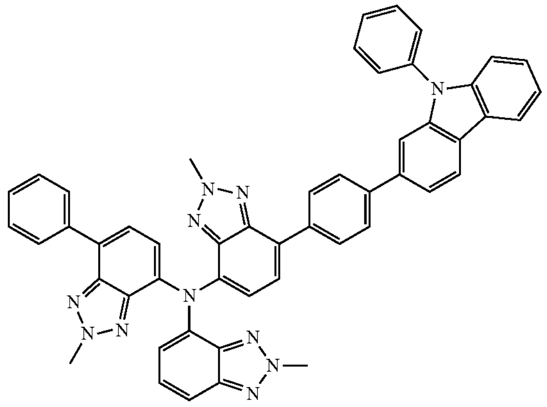
H160
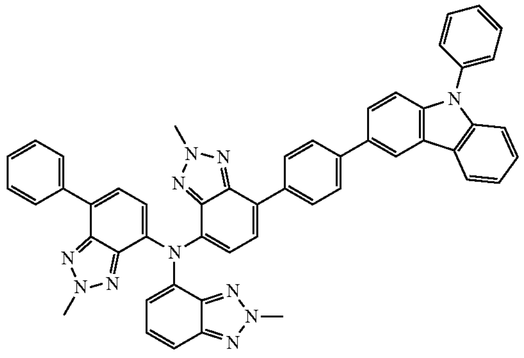
H161
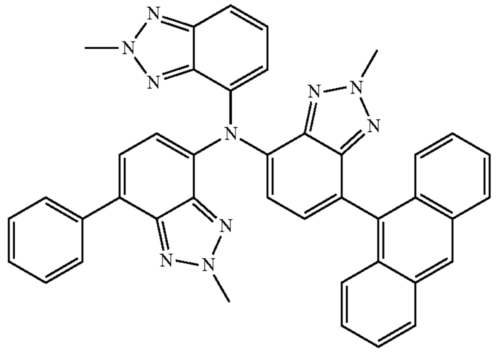
H162
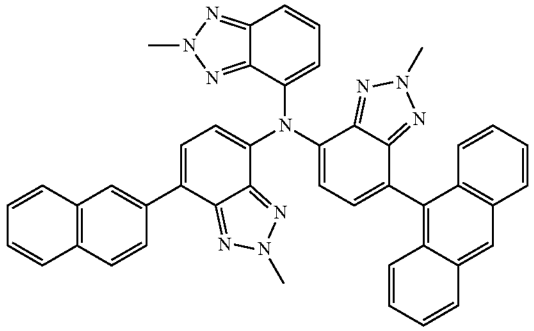
H163
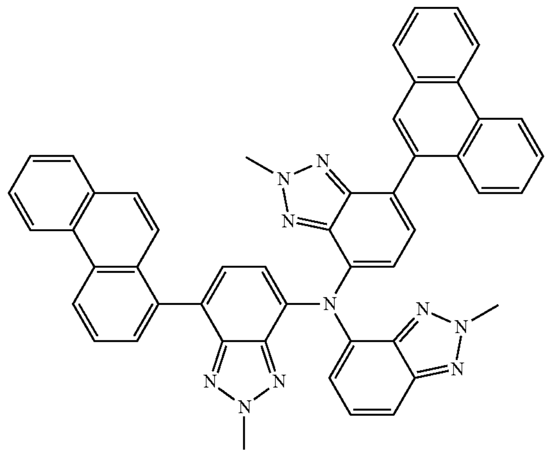
H164
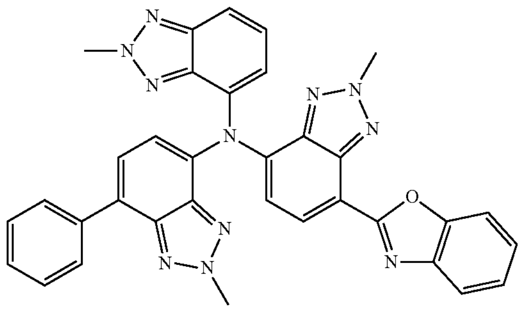

-continued
H165
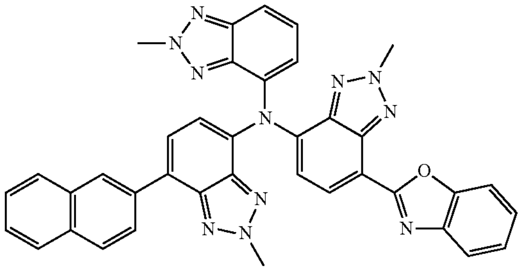
H166
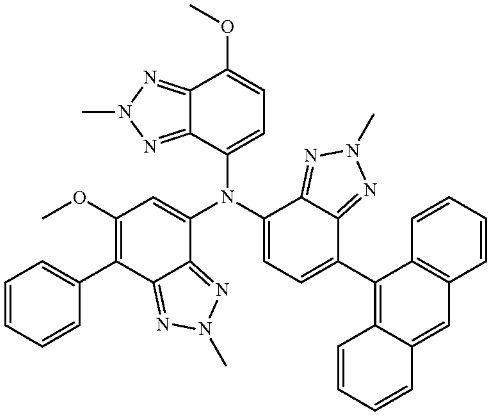
H167
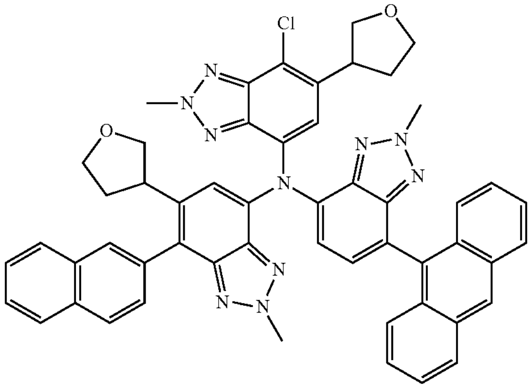
H168
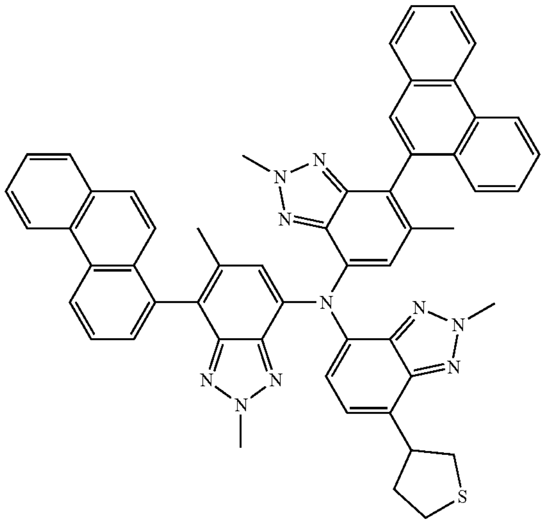
H169
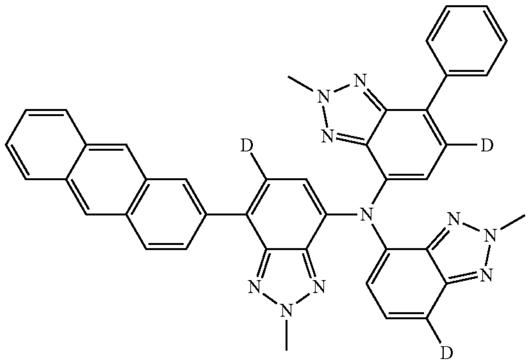
H170
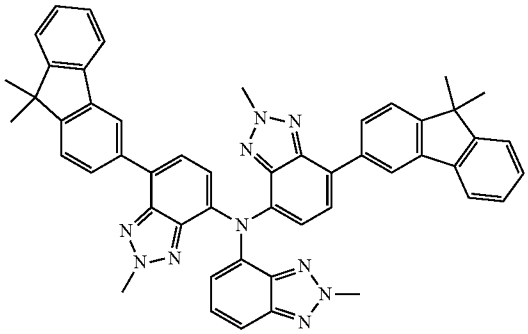

-continued
H171
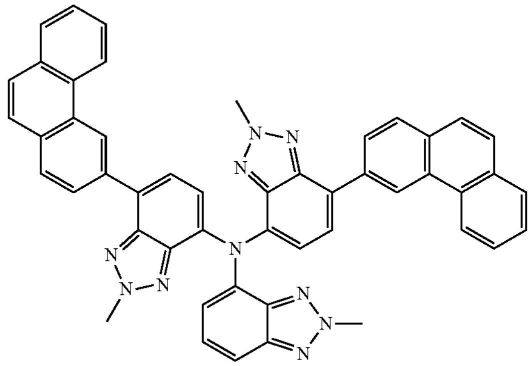
H172
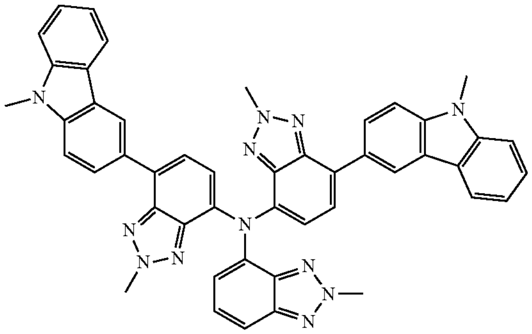
H173
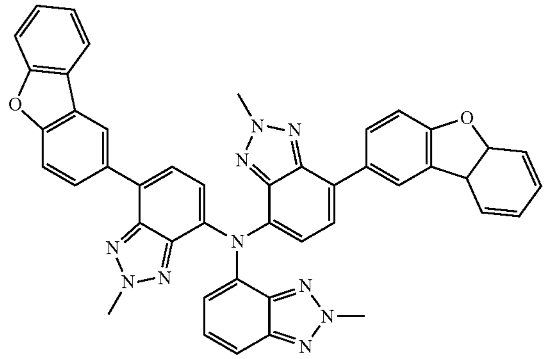
H174
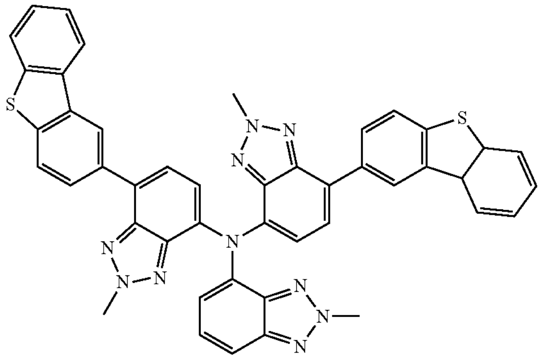
H175
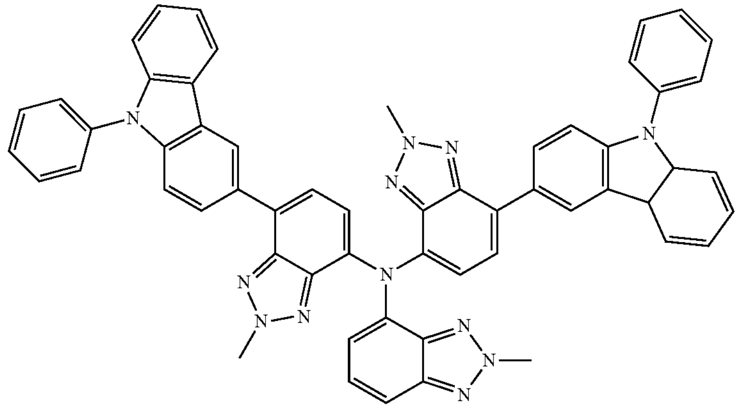
H176
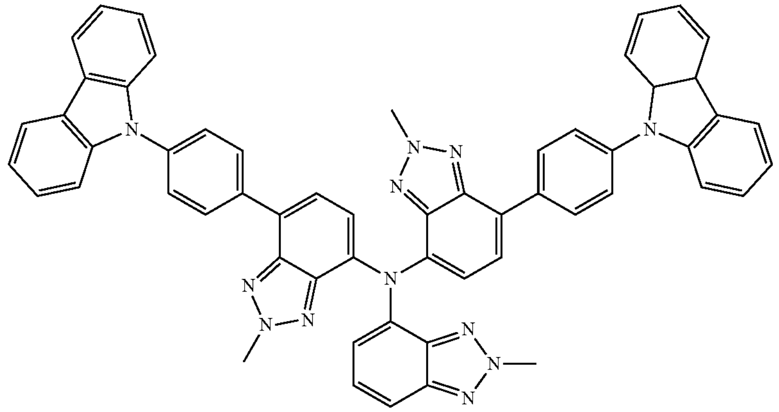

-continued

H177

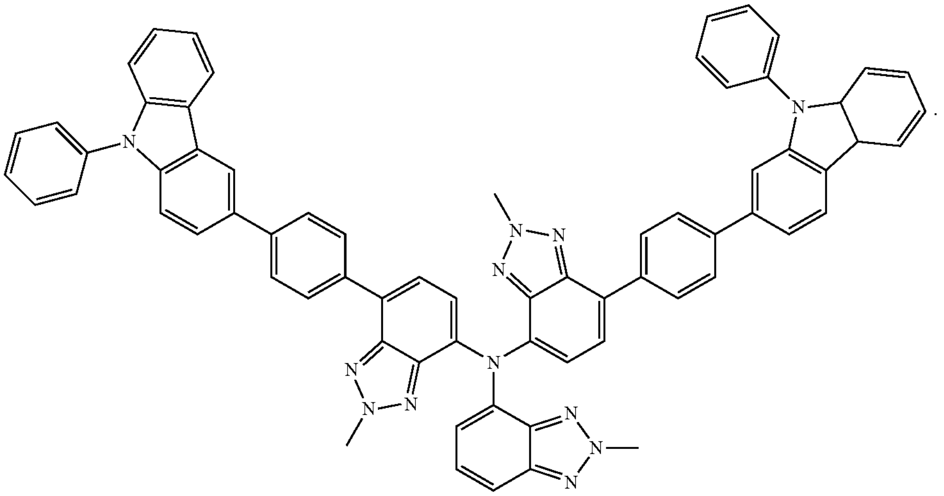

In some embodiments, $X_1$, $X_2$, and $X_3$ all represent $C(Y_2)_2$ or $Si(Y_3)_2$, and $Y_2$ and $Y_3$ each independently represent hydrogen, deuterium, tritium or the following group unsubstituted or substituted by $R^a$:

methyl, ethyl, propyl, butyl, methoxy, ethoxy, propoxy, cyclopropyl, cyclobutyl, cyclopentyl, cyclohexyl, tetrahydrofuranyl, tetrahydrothienyl, phenyl, naphthyl, anthryl, phenanthryl, biphenyl, terphenyl, tetraphenyl, triphenylenyl, pyrenyl, chrysenyl, perylenyl, indenyl, triphenylenyl, fluorenyl, 9,9-dimethylfluorenyl, spirobifluorenyl, pyrrolyl, furanyl, thienyl, indolyl, benzofuranyl, benzothienyl, dibenzofuran, dibenzothiophene, carbazolyl, indenocarbazolyl, indolocarbazolyl, pyridyl, pyrimidinyl, pyrazinyl, pyridazinyl, triazinyl, oxazolyl, isooxazolyl, thiazolyl, isothiazolyl, benzoxazolyl, benzoisoxazolyl, benzothiazolyl, or benzoisothiazolyl.

Optionally, $Y_2$ and $Y_3$ each independently represent hydrogen, deuterium, tritium or the following group unsubstituted or substituted by $R^a$:

methyl, ethyl, propyl, butyl, methoxy, ethoxy, propoxy, cyclopropyl, cyclobutyl, cyclopentyl, cyclohexyl, tetrahydrofuranyl, tetrahydrothienyl, or phenyl.

As an example, the compound is selected from any of the following,

H178

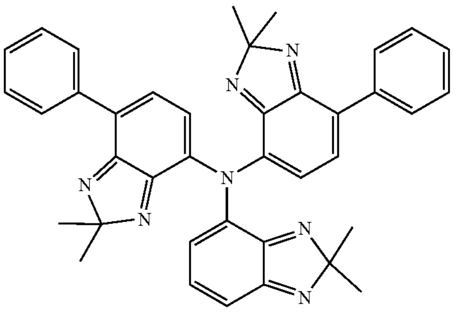

H179

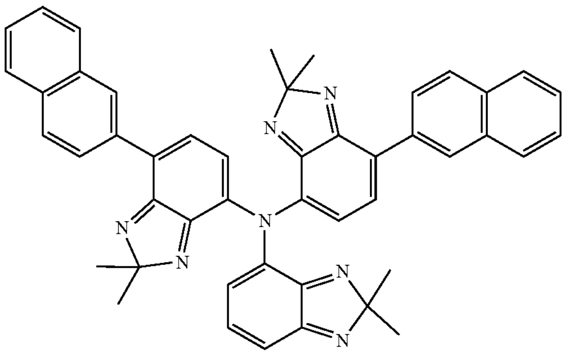

-continued
H180
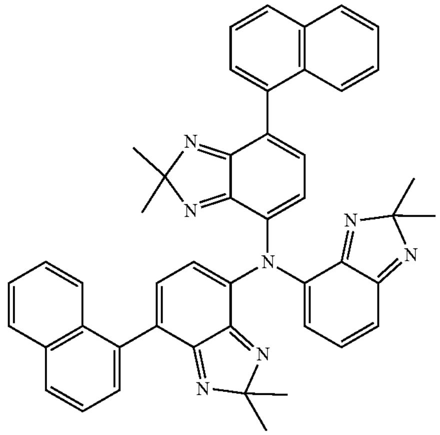
H181
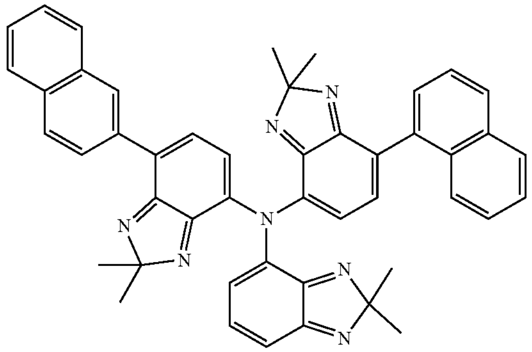
H182
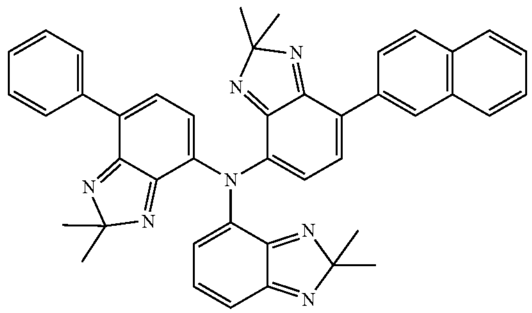
H183
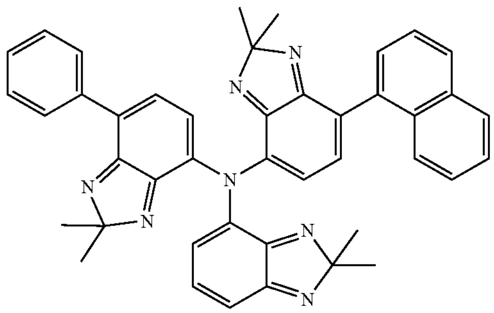
H184
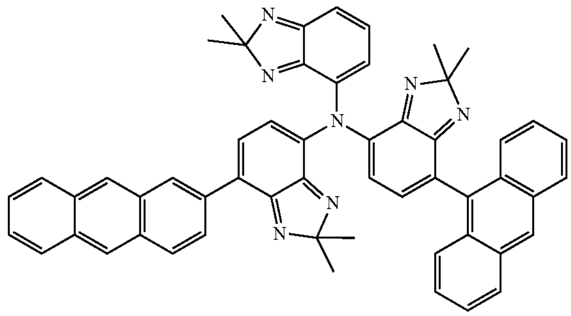
H185
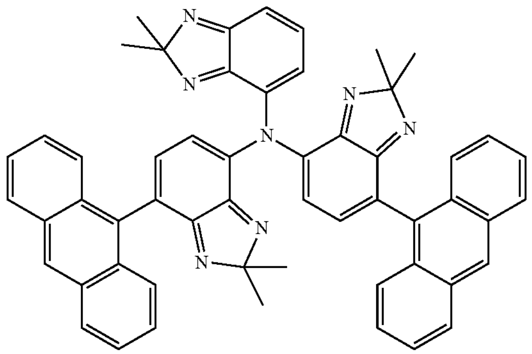
H186
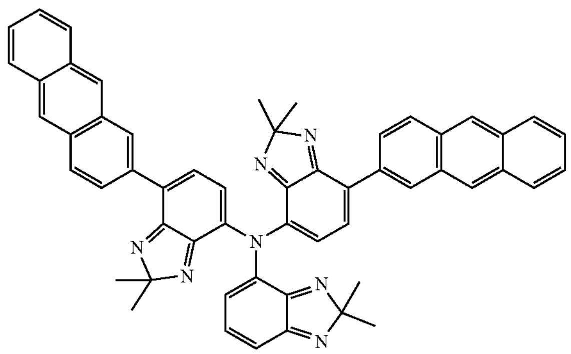
H187
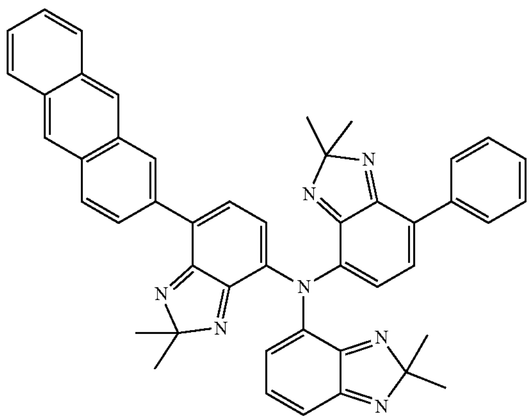

-continued
H188
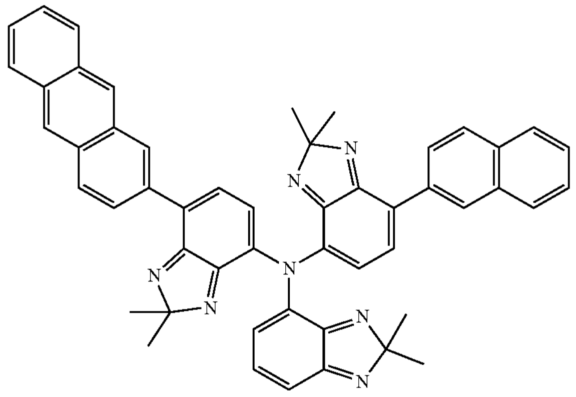
H189
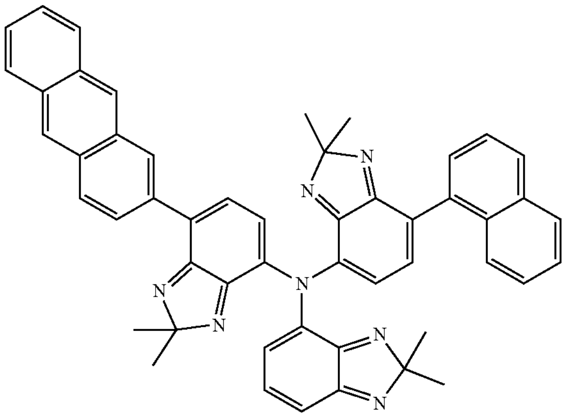
H190
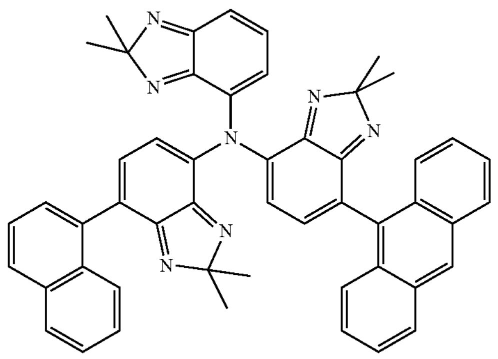
H191
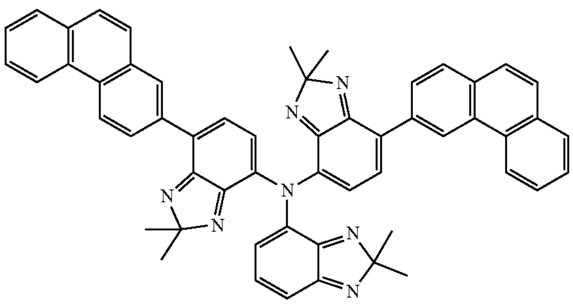
H192
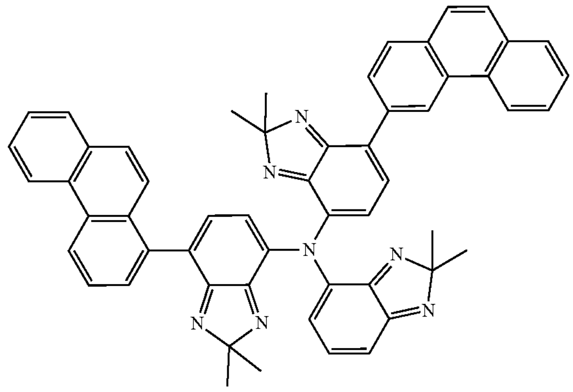
H193
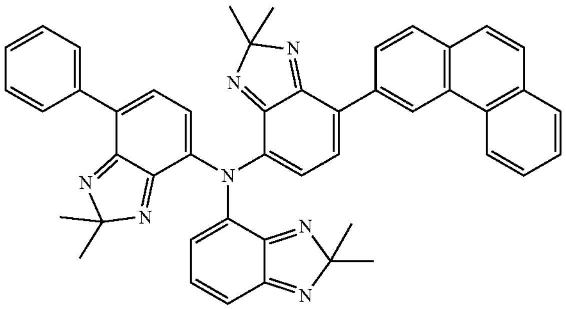
H194
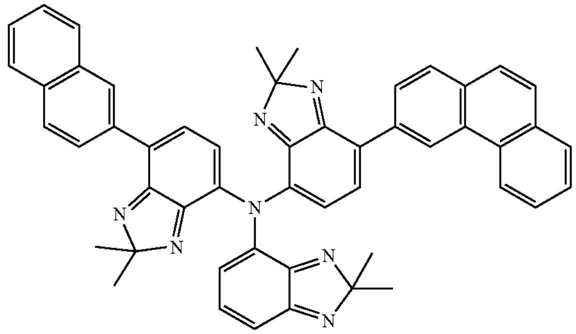
H195
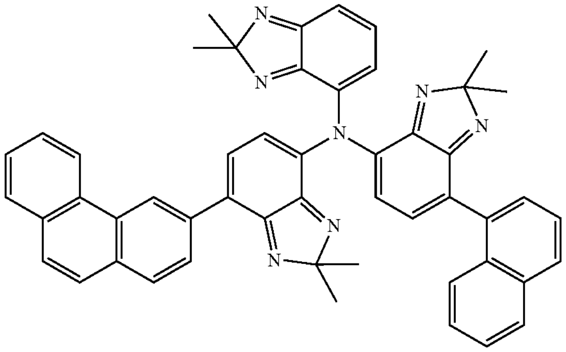

-continued
H196
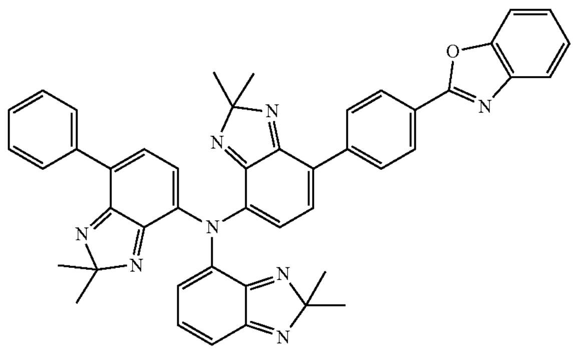
H197
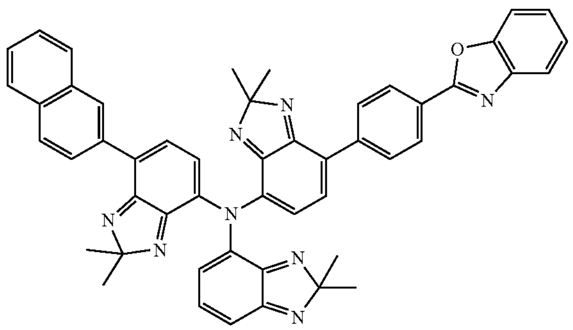
H198
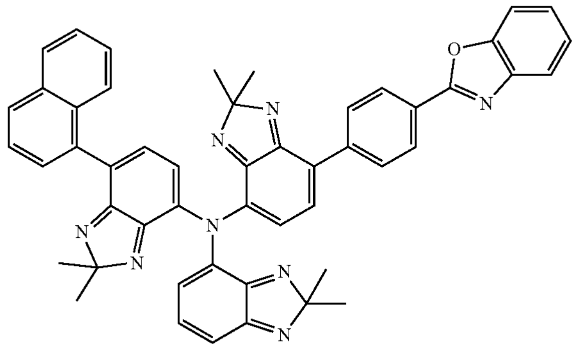
H199
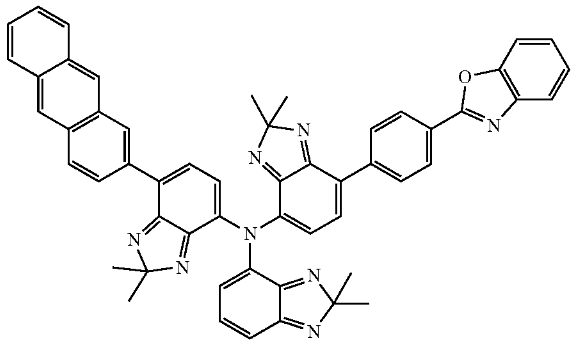
H200
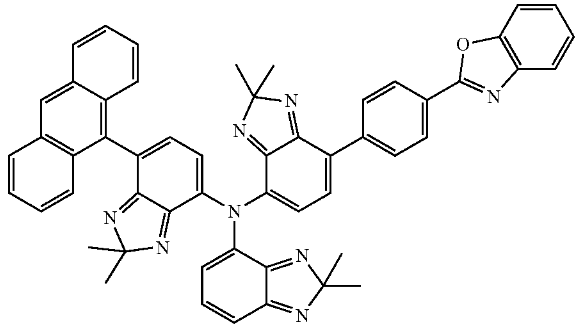
H201
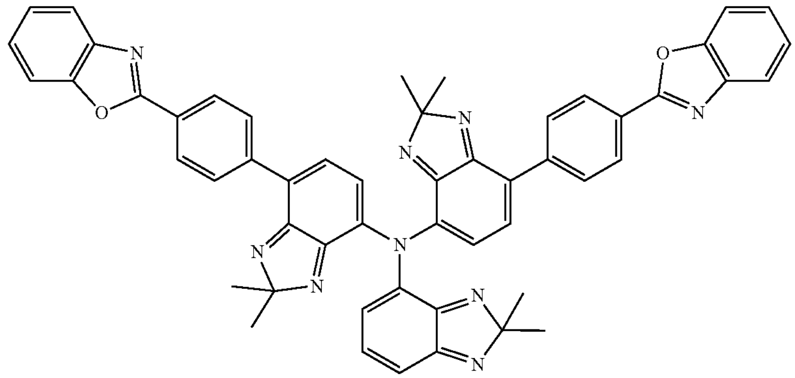

-continued
H202
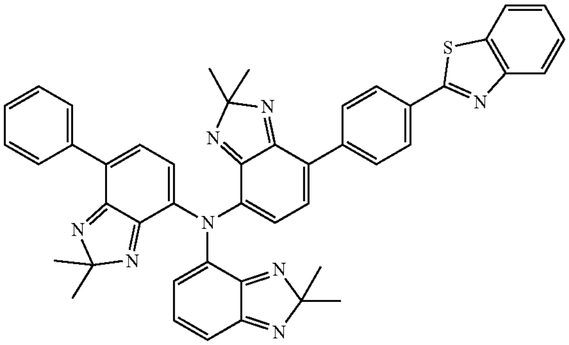
H203
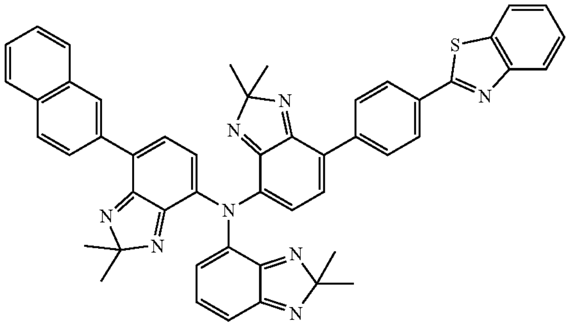
H204
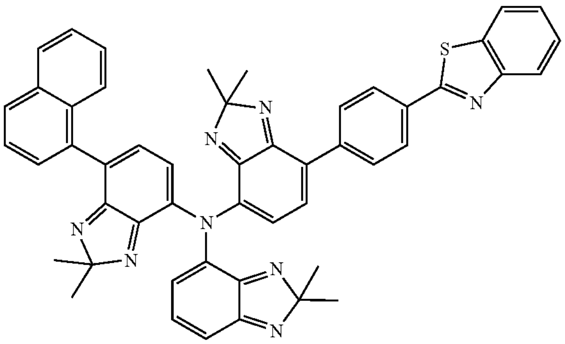
H205
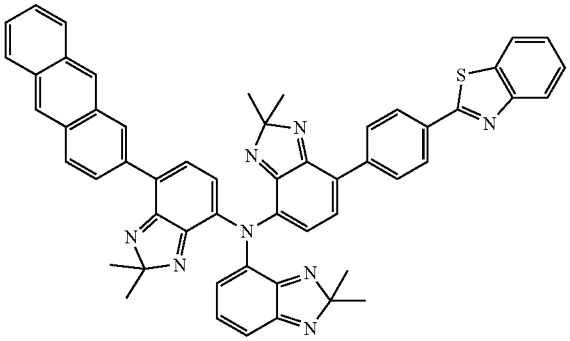
H206
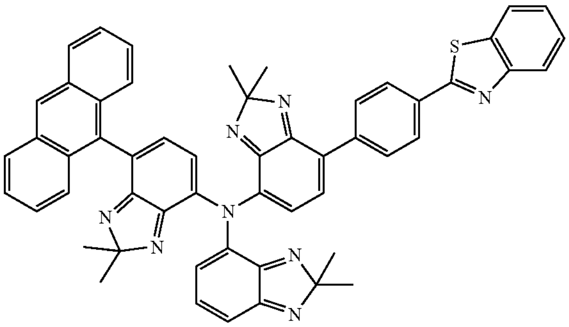
H207
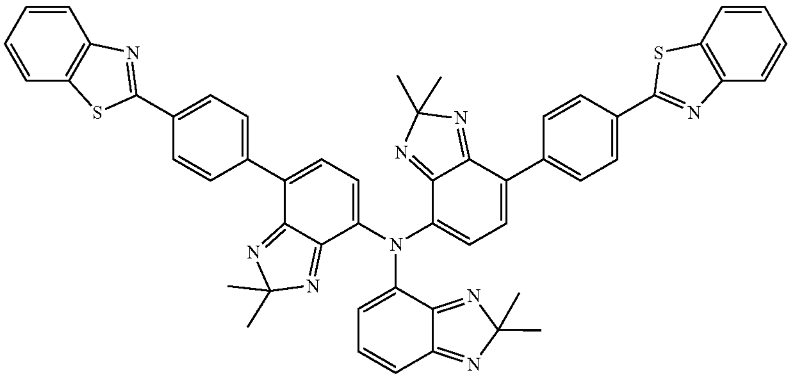

-continued
H208
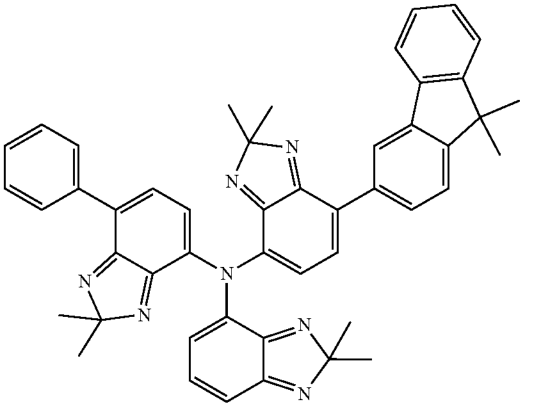
H209
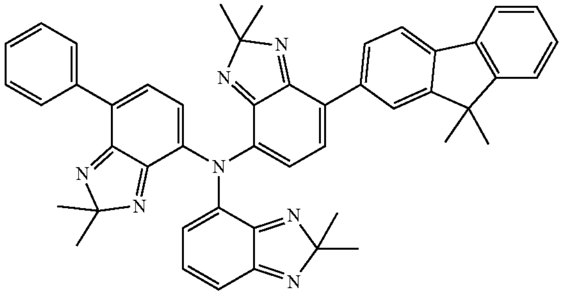
H210
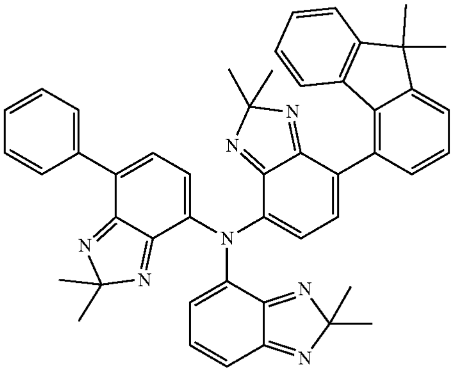
H211
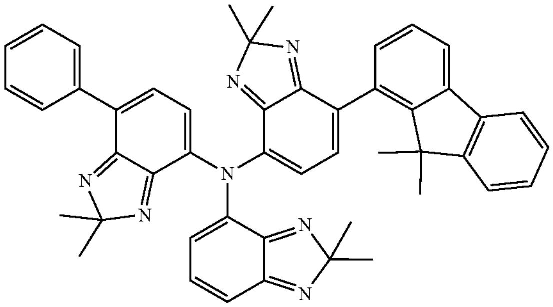
H212
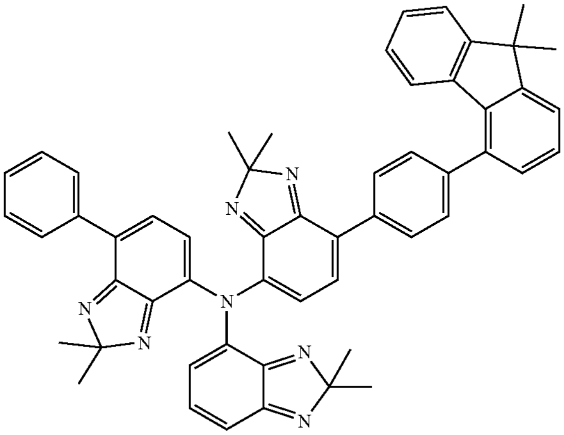
H213
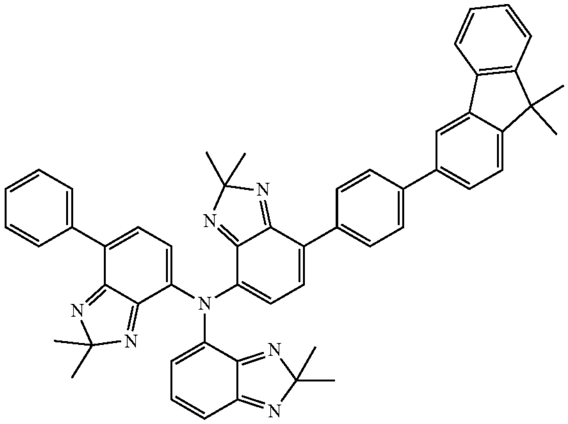
H214
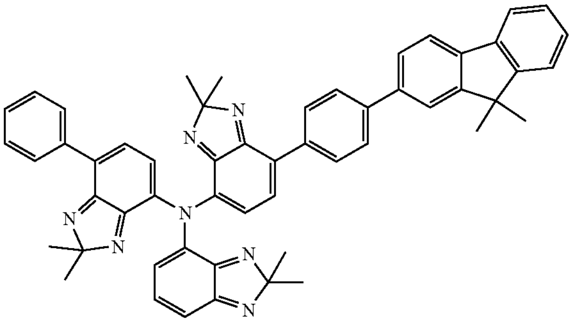
H215
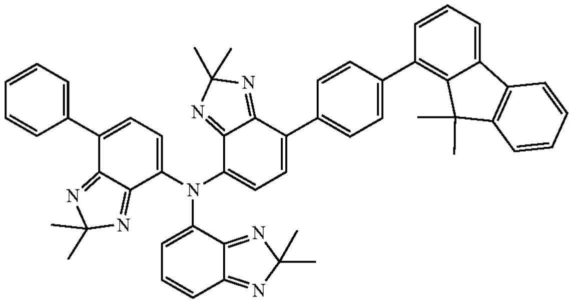

-continued
H216
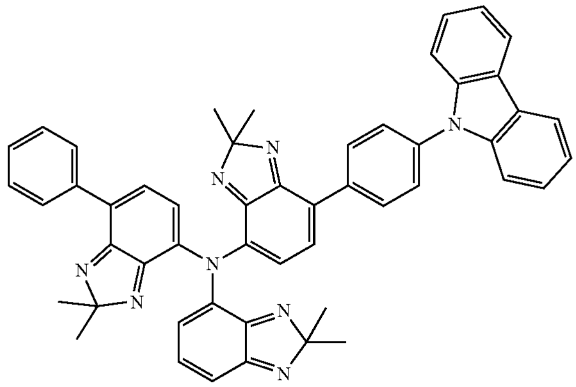
H217
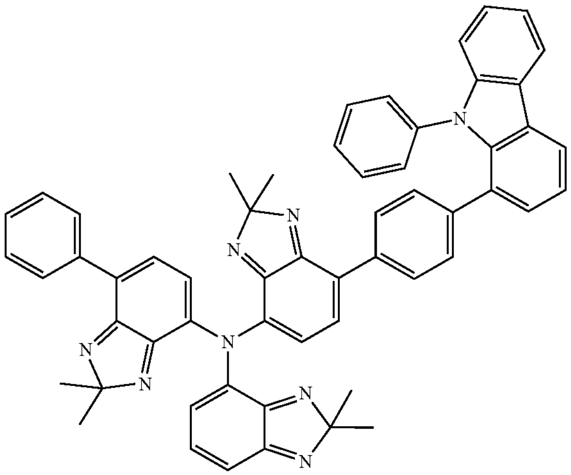
H218
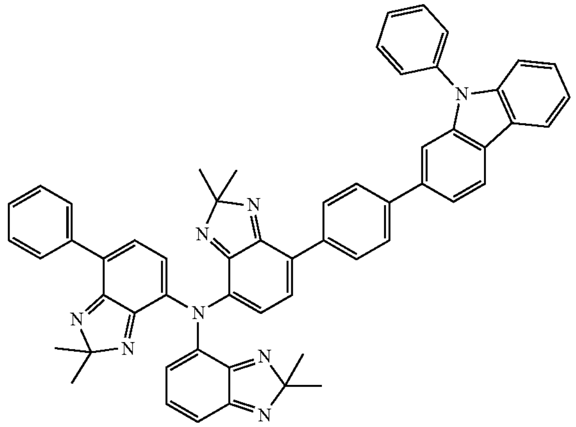
H219
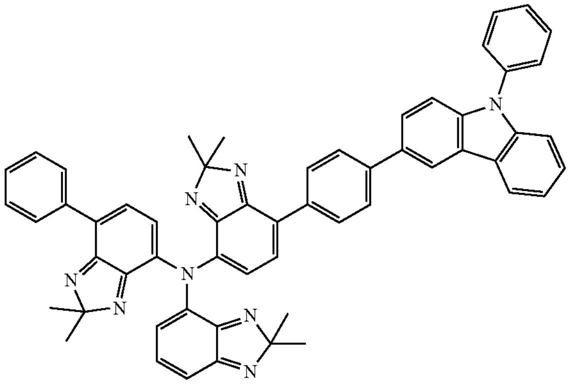
H220
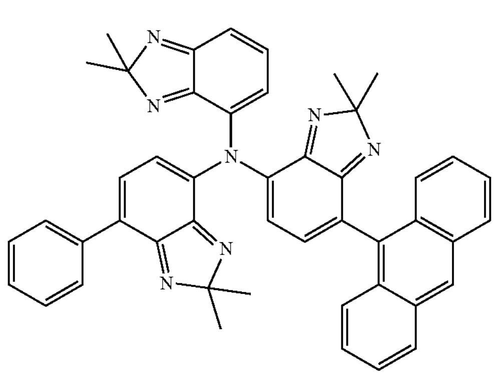
H221
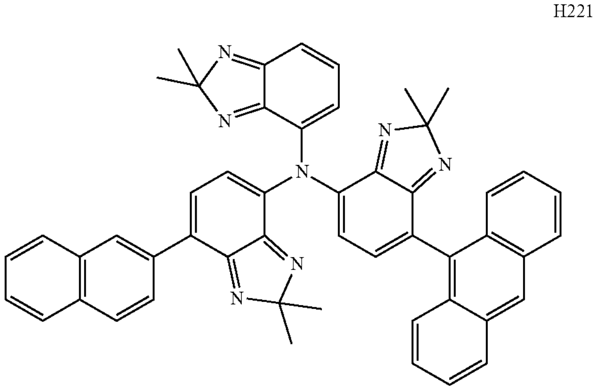

-continued
H222
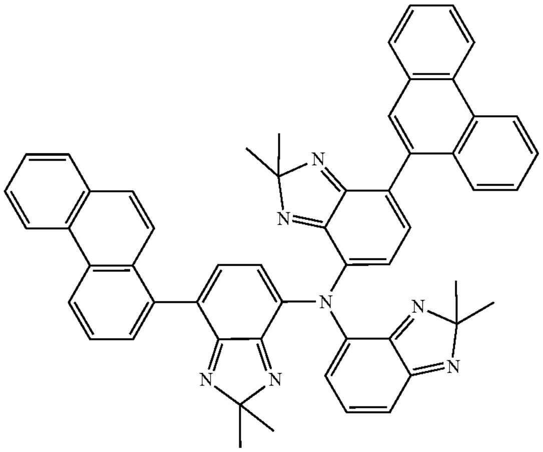
H223
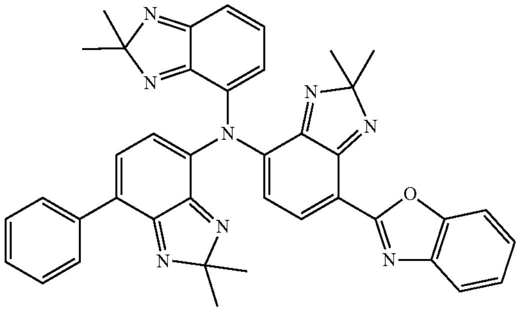
H224
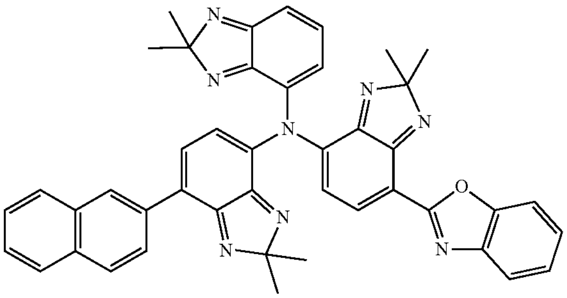
H225
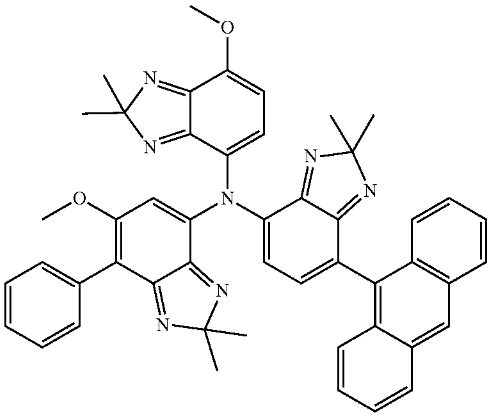
H226
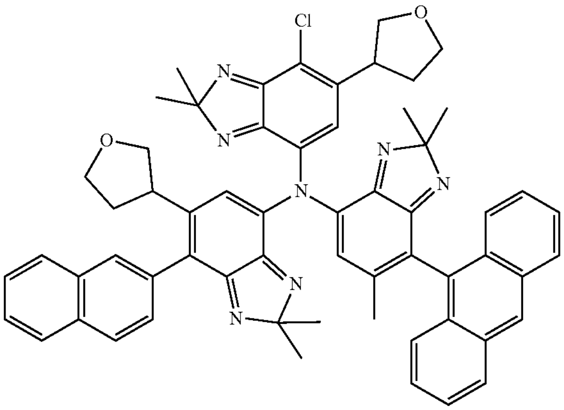
H227
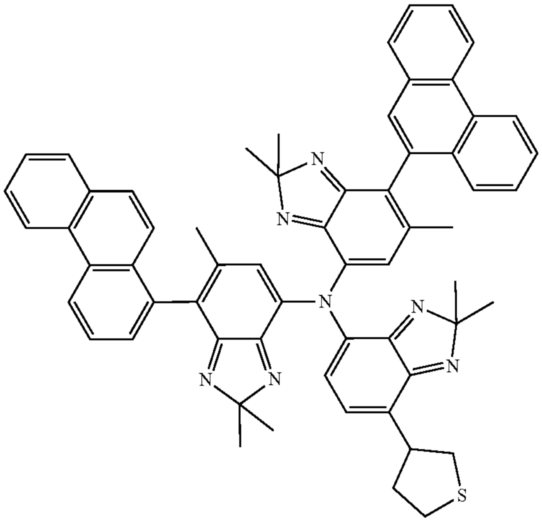

-continued
H228
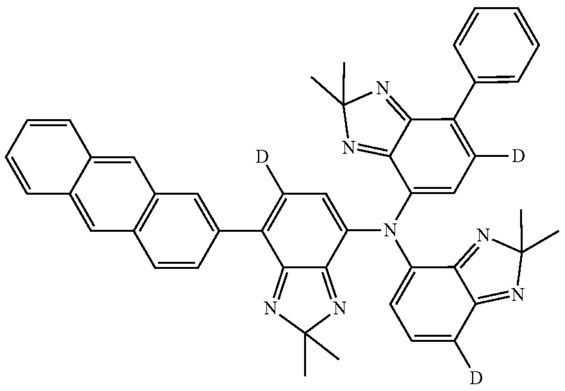
H229
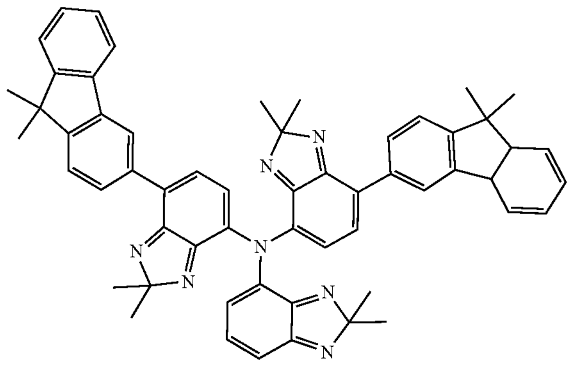
H230
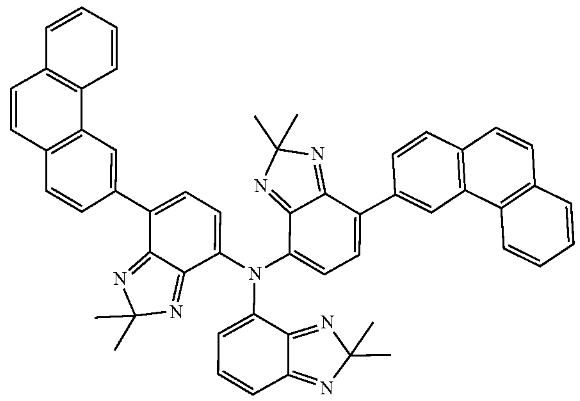
H231
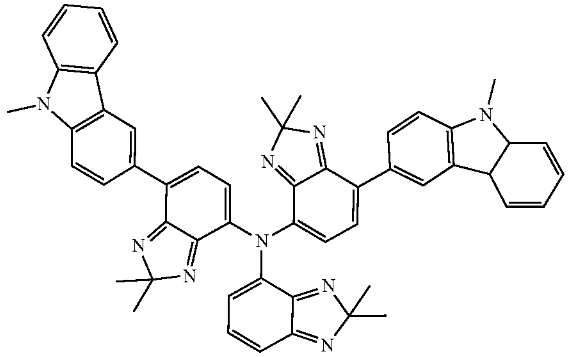
H232
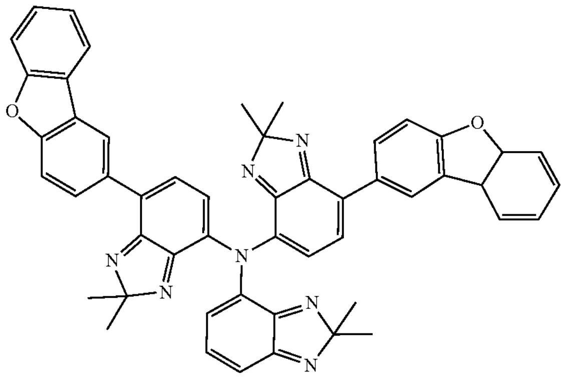
H233
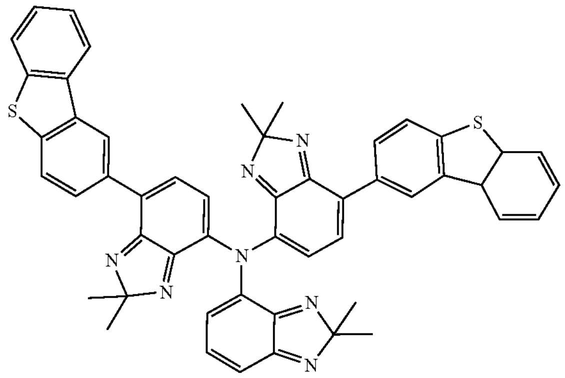
H234
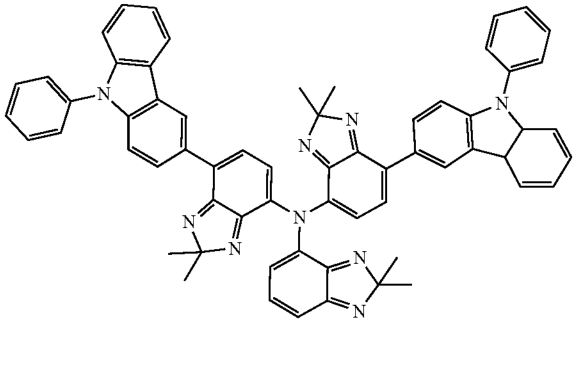
H235
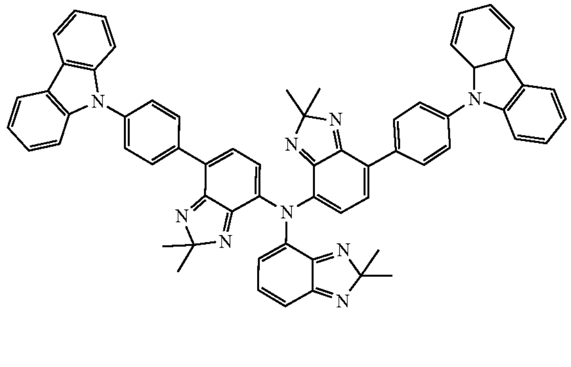

-continued
H236
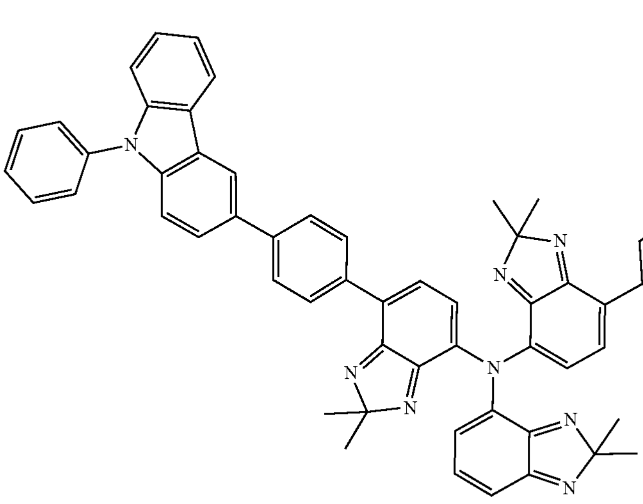
H237
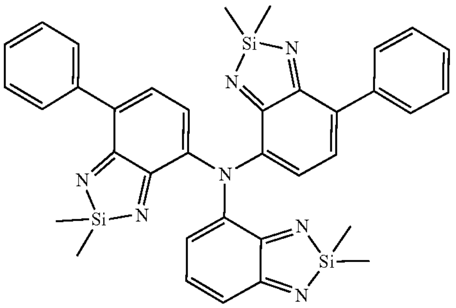
H238
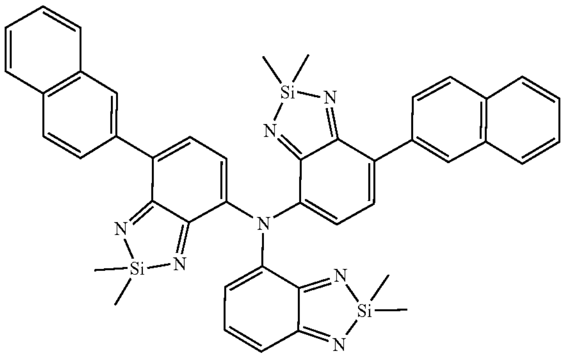
H239
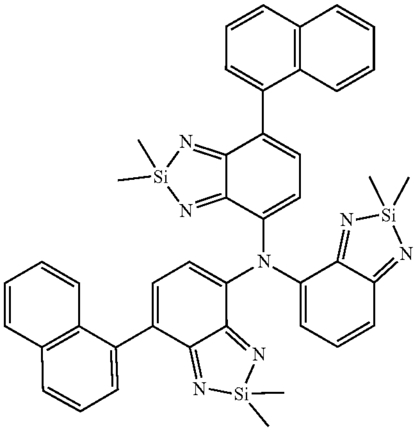
H240
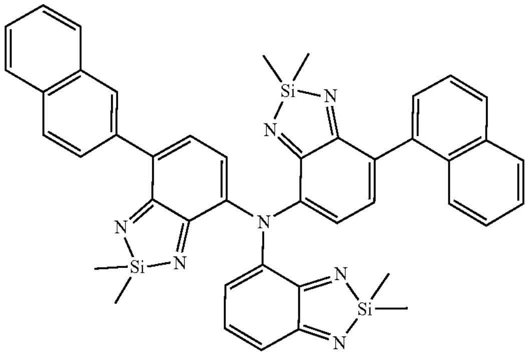
H241
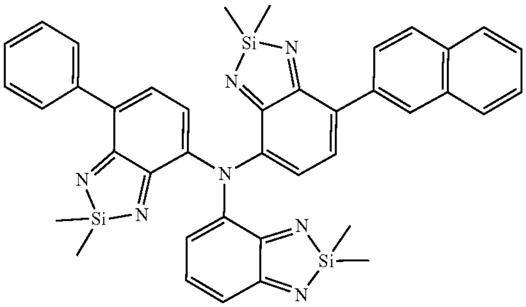
H242
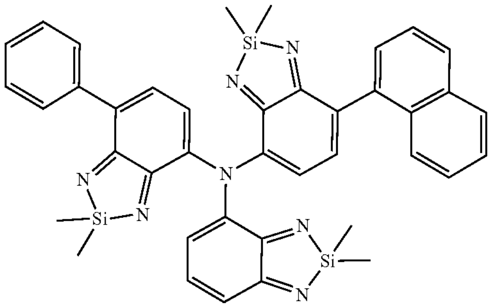

-continued
H243
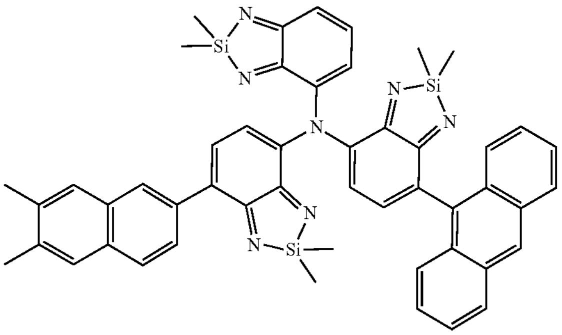
H244
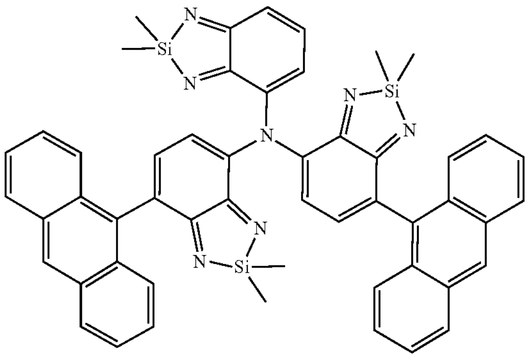
H245
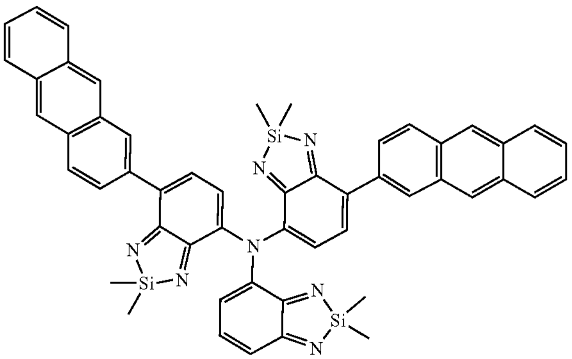
H246
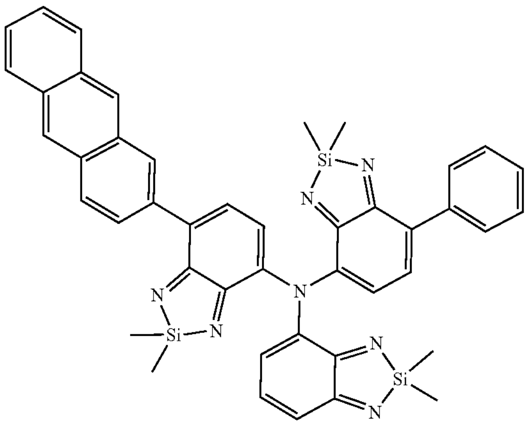
H247
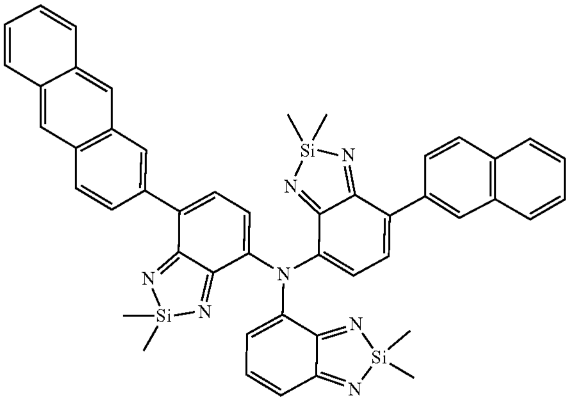
H248
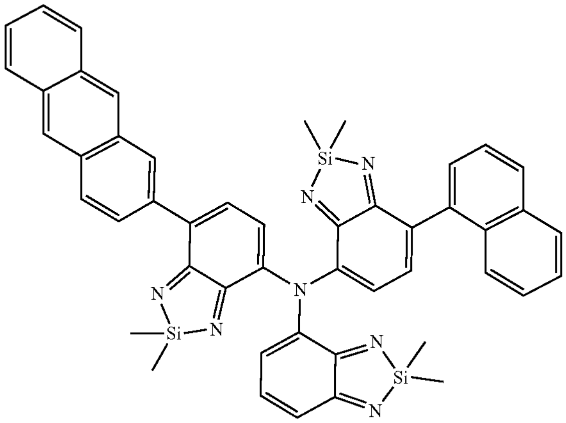
H249
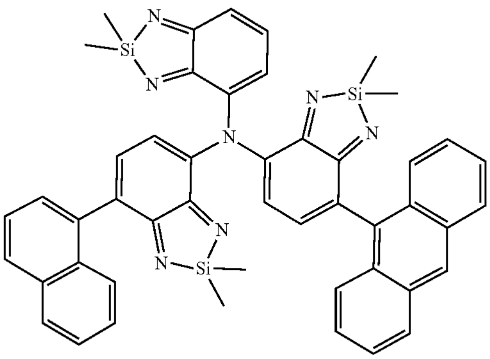
H250
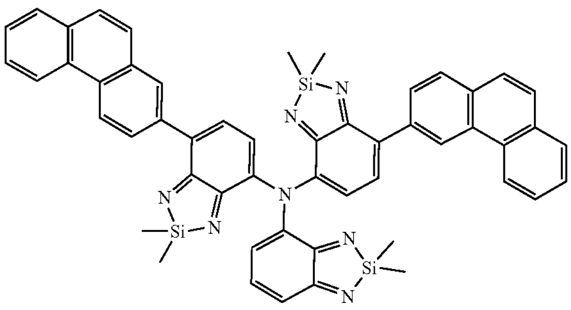

-continued
H251
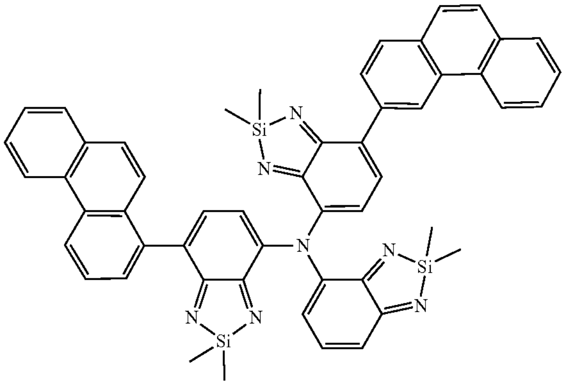
H252
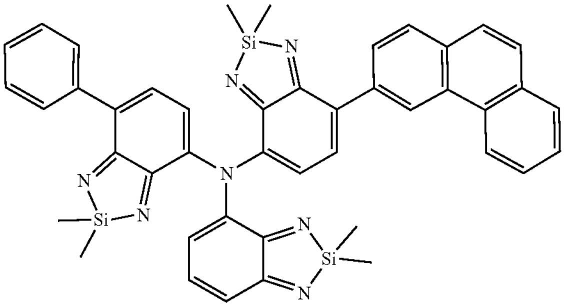
H253
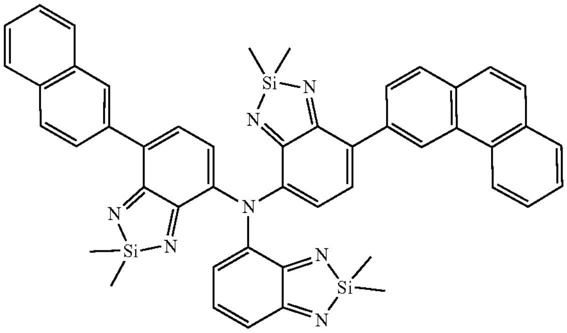
H254
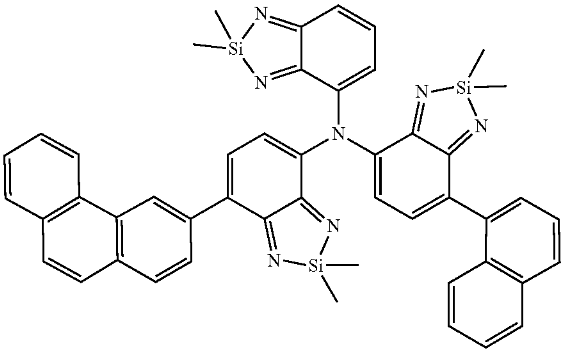
H255
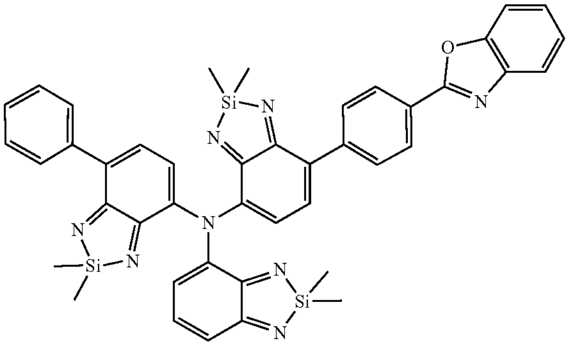
H256
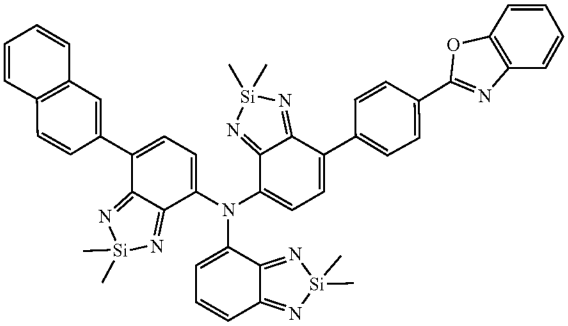
H257
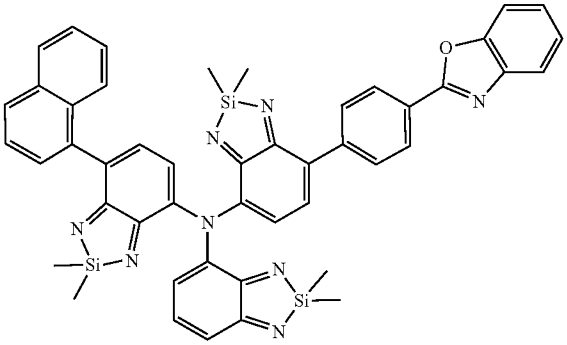
H258
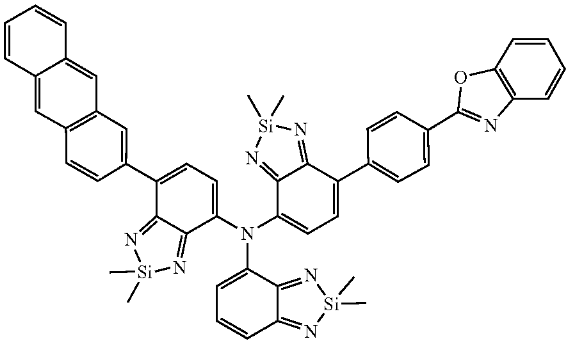

-continued
H259
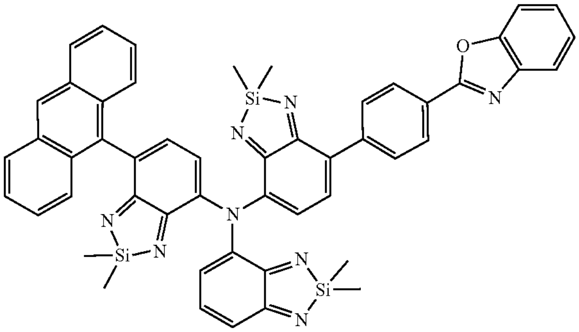
H260
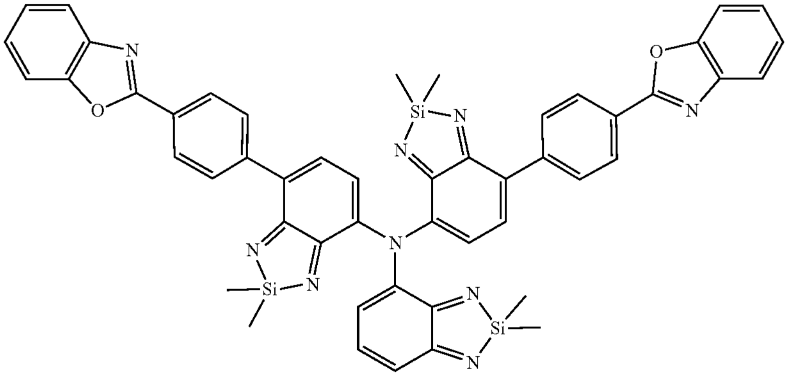
H261
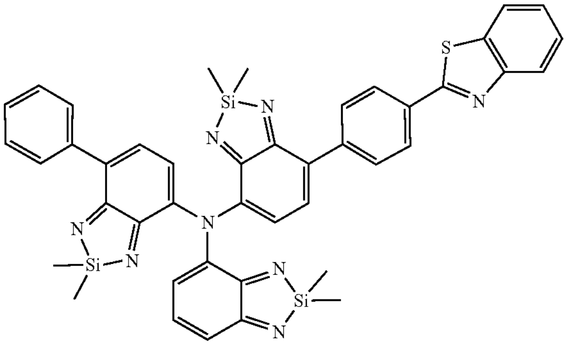
H262
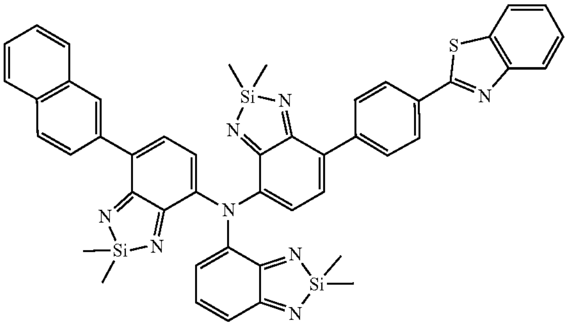
H263
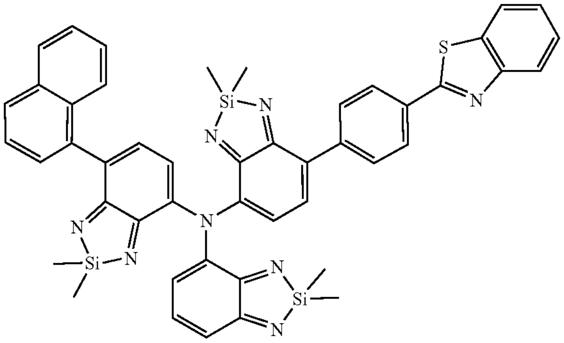
H264
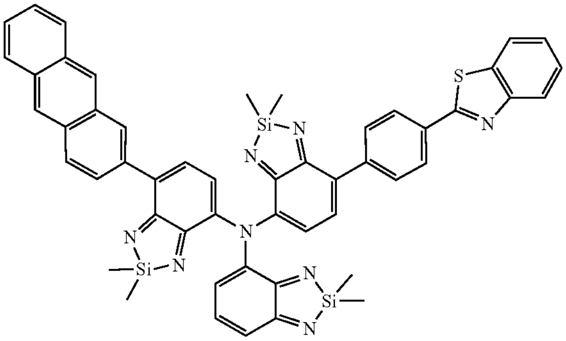

-continued
H265
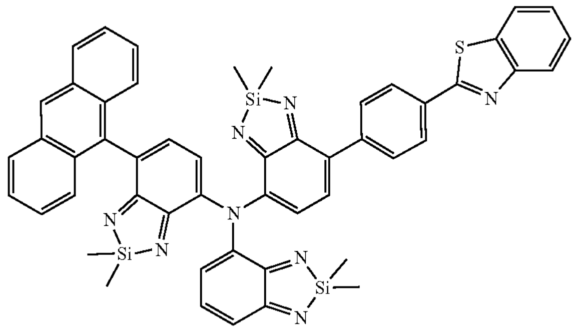
H266
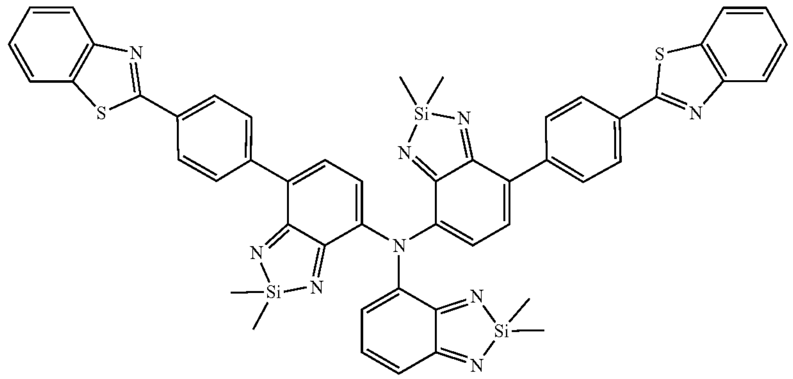
H267
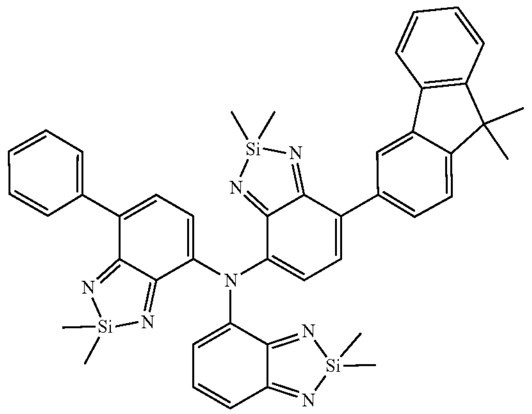
H268
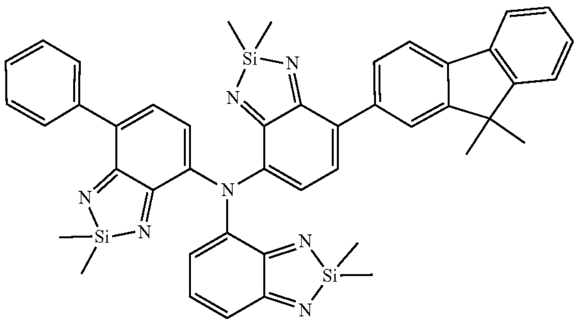
H269
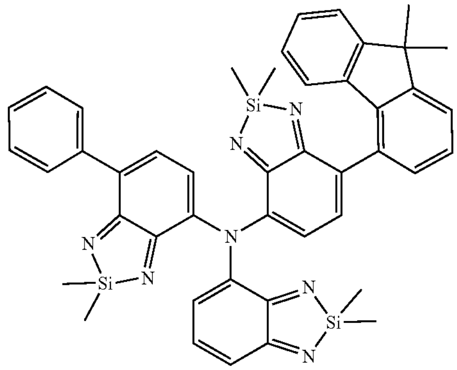
H270
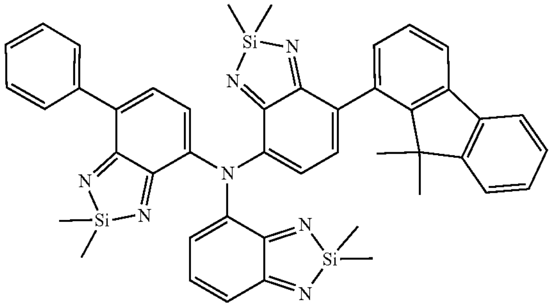

-continued
H271
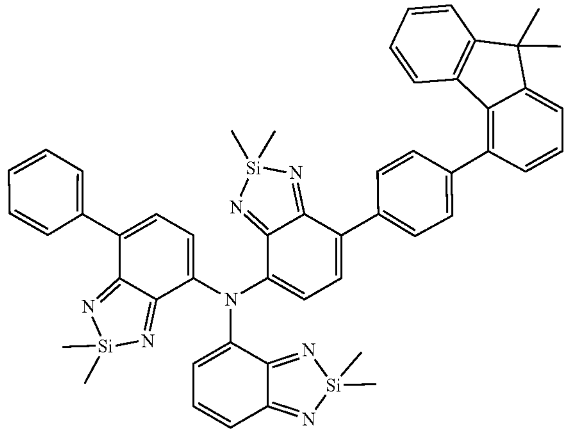
H272
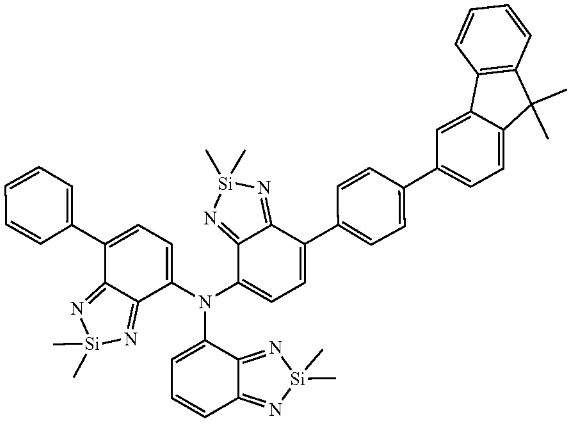
H273
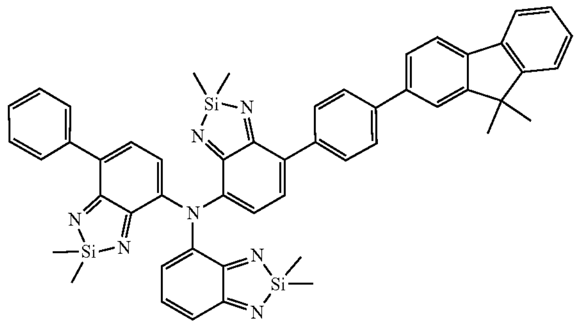
H274
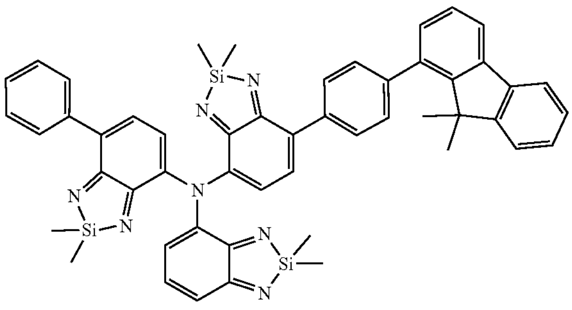
H275
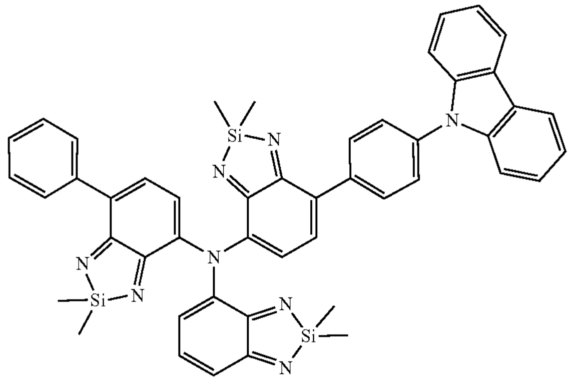
H276
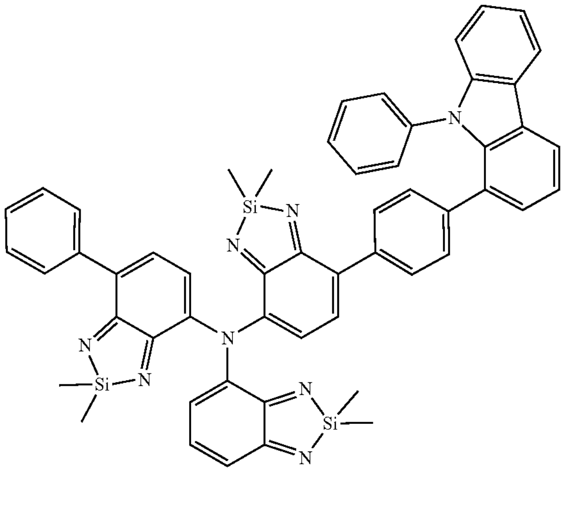

-continued
H277
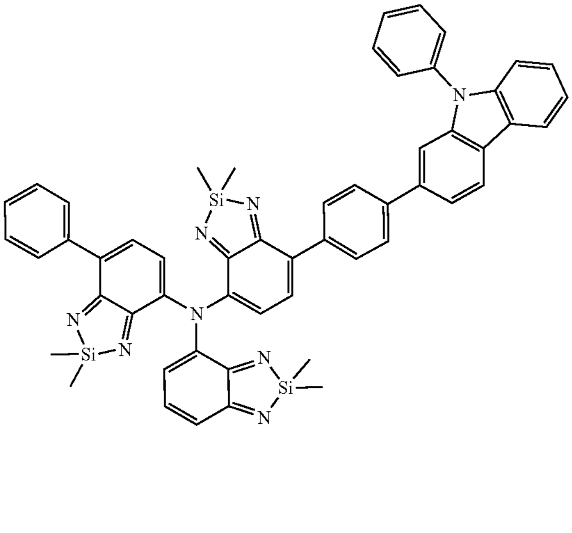
H278
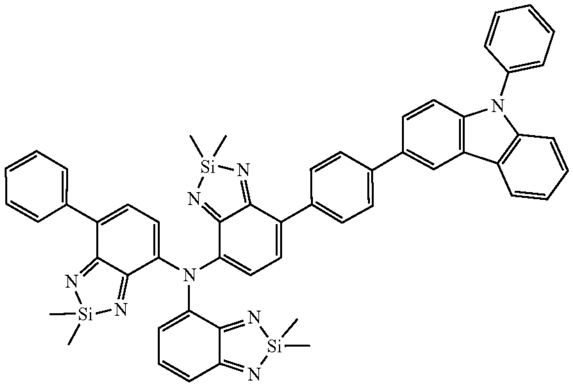
H279
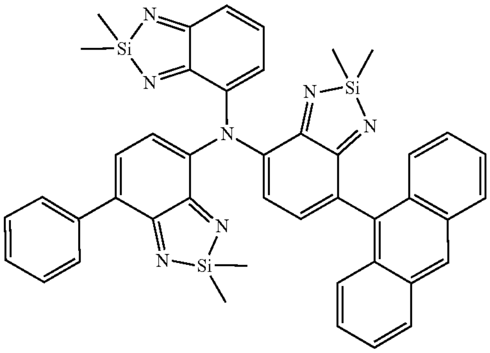
H280
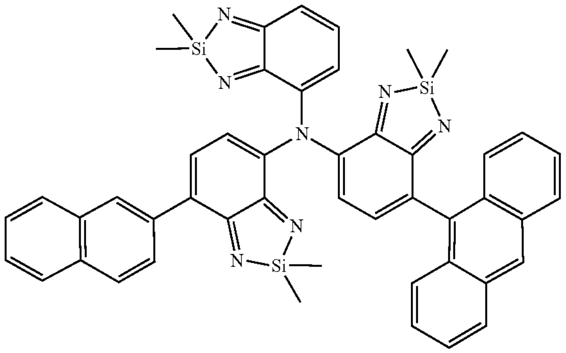
H281
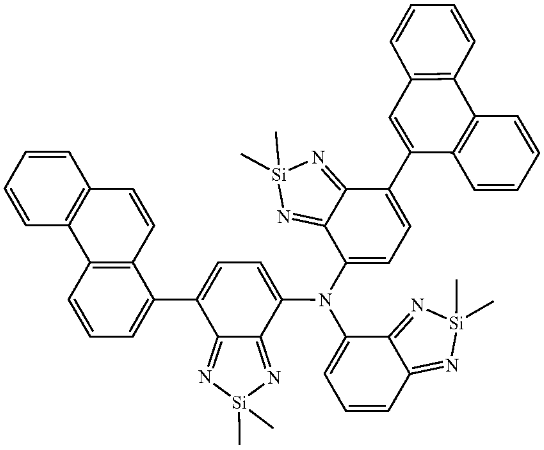
H282
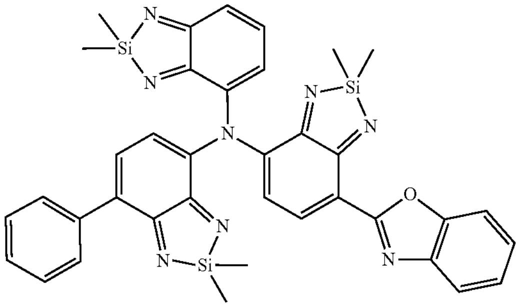

-continued
H283
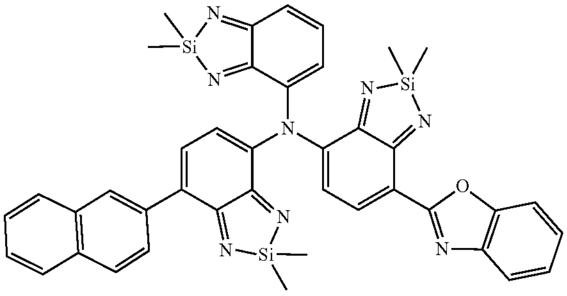
H284
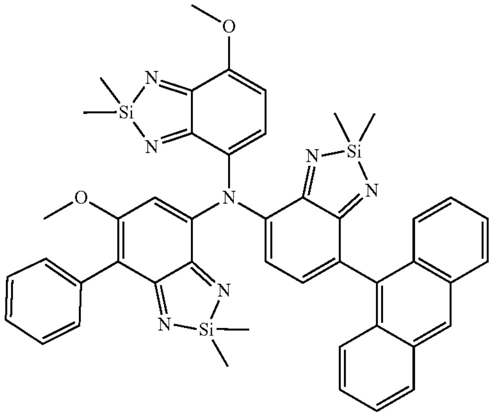
H285
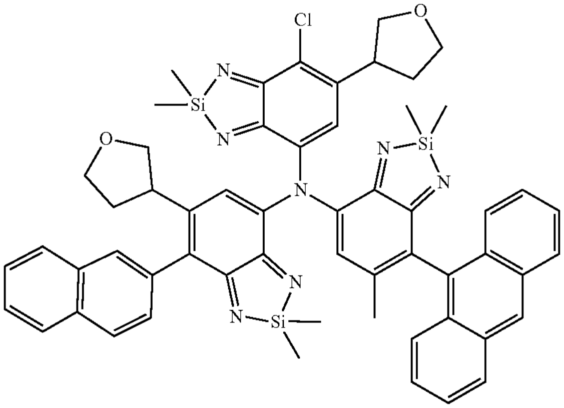
H286
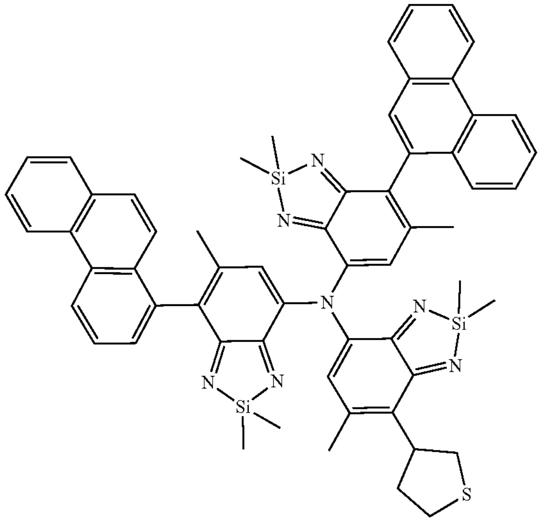
H287
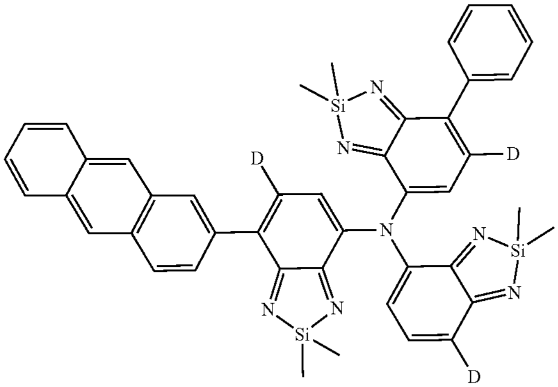
H288
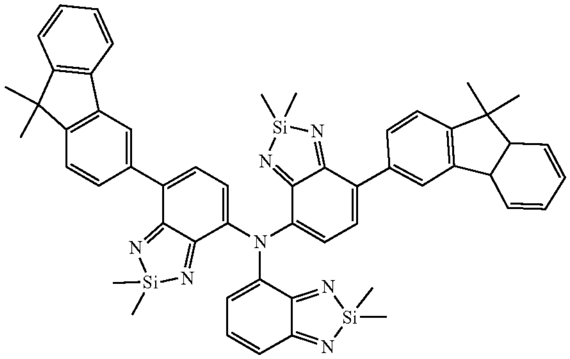

-continued
H289
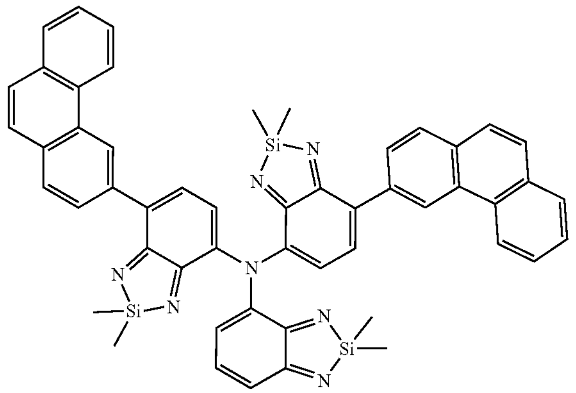
H290
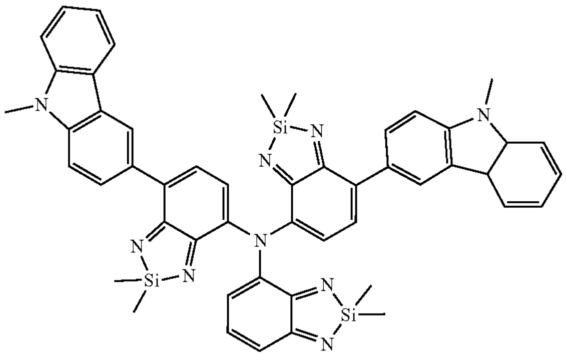
H291
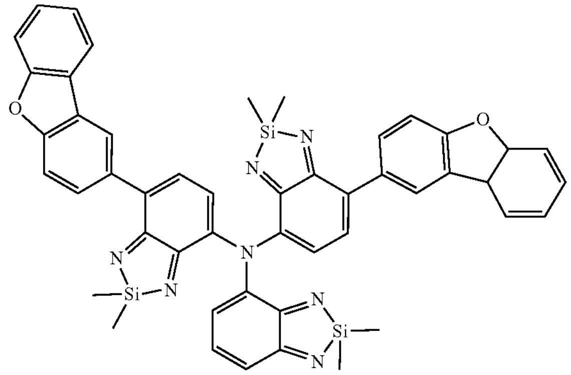
H292
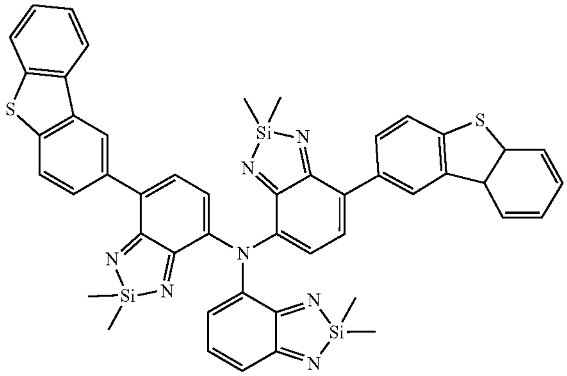
H293
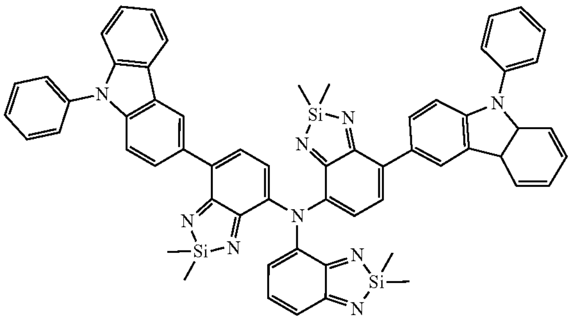
H294
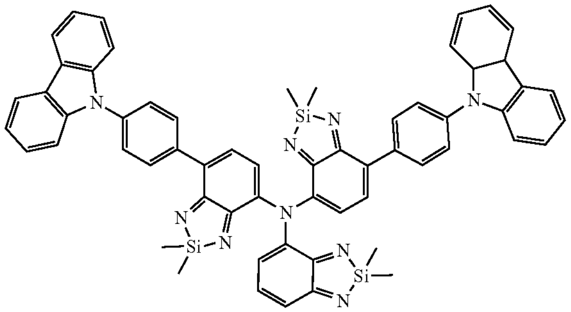

-continued

H295

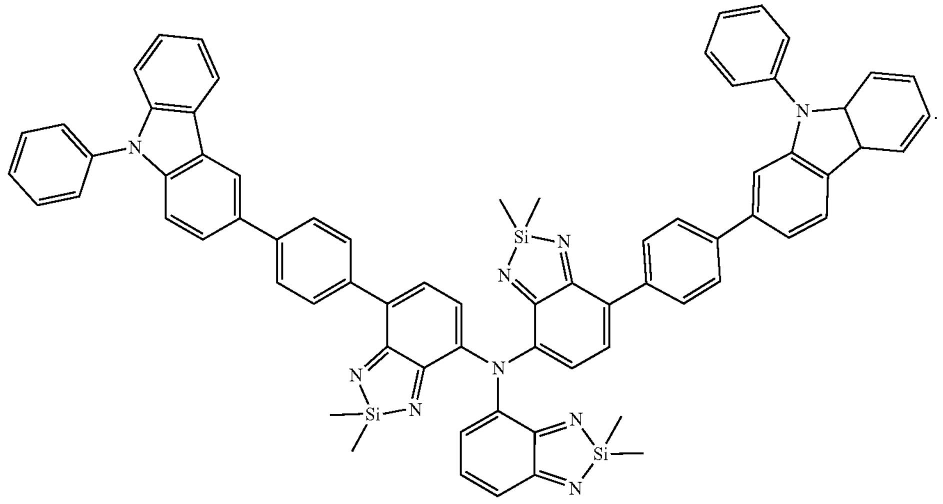

Display Panel

A second aspect of the present application provides a display panel, including an organic electroluminescent device, the organic electroluminescent device including a cathode, an anode arranged opposite to the cathode, a capping layer located on the side of the cathode away from the anode, and an organic film layer located between the cathode and the anode, wherein at least one of the capping layer and the organic film layer includes any one or more compounds according to the first aspect of the present application.

In some embodiments, the display panel is a foldable display panel. When any one or more compounds according to the first aspect of the present application are used in the foldable display panel, the difference Δn between refractive indexes of RGB light colors is small at multi-angle display, which can effectively reduce color shift.

The cathode material and anode material can independently be selected from corresponding materials known in the art. In some embodiments, the cathode may include a metal layer (e.g., aluminum, magnesium, silver, indium, tin, titanium, etc., and alloys thereof), or a metal layer and a multi-layer cathode formed by compounding layers including one or more of metal oxides and metal halides (e.g., LiF/Al, $LiO_2$/Al, $BaF_2$/Al, etc.). In addition to the above materials and combinations that facilitate electron injection, other known materials suitable for the cathode are also included. In some embodiments, the anode material may include metals (e.g., copper, gold, silver, iron, chromium, nickel, manganese, palladium, platinum, etc., and alloys thereof), metal oxides (e.g., indium oxide, zinc oxide, indium tin oxide (ITO), indium zinc oxide (IZO), etc.), conductive polymers (e.g., polyaniline, polypyrrole, poly(3-methylthiophene), etc.). In addition to the above materials and combinations that facilitate hole injection, other known materials suitable for the anode may also be included.

The organic film layer is arranged between the cathode and the anode, and the organic film layer is of a multi-layer thin film structure.

The organic film layer includes at least one luminescent layer, and the luminescent layer may include luminescent materials known in the art. Further, the luminescent material may include a host material and a guest material. In some embodiments, the luminescent layer may include any one or more compounds according to the first aspect of the present application, which may serve as the host material or guest material.

The guest material may also be selected from fluorescent luminescent materials, phosphorescent luminescent materials or thermally activated delayed fluorescence (TADF) luminescent materials known in the art depending on light emitting principles; and blue luminescent materials, green luminescent materials, red luminescent materials, etc. known in the art may be used depending on light emitting colors.

The host material may be selected depending on the light emitting principles and light emitting colors of the guest material, for example, may be a fluorescent host material, a unipolar host material, a bipolar host material, etc., and may also be a blue light host material, a green light host material, a red light host material, etc.

In some embodiments, the organic film layer may include, in addition to at least one luminescent layer, any one or more of a hole injection layer (HIL), a hole transport layer (HTL), an electron barrier layer (EBL), a hole barrier layer (HBL), an electron transport layer (ETL), and an electron injection layer (EIL). Materials for each layer, such as a hole injection material (HIM), a hole transport material (HTM), an electron barrier material (EBM), a hole barrier material (HBM), an electron transport material (ETM), and an electron injection material (EIM), may be respectively selected from corresponding materials known in the art.

As an example, the hole injection material, hole transport material and electron barrier material may be selected from 2,2'-dimethyl-N,N'-di-1-naphthyl-N,N'-diphenyl [1,1'-biphenyl]-4,4'-diamine (α-NPD), 4,4',4"-tris(carbazol-9-yl) triphenylamine (TCTA), 1,3-di carbazol-9-ylbenzene (mCP), 4,4'-bis(9-carbazole)biphenyl (CBP), 3,3'-bis(N-carbazolyl)-1,1'-biphenyl (mCBP), N,N-bisbiphenyl-4'-(9H-carbazolyl) biphenyl-4-amine, 2,3,6,7,10,11-hexacyano-1,4,5,8,9,12-hexaazatriphenylene (HAT-CN), 4,4'-cyclohexylbis[N,N-bis(4-methylphenyl)aniline (TAPC), N,N'-diphenyl-N,N'-(1-naphthyl)-1,1'-biphenyl-4,4'-diamine (α-NPB), N,N'-bis(naphthalen-2-yl)-N,N'-bis (phenyl) biphenyl-4,4'-diamine (NPB), poly(3,4-ethylenedioxythiophene)-polystyrenesulfonic acid (PEDOT:PSS), polyvinylcarbazole (PVK), 9-phenyl-3,9-bicarbazole (CCP), molybdenum trioxide ($MoO_3$) and other materials, but are not limited to the above materials.

As an example, the hole barrier material, electron transport material and electron injection material may be selected from 2,9-dimethyl-4,7-diphenyl-1,10-phenanthroline, 2,8-bis(diphenylphosphinyl)dibenzothiophene (PPT), TSPO 1,1,3,5-tris (1-phenyl-1H-benzimidazol-2-yl)benzene (TPBi), 2,8-bis(diphenylphosphinyl)dibenzofuran (PPF), bis(2-diphenylphosphinyl)diphenyl ether (DPEPO), lithium fluoride (LiF), 4,6-bis(3,5-bis(3-pyrid)ylphenyl)-2-methylpyrimidine (B3PYMPM), 4,7-diphenyl-1,10-phenanthroline (Bphen), 1,3,5-tris[(3-pyridyl)-3-phenyl]benzene (TmPyBP), tris[2,4,6-tri methyl-3-(3-pyridyl)phenyl]borane (3 TPYMB), 1,3-bis(3,5-bipyridin-3-ylphenyl) benzene (B3 PYPB), 1,3-bis[3,5-bis(pyridin-3-yl)phenyl]benzene (BMPYPHB), 2,4,6-tri s (biphenyl-3-yl)-1,3,5-tri azine (T2T), diphenylbis[4-pyridin-3-yl)phenyl]silane (DPPS), cesium carbonate ($Cs_2O_3$), bis(2-methyl-8-hydroxyquinoline-N1,O8)-(1,1'-biphenyl-4-hydroxy)aluminum (BAlq), 8-hydroxyquinoline-lithium (Liq), tris(8-hydroxyquinoline) aluminum (Alq3) and other materials, but are not limited to the above materials.

In some embodiments, the hole transport material may include any one or more compounds according to the first aspect of the present application.

FIG. 1 shows an exemplary organic electroluminescent device, which includes a substrate 1, an anode 2, a hole injection layer 3, a first hole transport layer 4, a second hole transport layer 5, a luminescent layer 6, a first electron transport layer 7, a second electron transport layer 8, a cathode 9 and a first capping layer 10 laminated in sequence.

In particular, the first capping layer 10 includes any one or more compounds according to the first aspect of the present application.

Figure 2:
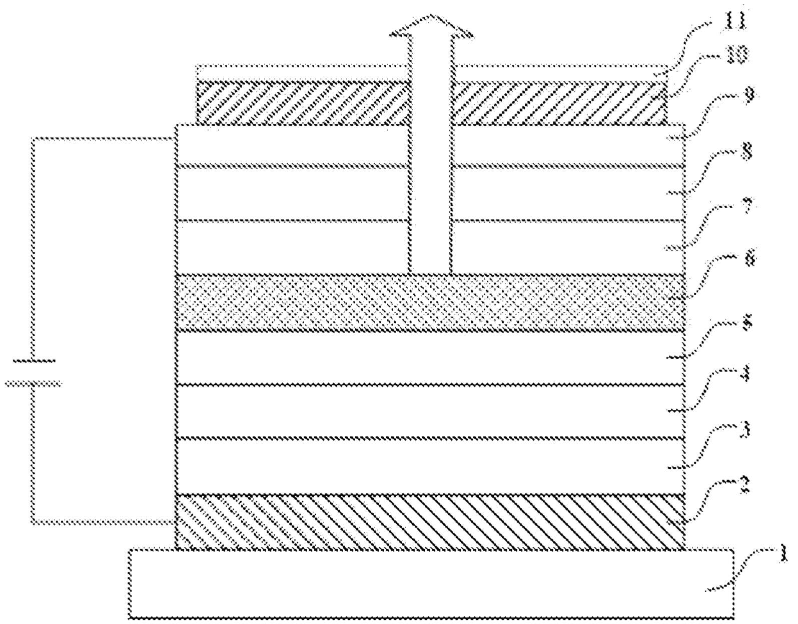
FIG. 2 is a schematic structural diagram of an organic electroluminescent device according to another embodiment of the present application.

In some embodiments, the organic electroluminescent device may further include a second capping layer on the side of the first capping layer away from the cathode. For example, FIG. 2 shows another exemplary organic electroluminescent device, which includes a substrate 1, an anode 2, a hole injection layer 3, a first hole transport layer 4, a second hole transport layer 5, a luminescent layer 6, a first electron transport layer 7, a second electron transport layer 8, a cathode 9, a first capping layer 10 and a second capping layer 11.

The material of the second capping layer includes lithium fluoride and/or organic small molecule materials having refractive indexes of 1.40 to 1.65 (e.g., 1.41, 1.42, 1.43, 1.44, 1.45, 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64, etc.). Optionally, the organic small molecule materials having refractive indexes of 1.40 to 1.65 include, but are not limited to, any one or a combination of at least two of polyfluorocarbon-containing compounds, boron-containing compounds, silicon-containing compounds, oxygen silicon-containing compounds, and adamantane-containing alkane compounds.

After any one or more compounds according to the first aspect of the present application is used as the material of the first capping layer and matched with the material of the second capping layer (such as lithium fluoride and/or an organic small molecule material having a refractive index of 1.40 to 1.65), the both can retard the total reflection of light by encapsulation glass, which is conducive to the transmission of visible light through the glass, further improves the light extraction effect, and especially significantly improves the external quantum efficiency.

The organic electroluminescent device may be manufactured by using methods known in the art. An exemplary manufacturing method includes: forming an anode on a substrate, forming an organic film layer on the anode, forming a cathode on the organic film layer, and forming a capping layer on the cathode. The substrate may be a rigid substrate (e.g., a glass substrate, a rigid plastic substrate, etc.), or a flexible substrate (e.g., a polyimide substrate, etc.). The organic film layer and the capping layer may be formed by known film forming methods such as evaporation-deposition, sputtering, spin coating, dipping, and ion plating.

Display Device

Figure 3:
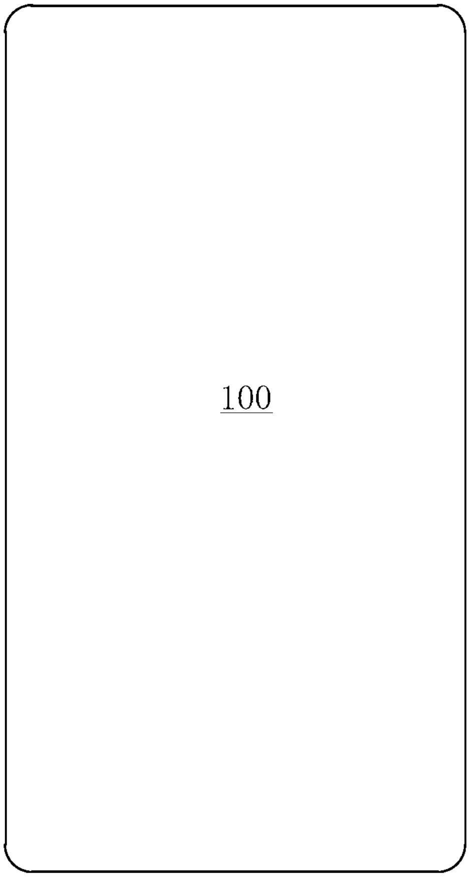
FIG. 3 is a schematic diagram of a display device according to the present application.

A third aspect of the present application provides a display device, including the display panel according to the second aspect of the present application. Examples of the display device include but are not limited to a mobile phone (mobile phone 100 shown in FIG. 3), a computer, a television, a smart watch, a smart car, a VR or AR helmet, etc., which are not specifically limited in the present application.

Some exemplary embodiments of the present disclosure are provided as follows.

Embodiment 1. A compound having the structure shown in Formula 1,

Formula 1

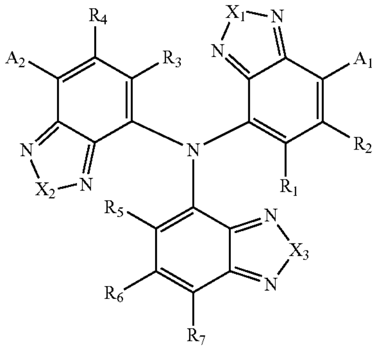

$A_1$ and $A_2$ each independently represent $-(L)_n-R$, where L each independently represents 6-membered to 60-membered divalent aryl unsubstituted or substituted by $R^a$ or to 60-membered divalent heteroaryl unsubstituted or substituted by $R^a$, R represents 6-membered to 60-membered monovalent aryl unsubstituted or substituted by $R^a$ or 5-membered to 60-membered monovalent heteroaryl unsubstituted or substituted by $R^a$, and n represents 0, 1 or 2;

$R_1$, $R_2$, $R_3$, $R_4$, $R_5$, $R_6$, and $R_7$ each independently represent hydrogen, deuterium, tritium, a halogen atom or the following group unsubstituted or substituted by $R^a$:

C1-C20 monovalent alkyl, C1-C20 monovalent alkoxy, C1-C20 monovalent alkylthio, C2-C20 monovalent alkenyl, C2-C20 monovalent alkynyl, 3-membered to monovalent alcyl, 3-membered to 20-membered monovalent heteroalcyl, 6-membered to 40-membered monovalent aryl, or 5-membered to 40-membered monovalent heteroaryl;

$X_1$, $X_2$, and $X_3$ each independently represent S, O, $N(Y_1)$, $C(Y_2)_2$ or $Si(Y_3)_2$, and $Y_1$, $Y_2$, and $Y_3$ each independently represent hydrogen, deuterium, tritium, or the following group unsubstituted or substituted by $R^a$:

C1-C20 monovalent alkyl, C1-C20 monovalent alkoxy, C1-C20 monovalent alkylthio, C2-C20 monovalent alkenyl, C2-C20 monovalent alkynyl, 3-membered to 20-membered monovalent alcyl, 3-membered to 20-membered monovalent heteroalcyl, 6-membered to 40-membered monovalent aryl, or 5-membered to 40-membered monovalent heteroaryl; and $R^a$ represents deuterium, tritium, a halogen atom, cyano, nitro, carboxyl, carbonyl, amino, C1-C20 monovalent alkyl, C1-C20 monovalent alkoxy, C1-C20 monovalent alkylthio, C2-C20 monovalent alkenyl, C2-C20 monovalent alkynyl, 3-membered to monovalent alcyl, 3-membered to 20-membered monovalent heteroalcyl, 6-membered to 40-membered monovalent aryl, or 5-membered to 40-membered monovalent heteroaryl, wherein one or more hydrogens of C1-C20 monovalent alkyl, C1-C20 monovalent alkoxy, C1-C20 monovalent alkylthio, C2-C20 monovalent alkenyl, C2-C20 monovalent alkynyl, 3-membered to 20-membered monovalent alcyl, 3-membered to 20-membered monovalent heteroalcyl, 6-membered to 40-membered monovalent aryl, or 5-membered to 40-membered monovalent heteroaryl each are independently replaced by deuterium, tritium, a halogen atom, cyano, nitro, carboxyl, carbonyl, or amino.

Embodiment 2. The compound according to Embodiment 1, wherein heteroatoms comprise at least one of N, O, S, Si, and Se.

Embodiment 3. The compound according to Embodiment 1 or 2, wherein $A_1$ and $A_2$ are the same.

Embodiment 4. The compound according to any one of Embodiments 1 to 3, wherein n represents 0 or 1.

Embodiment 5. The compound according to any one of Embodiments 1 to 4, wherein

L each independently represents phenyl, naphthyl, anthryl, phenanthryl, biphenyl, terphenyl, tetraphenyl, triphenylenyl, pyrenyl, chrysenyl, perylenyl, indenyl, triphenylenyl, fluorenyl, 9,9-dimethylfluorenyl, spirobifluorenyl, pyrrolyl, furanyl, thienyl, indolyl, benzofuranyl, benzothienyl, dibenzofuran, dibenzothiophene, carbazolyl, indenocarbazolyl, indolocarbazolyl, pyridyl, pyrimidinyl, pyrazinyl, pyridazinyl, triazinyl, oxazolyl, isooxazolyl, thiazolyl, isothiazolyl, benzoxazolyl, benzoisoxazolyl, benzothiazolyl, or benzoisothiazolyl unsubstituted or substituted by $R^a$, and R represents phenyl, naphthyl, anthryl, phenanthryl, biphenyl, terphenyl, tetraphenyl, triphenylenyl, pyrenyl, chrysenyl, perylenyl, indenyl, triphenylenyl, fluorenyl, 9,9-dimethylfluorenyl, spirobifluorenyl, pyrrolyl, furanyl, thienyl, indolyl, benzofuranyl, benzothienyl, dibenzofuran, dibenzothiophene, carbazolyl, indenocarbazolyl, indolocarbazolyl, pyridyl, pyrimidinyl, pyrazinyl, pyridazinyl, triazinyl, oxazolyl, isooxazolyl, thiazolyl, isothiazolyl, benzoxazolyl, benzoisoxazolyl, benzothiazolyl, or benzoisothiazolyl unsubstituted or substituted by $R^a$.

Embodiment 6. The compound according to any one of Embodiments 1 to 5, wherein n represents 0 or 1, L represents phenyl, and R represents phenyl, naphthyl, anthryl, phenanthryl, 9,9-dimethylfluorenyl, dibenzofuran, dibenzothiophene, carbazolyl, benzoxazolyl, or benzothiazolyl unsubstituted or substituted by $R^a$.

Embodiment 7. The compound according to any one of Embodiments 1 to 6, wherein $A_1$ and $A_2$ each independently represent any one of the following groups,

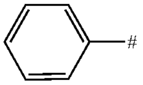
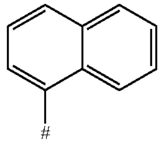
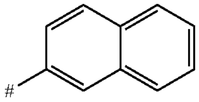
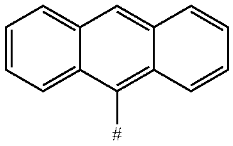
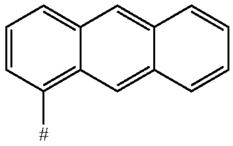
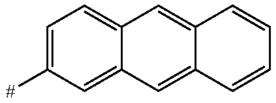
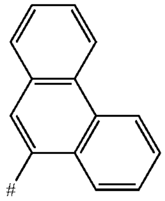
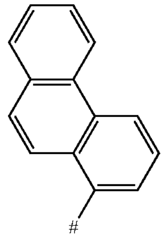
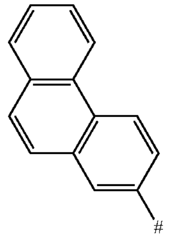
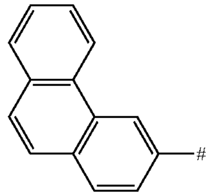
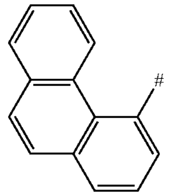
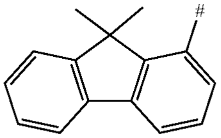
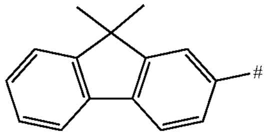
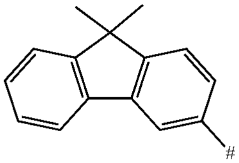
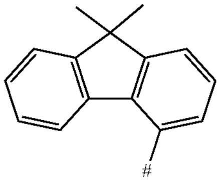
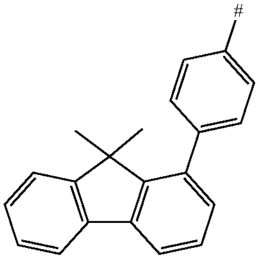
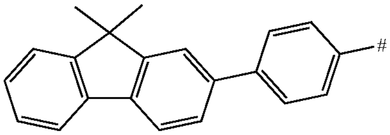

-continued

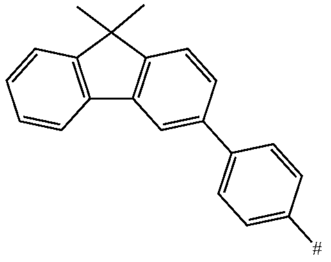

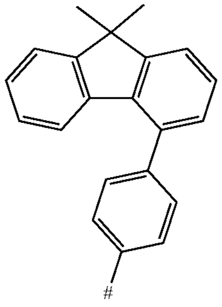

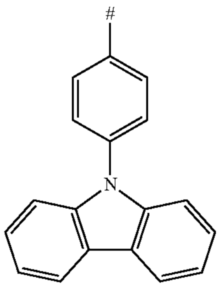

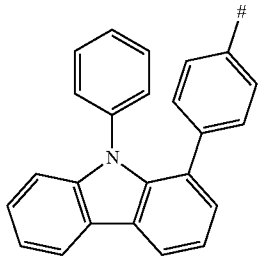

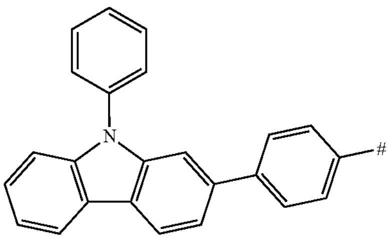

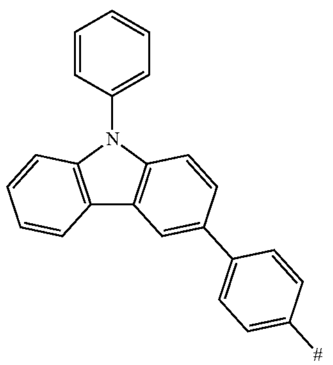

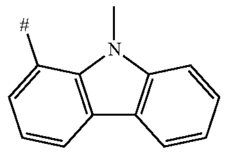

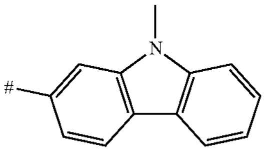

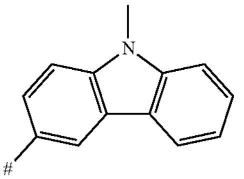

-continued

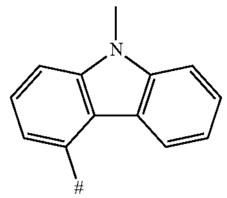

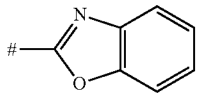

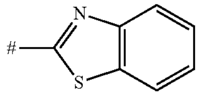

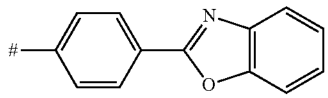

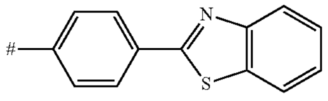

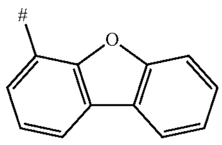

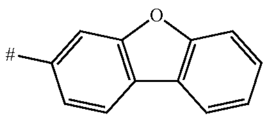

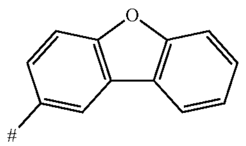

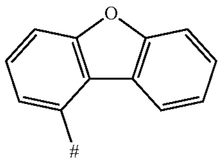

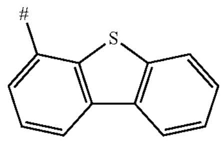

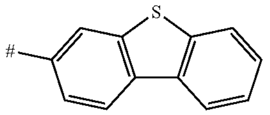

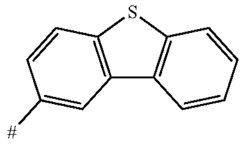

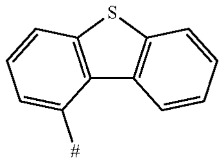

# represents an attachment position.

Embodiment 8. The compound according to any one of Embodiments 1 to 7, wherein $R_1$, $R_2$, $R_3$, $R_4$, $R_5$, $R_6$, and $R_7$ each independently represent hydrogen, deuterium, tritium, a halogen atom or the following group unsubstituted or substituted by $R^a$:

methyl, ethyl, propyl, butyl, methoxy, ethoxy, propoxy, cyclopropyl, cyclobutyl, cyclopentyl, cyclohexyl, tetrahydrofuranyl, tetrahydrothienyl, or phenyl.

Embodiment 9. The compound according to any one of Embodiments 1 to 8, wherein $X_1$, $X_2$, and $X_3$ all represent S or O.

Embodiment 10. The compound according to any one of Embodiments 1 to 9, wherein the compound is selected from any of the following, H01
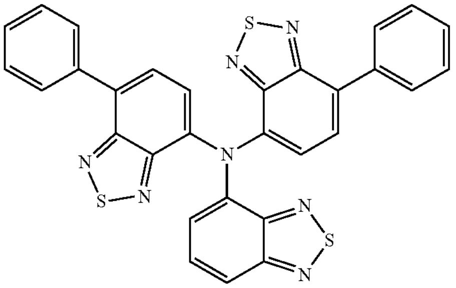
H02
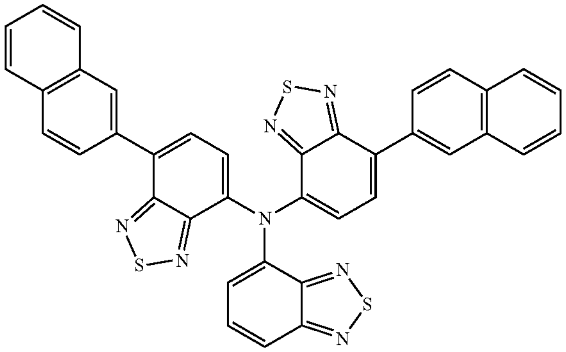
H03
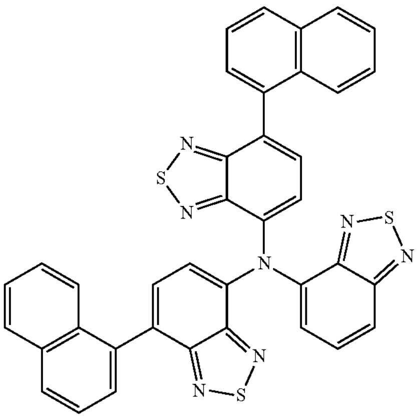
H04
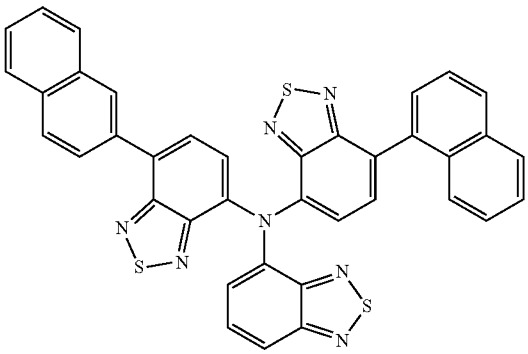
H05
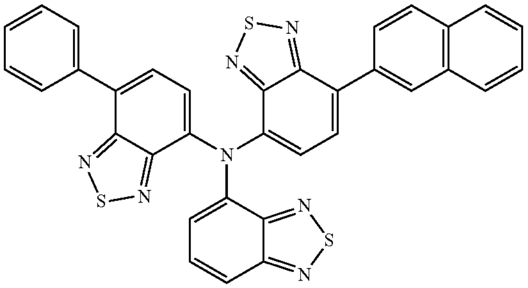
H06
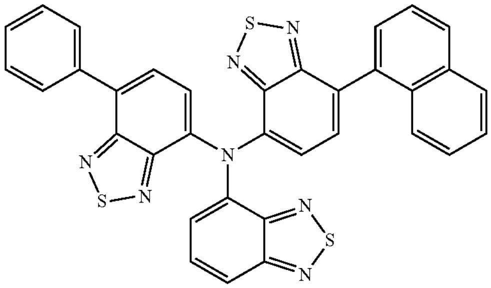
H07
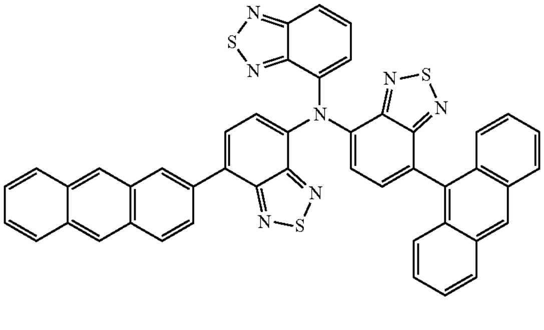
H08
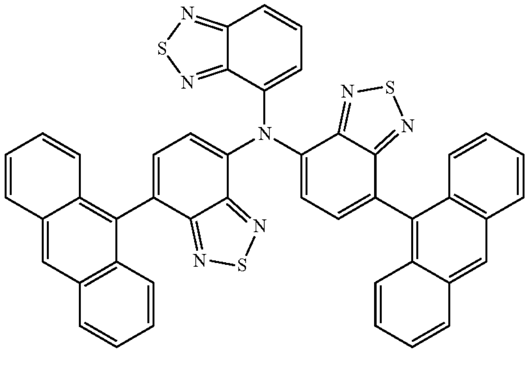

-continued
H09
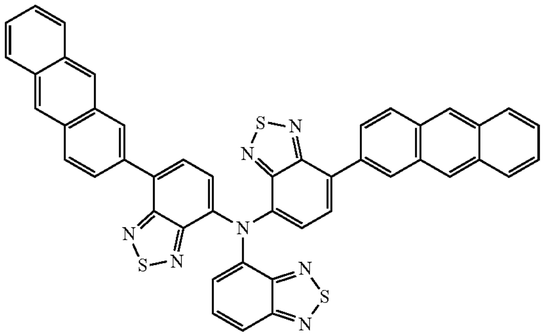
H10
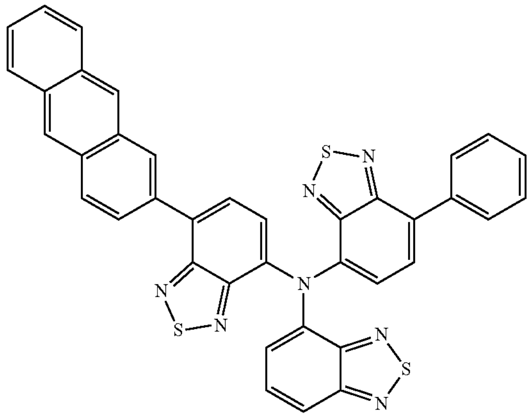
H11
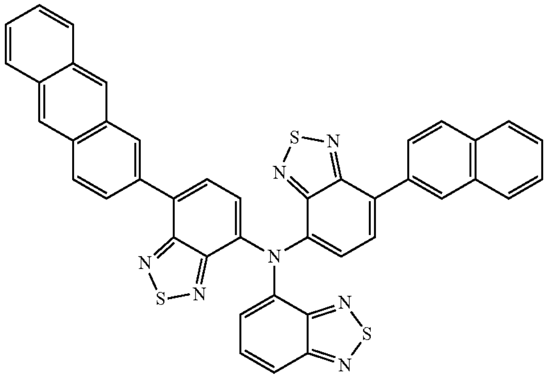
H12
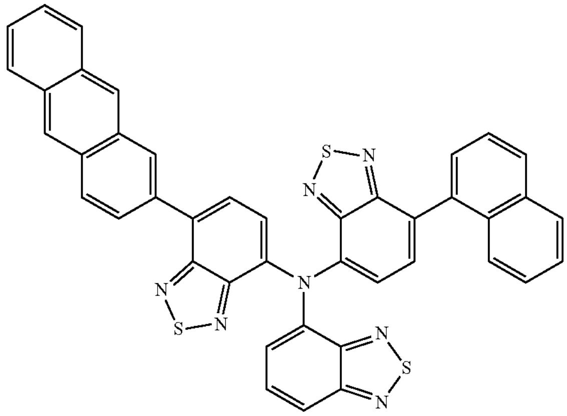
H13
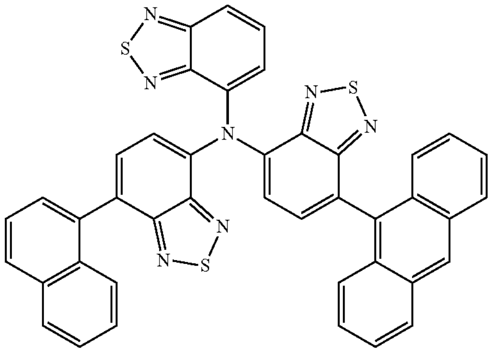
H14
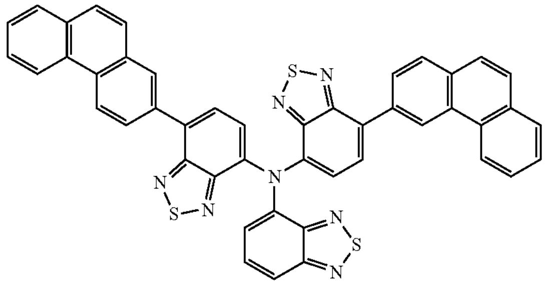
H15
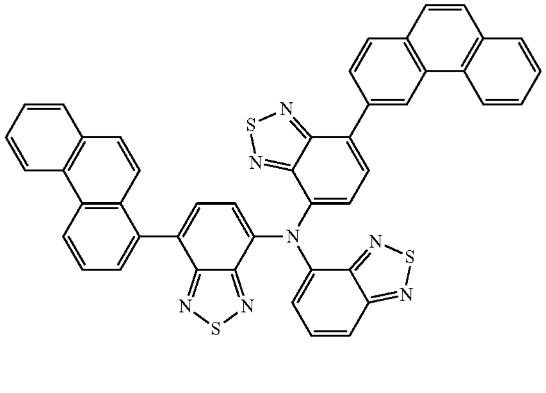
H16
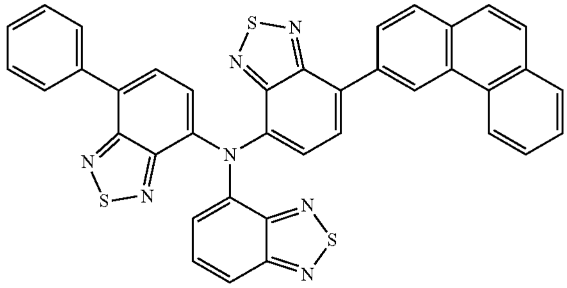

-continued
H17
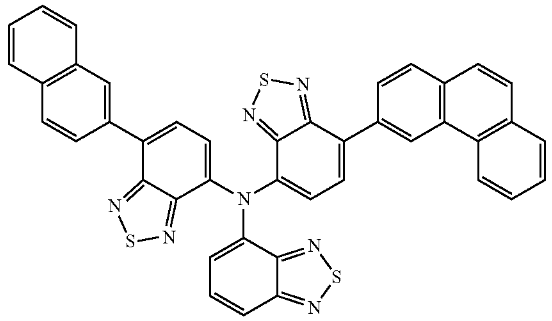
H18
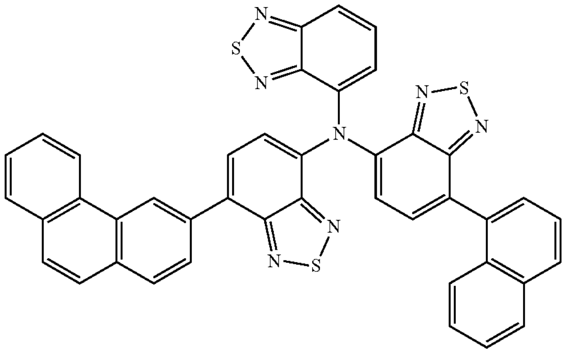
H19
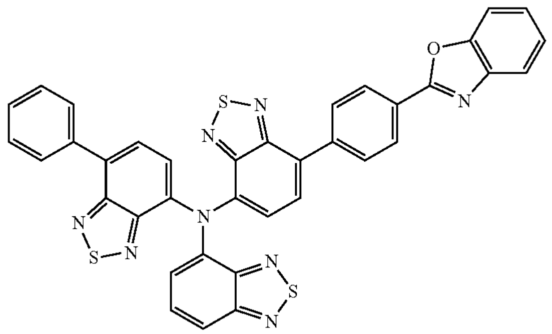
H20
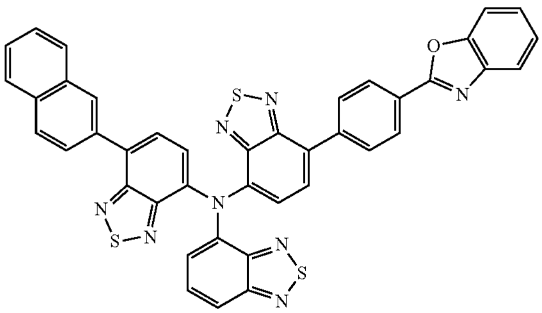
H21
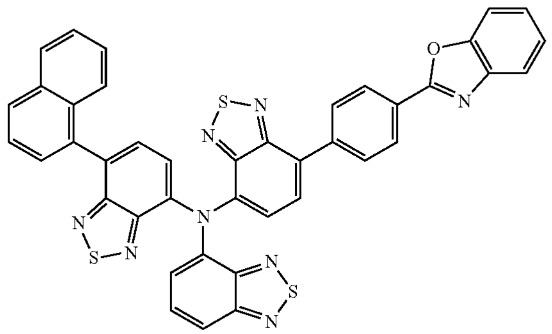
H22
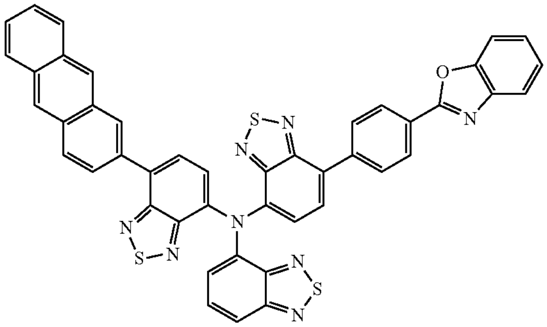
H23
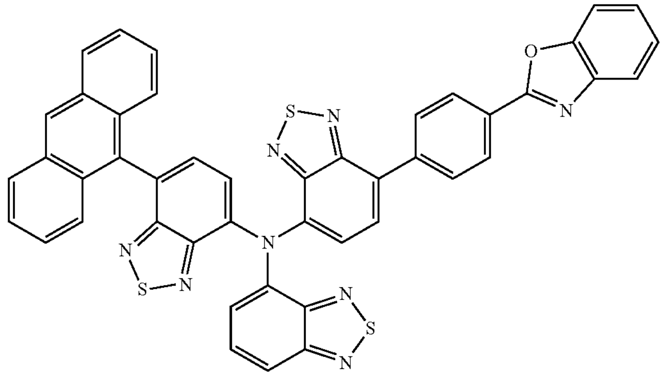

-continued
H24
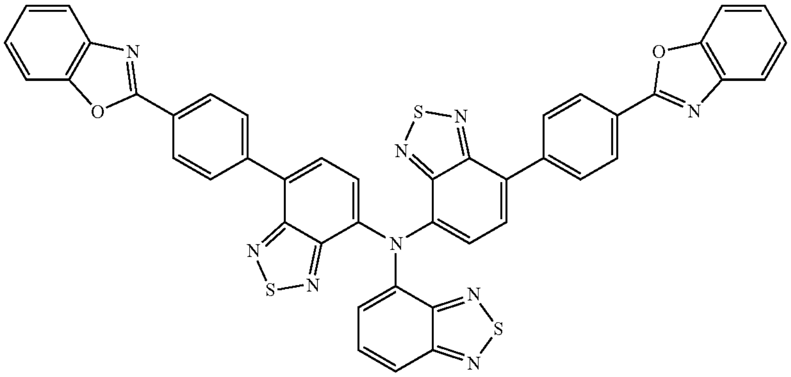
H25
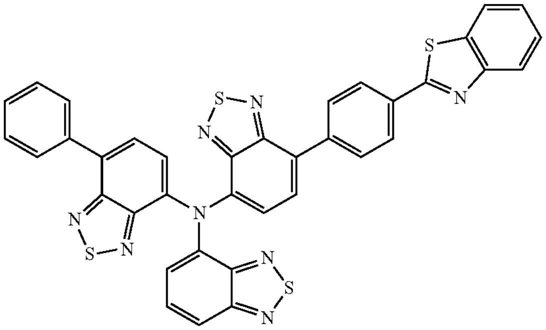
H26
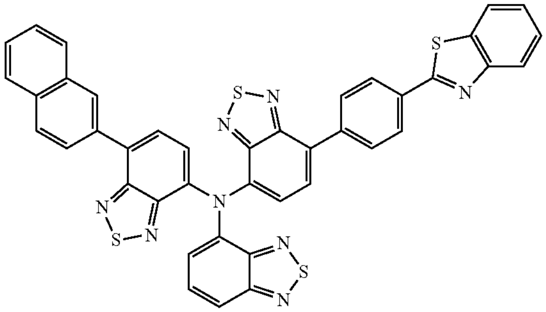
H27
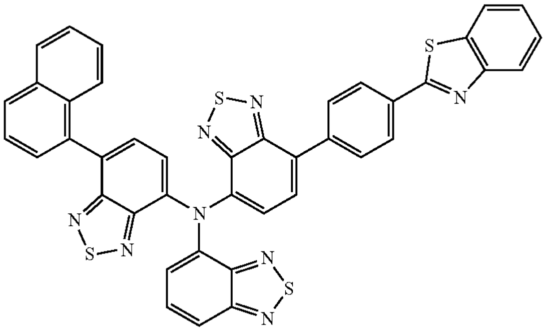
H28
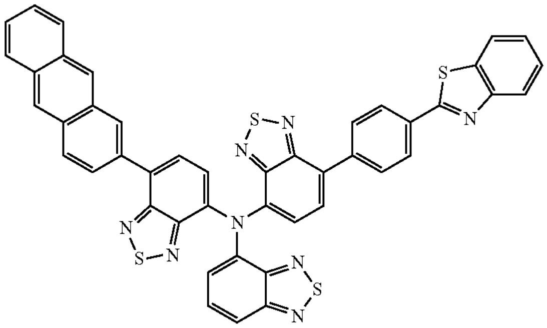
H29
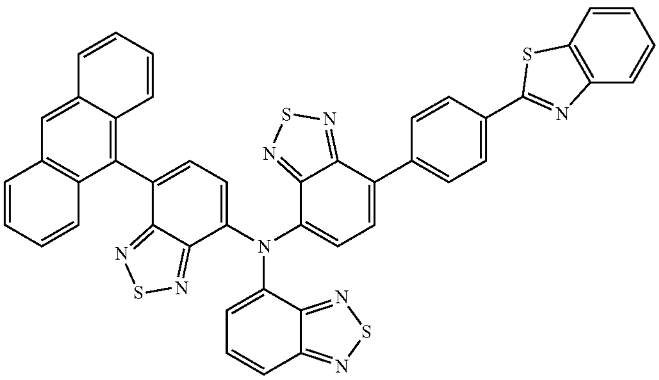

-continued
H30
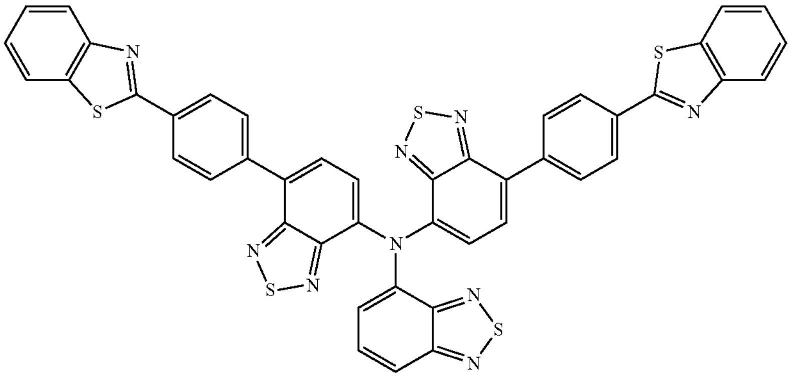
H31
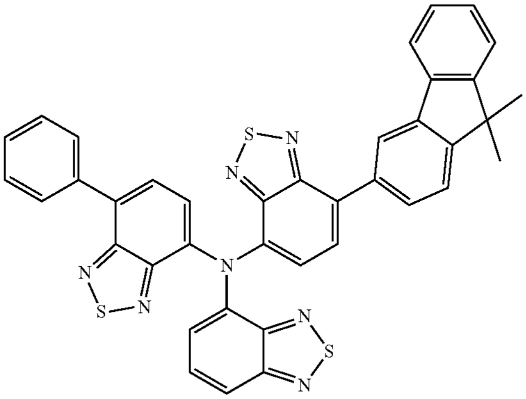
H32
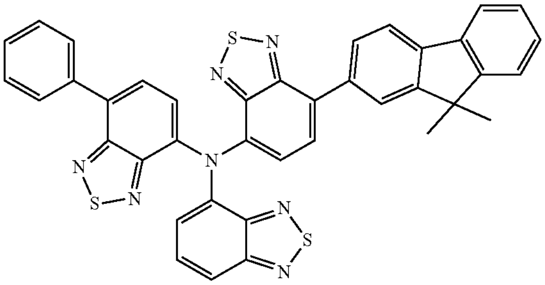
H33
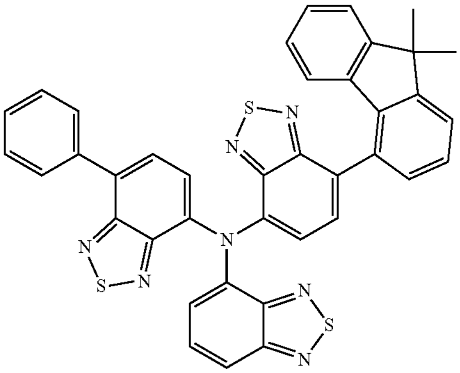
H34
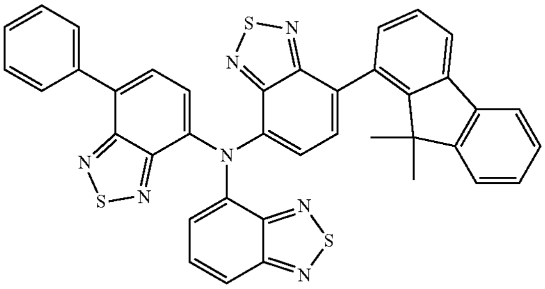
H35
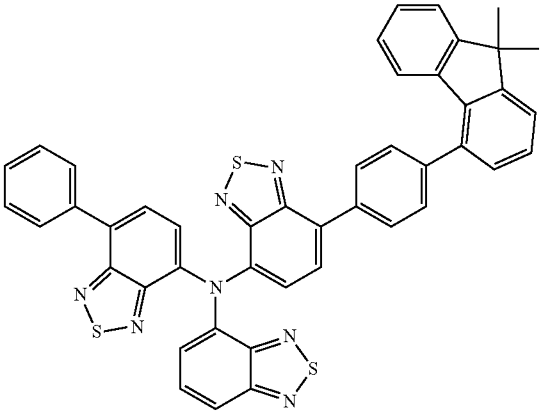
H36
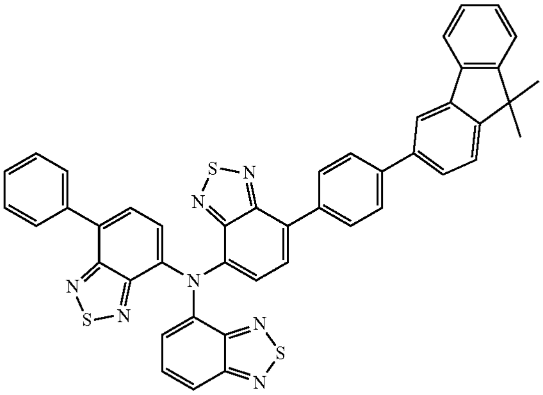

-continued
H37
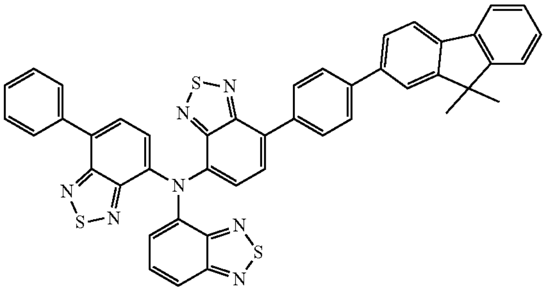
H38
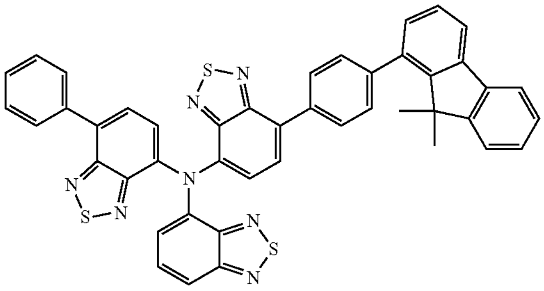
H39
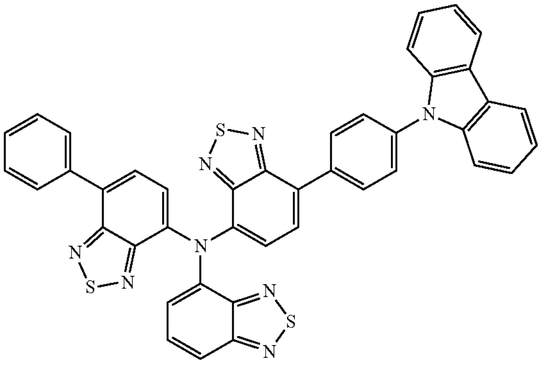
H40
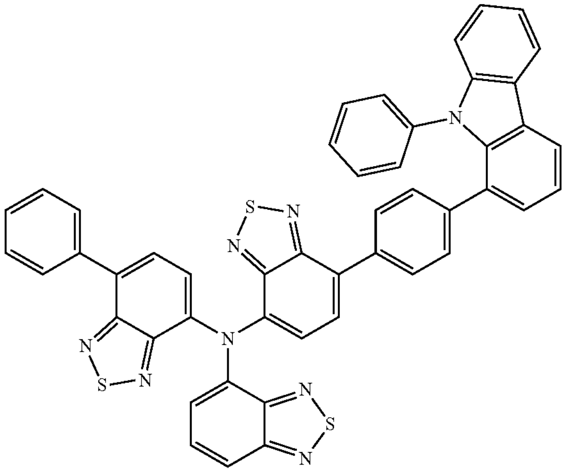
H41
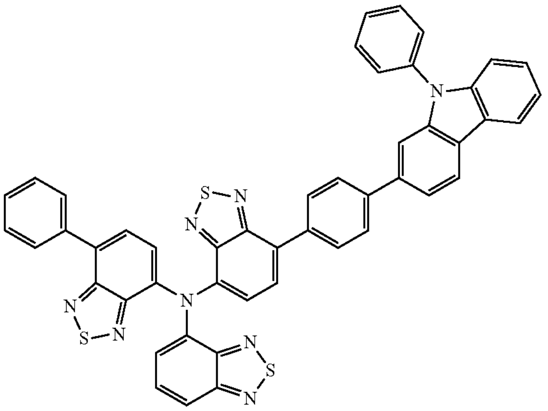
H42
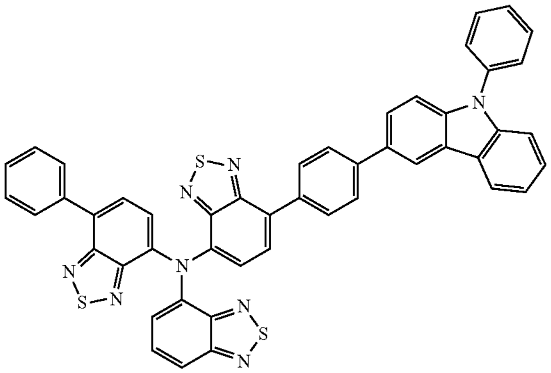
H43
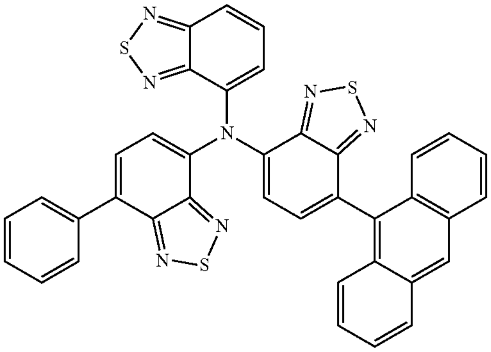
H44
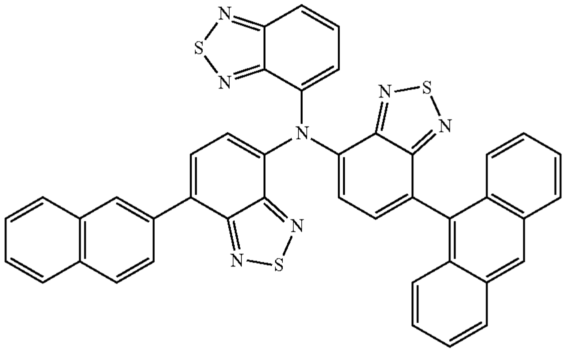

-continued
H45
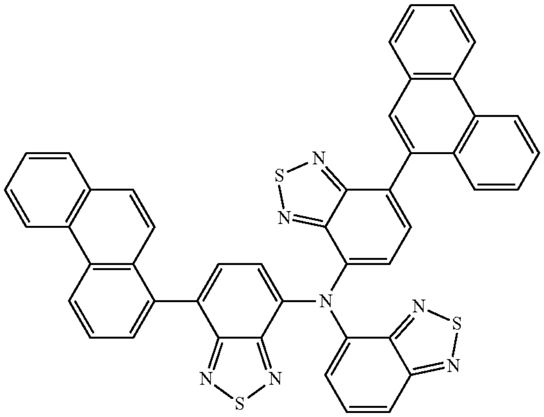
H46
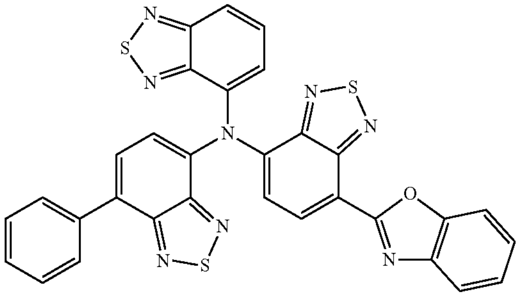
H47
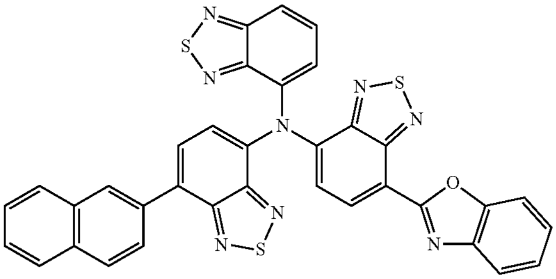
H48
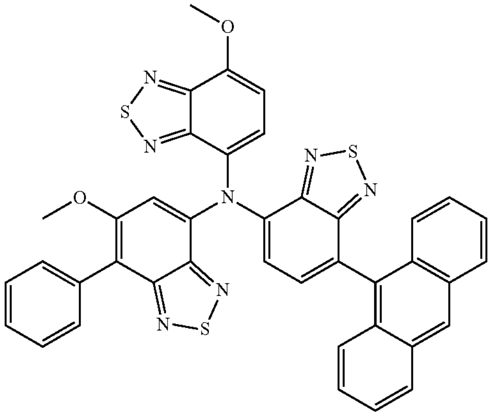
H49
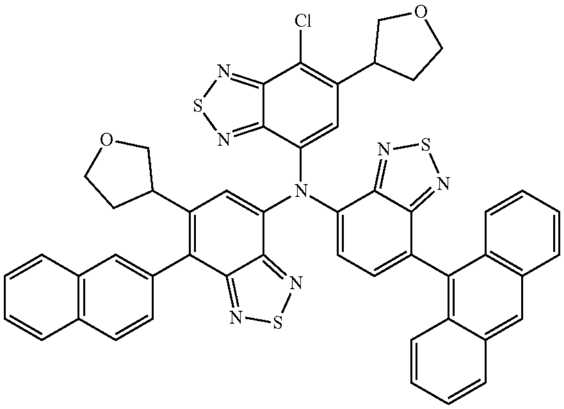
H50
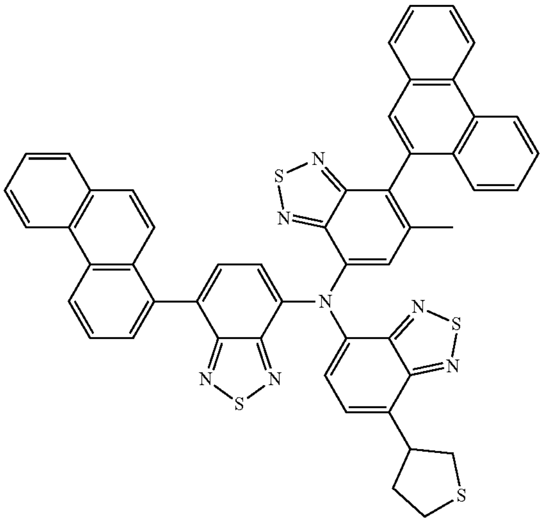

-continued
H51
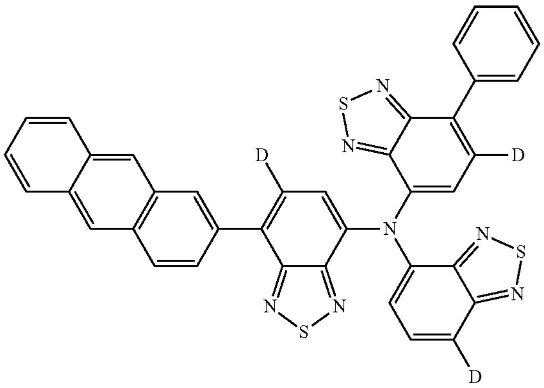
H52
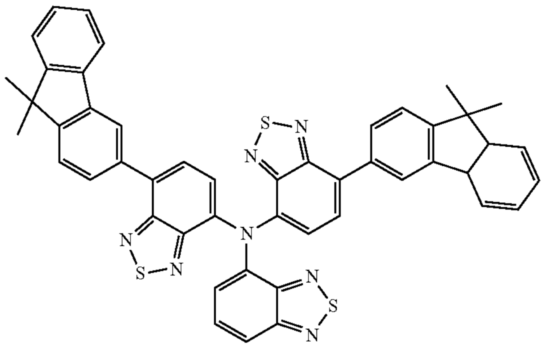
H53
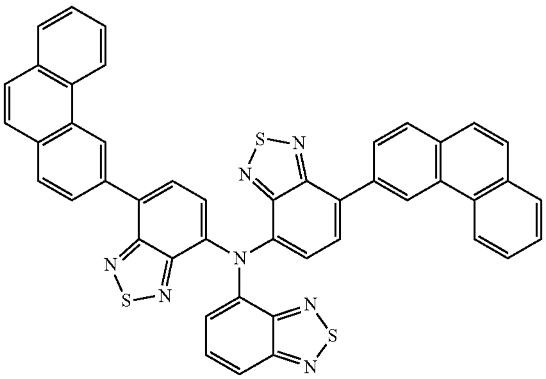
H54
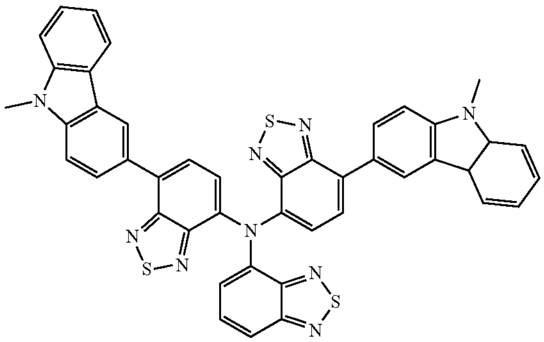
H55
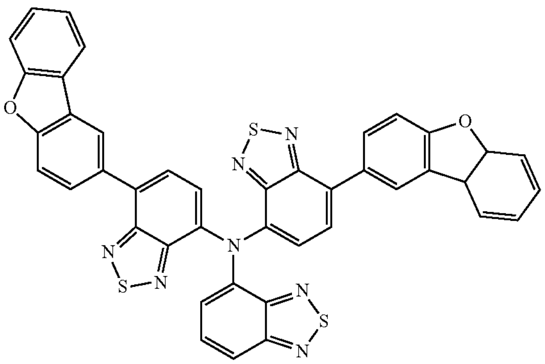
H56
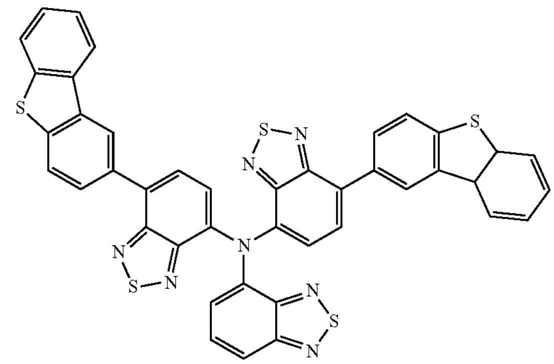
H57
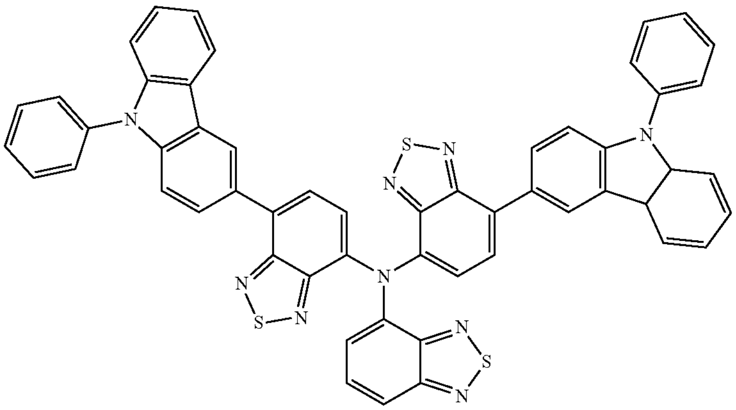

-continued
H58
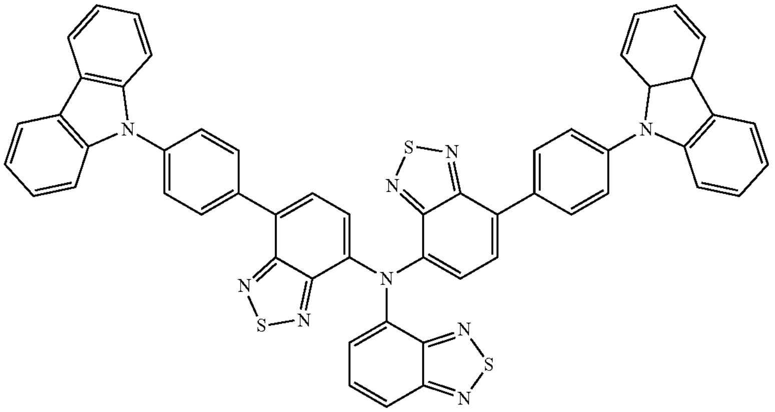
H59
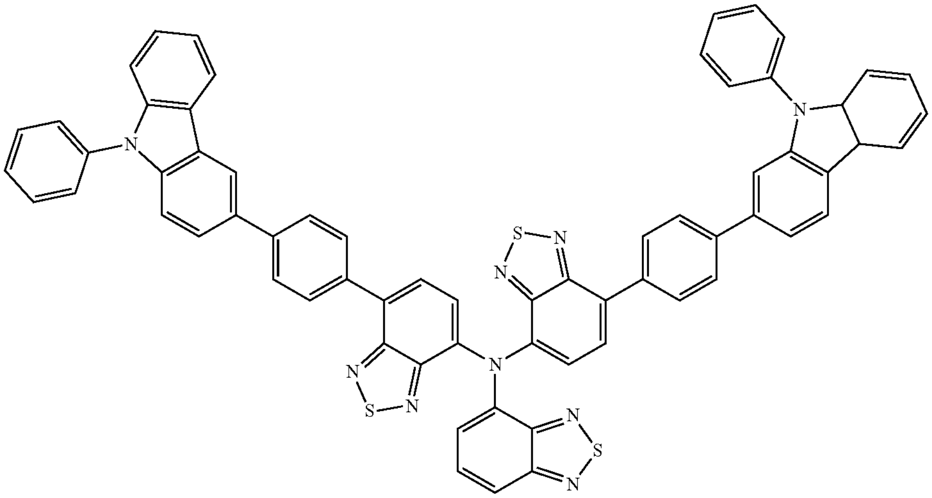
H60
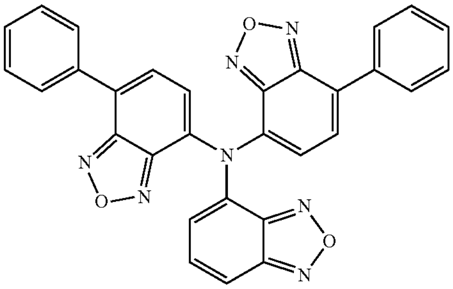
H61
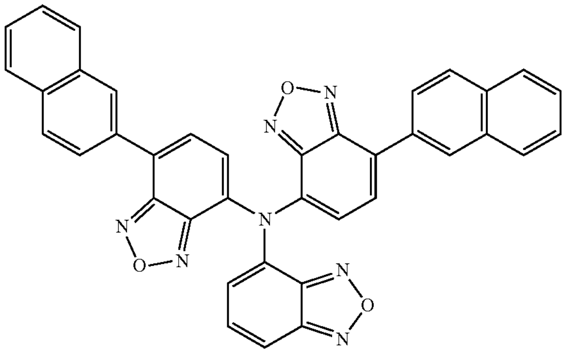

-continued
H62
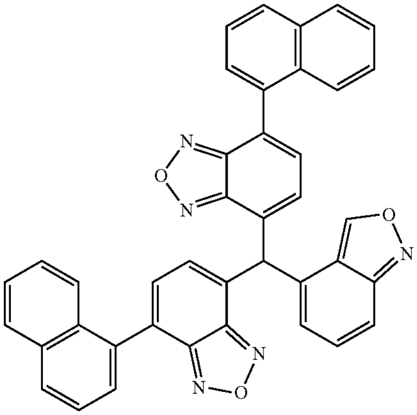
H63
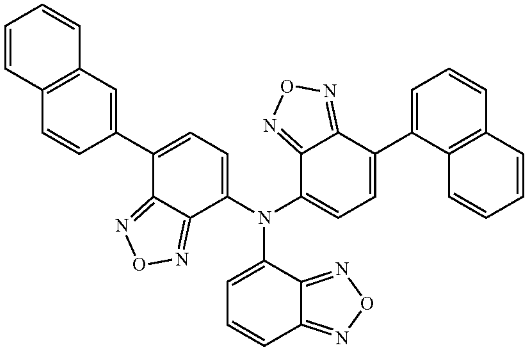
H64
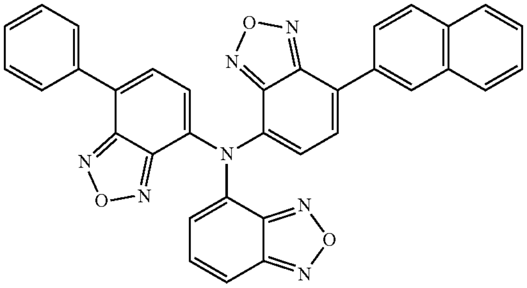
H65
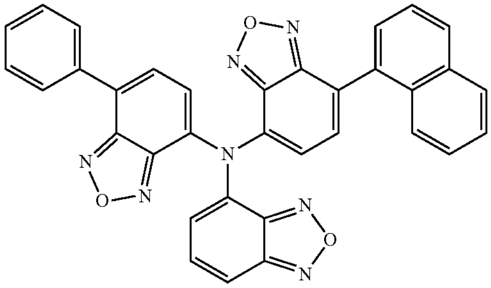
H66
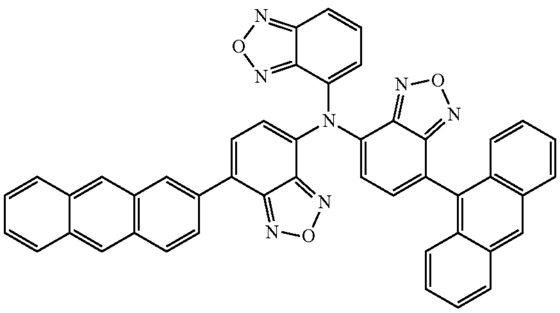
H67
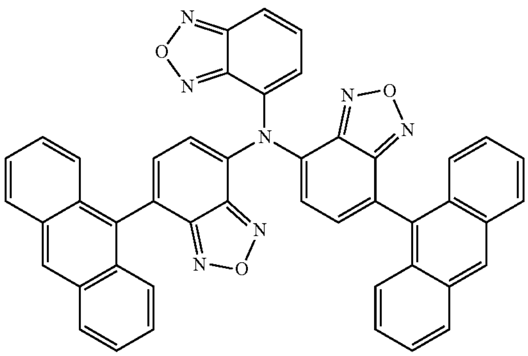
H68
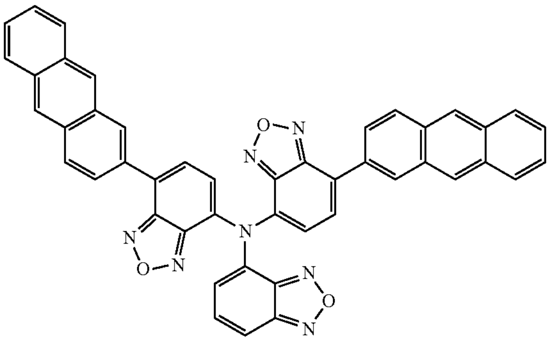
H69
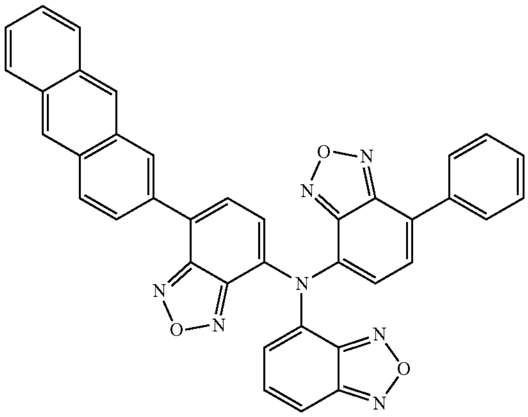

-continued
H70
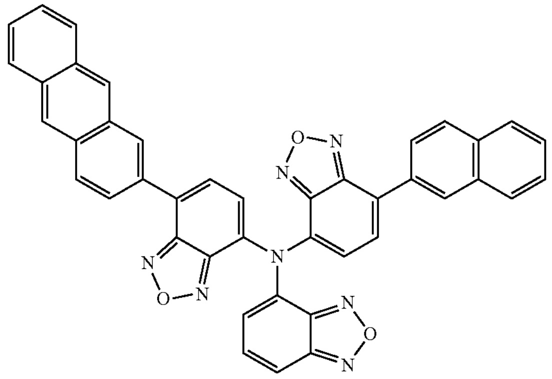
H71
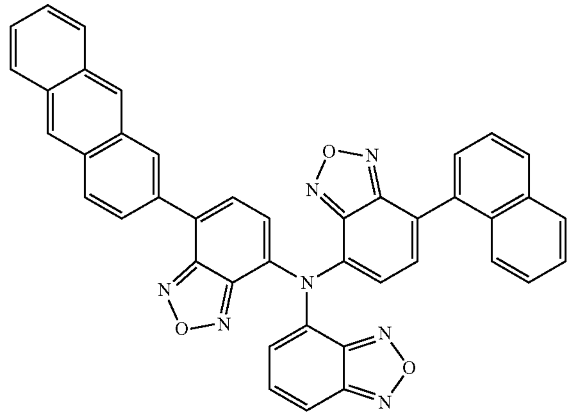
H72
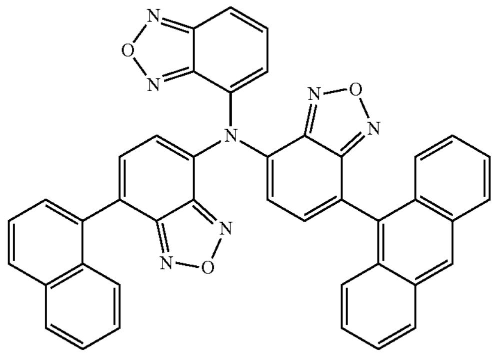
H73
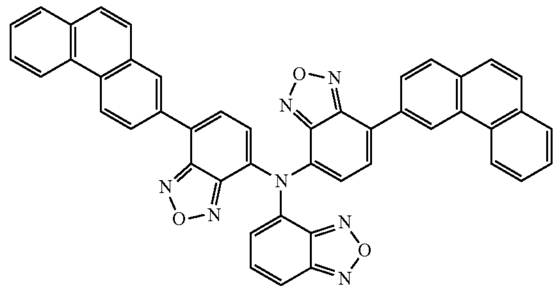
H74
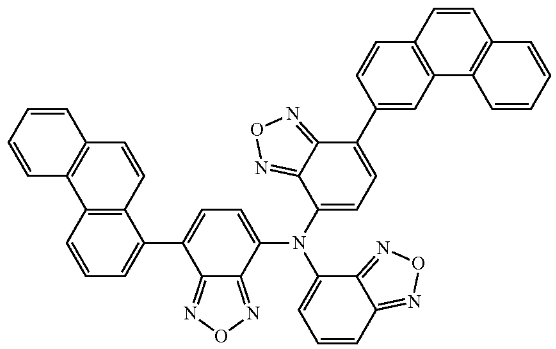
H75
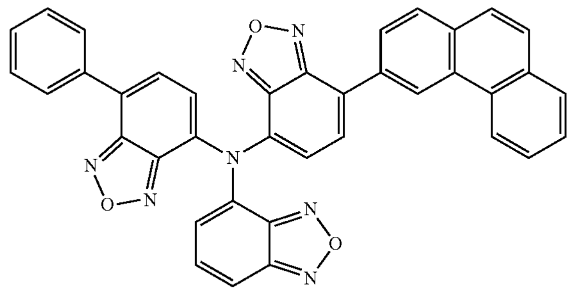
H76
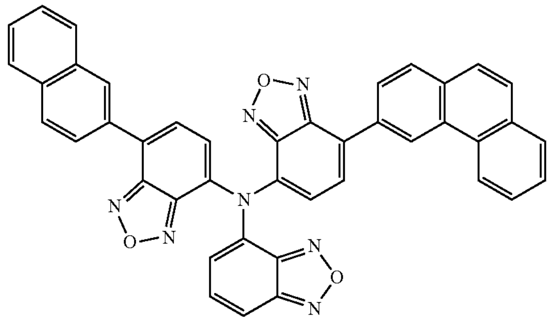
H77
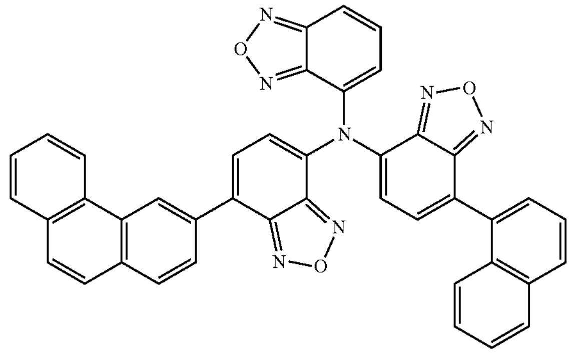

-continued
H78
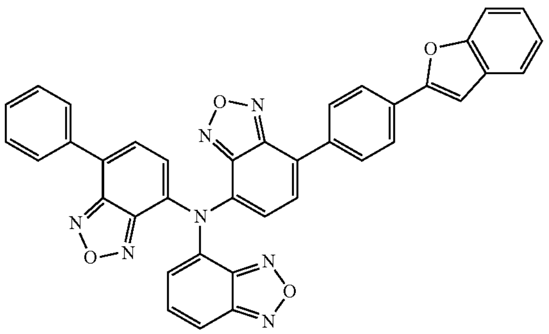
H79
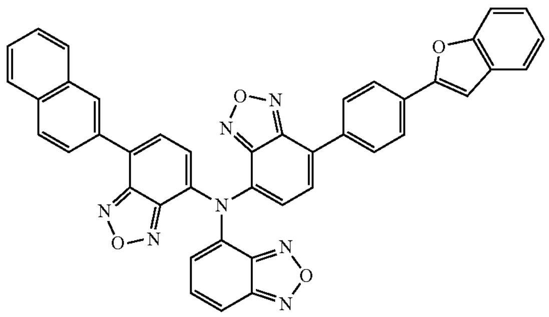
H80
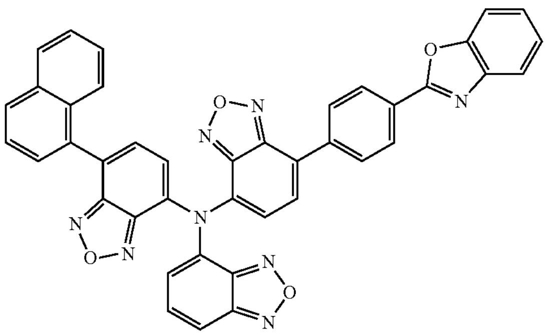
H81
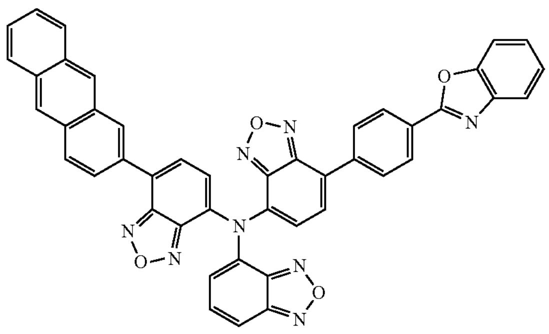
H82
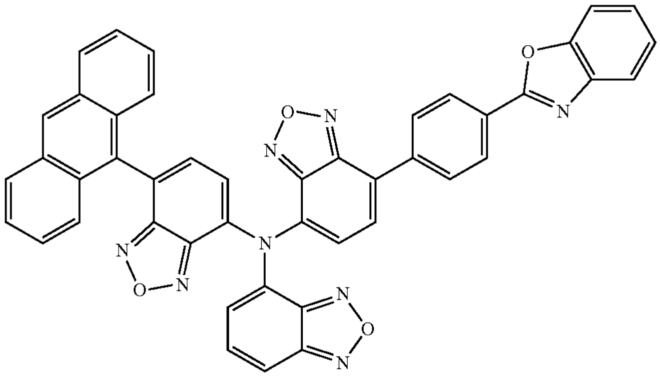
H83
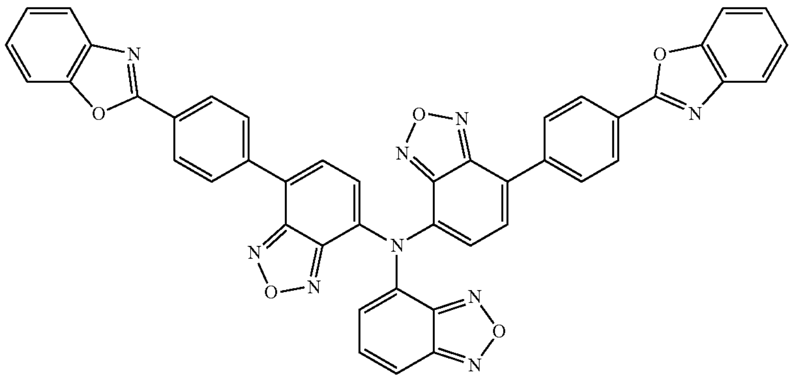

-continued
H84
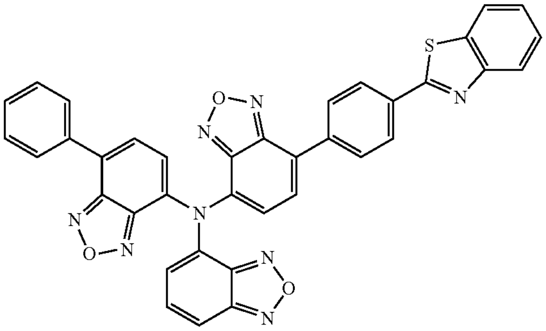
H85
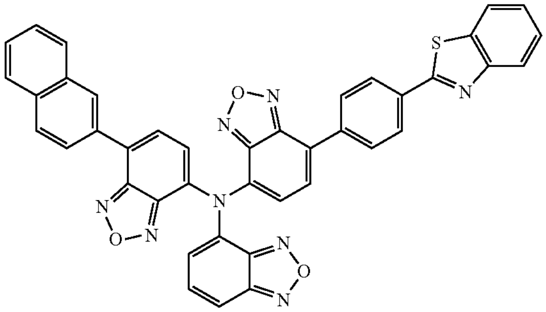
H86
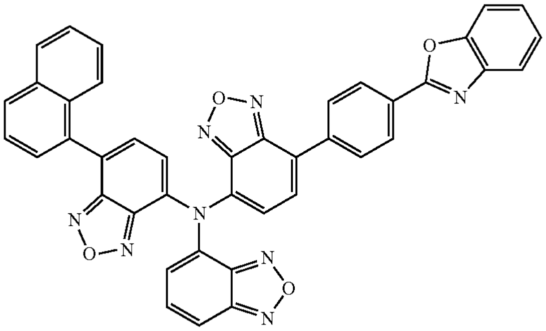
H87
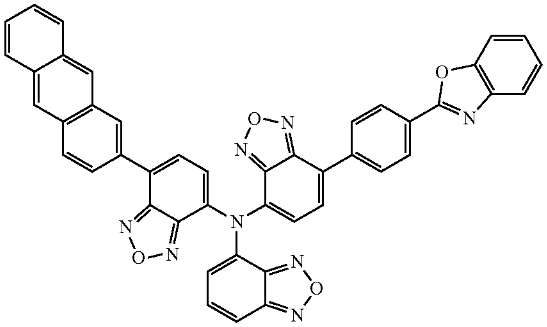
H88
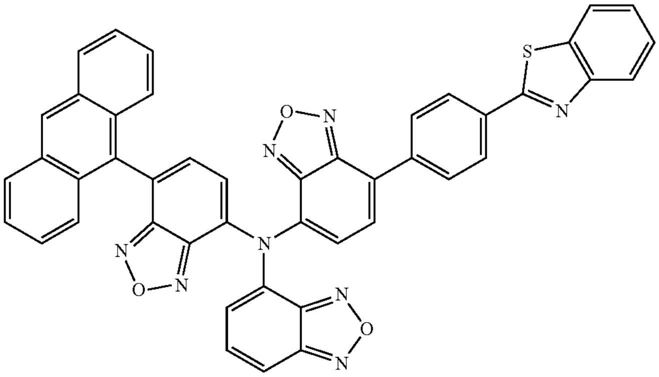
H89
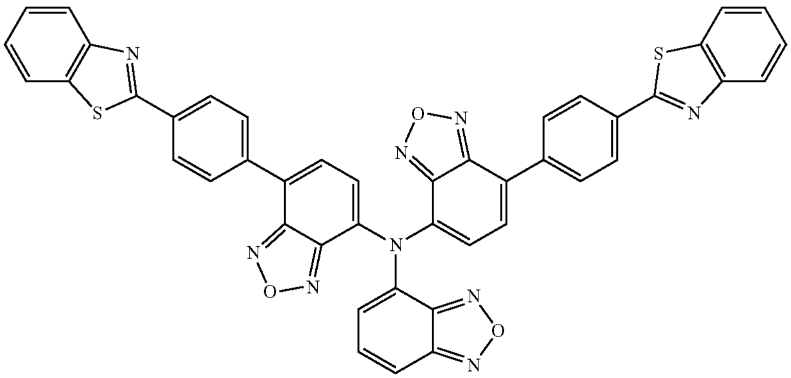

-continued
H90
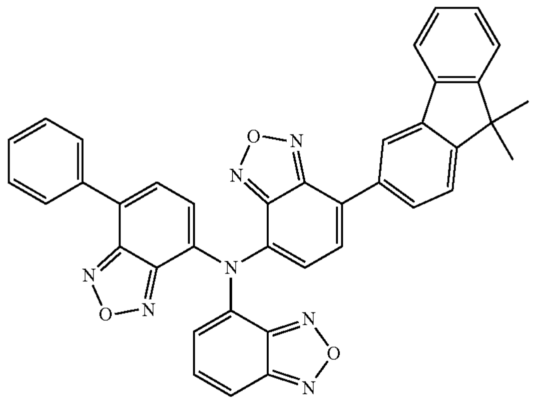
H91
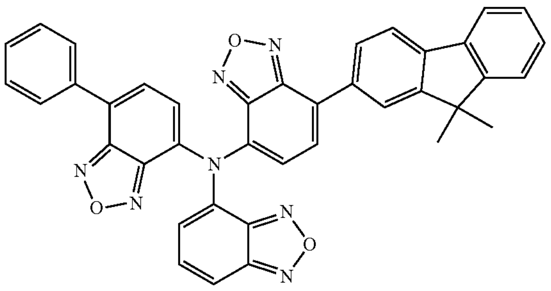
H92
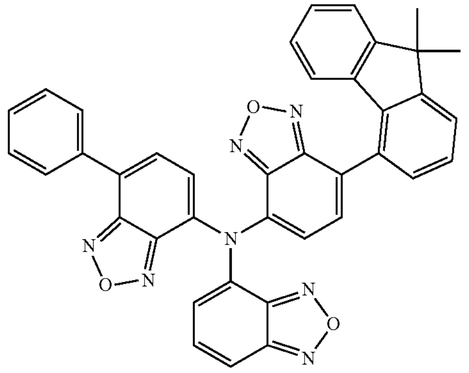
H93
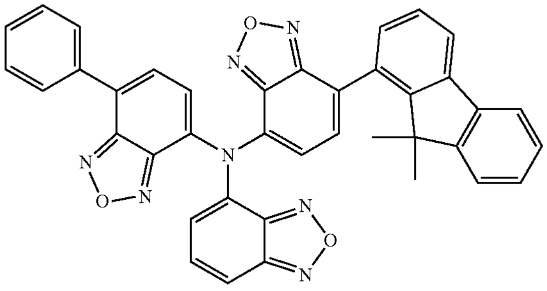
H94
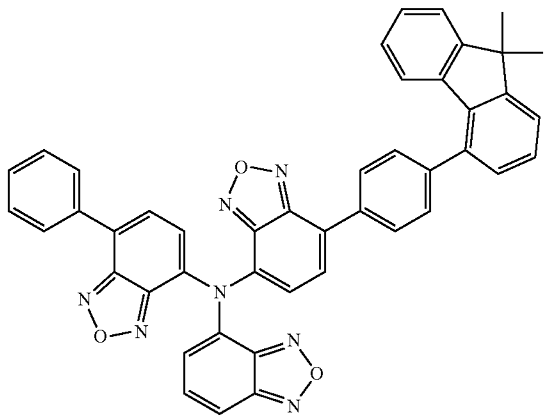
H95
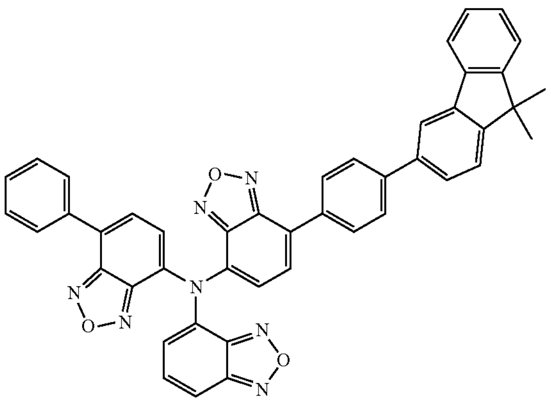
H96
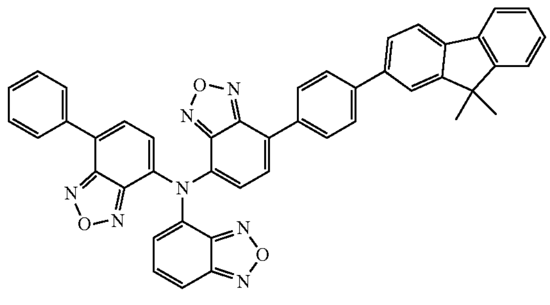
H97
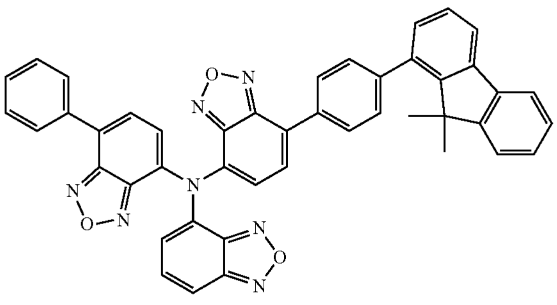

-continued
H98
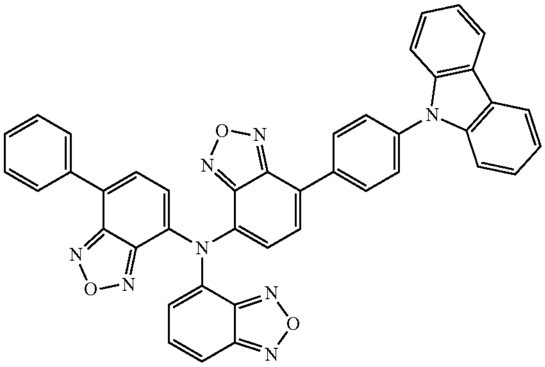
H99
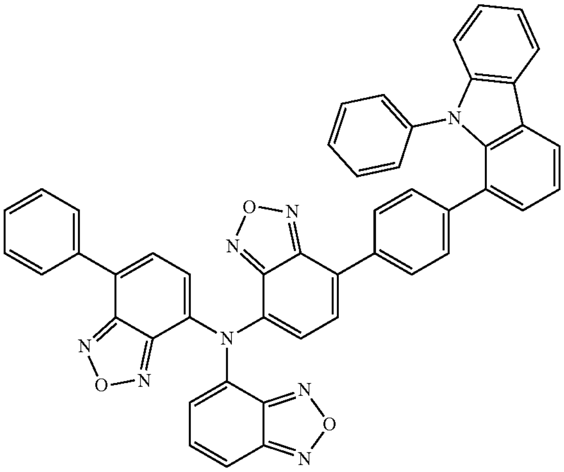
H100
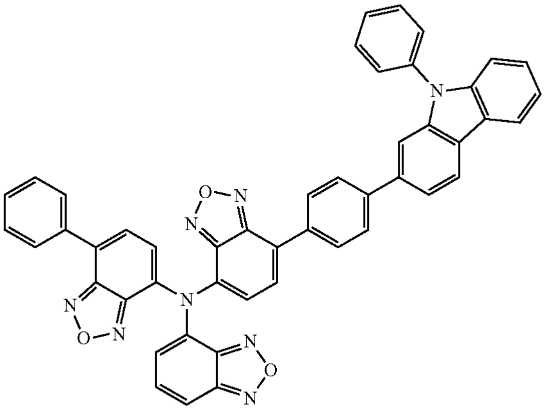
H101
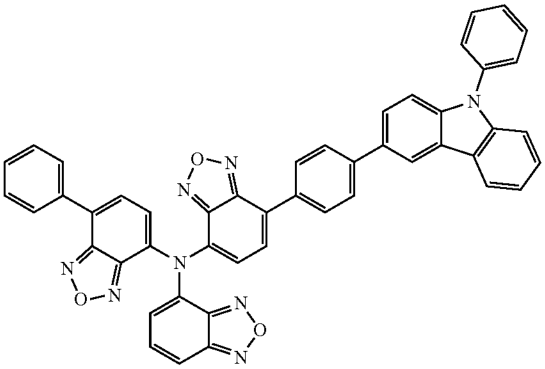
H102
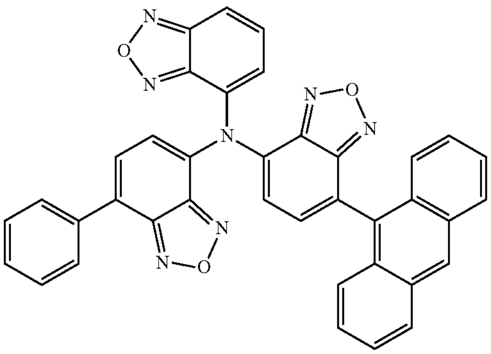
H103
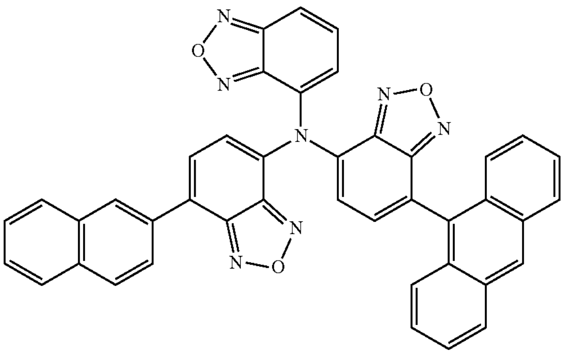

-continued
H104
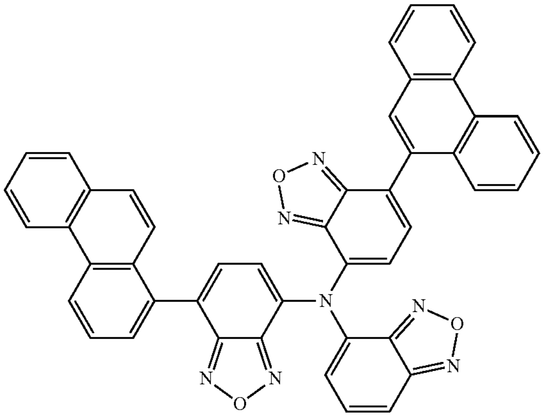
H105
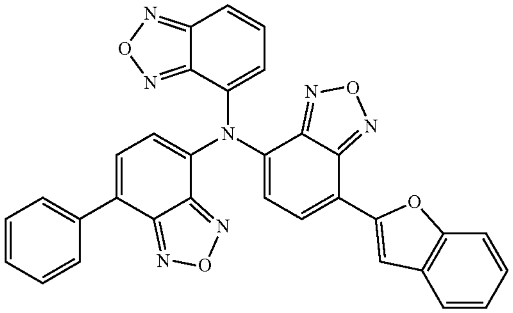
H106
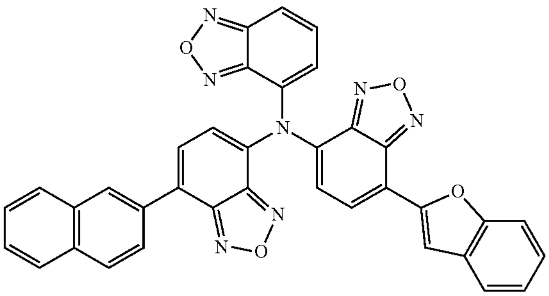
H107
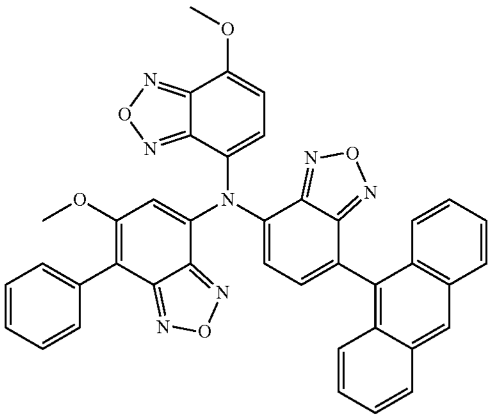
H108
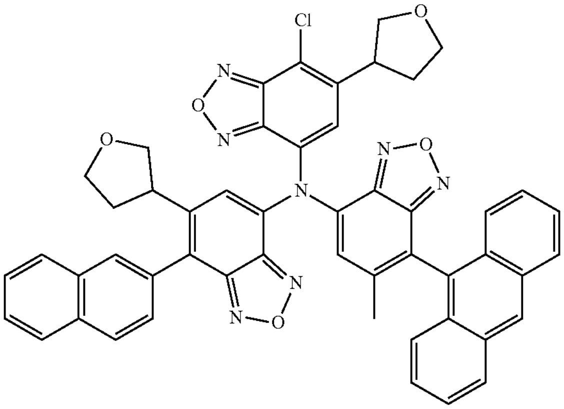
H109
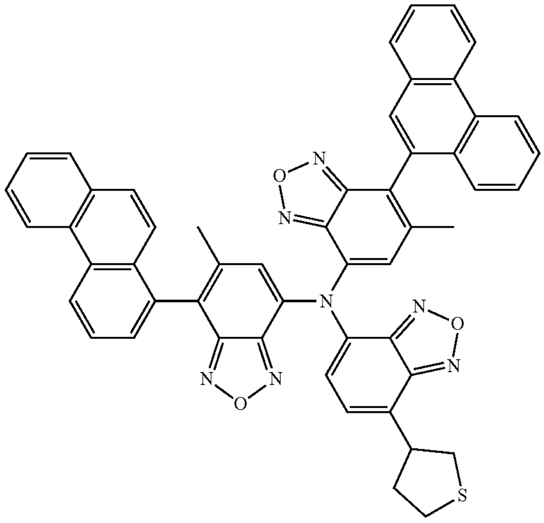

-continued
H110
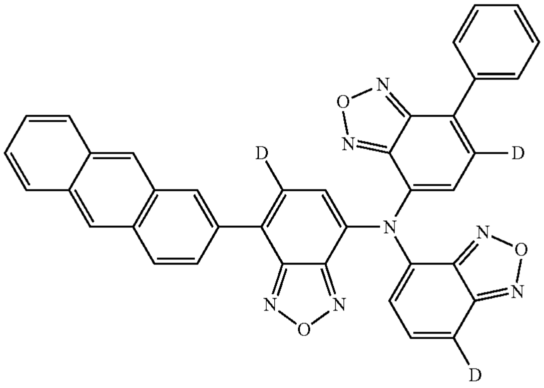
H111
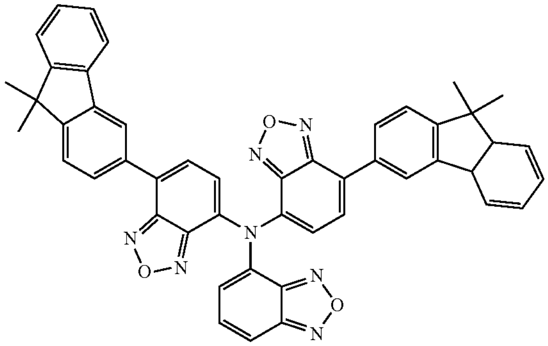
H112
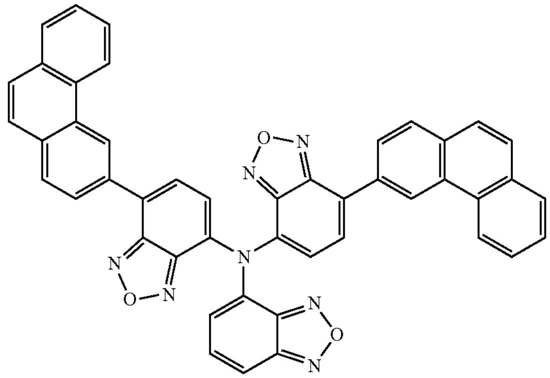
H113
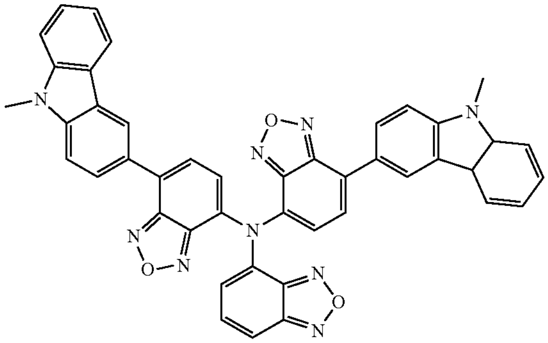
H114
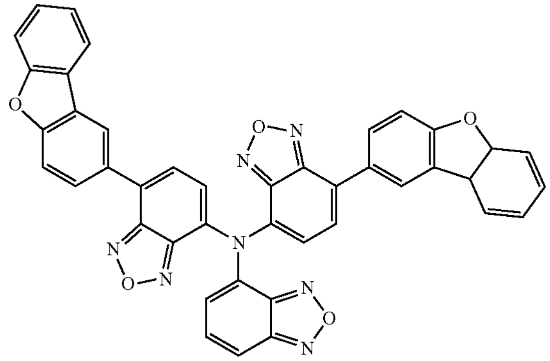
H115
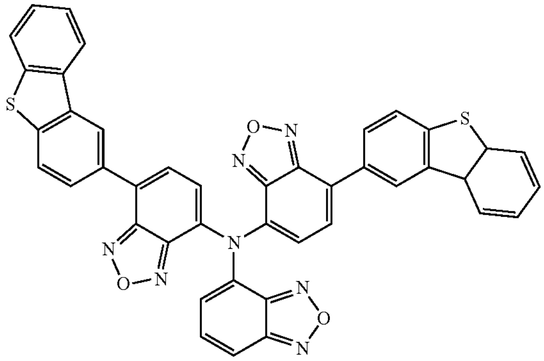
H116
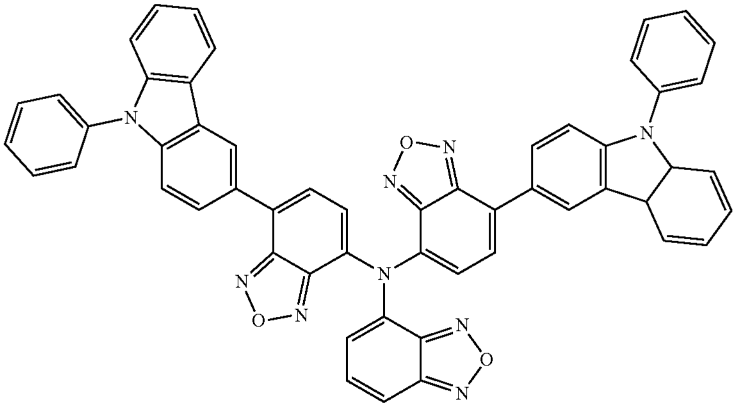

-continued

H117

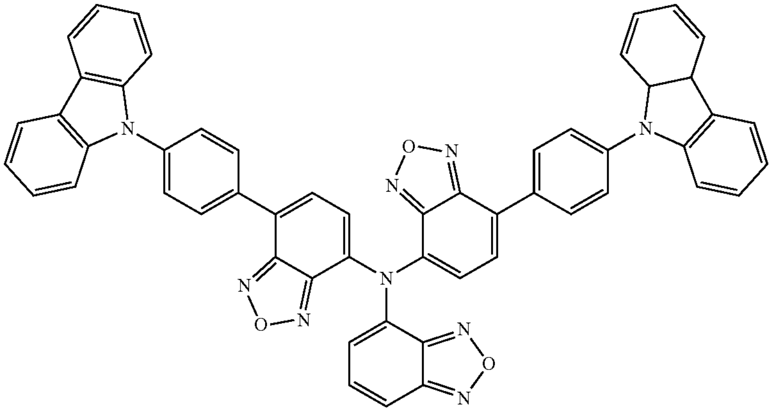

H118

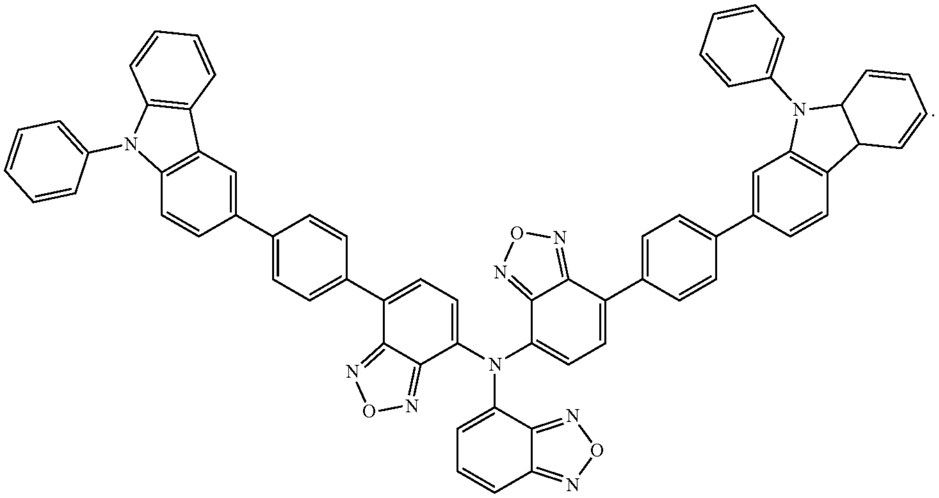

Embodiment 11. The compound according to any one of Embodiments 1 to 10, wherein $X_1$, $X_2$, and $X_3$ all represent $N(Y_1)$, and $Y_1$ represents hydrogen, deuterium, tritium or the following group unsubstituted or substituted by $R^a$:

methyl, ethyl, propyl, butyl, methoxy, ethoxy, propoxy, cyclopropyl, cyclobutyl, cyclopentyl, cyclohexyl, tetrahydrofuranyl, tetrahydrothienyl, or phenyl.

Embodiment 12. The compound according to any one of Embodiments 1 to 11, wherein the compound is selected from any of the following,

H119

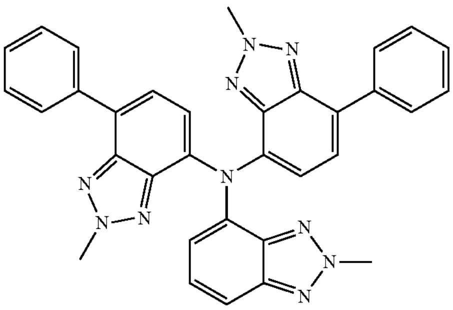

H120

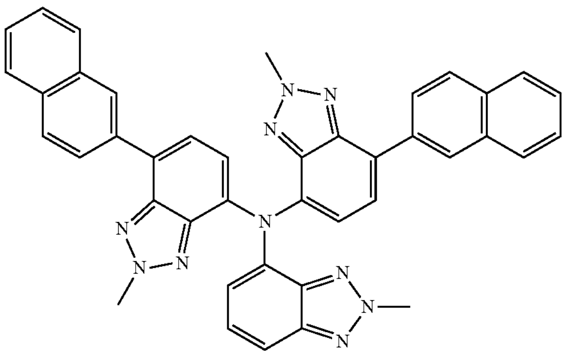

-continued
H121
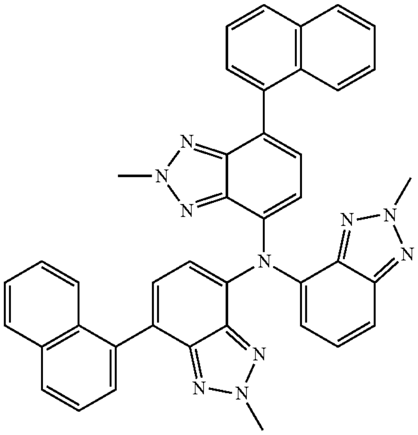
H122
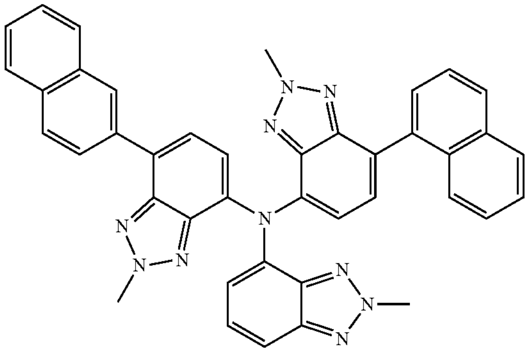
H123
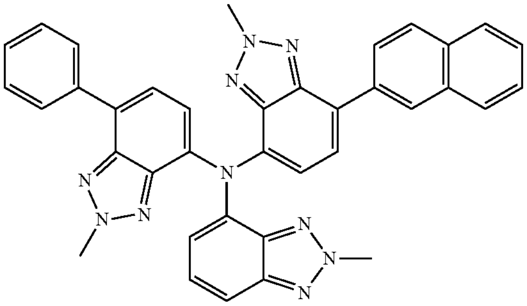
H124
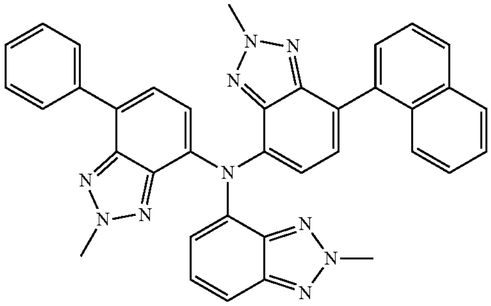
H125
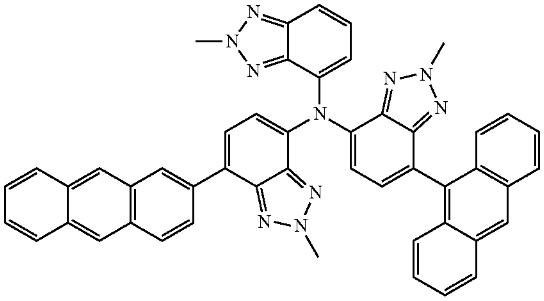
H126
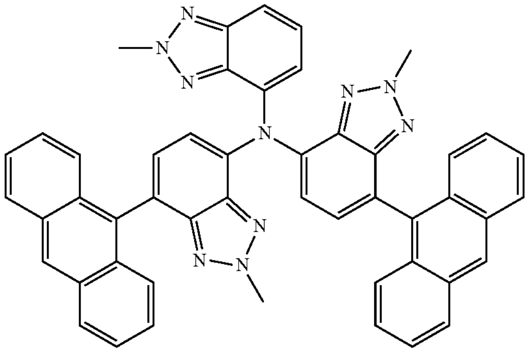
H127
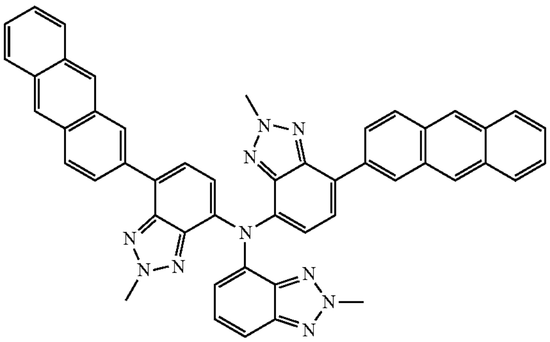
H128
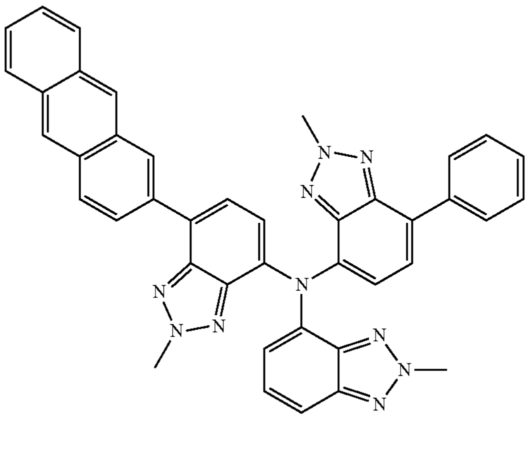

-continued
H129
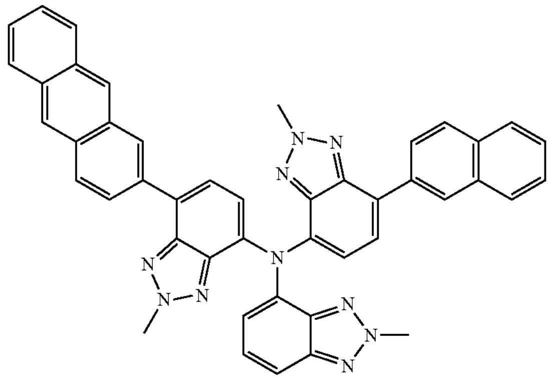
H130
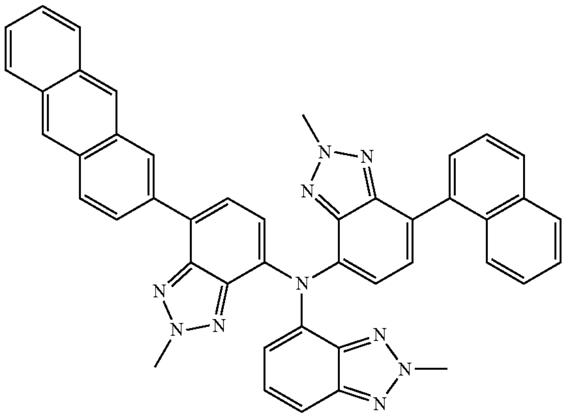
H131
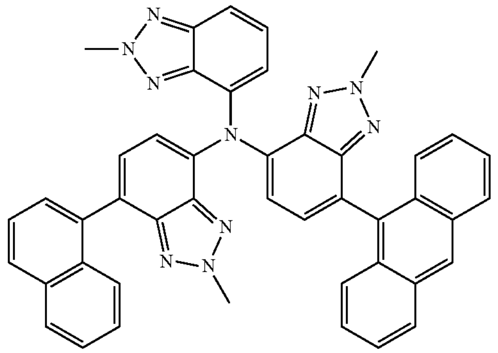
H132
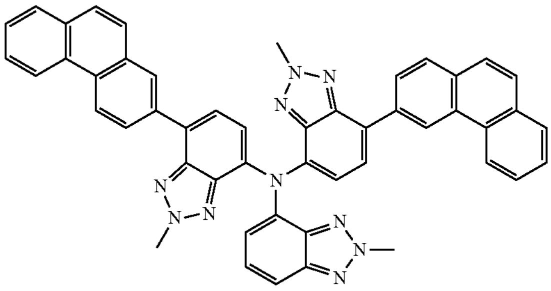
H133
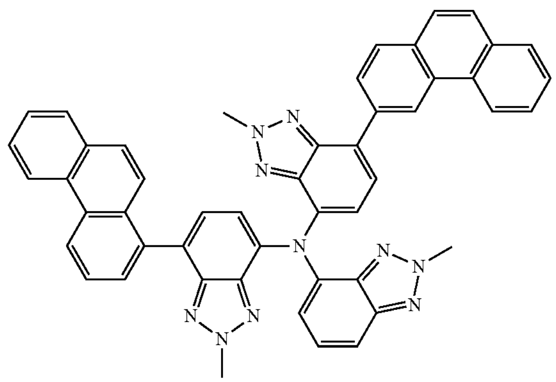
H134
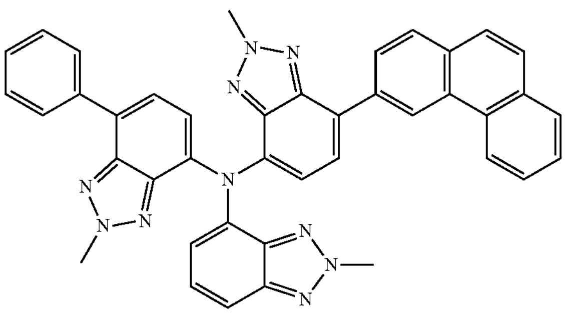
H135
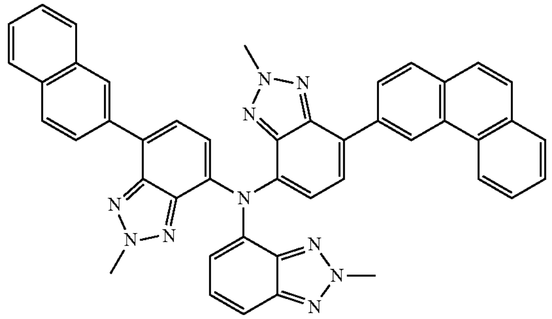
H136
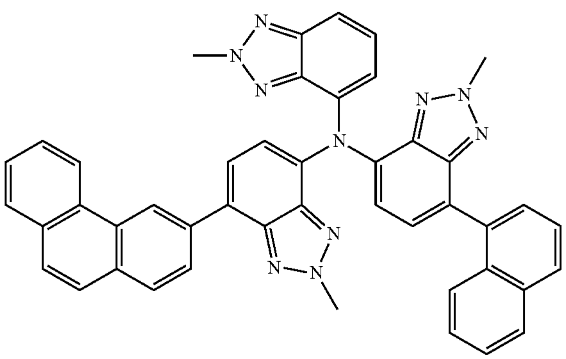

-continued
H137
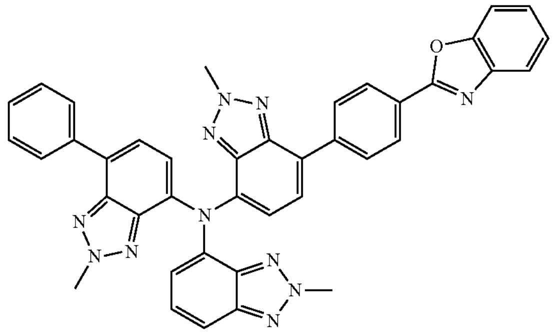
H138
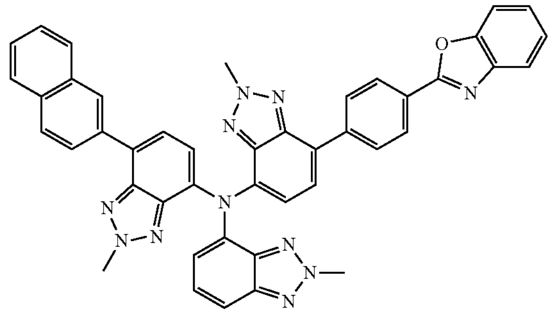
H139
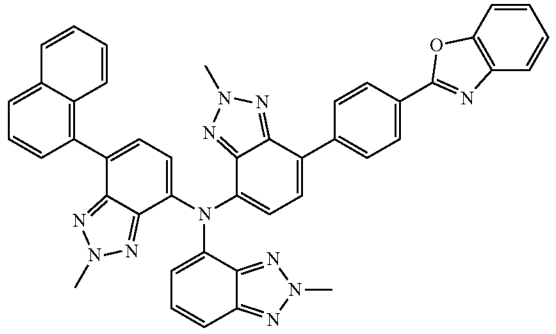
H140
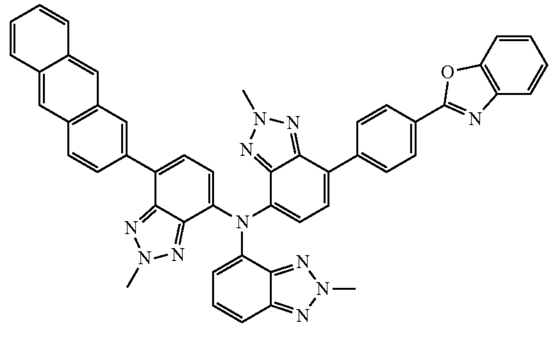
H141
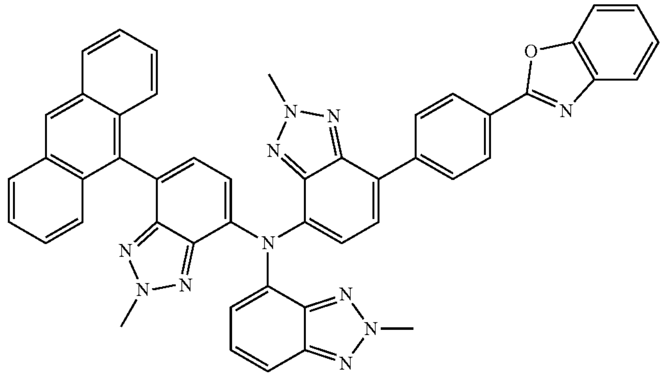
H142
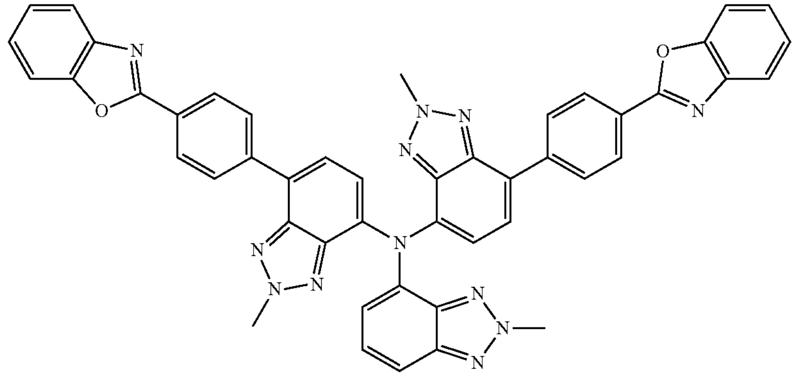

-continued
H143
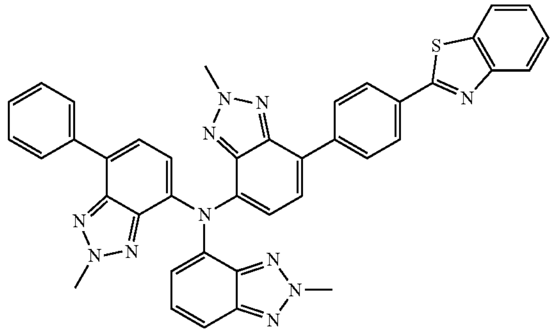
H144
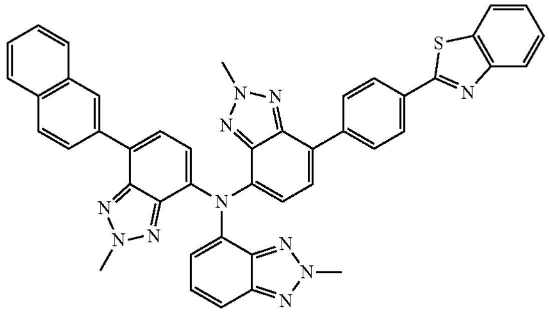
H145
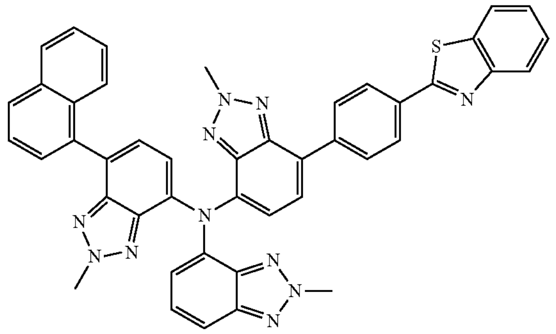
H146
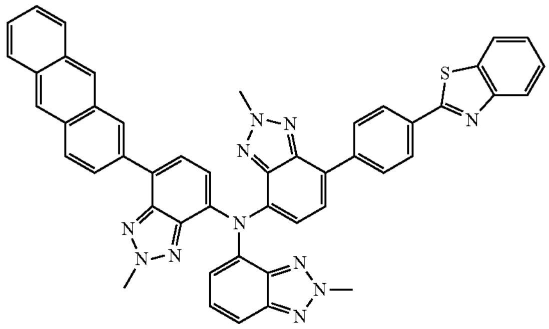
H147
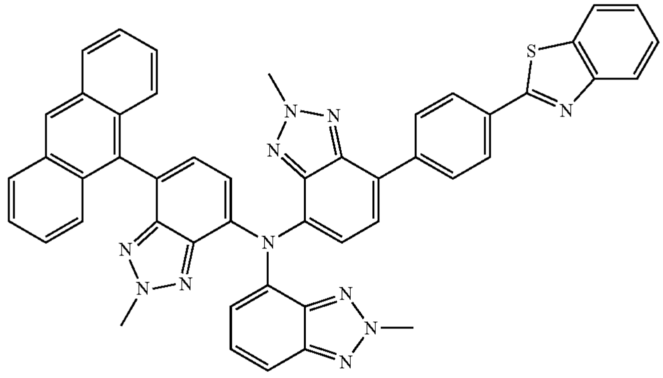
H148
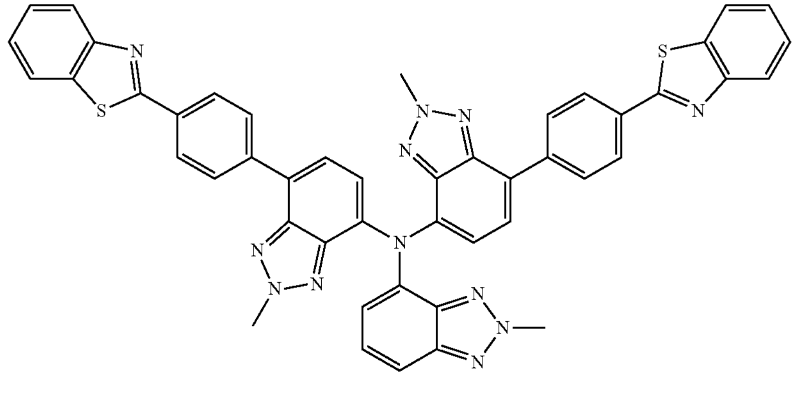

-continued
H149
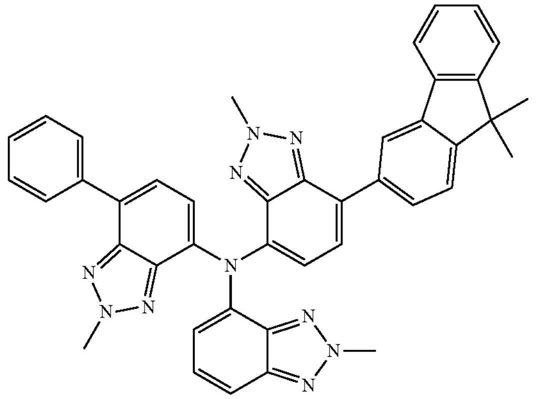
H150
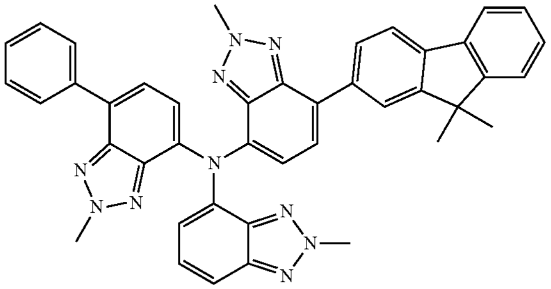
H151
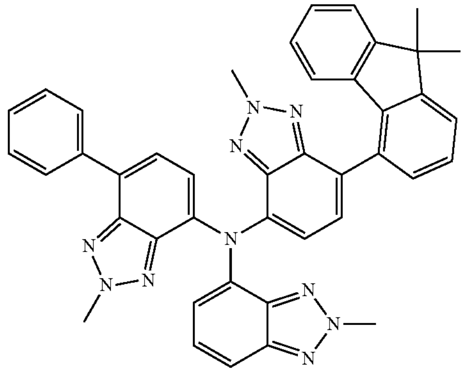
H152
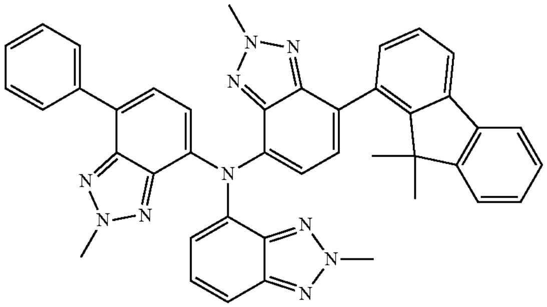
H153
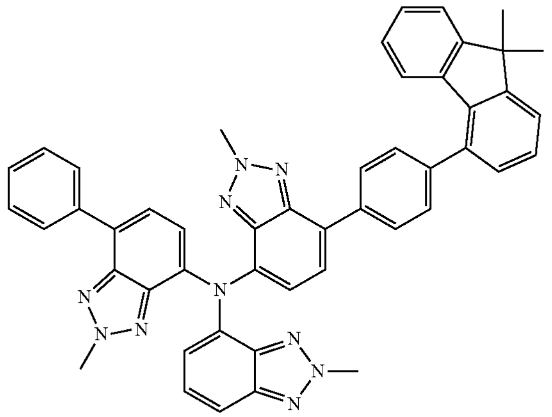
H154
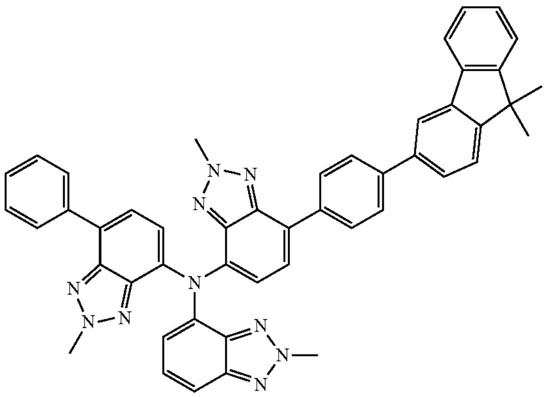
H155
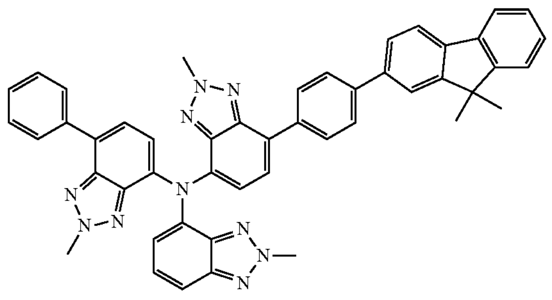
H156
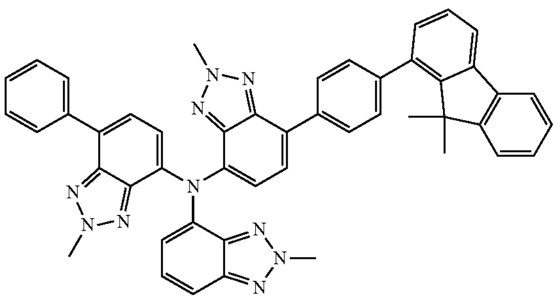

-continued
H157
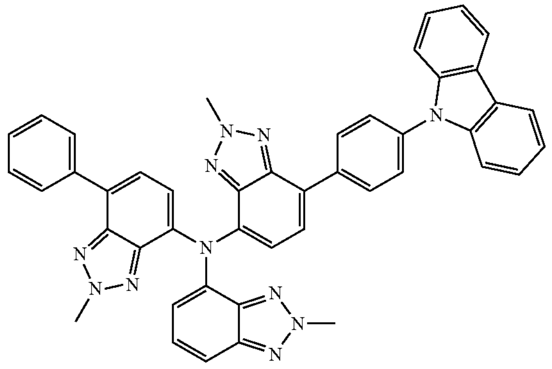
H158
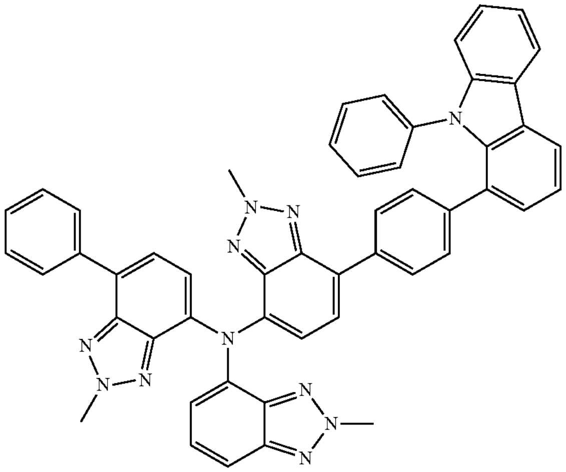
H159
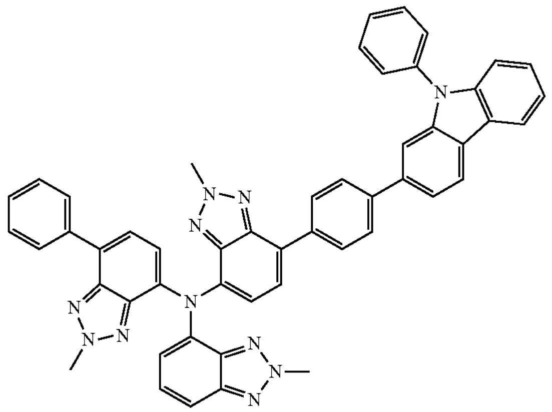
H160
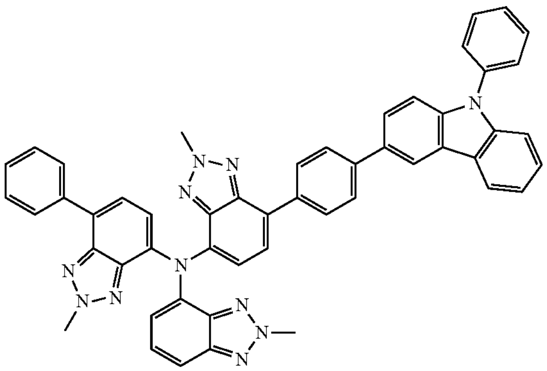
H161
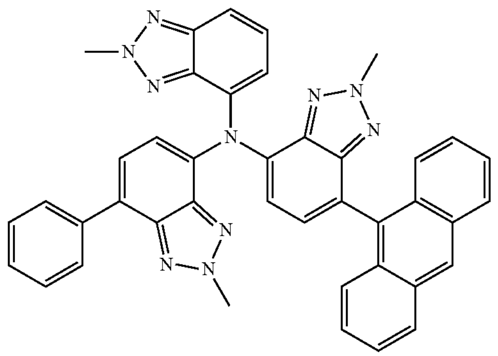
H162
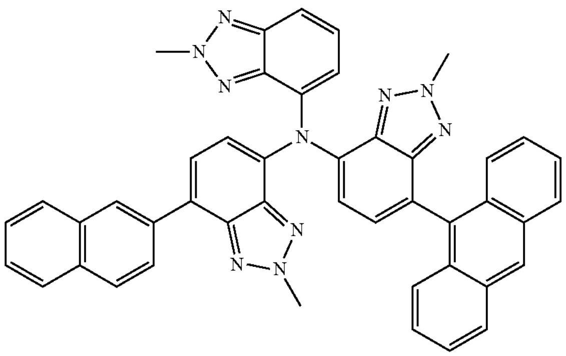

-continued
H163
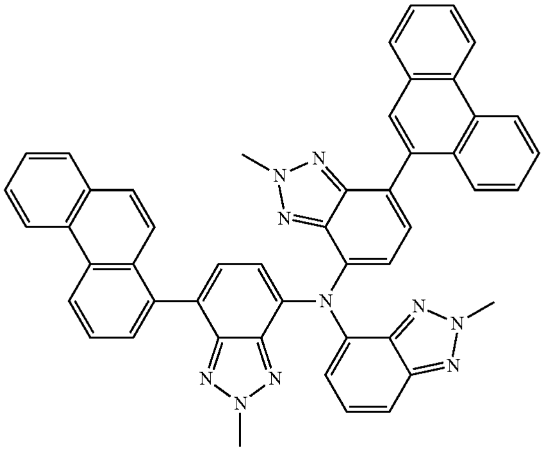
H164
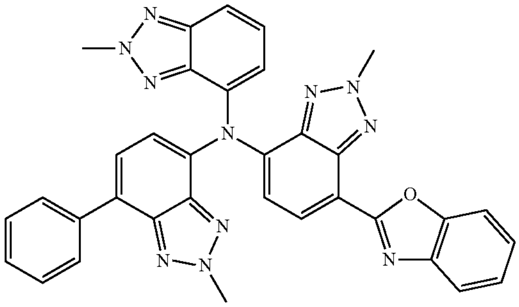
H165
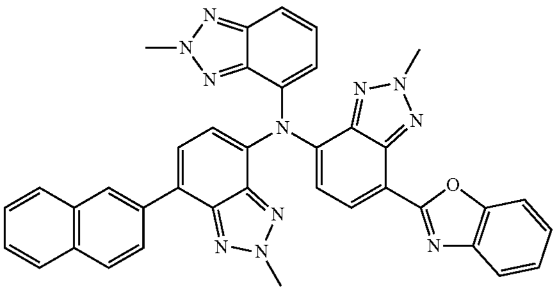
H166
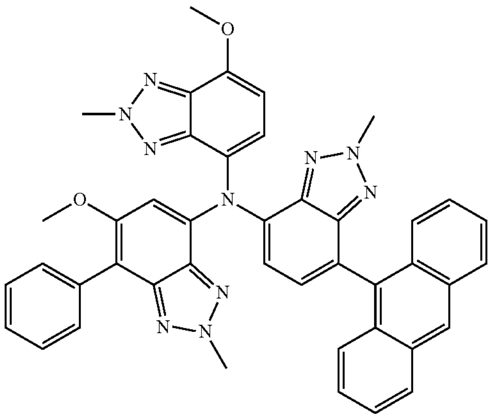
H167
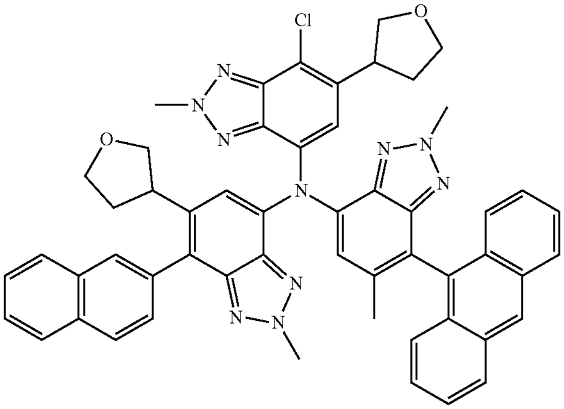
H168
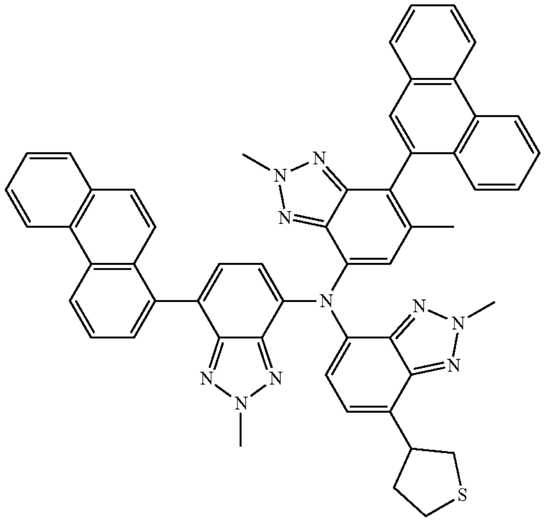

-continued
H169
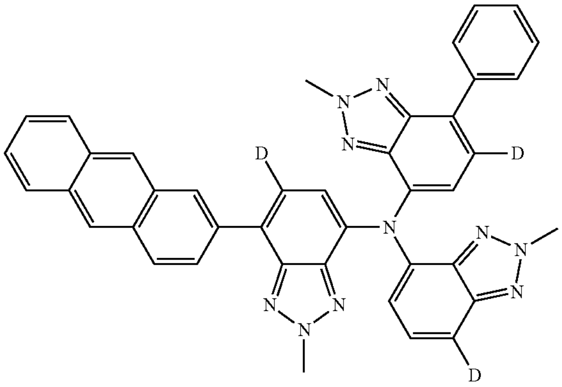
H170
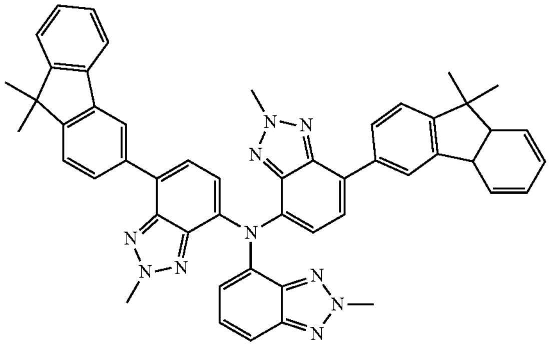
H171
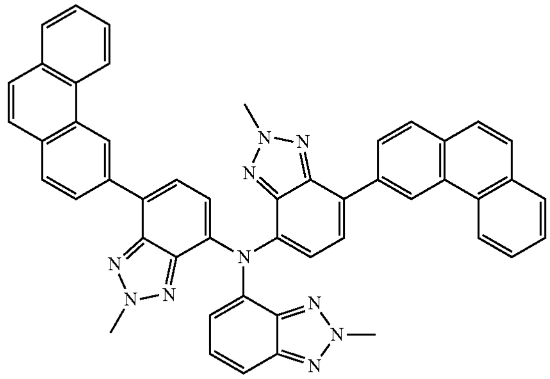
H172
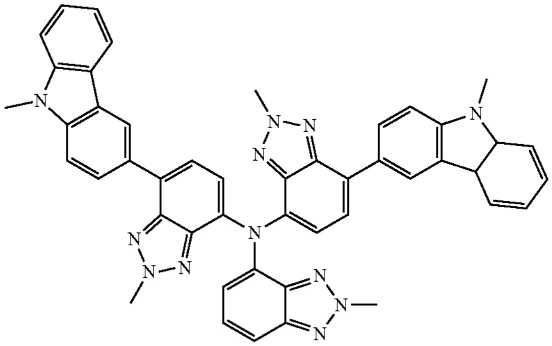
H173
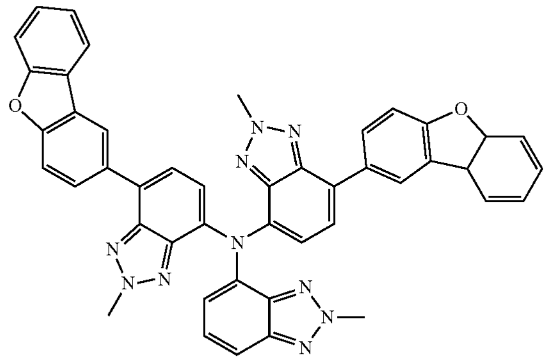
H174
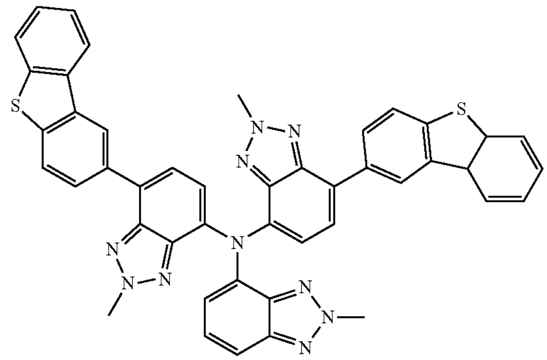
H175
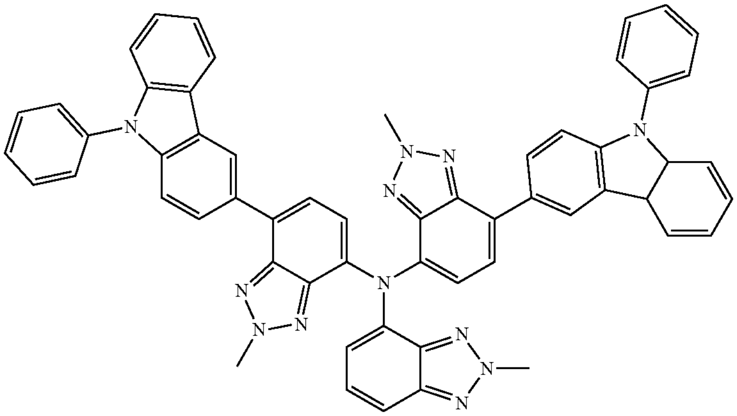

-continued

H176

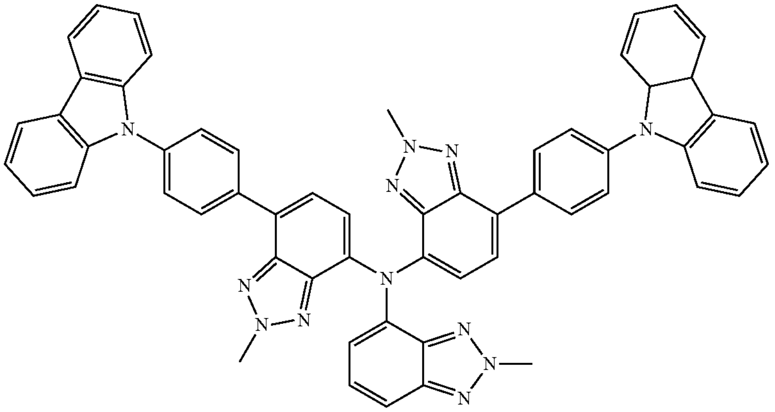

H177

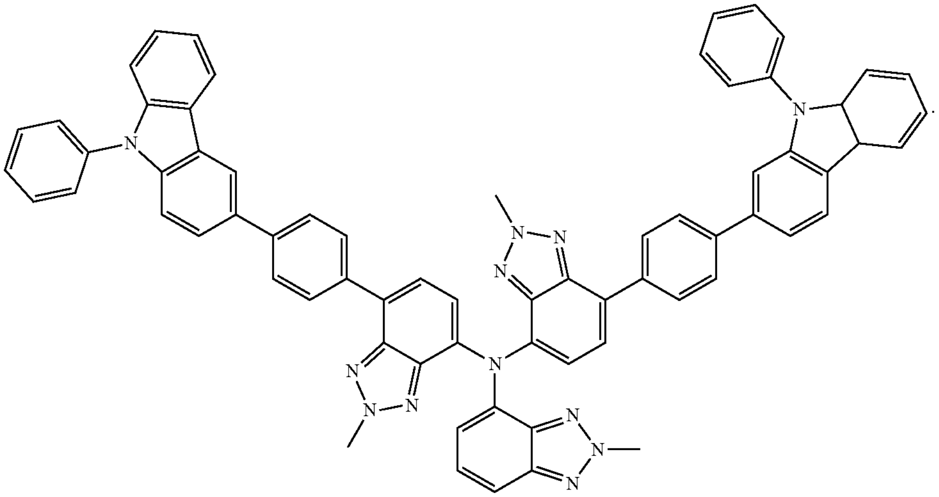

Embodiment 13. The compound according to any one of Embodiments 1 to 12, wherein $X_1$, $X_2$, and $X_3$ all represent $C(Y_2)_2$ or $Si(Y_3)_2$, and $Y_2$ and $Y_3$ each independently represent hydrogen, deuterium, tritium or the following group unsubstituted or substituted by $R^a$:

methyl, ethyl, propyl, butyl, methoxy, ethoxy, propoxy, cyclopropyl, cyclobutyl, cyclopentyl, cyclohexyl, tetrahydrofuranyl, tetrahydrothienyl, or phenyl.

Embodiment 14. The compound according to any one of Embodiments 1 to 13, wherein the compound is selected from any of the following,

H178

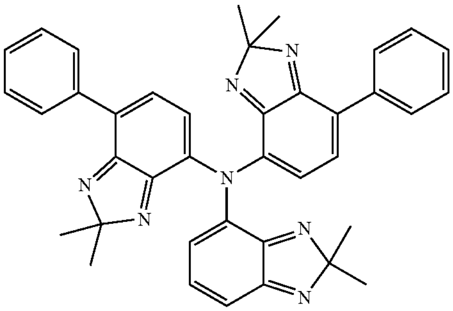

H179

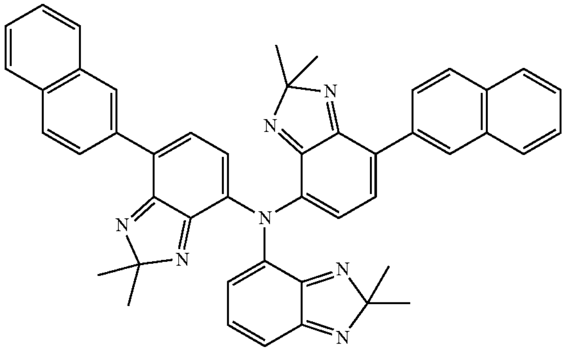

-continued
H180
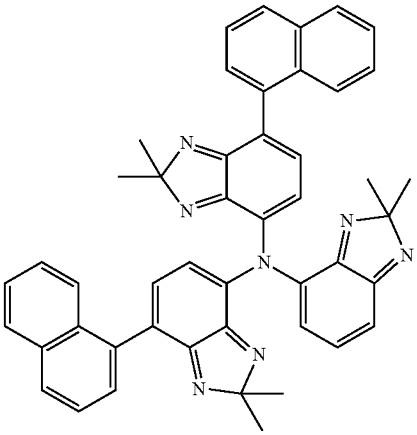
H181
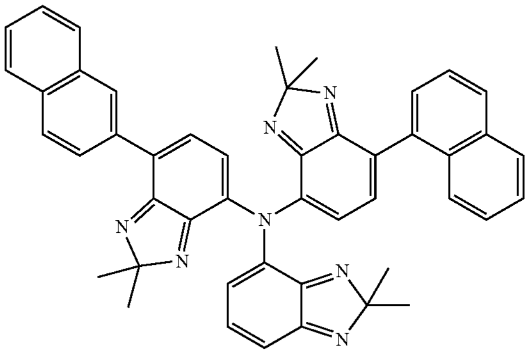
H182
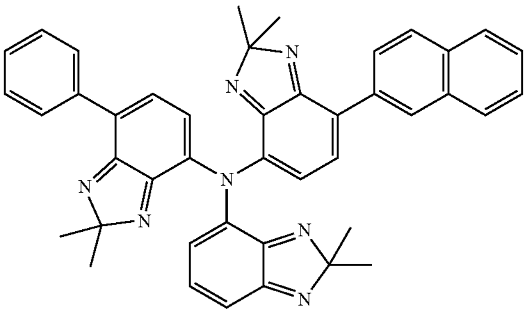
H183
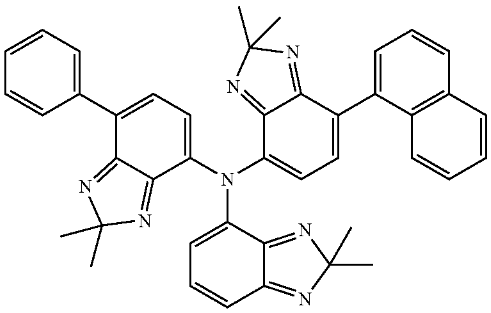
H184
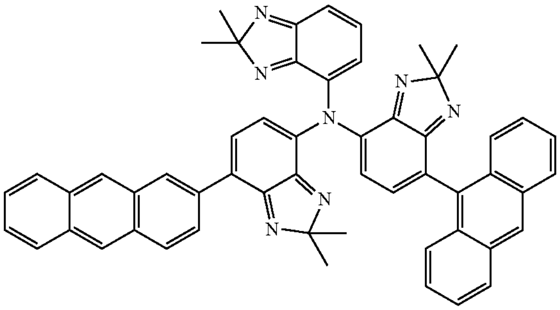
H185
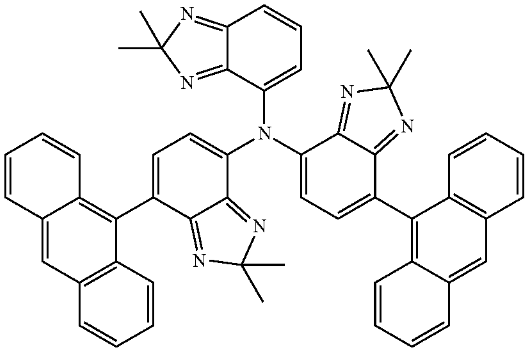
H186
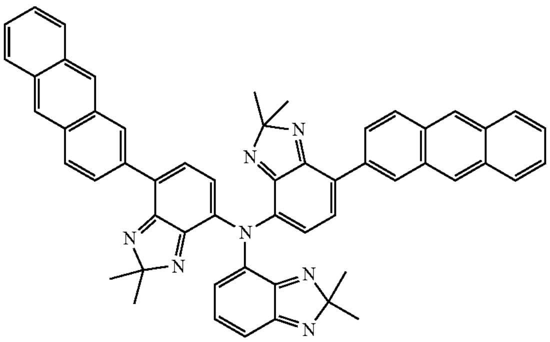
H187
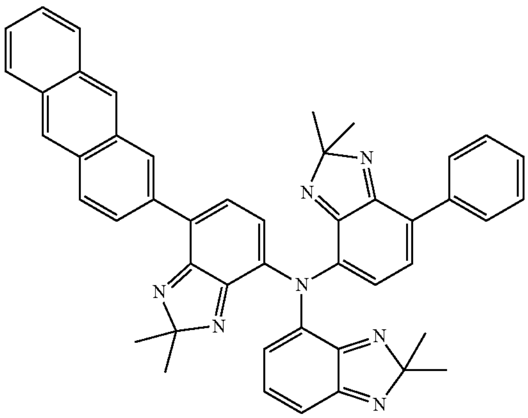

-continued
H188
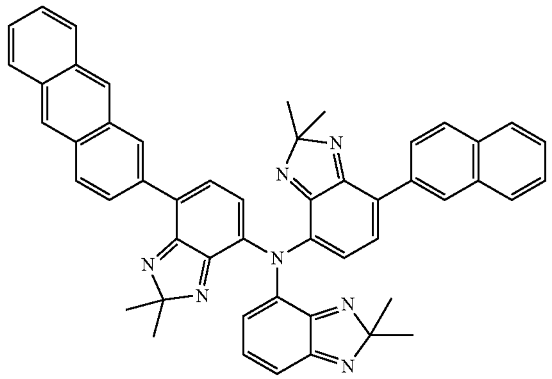
H189
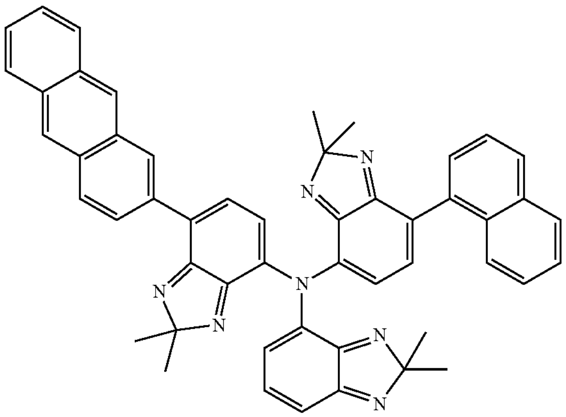
H190
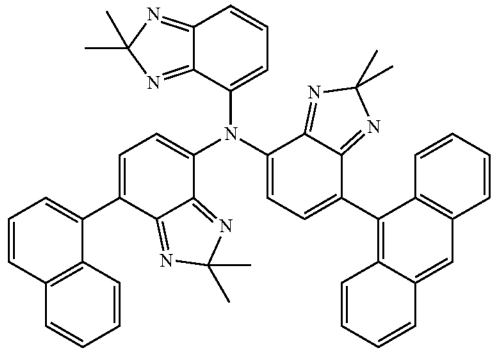
H191
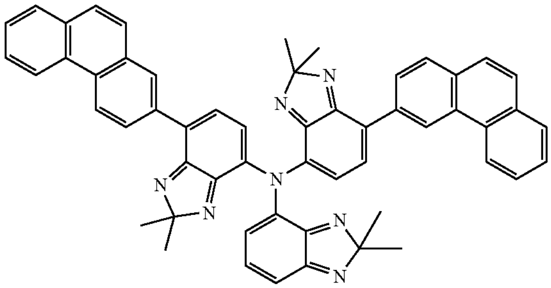
H192
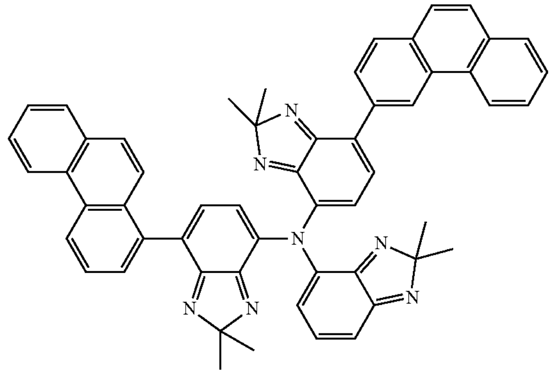
H193
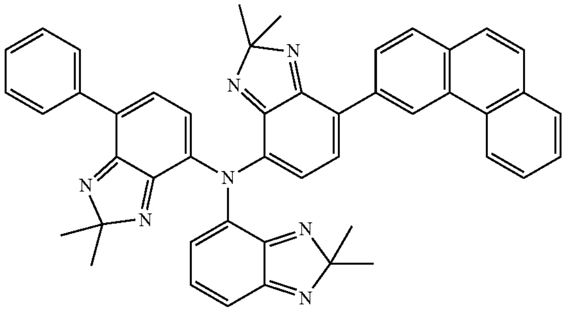
H194
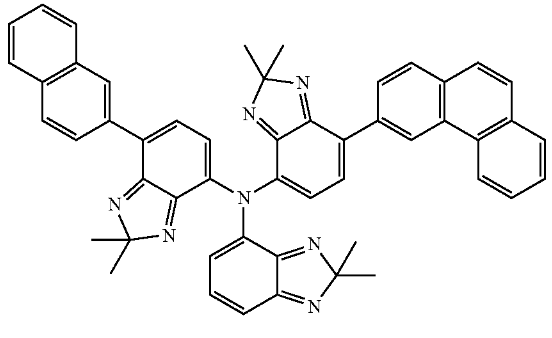
H195
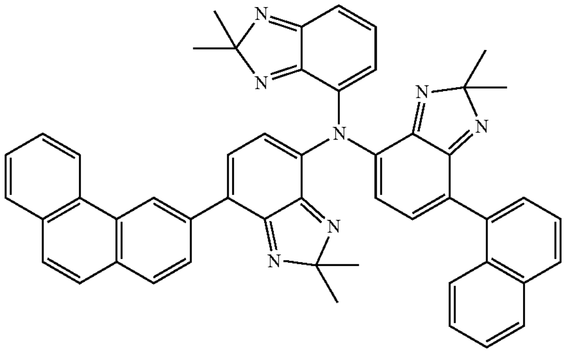

-continued
H196
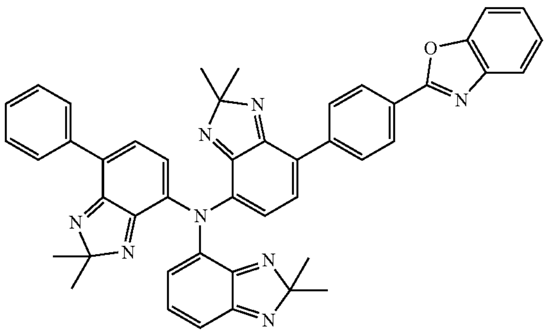
H197
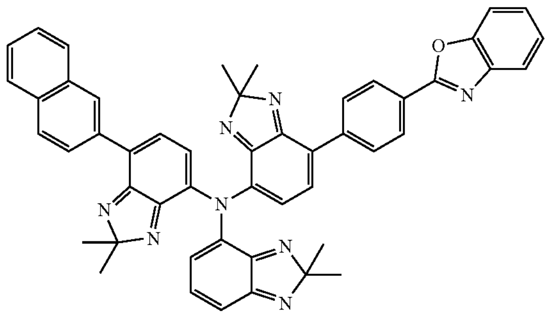
H198
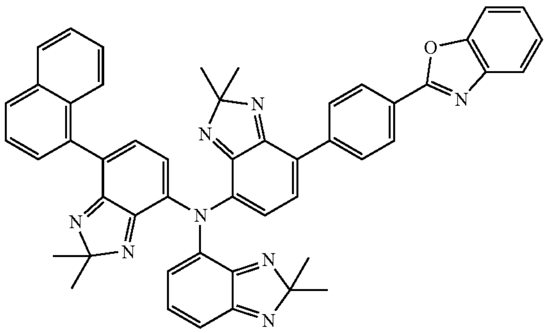
H199
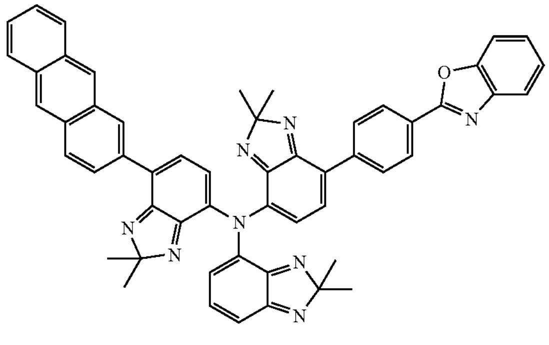
H200
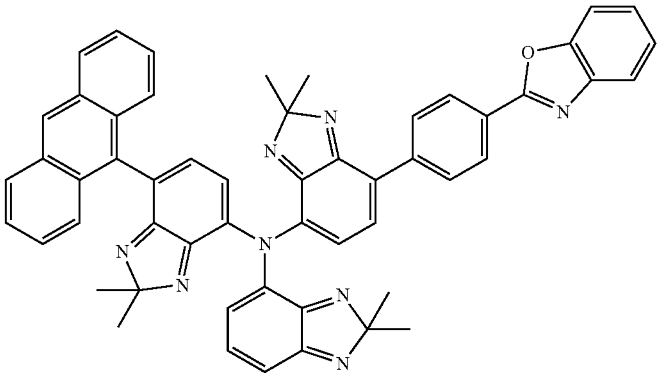
H201
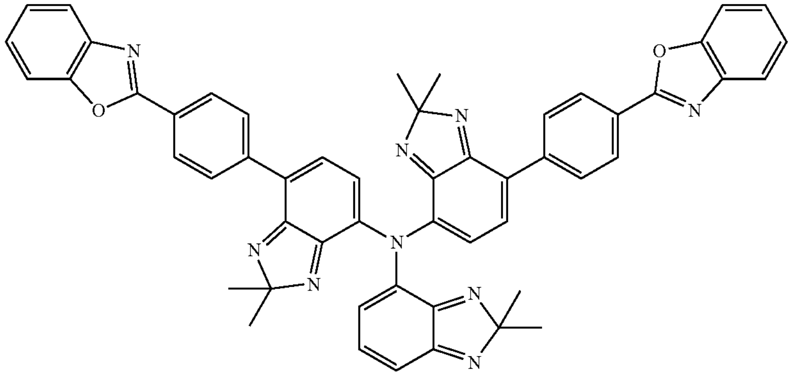

-continued
H202
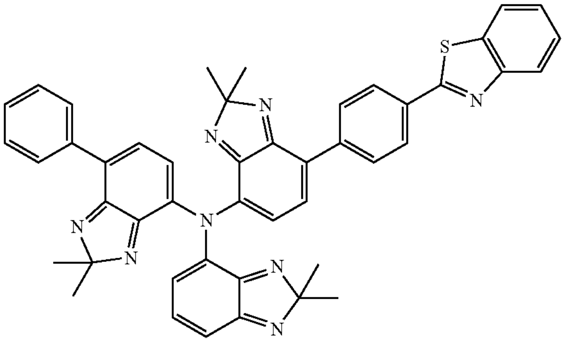
H203
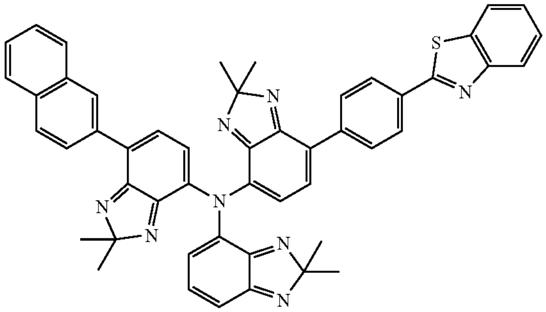
H204
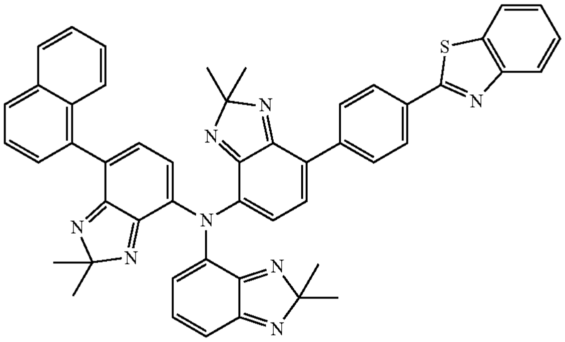
H205
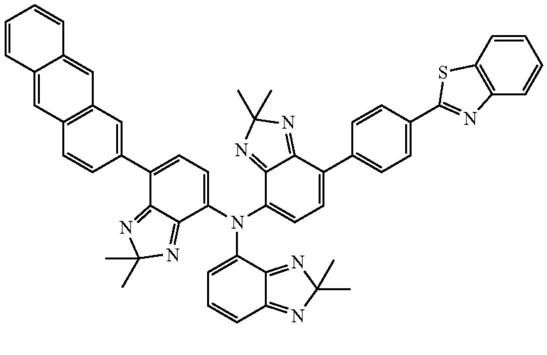
H206
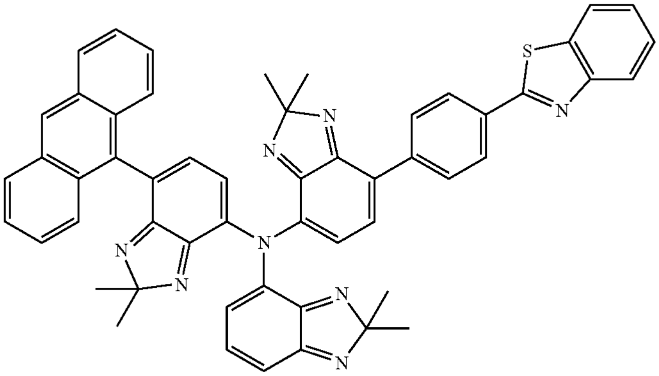
H207
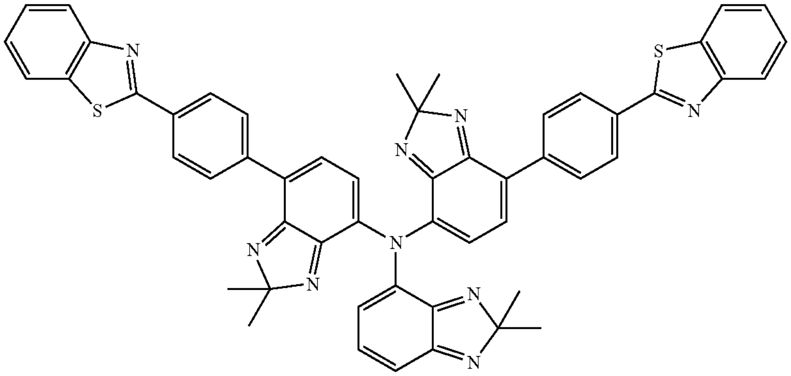

-continued
H208
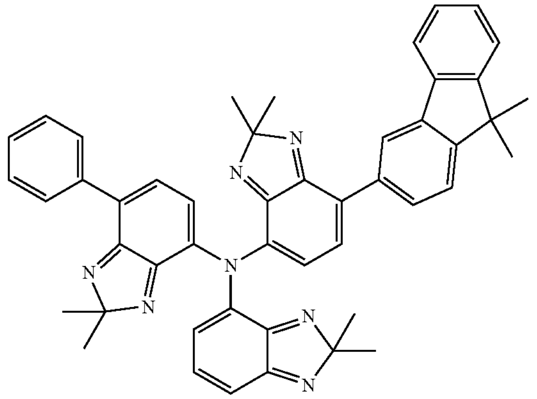
H209
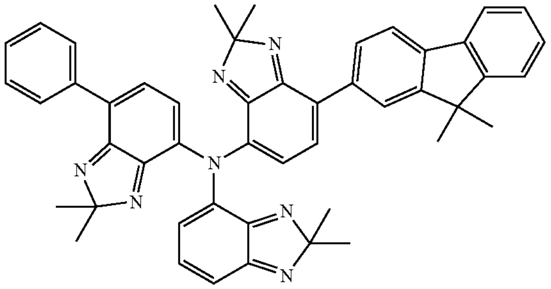
H210
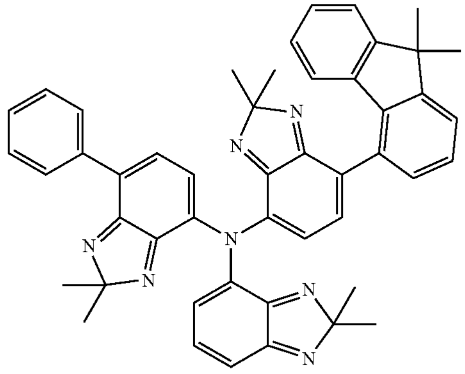
H211
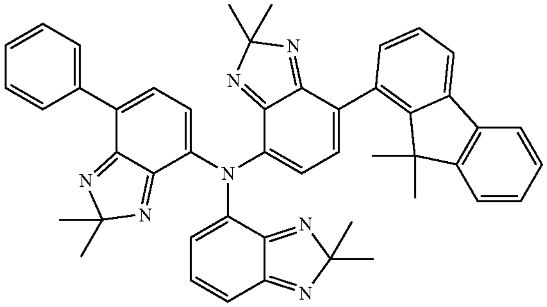
H212
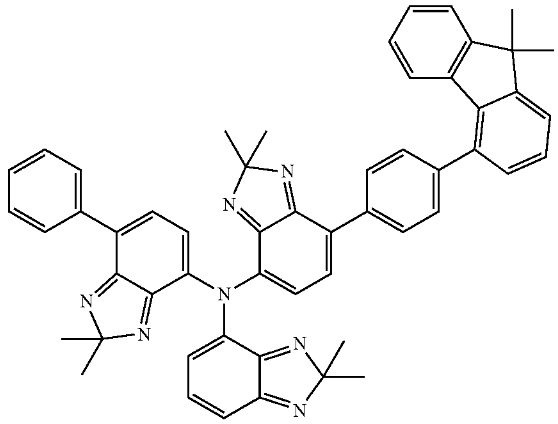
H213
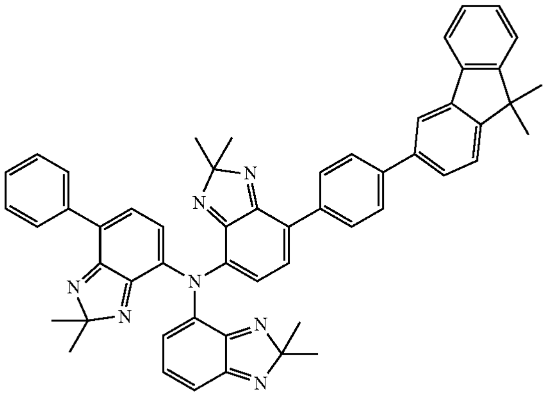
H214
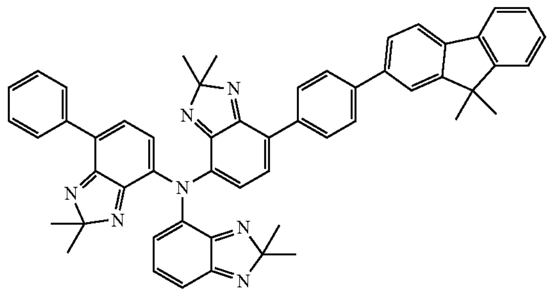
H215
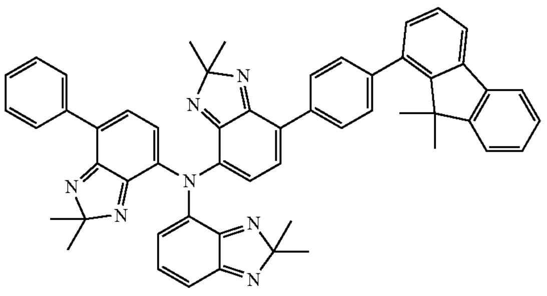

-continued
H216
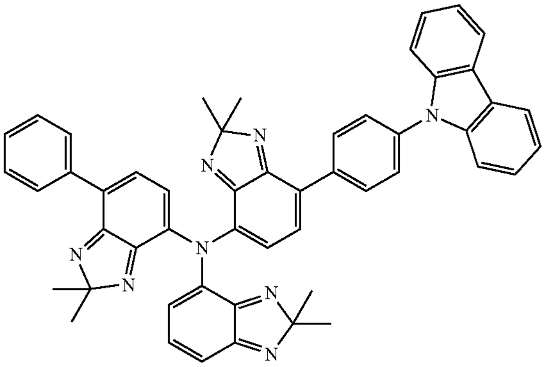
H217
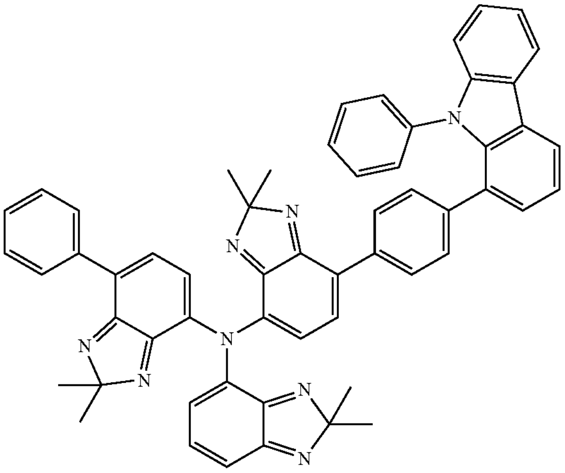
H218
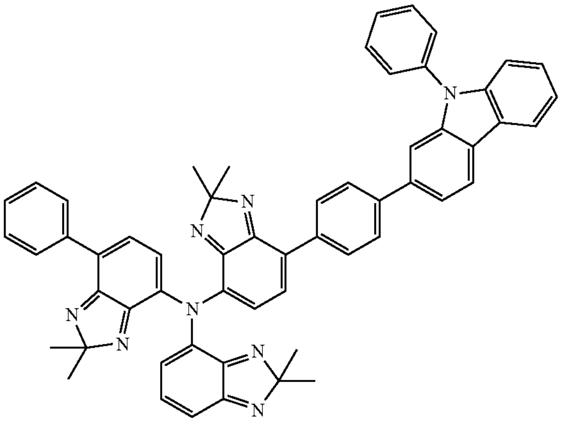
H219
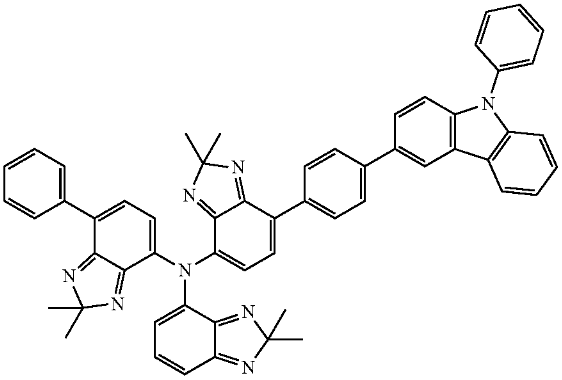
H220
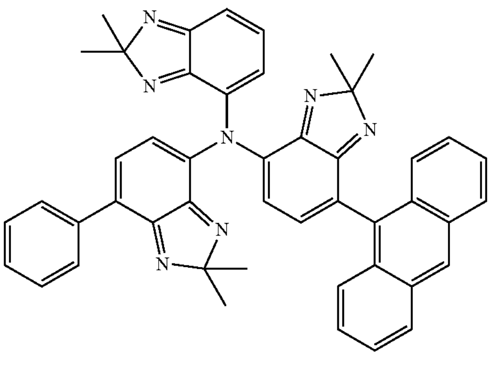
H221
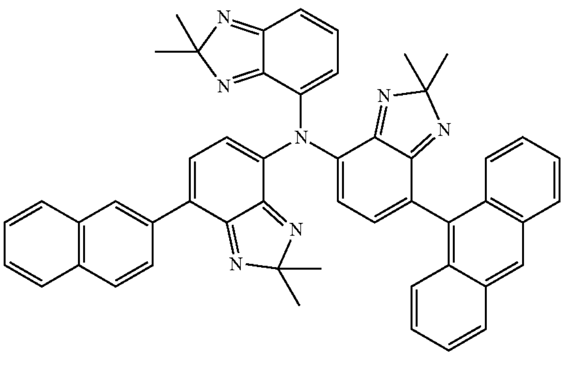

-continued
H222
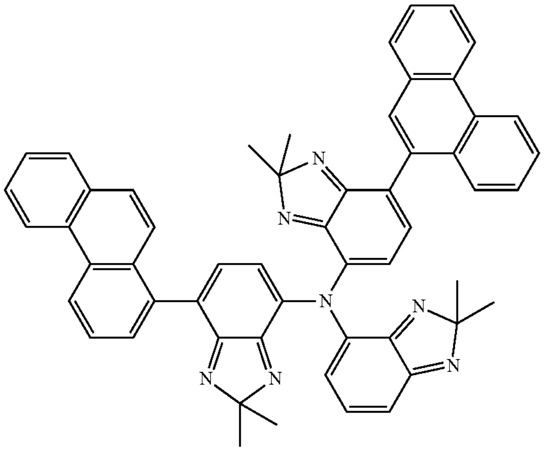
H223
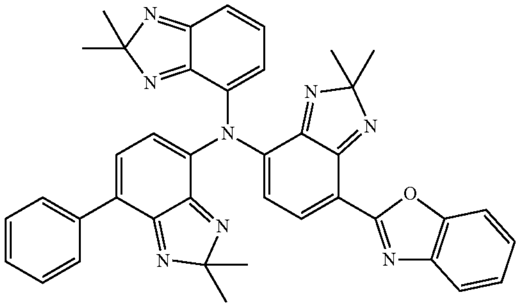
H224
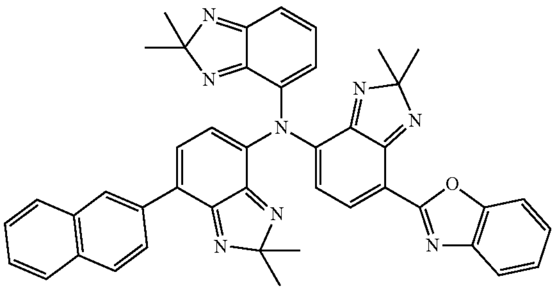
H225
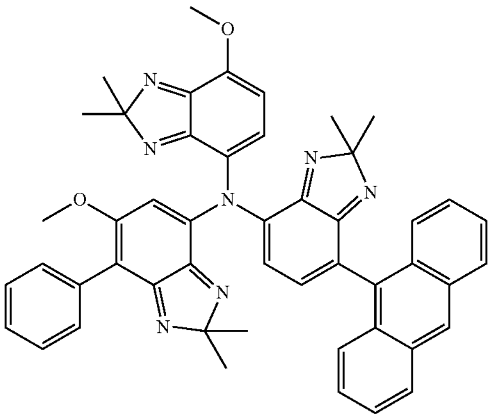
H226
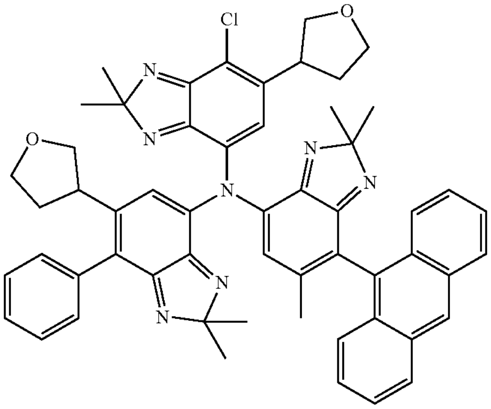
H227
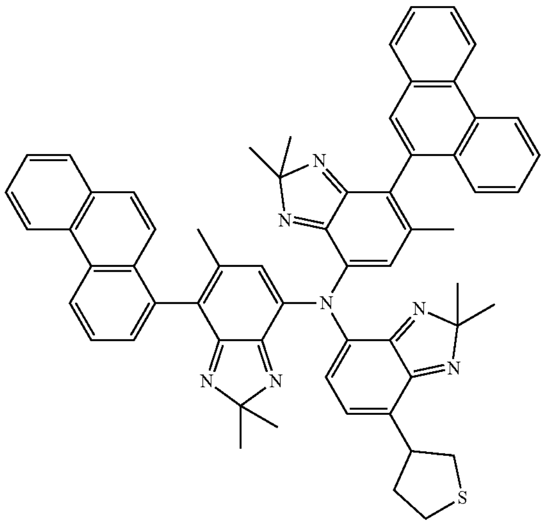

-continued
H228
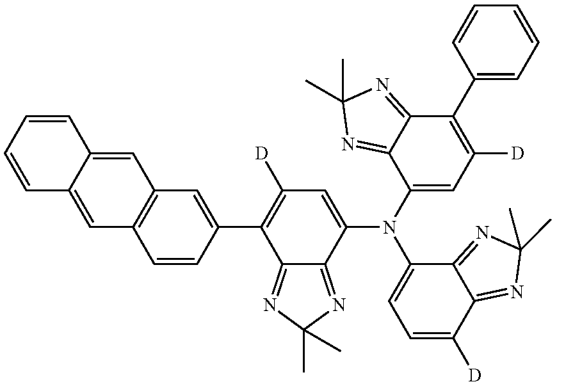
H229
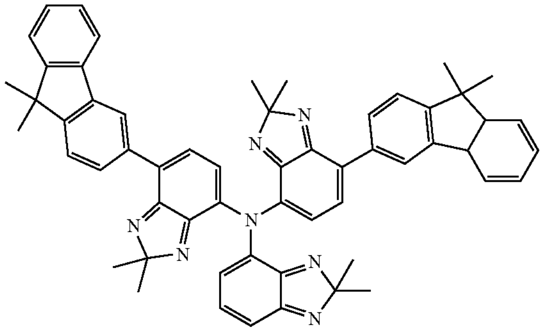
H230
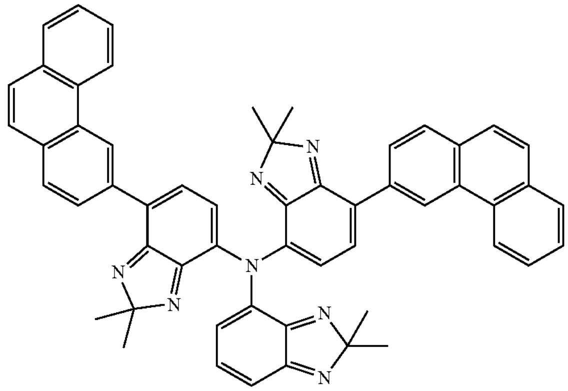
H231
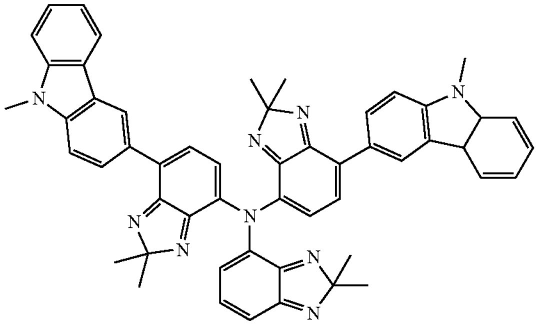
H232
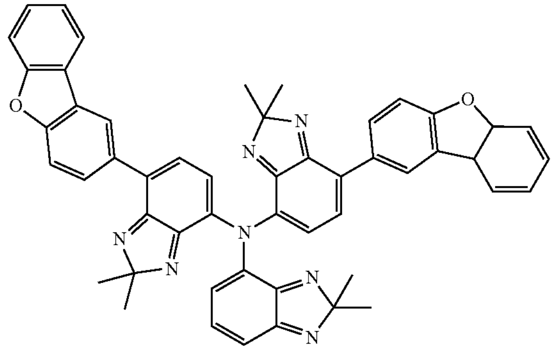
H233
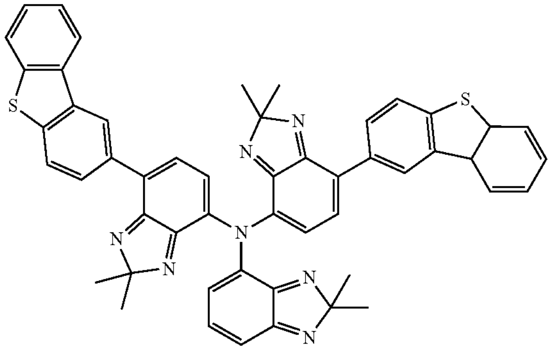
H234
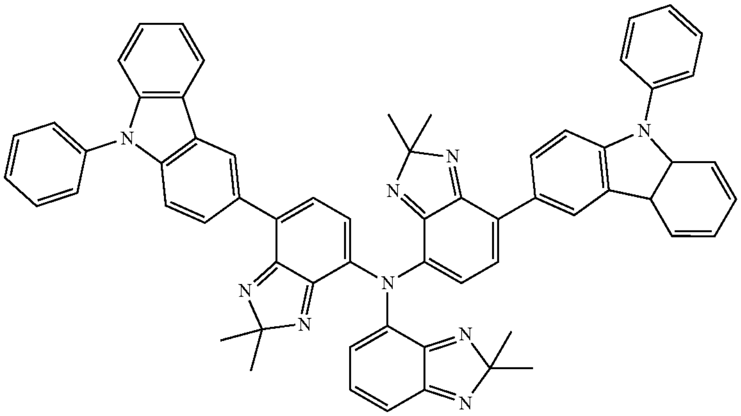

-continued
H235
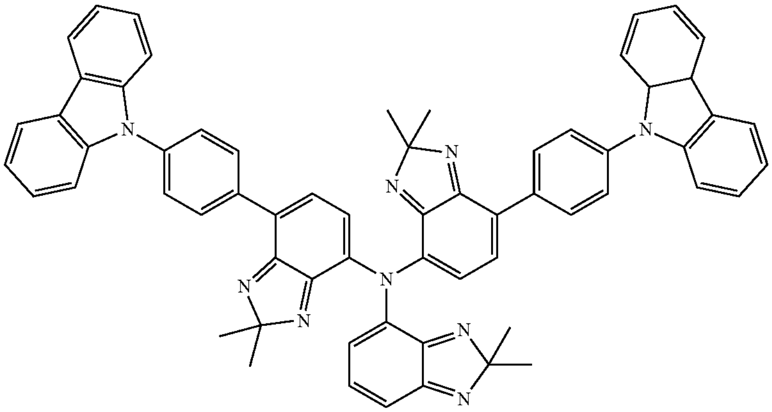
H236
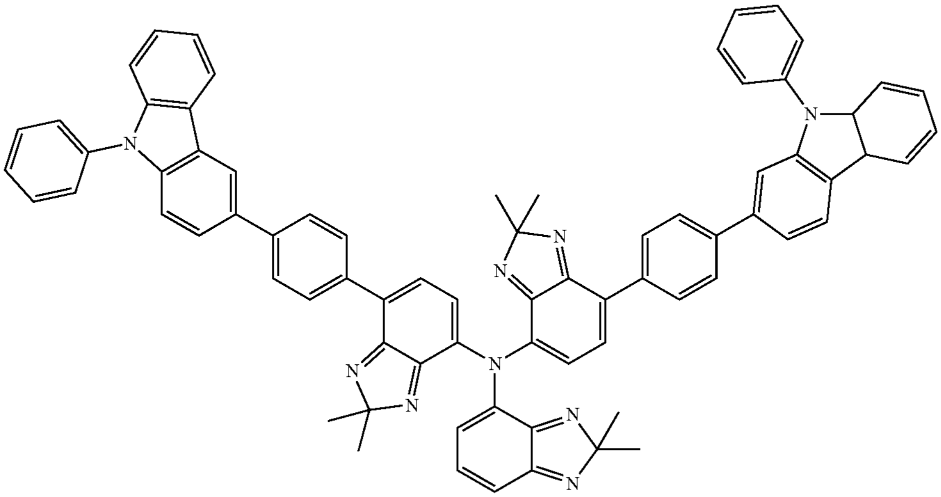
H237
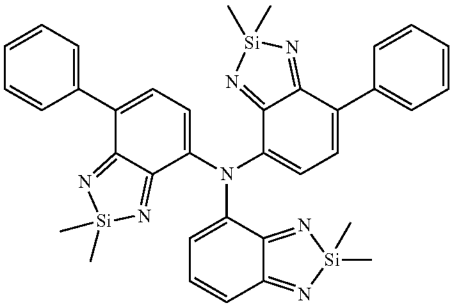
H238
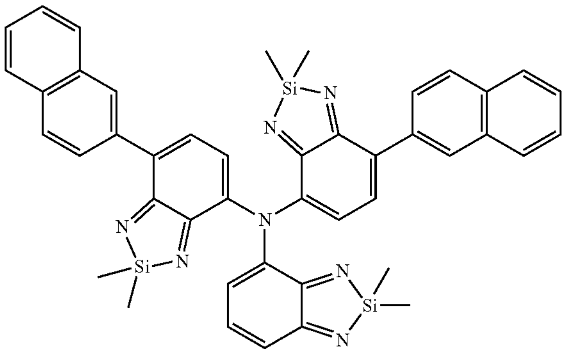

-continued
H239
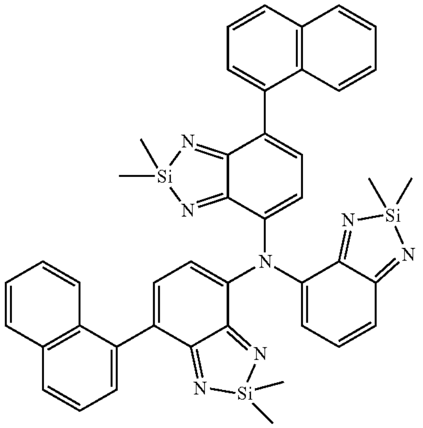
H240
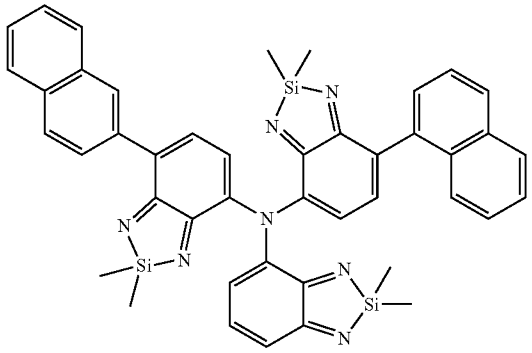
H241
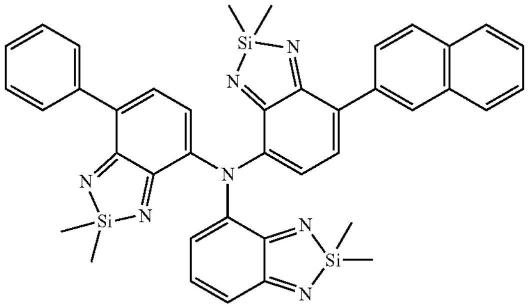
H242
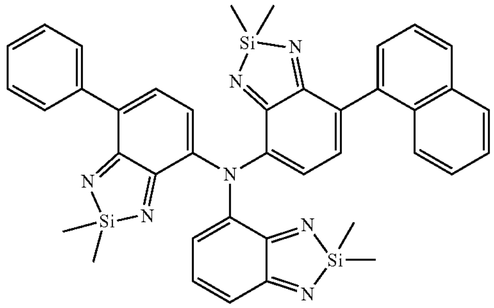
H243
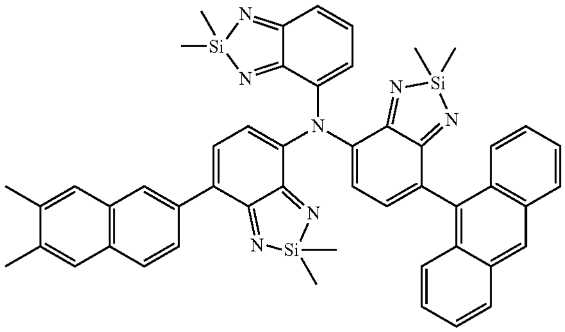
H244
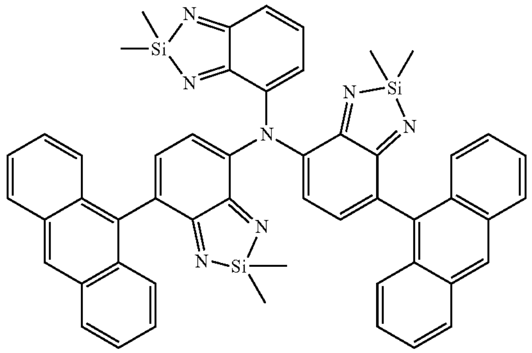
H245
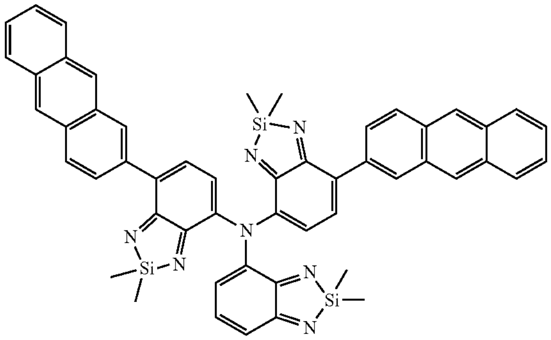
H246
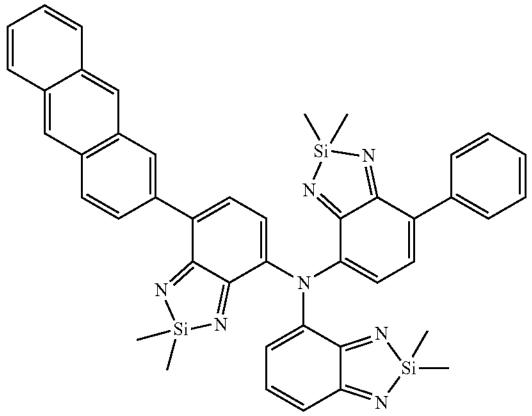

-continued
H247
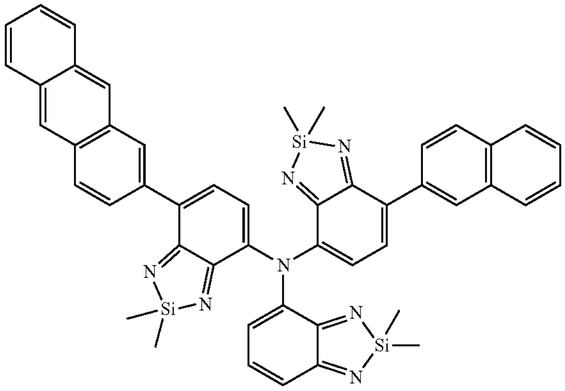
H248
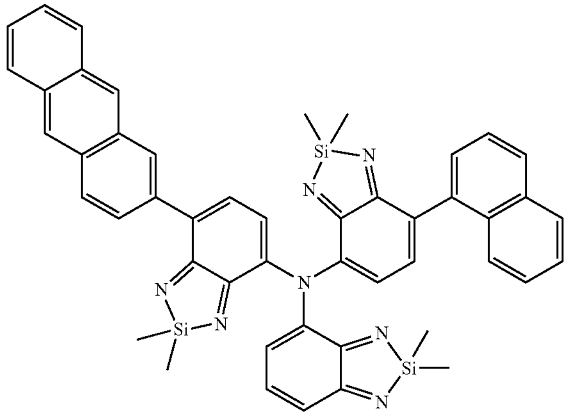
H249
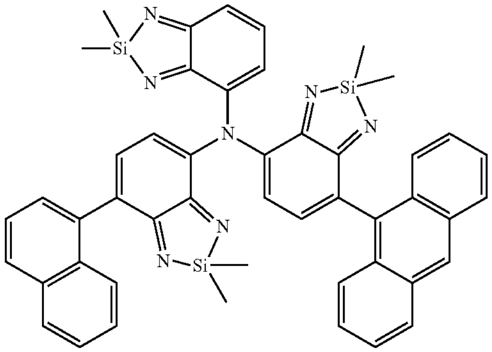
H250
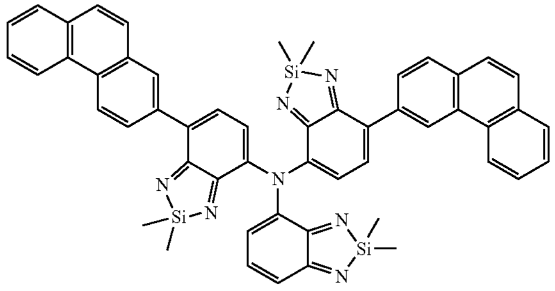
H251
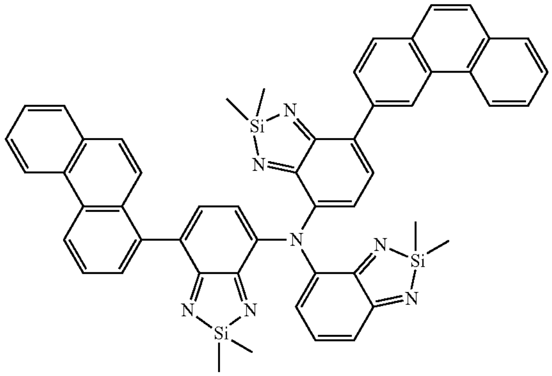
H252
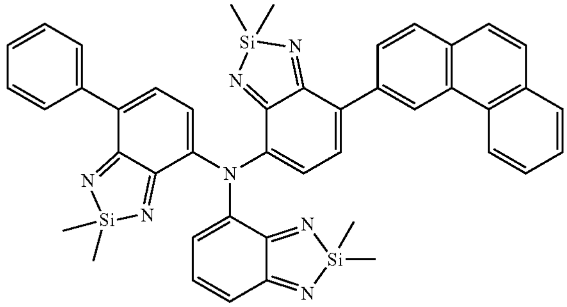
H253
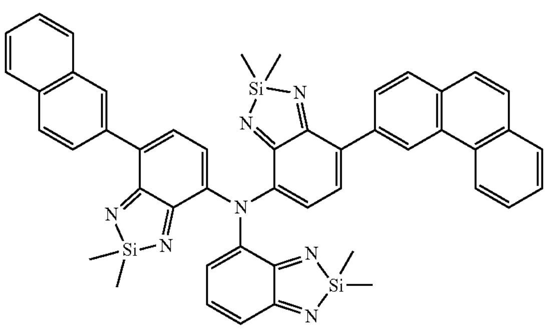
H254
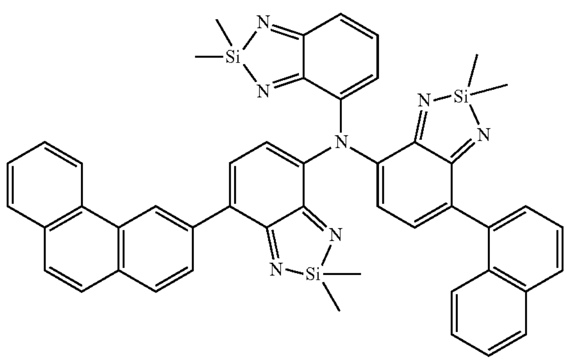

-continued
H255
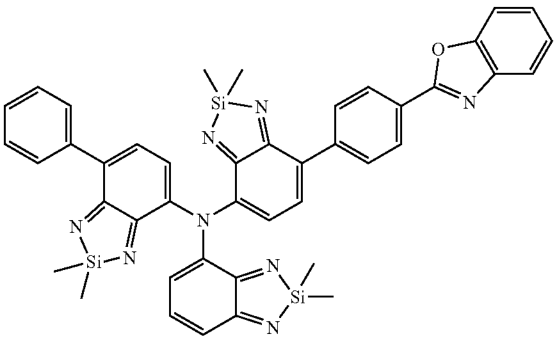
H256
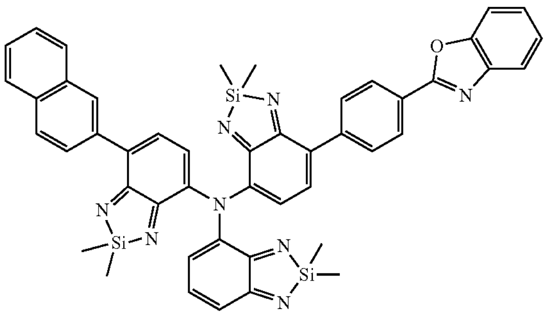
H257
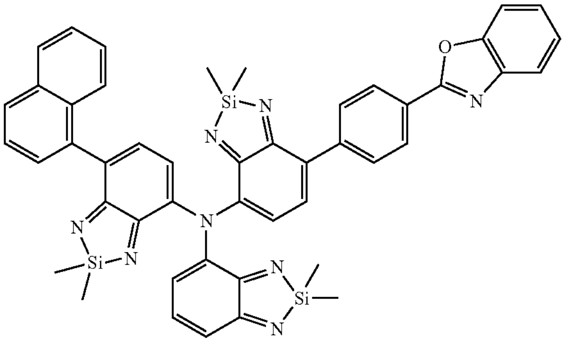
H258
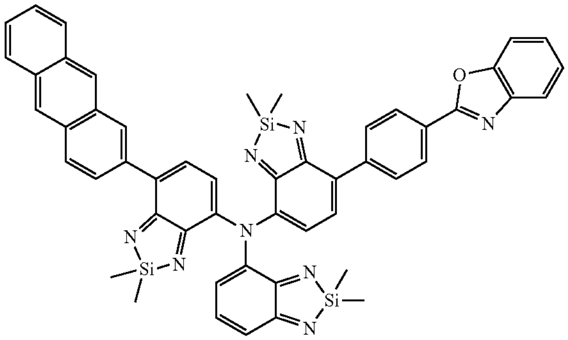
H259
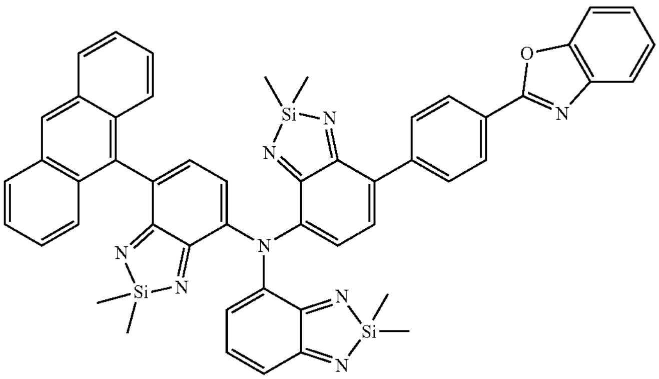
H260
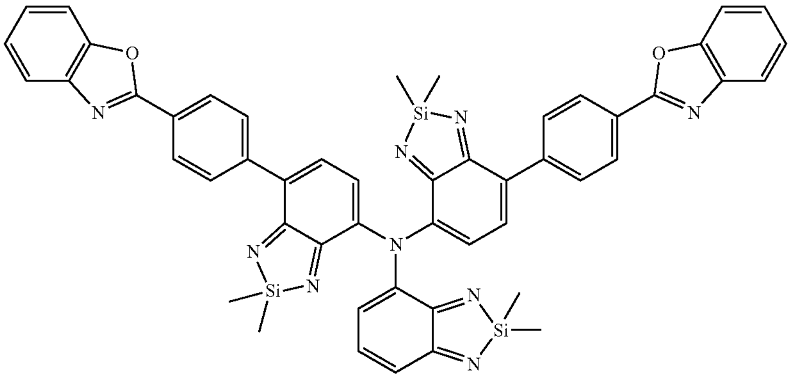

-continued
H261
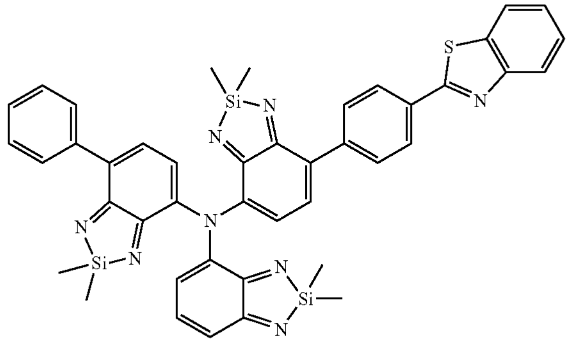
H262
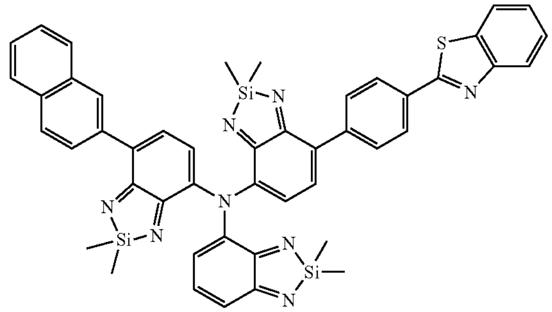
H263
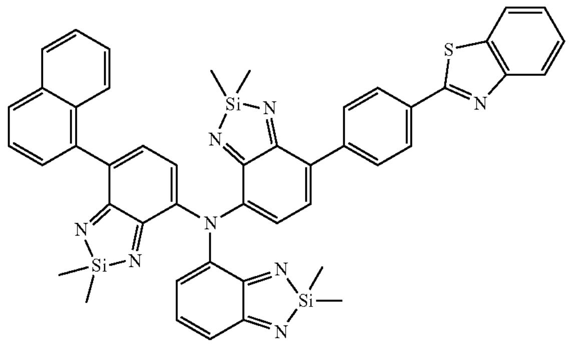
H264
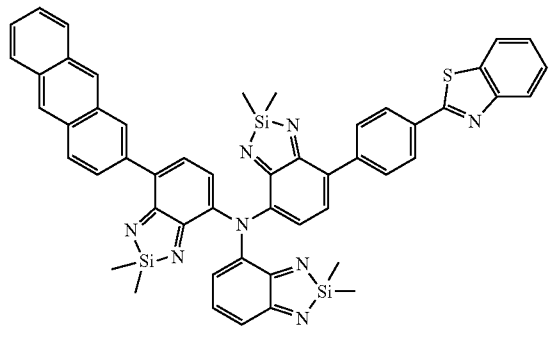
H265
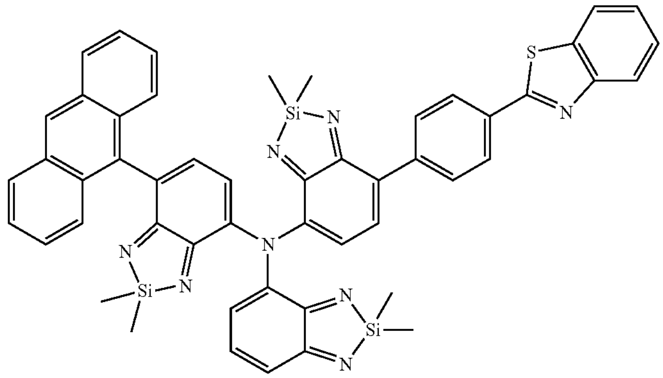
H266
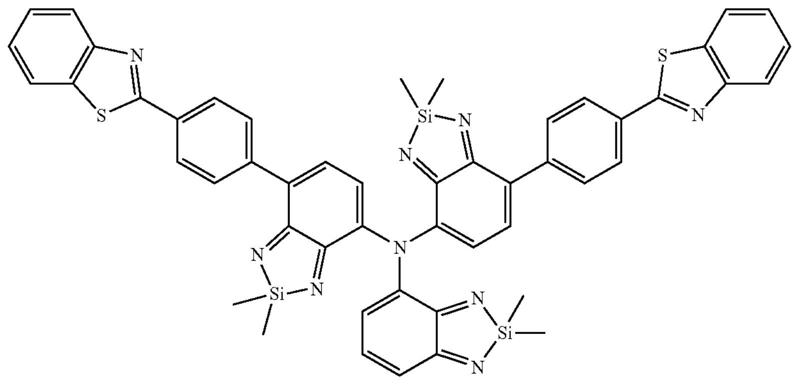

-continued
H267
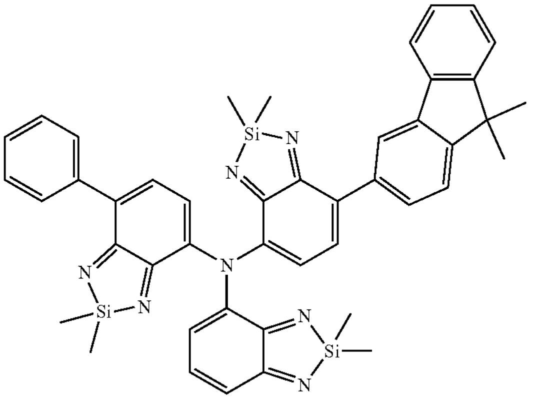
H268
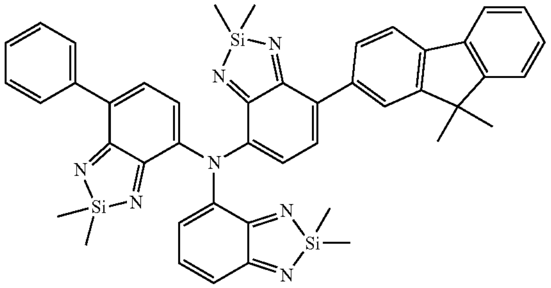
H269
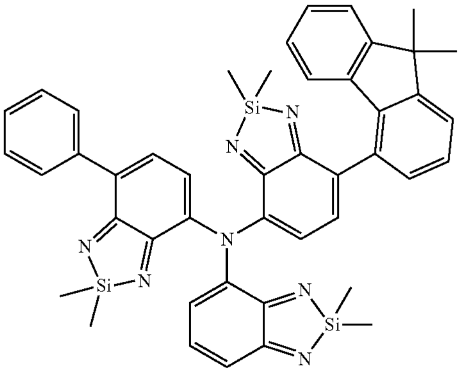
H270
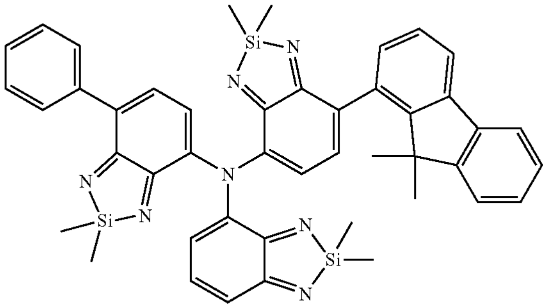
H271
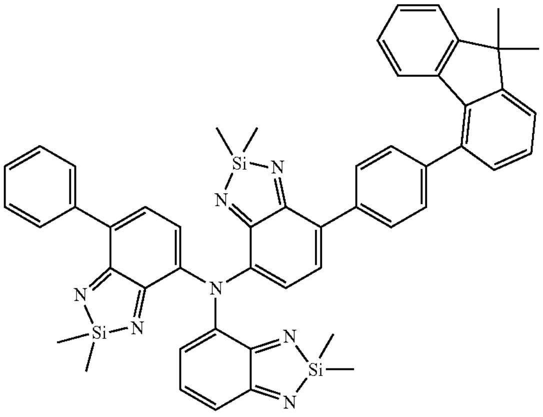
H272
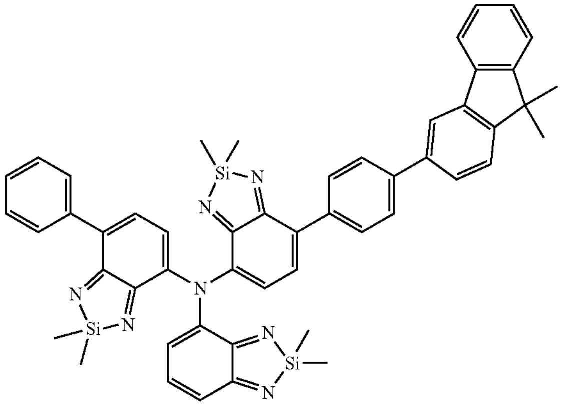
H273
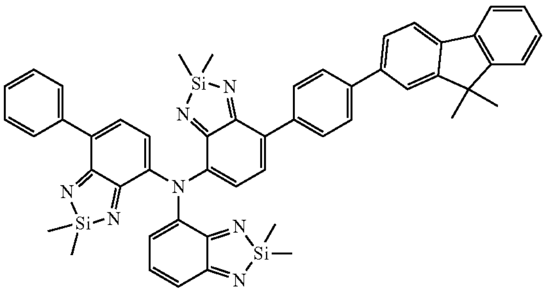
H274
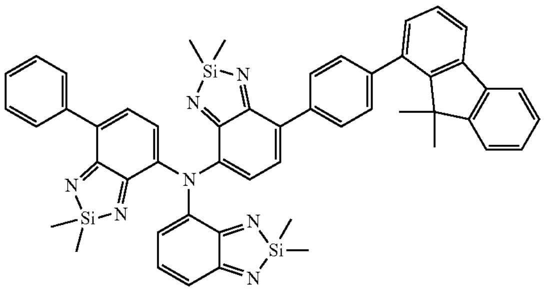

-continued
H275
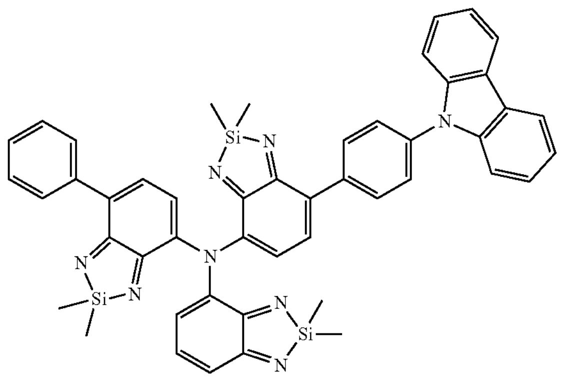
H276
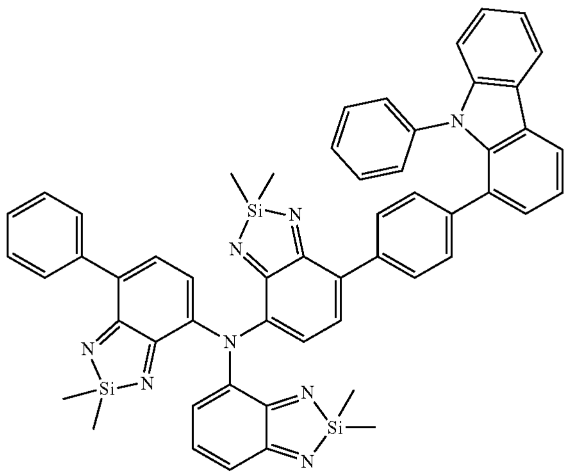
H277
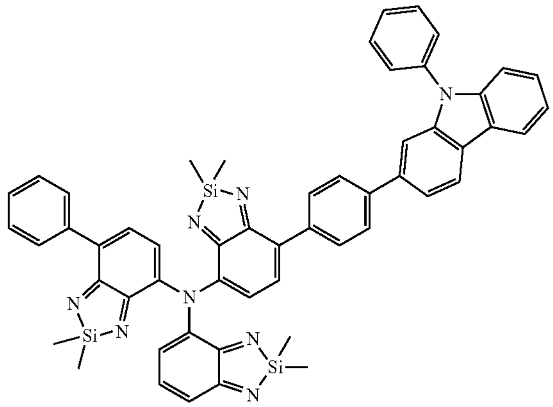
H278
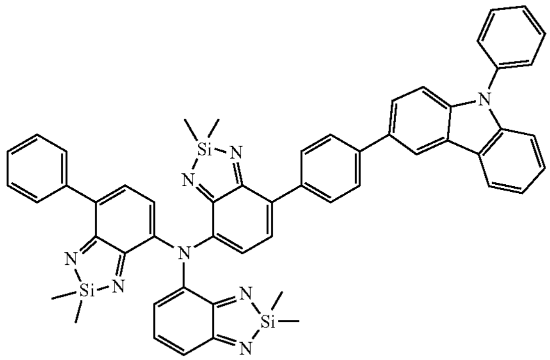
H279
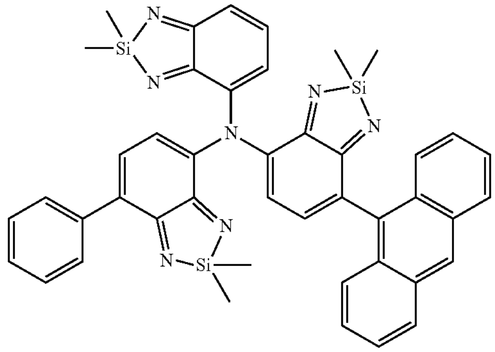
H280
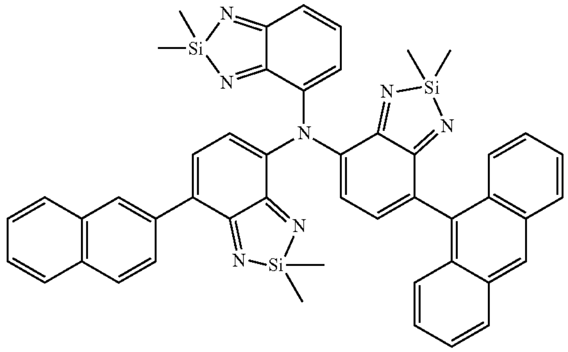

-continued
H281
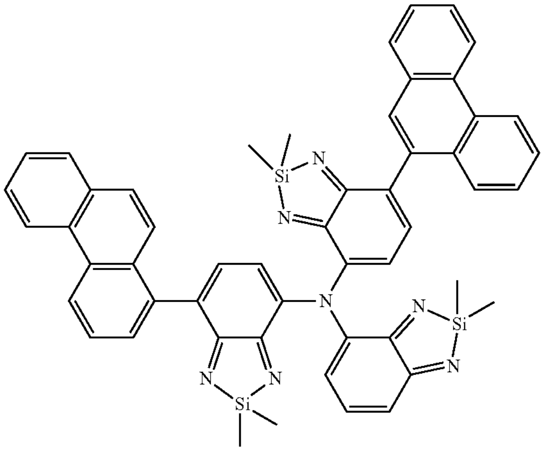
H282
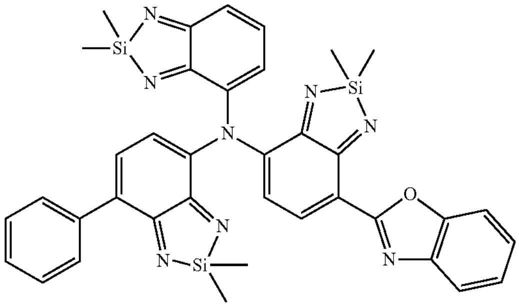
H283
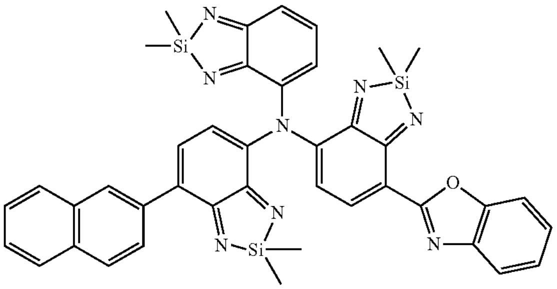
H284
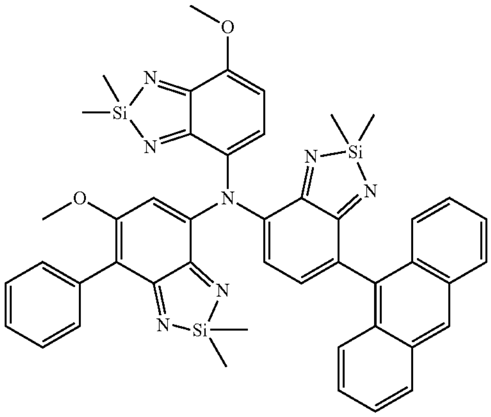
H285
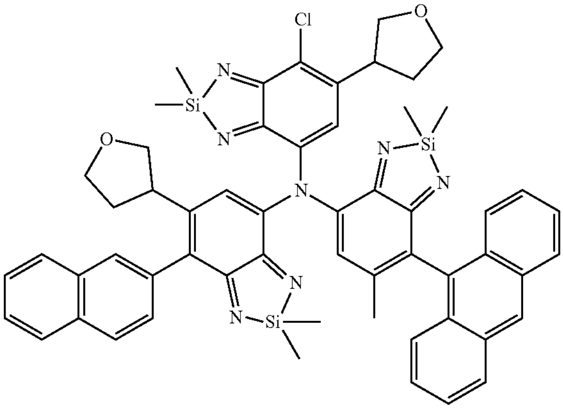
H286
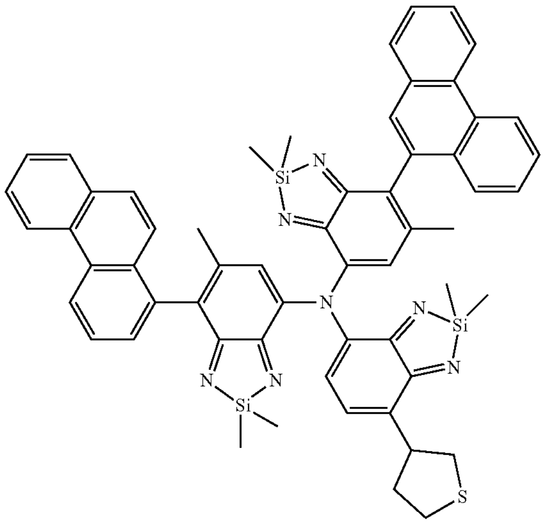

-continued
H287
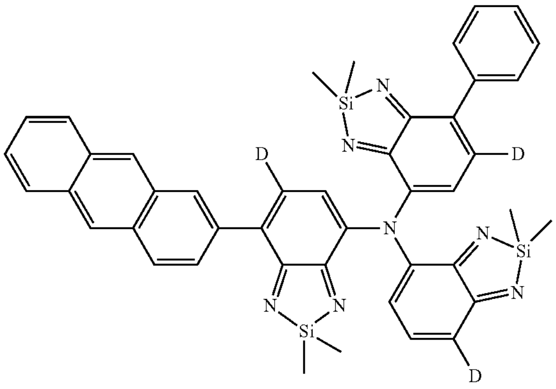
H288
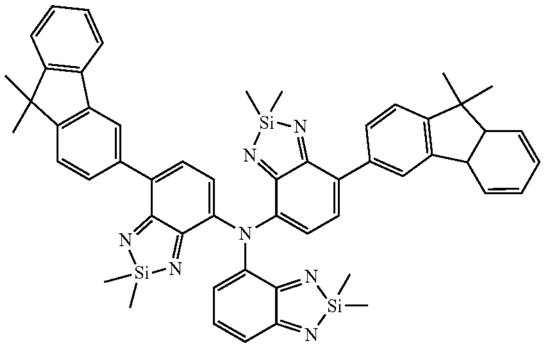
H289
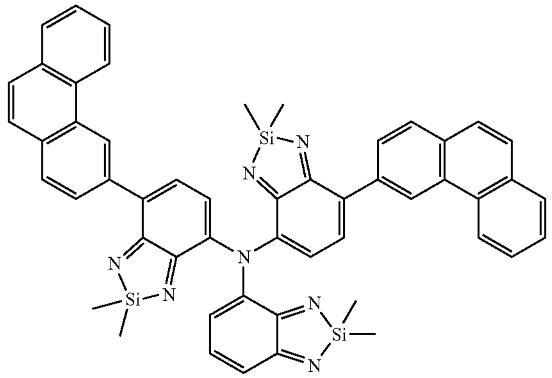
H290
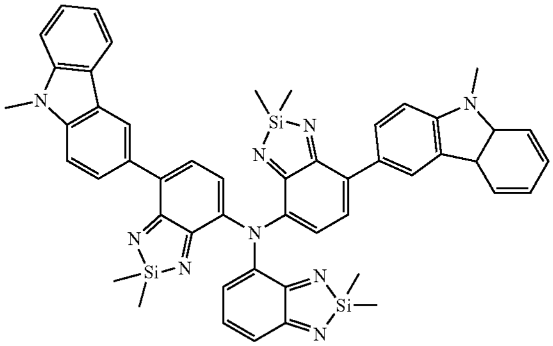
H291
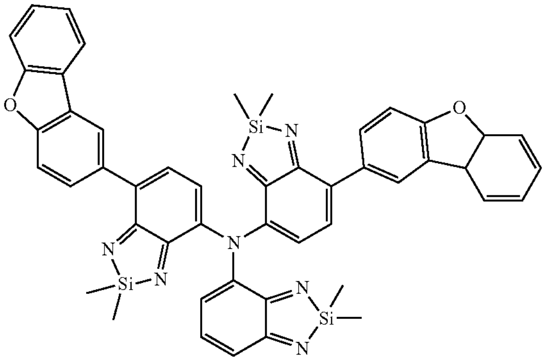
H292
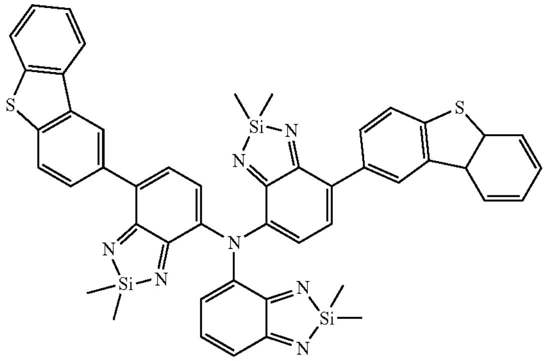
H293
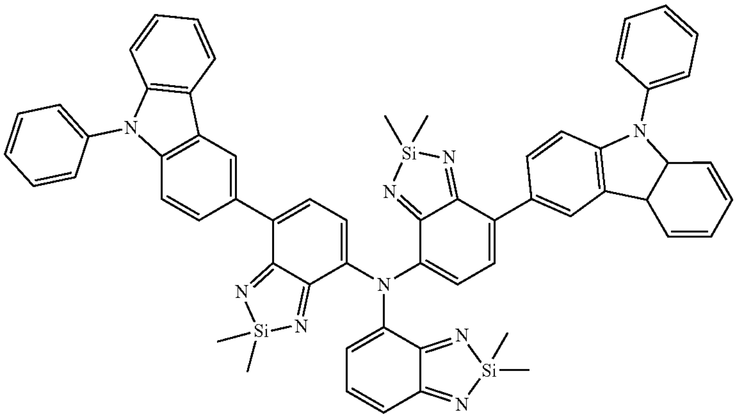

-continued

H294

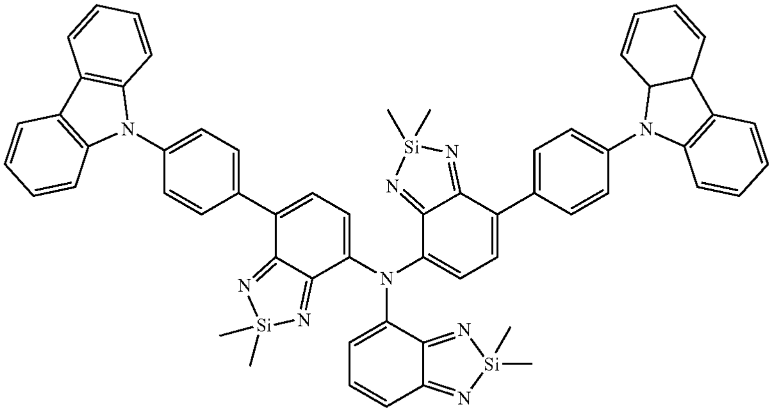

H295

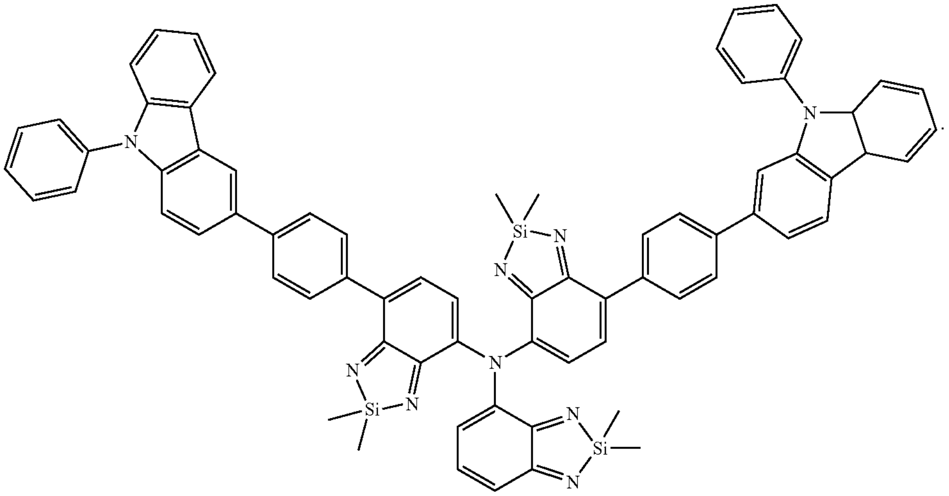

Embodiment 15. The compound according to any one of Embodiments 1-14, wherein the compound has a refractive index n≥2.1 at a wavelength of 460 nm, the compound has a difference between refractive index at a wavelength of 460 nm and refractive index at a wavelength of 530 nm being 0.09-0.17, the compound has a difference between refractive index at a wavelength of 530 nm and refractive index at a wavelength of 620 nm being 0.03-0.11, and the compound has a difference between refractive index at a wavelength of 460 nm and refractive index at a wavelength of 620 nm being 0.15-0.24.

Embodiment 16. A display panel, comprising an organic electroluminescent device, the organic electroluminescent device comprising a cathode, an anode arranged opposite to the cathode, a capping layer located on the side of the cathode away from the anode, and an organic film layer located between the cathode and the anode, wherein at least one of the capping layer and the organic film layer comprises the compound according to any one of Embodiments 1-15.

Embodiment 17. The display panel according to Embodiment 16, wherein the organic film layer comprises a hole transport layer and a luminescent layer, and at least one of the hole transport layer and the luminescent layer comprises the compound according to any one of Embodiments 1-15.

Embodiment 18. A display device, comprising the display panel according to Embodiment 16 or 17.

EXAMPLES

The following examples more specifically describe the content disclosed in the present application, and these examples are only used for explanatory description, because various modifications and changes within the scope of the present disclosure are apparent to those skilled in the art. Unless otherwise stated, all parts, percentages, and ratios described in the following examples are based on weight, all reagents used in the examples are commercially available or synthesized according to conventional methods and can be directly used without further treatment, and all instruments used in the examples are commercially available.

Synthesis of Compounds

The present application exemplarily provides a method for preparing several compounds. Other compounds of the present application may be prepared with reference to this exemplary method. According to the exemplary method for preparing the compounds, those skilled in the art may easily obtain specific methods for implementing synthesis steps from relevant scientific literature or standard textbooks in the art. Unless otherwise specified, compounds that are commercially available or known in the literature are used as raw materials for synthesis. Those skilled in the art of organic synthesis will recognize that the nature and order of the proposed synthesis steps may be varied for the purpose of optimizing the generation of the compounds described herein.

The processes described herein may be monitored according to any suitable method known in the art. For example, product generation may be monitored by spectroscopic means, such as nuclear magnetic resonance spectroscopy (NMR, e.g., $^{1}H$ or $^{13}C$), infrared spectroscopy (IR), spectrophotometry (e.g., UV-visible) and mass spectrometry (MS), or by chromatography, such as high performance liquid chromatography (HPLC), gas chromatography (GC), gel permeation chromatography (GPC) or thin layer chromatography (TLC).

Example 1-1: Synthesis of Compound H02

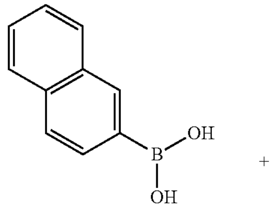

Compound 1

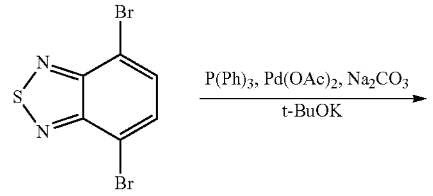

Compound 2

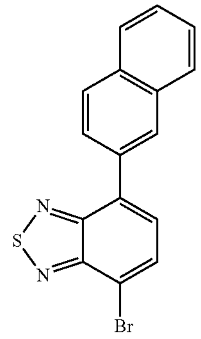

Compound 3

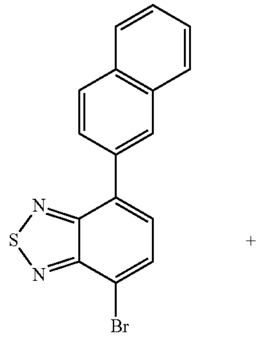

Compound 3

-continued

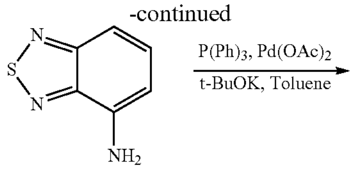

Compound 4

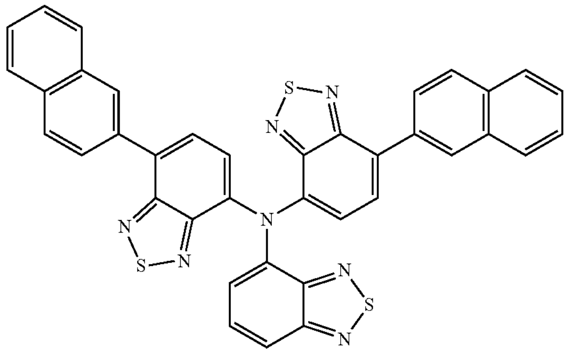

H02

After a compound 1 (0.5 mmol), a compound 2 (0.5 mmol), $P(ph)_3$ (0.15 mmol), $Pd(OAc)_2$ (0.2 mmol), t-BuOK (0.15 mmol), and $Na_2CO_3$ (0.15 mmol) were added to toluene (3 mL) and mixed uniformly, the mixture was put into a 50 mL flask and reacted at 80° C. for 12 hours. After the reaction was completed, the solution was cooled to room temperature, followed by slowly adding a saturated aqueous $MgSO_4$ solution and ethyl acetate to the solution for extraction three times. The organic layers were collected and then the solvent was removed with a rotary evaporator. After purification by column chromatography, a compound 3 was obtained.

After the compound 3 (1 mmol), a compound 4 (0.5 mmol), $P(ph)_3$ (0.15 mmol), $Pd(OAc)_2$ (0.2 mmol), and t-BuOK (0.15 mmol) were added to toluene (3 mL) and mixed uniformly, the mixture was put into a 50 mL flask and reacted at 80° C. for 12 hours. After the reaction was completed, the solution was cooled to room temperature, followed by slowly adding a saturated aqueous $MgSO_4$ solution and ethyl acetate to the solution for extraction three times. The organic layers were collected and then the solvent was removed with the rotary evaporator. After purification by column chromatography, a compound H02 was obtained.

The following were obtained by matrix-assisted laser desorption ionization time-of-flight mass spectrometry (MALDI-TOF MS) (m/z): calculated value 671.1; test value 671.0.

Elemental analysis results: theoretical values: C, 67.94; H, 3.15; N, 14.59; S, 14.32. Actual values: C, 67.93; H, 3.13; N, 14.58; S, 14.30.

Example 1-2: Synthesis of Compound H09

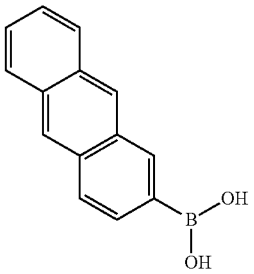

+

Compound 5

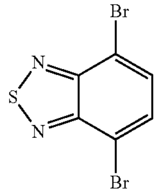

Compound 2

P(Ph)3, Pd(OAc)2, Na2CO3
t-BuOK

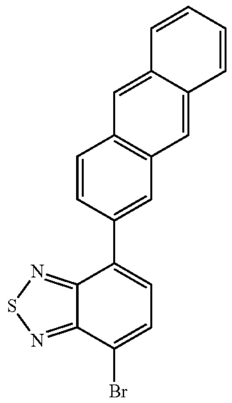

Compound 6

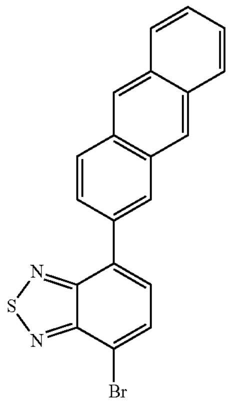

+

Compound 6

-continued

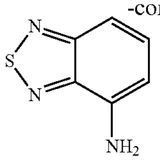

Compound 4

P(Ph)3, Pd(OAc)2
t-BuOK, Toluene

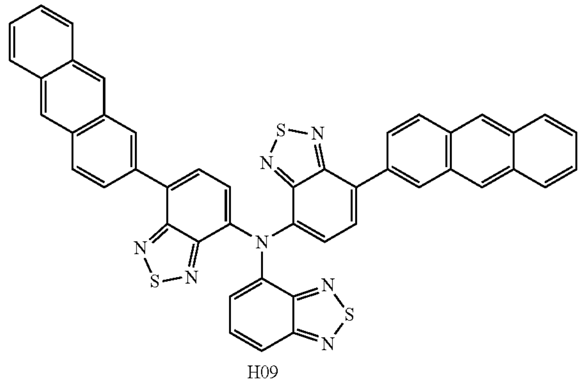

H09

After a compound 2 (0.5 mmol), a compound 5 (0.5 mmol), $P(ph)_3$ (0.15 mmol), $Pd(OAc)_2$ (0.2 mmol), t-BuOK (0.15 mmol), and $Na_2CO_3$ (0.15 mmol) were added to toluene (3 mL) and mixed uniformly, the mixture was put into a 50 mL flask and reacted at 80° C. for 12 hours. After the reaction was completed, the solution was cooled to room temperature, followed by slowly adding a saturated aqueous $MgSO_4$ solution and ethyl acetate to the solution for extraction three times. The organic layers were collected and then the solvent was removed with a rotary evaporator. After purification by column chromatography, a compound 6 was obtained.

After the compound 6 (1 mmol), a compound 4 (0.5 mmol), $P(ph)_3$ (0.15 mmol), $Pd(OAc)_2$ (0.2 mmol), and t-BuOK (0.15 mmol) were added to toluene (3 mL) and mixed uniformly, the mixture was put into a 50 mL flask and reacted at 80° C. for 12 hours. After the reaction was completed, the solution was cooled to room temperature, followed by slowly adding a saturated aqueous $MgSO_4$ solution and ethyl acetate to the solution for extraction three times. The organic layers were collected and then the solvent was removed with the rotary evaporator. After purification by column chromatography, a compound H09 was obtained.

The following were obtained by matrix-assisted laser desorption ionization time-of-flight mass spectrometry (MALDI-TOF MS) (m/z): calculated value 771.1; test value 771.0.

Elemental analysis results: theoretical values: C, 71.57; H, 3.26; N, 12.70; S, 12.46. Actual values: C, 71.55; H, 3.25; N, 12.69; S, 12.45.

Example 1-3: Synthesis of Compound H24

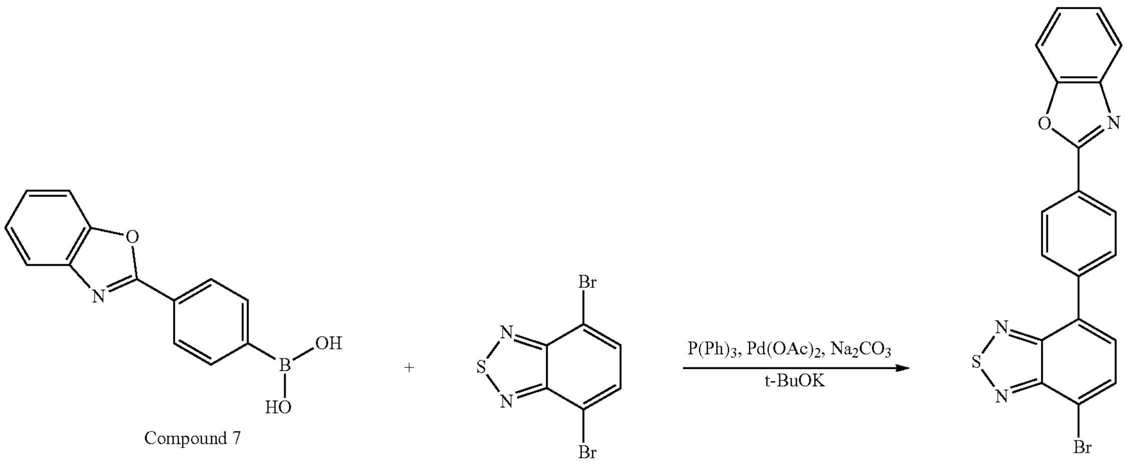

Compound 7

Compound 2

Compound 8

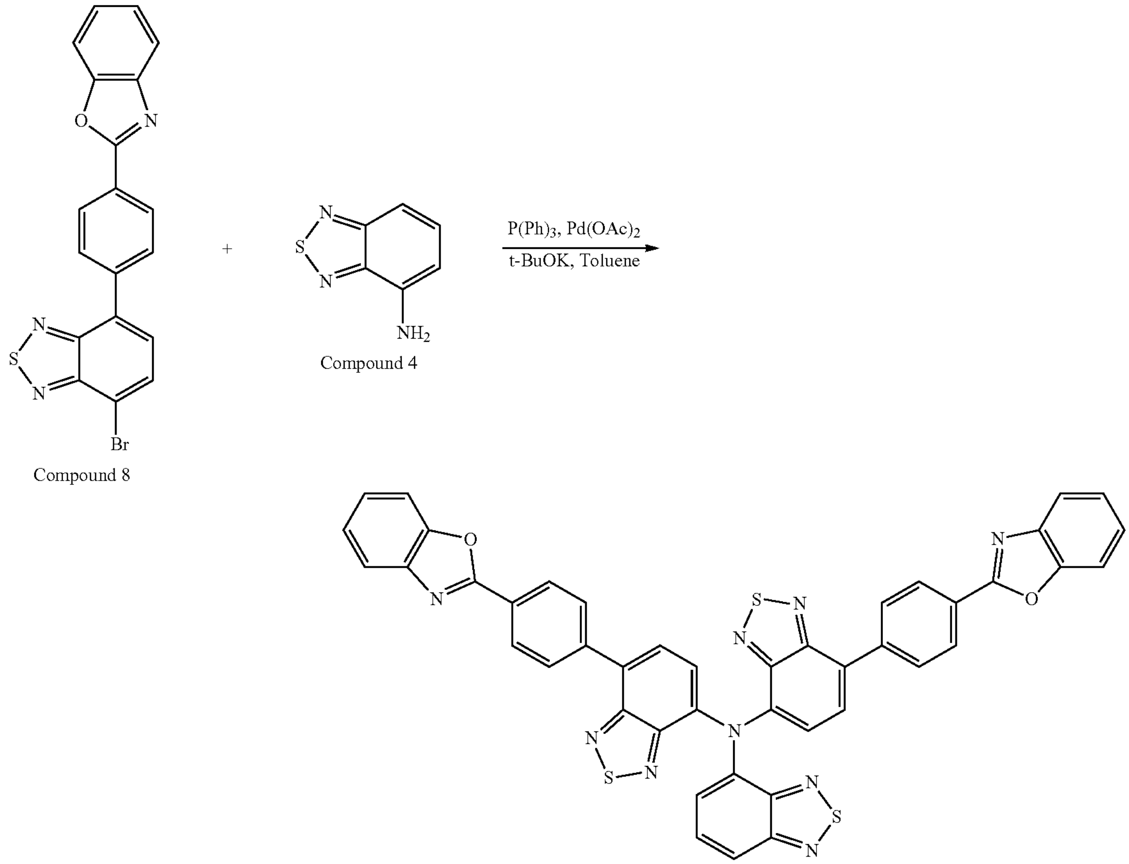

Compound 8

Compound 4

H24

After a compound 2 (0.5 mmol), a compound 7 (0.5 mmol), $P(ph)_3$ (0.15 mmol), $Pd(OAc)_2$ (0.2 mmol), t-BuOK (0.15 mmol), and $Na_2CO_3$ (0.15 mmol) were added to toluene (3 mL) and mixed uniformly, the mixture was put into a 50 mL flask and reacted at 80° C. for 12 hours. After the reaction was completed, the solution was cooled to room temperature, followed by slowly adding a saturated aqueous $MgSO_4$ solution and ethyl acetate to the solution for extraction three times. The organic layers were collected and then the solvent was removed with a rotary evaporator. After purification by column chromatography, a compound 8 was obtained.

After the compound 8 (1 mmol), a compound 4 (0.5 mmol), $P(ph)_3$ (0.15 mmol), $Pd(OAc)_2$ (0.2 mmol), and t-BuOK (0.15 mmol) were added to toluene (3 mL) and mixed uniformly, the mixture was put into a 50 mL flask and reacted at 80° C. for 12 hours. After the reaction was completed, the solution was cooled to room temperature, followed by slowly adding a saturated aqueous $MgSO_4$ solution and ethyl acetate to the solution for extraction three times. The organic layers were collected and then the solvent was removed with the rotary evaporator. After purification by column chromatography, a compound H24 was obtained.

The following were obtained by matrix-assisted laser desorption ionization time-of-flight mass spectrometry (MALDI-TOF MS) (m/z): calculated value 805.1; test value 805.0.

Elemental analysis results: theoretical values: C, 65.57; H, 2.88; N, 15.64; 0, 3.97; S, 11.94. Actual values: C, 65.55; H, 2.85; N, 15.63; 0, 3.97; S, 11.94.

Example 1-4: Synthesis of Compound H52

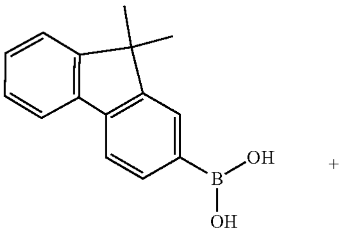

Compound 9

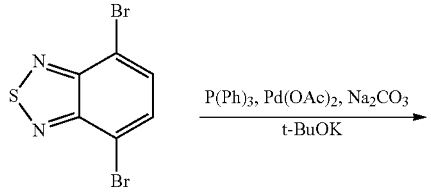

Compound 2

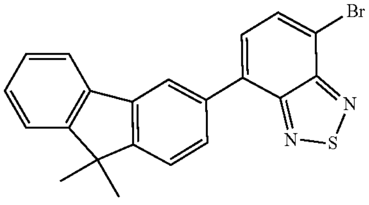

Compound 10

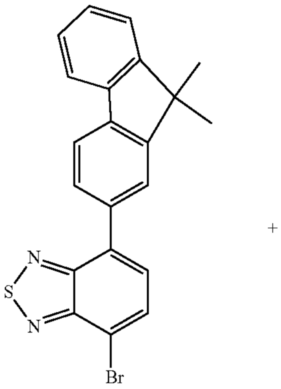

Compound 10

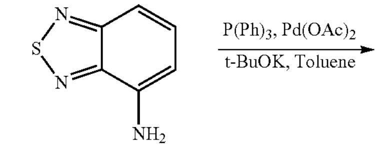

Compound 4

-continued

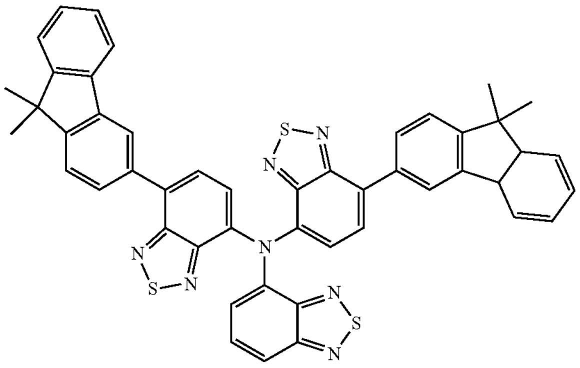

H52

After a compound 2 (0.5 mmol), a compound 9 (0.5 mmol), $P(ph)_3$ (0.15 mmol), $Pd(OAc)_2$ (0.2 mmol), t-BuOK (0.15 mmol), and $Na_2CO_3$ (0.15 mmol) were added to toluene (3 mL) and mixed uniformly, the mixture was put into a 50 mL flask and reacted at 80° C. for 12 hours. After the reaction was completed, the solution was cooled to room temperature, followed by slowly adding a saturated aqueous $MgSO_4$ solution and ethyl acetate to the solution for extraction three times. The organic layers were collected and then the solvent was removed with a rotary evaporator. After purification by column chromatography, a compound 10 was obtained.

After the compound 10 (1 mmol), a compound 4 (0.5 mmol), P(ph) 3 (0.15 mmol), Pd(OAc) 2 (0.2 mmol), and t-BuOK (0.15 mmol) were added to toluene (3 mL) and mixed uniformly, the mixture was put into a 50 mL flask and reacted at 80° C. for 12 hours. After the reaction was completed, the solution was cooled to room temperature, followed by slowly adding a saturated aqueous $MgSO_4$ solution and ethyl acetate to the solution for extraction three times. The organic layers were collected and then the solvent was removed with the rotary evaporator. After purification by column chromatography, a compound H52 was obtained.

The following were obtained by matrix-assisted laser desorption ionization time-of-flight mass spectrometry (MALDI-TOF MS) (m/z): calculated value 805.2; test value 805.0.

Elemental analysis results: theoretical values: C, 71.52; H, 4.38; N, 12.16; S, 11.93. Actual values: C, 71.51; H, 12.15; N, 12.15; S, 11.92.

Example 1-5: Synthesis of Compound H53

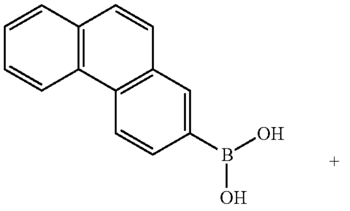

Compound 11

-continued

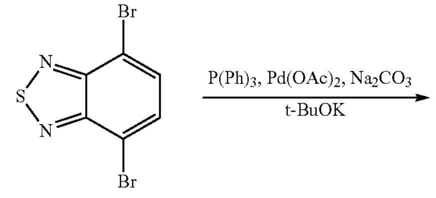

Compound 2

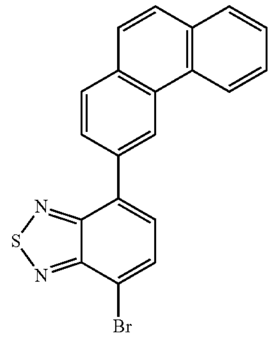

Compound 12

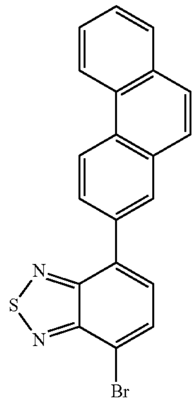

+

Compound 12

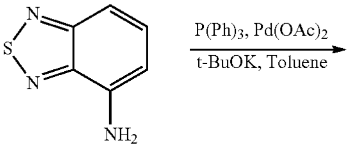

Compound 4

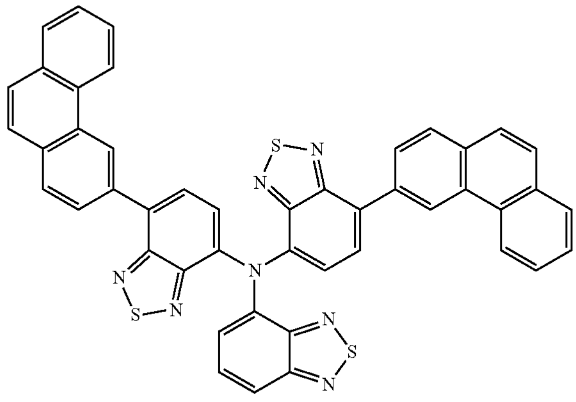

H53

After a compound 2 (0.5 mmol), a compound 11 (0.5 mmol), $P(ph)_3$ (0.15 mmol), $Pd(OAc)_2$ (0.2 mmol), t-BuOK (0.15 mmol), and $Na_2CO_3$ (0.15 mmol) were added to toluene (3 mL) and mixed uniformly, the mixture was put into a 50 mL flask and reacted at 80° C. for 12 hours. After the reaction was completed, the solution was cooled to room temperature, followed by slowly adding a saturated aqueous $MgSO_4$ solution and ethyl acetate to the solution for extraction three times. The organic layers were collected and then the solvent was removed with a rotary evaporator. After purification by column chromatography, a compound 12 was obtained.

After the compound 12 (1 mmol), a compound 4 (0.5 mmol), $P(ph)_3$ (0.15 mmol), $Pd(OAc)_2$ (0.2 mmol), and t-BuOK (0.15 mmol) were added to toluene (3 mL) and mixed uniformly, the mixture was put into a 50 mL flask and reacted at 80° C. for 12 hours. After the reaction was completed, the solution was cooled to room temperature, followed by slowly adding a saturated aqueous $MgSO_4$ solution and ethyl acetate to the solution for extraction three times. The organic layers were collected and then the solvent was removed with the rotary evaporator. After purification by column chromatography, a compound H53 was obtained.

The following were obtained by matrix-assisted laser desorption ionization time-of-flight mass spectrometry (MALDI-TOF MS) (m/z): calculated value 771.1; test value 771.0.

Elemental analysis results: theoretical value: C, 71.57: H, 3.26; N, 12.70; S, 12.46. Actual values: C, 71.55: H, 3.25; N, 12.69; S, 12.45.

Examples 1-6: Synthesis of Compound H54

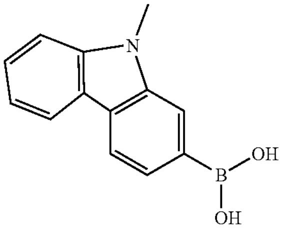

+

Compound 13

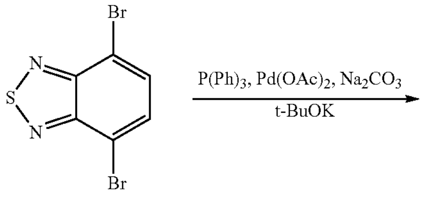

Compound 2

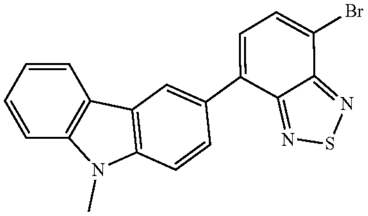

Compound 14

-continued

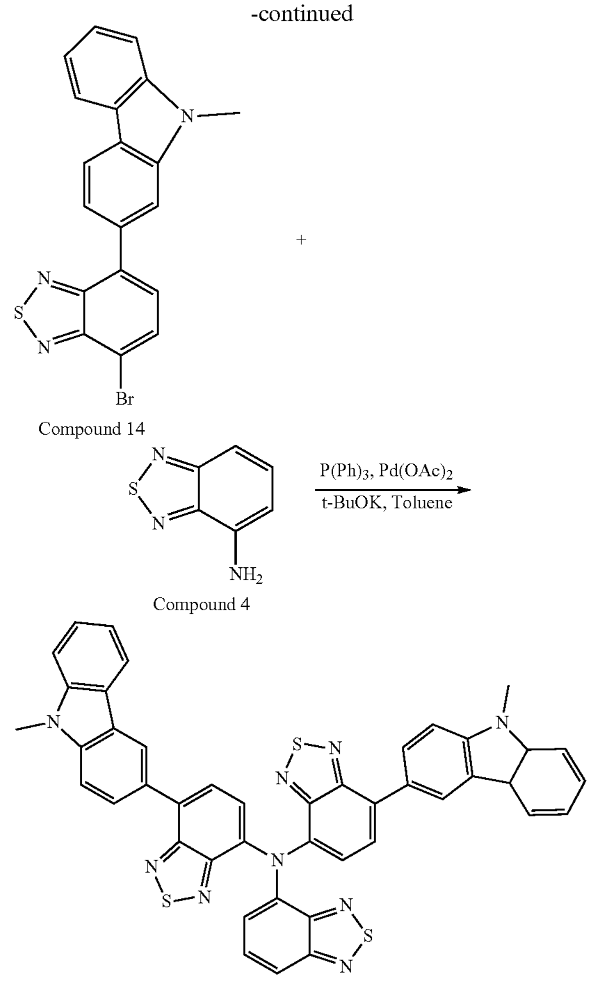

Compound 14

Compound 4

H54

After a compound 2 (0.5 mmol), a compound 13 (0.5 mmol), $P(ph)_3$ (0.15 mmol), $Pd(OAc)_2$ (0.2 mmol), t-BuOK (0.15 mmol), and $Na_2CO_3$ (0.15 mmol) were added to toluene (3 mL) and mixed uniformly, the mixture was put into a 50 mL flask and reacted at 80° C. for 12 hours. After the reaction was completed, the solution was cooled to room temperature, followed by slowly adding a saturated aqueous $MgSO_4$ solution and ethyl acetate to the solution for extraction three times. The organic layers were collected and then the solvent was removed with a rotary evaporator. After purification by column chromatography, a compound 14 was obtained.

After the compound 14 (1 mmol), a compound 4 (0.5 mmol), $P(ph)_3$ (0.15 mmol), $Pd(OAc)_2$ (0.2 mmol), and t-BuOK (0.15 mmol) were added to toluene (3 mL) and mixed uniformly, the mixture was put into a 50 mL flask and reacted at 80° C. for 12 hours. After the reaction was completed, the solution was cooled to room temperature, followed by slowly adding a saturated aqueous $MgSO_4$ solution and ethyl acetate to the solution for extraction three times. The organic layers were collected and then the solvent was removed with the rotary evaporator. After purification by column chromatography, a compound H54 was obtained.

The following were obtained by matrix-assisted laser desorption ionization time-of-flight mass spectrometry (MALDI-TOF MS) (m/z): calculated value 779.2; test value 779.1.

Elemental analysis results: theoretical values: C, 67.76: H, 3.75; N, 16.16; S, 12.33. Actual values: C, 67.75: H, 3.73; N, 16.15; S, 12.31.

Example 1-7: Synthesis of Compound H55

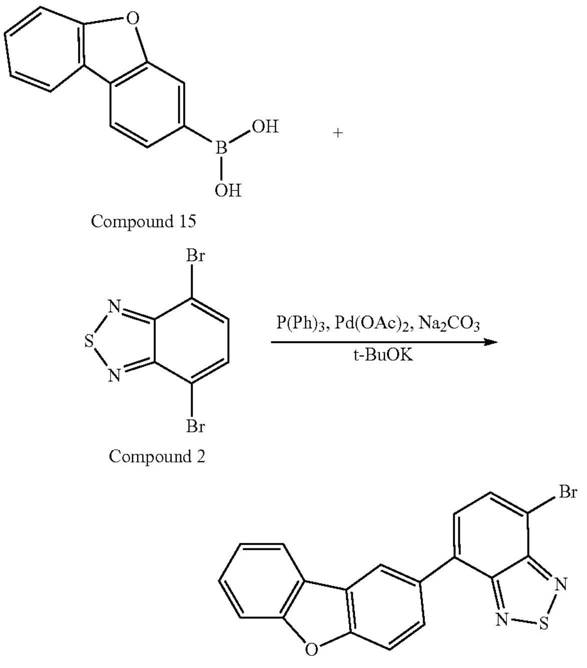

Compound 15

Compound 2

Compound 16

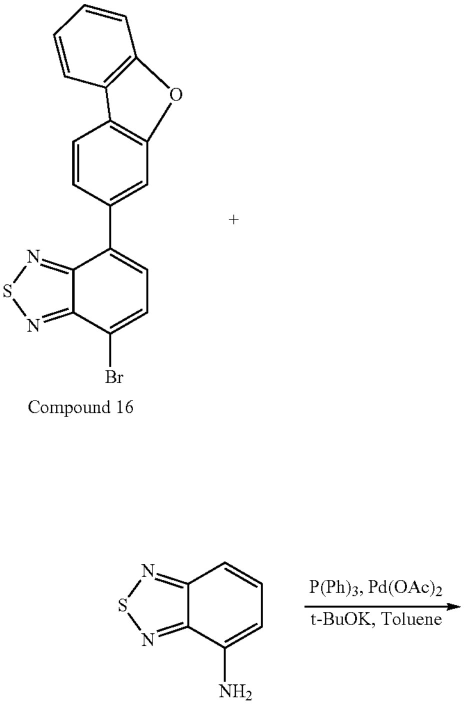

Compound 16

Compound 4

-continued

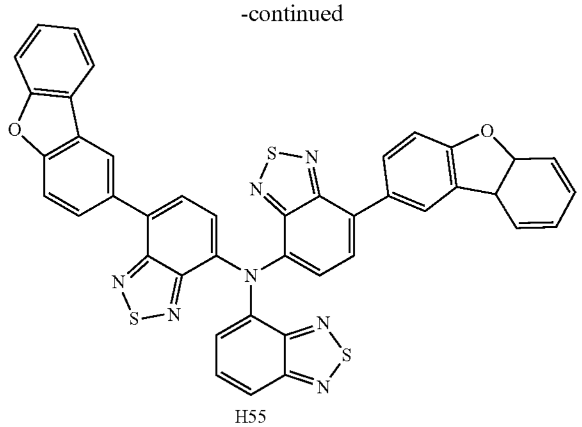

H55

After a compound 2 (0.5 mmol), a compound 15 (0.5 mmol), $P(ph)_3$ (0.15 mmol), $Pd(OAc)_2$ (0.2 mmol), t-BuOK (0.15 mmol), and $Na_2CO_3$ (0.15 mmol) were added to toluene (3 mL) and mixed uniformly, the mixture was put into a 50 mL flask and reacted at 80° C. for 12 hours. After the reaction was completed, the solution was cooled to room temperature, followed by slowly adding a saturated aqueous $MgSO_4$ solution and ethyl acetate to the solution for extraction three times. The organic layers were collected and then the solvent was removed with a rotary evaporator. After purification by column chromatography, a compound 16 was obtained.

After the compound 16 (1 mmol), a compound 4 (0.5 mmol), $P(ph)_3$ (0.15 mmol), $Pd(OAc)_2$ (0.2 mmol), and t-BuOK (0.15 mmol) were added to toluene (3 mL) and mixed uniformly, the mixture was put into a 50 mL flask and reacted at 80° C. for 12 hours. After the reaction was completed, the solution was cooled to room temperature, followed by slowly adding a saturated aqueous $MgSO_4$ solution and ethyl acetate to the solution for extraction three times. The organic layers were collected and then the solvent was removed with the rotary evaporator. After purification by column chromatography, a compound H55 was obtained.

The following were obtained by matrix-assisted laser desorption ionization time-of-flight mass spectrometry (MALDI-TOF MS) (m/z): calculated value 753.1; test value 753.0.

Elemental analysis results: theoretical values: C, 66.91: H, 3.08; N, 13.01; 0, 4.24; S, 12.76. Actual values: C, 66.90; H, 3.07; N, 13.0; 0, 4.24; S, 12.79.

Example 1-8: Synthesis of Compound H01

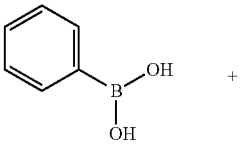

+

Compound 17

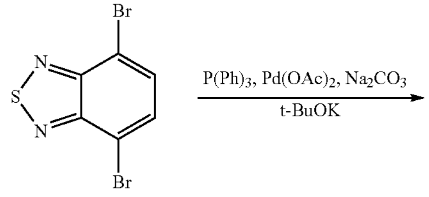

Compound 2

-continued

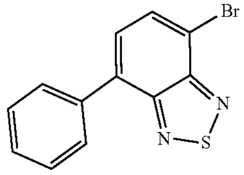

Compound 18

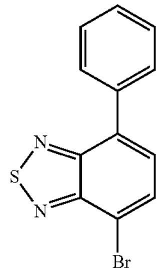

+

Compound 18

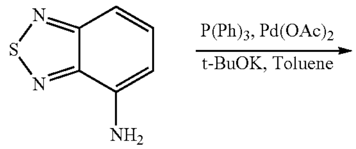

Compound 4

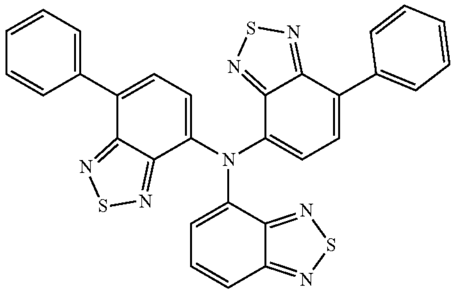

H01

After a compound 2 (0.5 mmol), a compound 17 (0.5 mmol), $P(ph)_3$ (0.15 mmol), $Pd(OAc)_2$ (0.2 mmol), t-BuOK (0.15 mmol), and $Na_2CO_3$ (0.15 mmol) were added to toluene (3 mL) and mixed uniformly, the mixture was put into a 50 mL flask and reacted at 80° C. for 12 hours. After the reaction was completed, the solution was cooled to room temperature, followed by slowly adding a saturated aqueous $MgSO_4$ solution and ethyl acetate to the solution for extraction three times, the solvent was removed with a rotary evaporator. After purification by column chromatography, a compound 18 was obtained.

After the compound 18 (1 mmol), a compound 4 (0.5 mmol), $P(ph)_3$ (0.15 mmol), $Pd(OAc)_2$ (0.2 mmol), and t-BuOK (0.15 mmol) were added to toluene (3 mL) and mixed uniformly, the mixture was put into a 50 mL flask and reacted at 80° C. for 12 hours. After the reaction was completed, the solution was cooled to room temperature, followed by slowly adding a saturated aqueous $MgSO_4$ solution and ethyl acetate to the solution for extraction three times. The organic layers were collected and then the solvent was removed with the rotary evaporator. After purification by column chromatography, a compound H01 was obtained.

The following were obtained by matrix-assisted laser desorption ionization time-of-flight mass spectrometry (MALDI-TOF MS) (m/z): calculated value 571.7; test value 571.5.

Elemental analysis results: theoretical values: C, 63.03; H, 3.00; N, 17.15; S, 16.83. Actual values: C, 63.02; H, 2.99; N, 17.15; S, 16.82.

Comparative Example 1-1

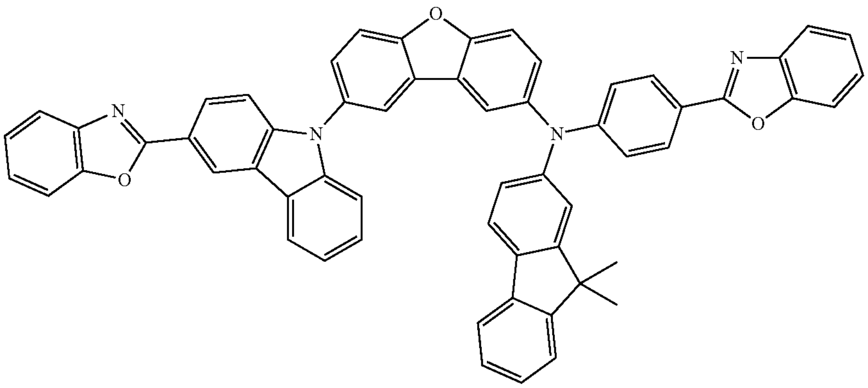

Compound C1

Comparative Example 1-2

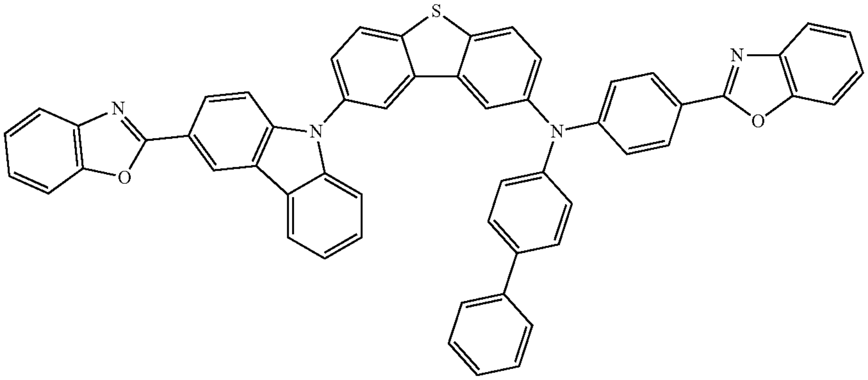

Compound C2

Characterization of Refractive Index

The refractive indexes of the compounds at the wavelengths of 460 nm, 530 nm and 620 nm were tested by an ellipsometer (model ALPHA-SE), and the difference between the refractive index at the wavelength of 460 nm and the refractive index at the wavelength of 530 nm $\Delta n_1$ ($\Delta n_1 = n_{460\ nm} - n_{530\ nm}$), the difference between the refractive index at the wavelength of 530 nm and the refractive index at the wavelength of 620 nm $\Delta n_2$ ($\Delta n_1 = n_{530\ nm} - n_{620\ nm}$), and the difference between the refractive index at the wavelength of 460 nm and the refractive index at the wavelength of 620 nm $\Delta n_3$ ($\Delta n_1 = n_{460\ nm} - n_{620\ nm}$) were obtained by calculation. The test results were shown in Table 1.

TABLE 1

| Number | Compound | $n_{460\ nm}$ | $n_{530\ nm}$ | $n_{620\ nm}$ | $\Delta n_1$ | $\Delta n_2$ | $\Delta n_3$ |
|---|---|---|---|---|---|---|---|
| Example 1-1 | H02 | 2.21 | 2.08 | 2.03 | 0.13 | 0.05 | 0.18 |
| Example 1-2 | H09 | 2.20 | 2.07 | 2.01 | 0.13 | 0.06 | 0.19 |
| Example 1-3 | H24 | 2.18 | 2.07 | 2.00 | 0.11 | 0.07 | 0.18 |
| Example 1-4 | H52 | 2.31 | 2.16 | 2.08 | 0.15 | 0.08 | 0.23 |
| Example 1-5 | H53 | 2.18 | 2.06 | 1.99 | 0.12 | 0.07 | 0.19 |
| Example 1-6 | H54 | 2.30 | 2.17 | 2.10 | 0.13 | 0.07 | 0.20 |
| Example 1-7 | H55 | 2.21 | 2.06 | 1.97 | 0.15 | 0.09 | 0.24 |

TABLE 1-continued

| Number | Compound | $n_{460\ nm}$ | $n_{530\ nm}$ | $n_{620\ nm}$ | $\Delta n_1$ | $\Delta n_2$ | $\Delta n_3$ |
|---|---|---|---|---|---|---|---|
| Example 1-8 | H01 | 2.15 | 2.02 | 1.94 | 0.13 | 0.08 | 0.21 |
| Comparative Example 1-1 | C1 | 2.18 | 2.00 | 1.93 | 0.18 | 0.07 | 0.25 |
| Comparative Example 1-2 | C2 | 2.20 | 2.05 | 1.93 | 0.15 | 0.12 | 0.27 |

It can be seen from Table 1 that the compounds provided by the present applications had a relatively high refractive index at the wavelength of 460 nm, and the differences between the refractive indexes at the wavelengths of 460 nm, 530 nm and 620 nm were all small. The compounds provided by the present application further satisfied: the difference between the refractive index at the wavelength of 460 nm and the refractive index at the wavelength of 530 nm was between 0.09 and 0.17; the difference between the refractive index at the wavelength of 530 nm and the refractive index at the wavelength of 620 was between 0.03 and 0.11; and the difference between the refractive index at the wavelength of 460 nm and the refractive index at the wavelength of 620 nm was between 0.15 and 0.24. Therefore, the compounds provided by the present application can effectively improve the color shift of a device at multi-angle display.

The differences between the refractive indexes of the compound C 1 and the compound C2 at the wavelengths of 460 nm, 530 nm and 620 nm were relatively large, which was not conducive to improving the color shift of the device at multi-angle display.

Examples 2-1 to 2-16

The compounds synthesized in Examples 2-1 to 2-16 were shown in Table 2. The synthesis methods for the compounds may refer to the synthesis methods shown in Examples 1-4 to 1-7, except that the types of raw compounds 2 and 4 in Examples 1-4 to 1-7 were changed. Details were shown in Table 2. The method for testing the refractive index of each compound was the same as that of Examples 1-1 to 1-8.

TABLE 2

| Number | Raw compound 2 | Raw compound 4 | Compound | $n_{46nm}$ | $n_{530nm}$ | $n_{620nm}$ | $\Delta n_1$ | $\Delta n_2$ | $\Delta n_3$ |
|---|---|---|---|---|---|---|---|---|---|
| Example 2-1 | 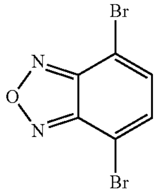 [SMILES: Brc1ccc(Br)c2nonc12] | 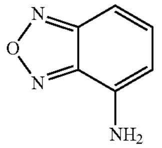 | H111 | 2.39 | 2.28 | 2.19 | 0.11 | 0.09 | 0.20 |
| Example 2-2 | 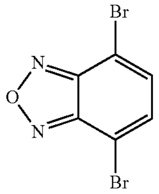 [SMILES: Brc1ccc(Br)c2nonc12] | 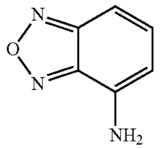 | H112 | 2.58 | 2.49 | 2.40 | 0.09 | 0.09 | 0.18 |
| Example 2-3 | 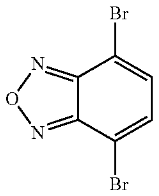 [SMILES: Brc1ccc(Br)c2nonc12] | 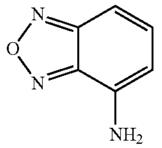 | H113 | 2.61 | 2.50 | 2.41 | 0.11 | 0.09 | 0.20 |
| Example 2-4 | 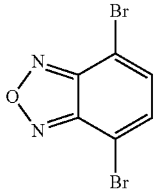 [SMILES: Brc1ccc(Br)c2nonc12] | 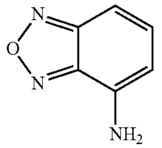 | H114 | 2.33 | 2.23 | 2.14 | 0.10 | 0.09 | 0.19 |
| Example 2-5 | 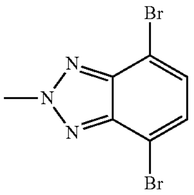 | 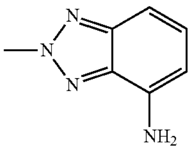 | H170 | 2.21 | 2.10 | 2.00 | 0.11 | 0.10 | 0.21 |
| Example 2-6 | 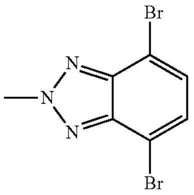 | 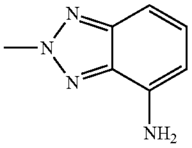 | H171 | 2.35 | 2.26 | 2.15 | 0.09 | 0.11 | 0.20 |

TABLE 2-continued
| Number | Raw compound 2 | Raw compound 4 | Compound | $n_{46nm}$ | $n_{530nm}$ | $n_{620nm}$ | $\Delta n_1$ | $\Delta n_2$ | $\Delta n_3$ |
|---|---|---|---|---|---|---|---|---|---|
| Example 2-7 | 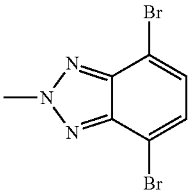 | 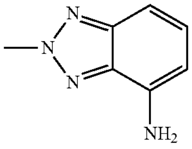 | H172 | 2.24 | 2.15 | 2.04 | 0.09 | 0.11 | 0.20 |
| Example 2-8 | 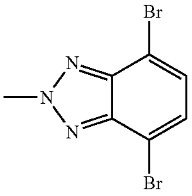 | 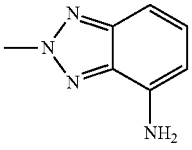 | H173 | 2.35 | 2.25 | 2.15 | 0.10 | 0.10 | 0.20 |
| Example 2-9 | 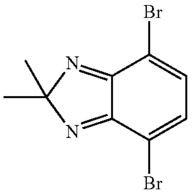 | 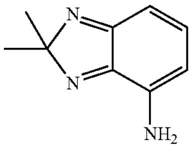 | H229 | 2.54 | 2.44 | 2.35 | 0.10 | 0.09 | 0.19 |
| Example 2-10 | 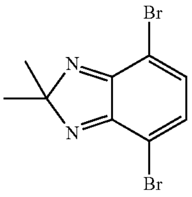 | 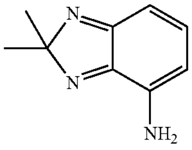 | H230 | 2.32 | 2.21 | 2.10 | 0.11 | 0.11 | 0.22 |
| Example 2-11 | 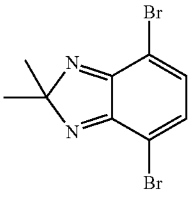 | 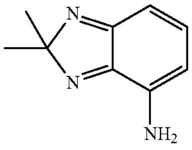 | H231 | 2.39 | 2.28 | 2.20 | 0.11 | 0.08 | 0.19 |
| Example 2-12 | 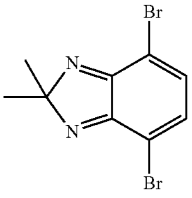 | 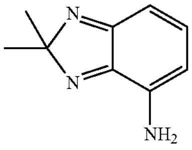 | H232 | 2.42 | 2.30 | 2.21 | 0.12 | 0.09 | 0.21 |
| Example 2-13 | 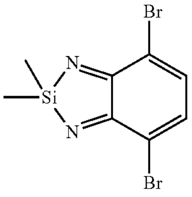 | 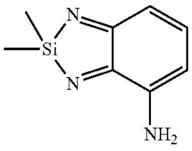 | H288 | 2.26 | 2.15 | 2.04 | 0.11 | 0.11 | 0.22 |

TABLE 2-continued

| Number | Raw compound 2 | Raw compound 4 | Compound | $n_{46nm}$ | $n_{530nm}$ | $n_{620nm}$ | $\Delta n_1$ | $\Delta n_2$ | $\Delta n_3$ |
|---|---|---|---|---|---|---|---|---|---|
| Example 2-14 | 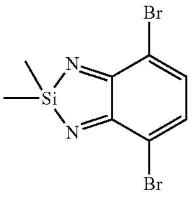 | 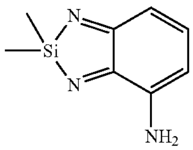 | H289 | 2.30 | 2.19 | 2.10 | 0.11 | 0.09 | 0.20 |
| Example 2-15 | 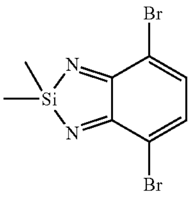 | 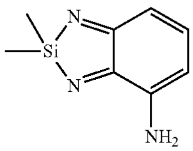 | H290 | 2.39 | 2.30 | 2.21 | 0.09 | 0.09 | 0.18 |
| Example 2-16 | 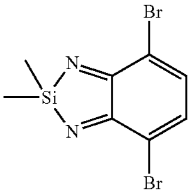 | 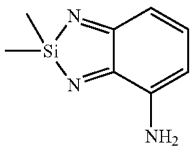 | H291 | 2.21 | 2.11 | 2.01 | 0.10 | 0.10 | 0.20 |

It can be seen from Table 2 that the compounds provided by the present application had a relatively high refractive index at the wavelength of 460 nm, and the differences between the refractive indexes at the wavelengths of 460 nm, 530 nm and 620 nm were all small.

The following lists several examples in which the compound described in the present application was used in an organic electroluminescent device.

Example 3-1

The structure of an organic electroluminescent device is shown in FIG. 1, including a substrate 1, an anode 2, a hole injection layer 3, a first hole transport layer 4, a second hole transport layer 5, a luminescent layer 6, a first electron transport layer 7, a second electron transport layer 8, a cathode 9 and a first capping layer 10 laminated in sequence.

The specific manufacturing steps of the above organic electroluminescent device were as follows:

1) A glass substrate (15 nm thick) with an indium tin oxide (ITO) anode 2 was cut into a size of 50 mm×50 mm×0.7 mm, ultrasonically treated in isopropanol and deionized water respectively for 30 minutes, and then exposed to ozone for about 10 min for cleaning, and the cleaned substrate 1 was installed on vacuum deposition equipment;
2) On the ITO anode 2, a hole injection material compound b and a p-type doping material compound a (at doping ratio of 3%, mass ratio) were evaporated and deposited in vacuum to form and serve as a hole injection layer 3 with a thickness of 5 nm;
3) A hole transport material compound b was evaporated and deposited in vacuum on the hole injection layer 3 to form and serve as a first hole transport layer 4 with a thickness of 100 nm;
4) A hole transport material compound c was evaporated and deposited in vacuum on the first hole transport layer 4 to form and serve as a second hole transport layer 5 with a thickness of 5 nm;
5) A luminescent layer 6 was evaporated and deposited in vacuum on the second hole transport layer 5, with compound d as a host material, compound e as a doping material at a doping ratio of 3% (mass ratio), and had a thickness of 30 nm;
6) An electron transport material compound f was evaporated and deposited in vacuum on the luminescent layer 6 to form and serve as a first electron transport layer 7 with a thickness of 30 nm;
7) An electron transport material compound g and an n-type doping material compound h (at a doping mass ratio of 1:1) were co-evaporated and deposited in vacuum on the first electron transport layer 7 to form and serve as a second electron transport layer 8 with a thickness of 5 nm;
8) A magnesium-silver electrode (the mass ratio of Mg and Ag was 9:1) was evaporated and deposited in vacuum on the second electron transport layer 8 to form and serve as a cathode 9 with a thickness of 10 nm; and
9) The compound H02 provided by the present application was evaporated and deposited in vacuum on the cathode 9 to form and serve as a capping layer 10 with a thickness of 100 nm.

-continued
Compound a
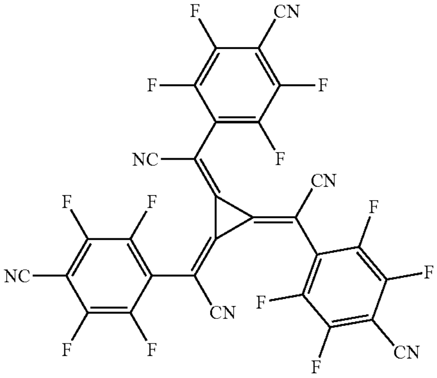
Compound b
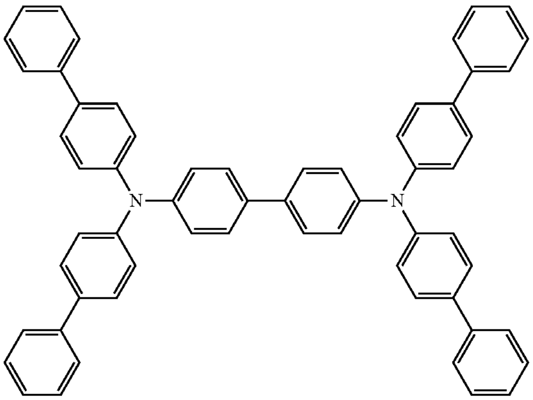
Compound c
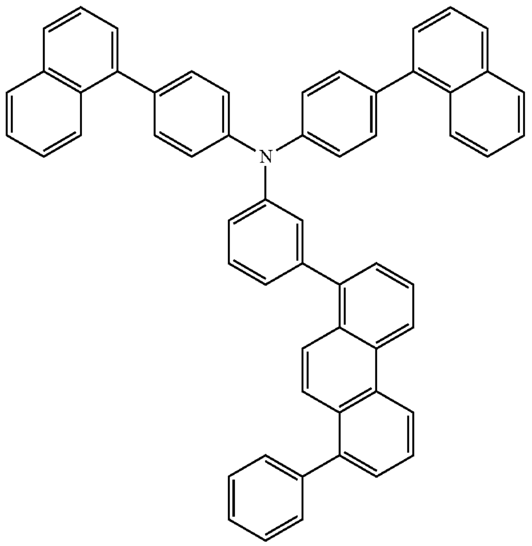
Compound d
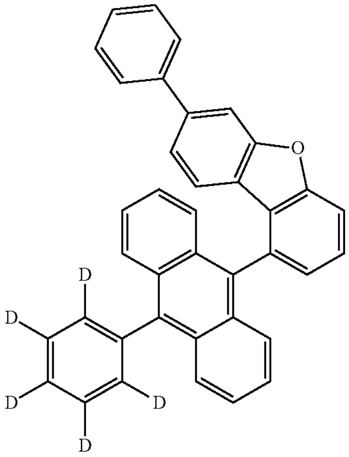
Compound e
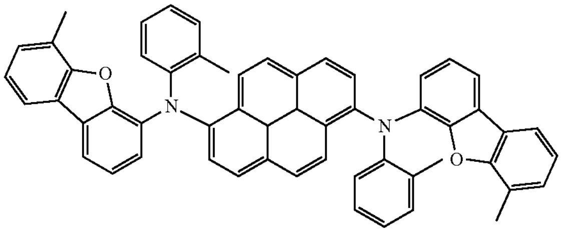
Compound f
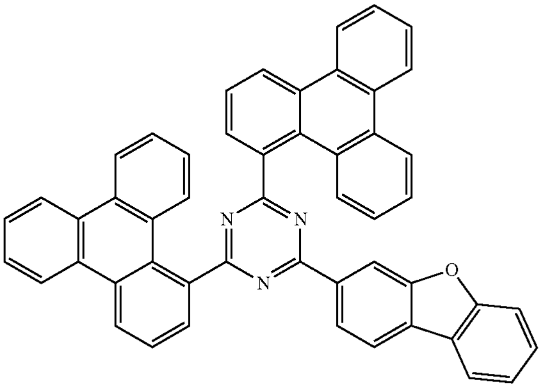
Compound g
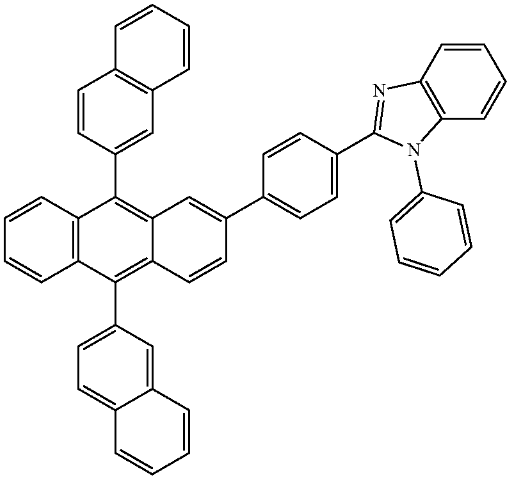

-continued

Compound h

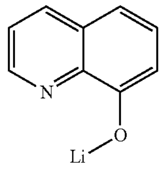

Examples 3-2 to 3-8

The methods for manufacturing organic electroluminescent devices were similar to the method in Example 3-1, except that in step 9), the compound H02 was replaced with the compounds provided in Examples 1-2 to 1-8, respectively.

Comparative Example 3-1

The methods for manufacturing organic electroluminescent devices were similar to the method in Example 3-1, except that in step 9), the compound H02 was replaced with the compound C1 in Comparative Example 1-1.

Comparative Example 3-2

The methods for manufacturing organic electroluminescent devices were similar to the method in Example 3-1, except that in step 9), the compound H02 was replaced with the compound C2 in Comparative Example 1-2.

Evaluation on the Performance of Organic Electroluminescent Device

Currents of an organic electroluminescent device at different voltages were tested with a Keithley 2365A digital nanovoltmeter, and then the currents were divided by a light emitting area to obtain current densities at different voltages. The brightnesses and radiant flux densities of the organic electroluminescent device at different voltages were tested with a Konicaminolta CS-2000 spectroradiometer, and a working voltage $V_{on}$ (V), a current efficiency CE (cd/A), an external quantum efficiency $EQE_{(max)}$ and a life LT95 at the same current density (10 mA/cm 2) were obtained according to the current densities and brightnesses at different voltages (the life LT95 was obtained by measuring the time when the brightness of the organic electroluminescent device reached 95% of the initial brightness under the test condition of 50 mA/cm 2). The results were shown in Table 3.

TABLE 3

| Number | Compound | $V_{on}$ (V) | CE (cd/A) | $EQE_{(max)}$ (%) | LT95 (h) |
|---|---|---|---|---|---|
| Example 3-1 | H02 | 3.42 | 7.79 | 17.5 | 68 |
| Example 3-2 | H09 | 3.41 | 7.62 | 18.1 | 71 |
| Example 3-3 | H24 | 3.36 | 7.86 | 18.3 | 70 |
| Example 3-4 | H52 | 3.41 | 7.90 | 18.1 | 69 |
| Example 3-5 | H53 | 3.36 | 7.70 | 18.2 | 68 |
| Example 3-6 | H54 | 3.35 | 7.85 | 17.9 | 68 |
| Example 3-7 | H55 | 3.36 | 8.01 | 18.5 | 67 |
| Example 3-8 | H01 | 3.45 | 7.89 | 18.2 | 71 |
| Comparative Example 3-1 | C1 | 3.46 | 6.89 | 14.9 | 68 |
| Comparative Example 3-2 | C2 | 3.51 | 6.88 | 14.4 | 67 |

It can be seen from Table 3 that, when the compounds provided by the present application were used as a capping layer material of the organic electroluminescent device, the color shift of the device can be effectively reduced, meanwhile the current efficiency and external quantum efficiency of the device can be improved, and the device can also have a longer life.

Examples 4-1 to 4-11

The structure of an organic electroluminescent device is shown in FIG. 2, including a substrate 1, an anode 2, a hole injection layer 3, a first hole transport layer 4, a second hole transport layer 5, a luminescent layer 6, a first electron transport layer 7, a second electron transport layer 8, a cathode 9, a first capping layer 10 and a second capping layer 11.

The specific manufacturing steps of the above organic electroluminescent device were as follows:

1) A glass substrate (15 nm thick) with an indium tin oxide (ITO) anode 2 was cut into a size of 50 mm×50 mm×0.7 mm, ultrasonically treated in isopropanol and deionized water respectively for 30 minutes, and then exposed to ozone for about 10 min for cleaning, and the cleaned substrate 1 was installed on vacuum deposition equipment;
2) On the ITO anode 2, a hole injection material compound b and a p-type doping material compound a (at doping ratio of 3%, mass ratio) were evaporated and deposited in vacuum to form and serve as a hole injection layer 3 with a thickness of 5 nm;
3) A hole transport material compound b was evaporated and deposited in vacuum on the hole injection layer 3 to form and serve as a first hole transport layer 4 with a thickness of 100 nm;
4) A hole transport material compound c was evaporated and deposited in vacuum on the first hole transport layer 4 to form and serve as a second hole transport layer 5 with a thickness of 5 nm;
5) A luminescent layer 6 was evaporated and deposited in vacuum on the second hole transport layer 5, with compound d as a host material, compound e as a doping material at a doping ratio of 3% (mass ratio), and had a thickness of 30 nm;
6) An electron transport material compound f was evaporated and deposited in vacuum on the luminescent layer 6 to form and serve as a first electron transport layer 7 with a thickness of 30 nm;
7) An electron transport material compound g and an n-type doping material compound h (at a doping mass ratio of 1:1) were co-evaporated and deposited in vacuum on the first electron transport layer 7 to form and serve as a second electron transport layer 8 with a thickness of 5 nm;
8) A magnesium-silver electrode (the mass ratio of Mg and Ag was 9:1) was evaporated and deposited in vacuum on the second electron transport layer 8 to form and serve as a cathode 9 with a thickness of 10 nm;
9) The compound H02 provided by the present application was evaporated and deposited in vacuum on the cathode 9 to form and serve as a first capping layer 10 with a thickness of 100 nm; and
10) An organic small molecule material with a low refractive index was evaporated and deposited in vacuum on the first capping layer 10 to form and serve as a second capping layer 11 with a thickness of 20 nm.

The structures of the organic small molecule materials with low refractive indexes used in Examples 4-1 to 4-11 were respectively as follows:

D1
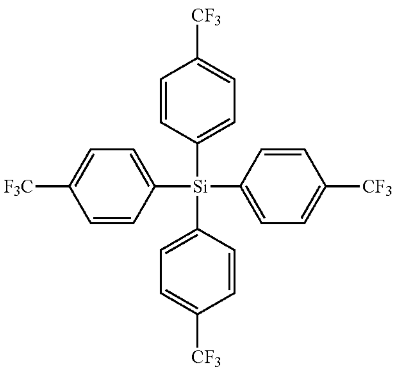
D2
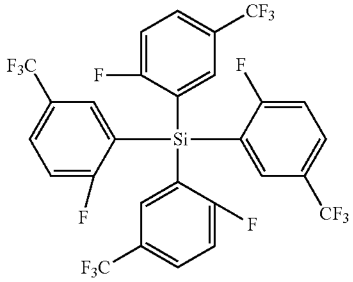
D3
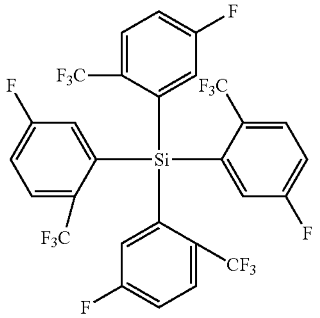
D4
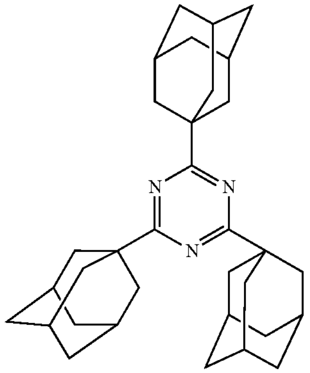
D5
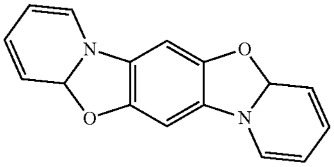
-continued
D6
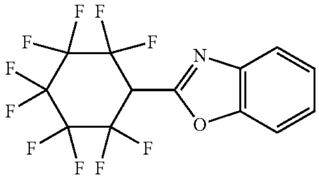
D7
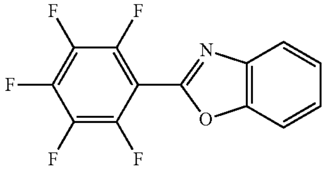
D8
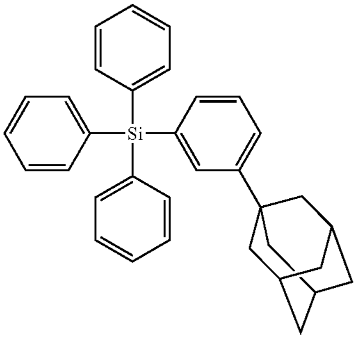
D9
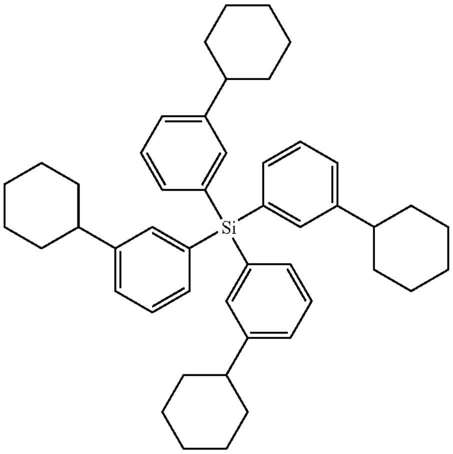
D10
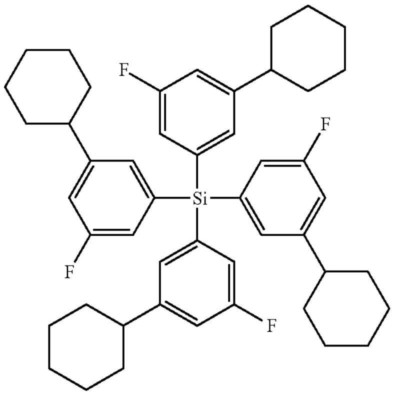

-continued

D11

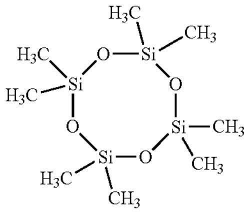

Example 4-12

The methods for manufacturing an organic electroluminescent device were similar to the method in Example 4-1, except that in step 9), the compound H02 was replaced with the compound H24.

Example 4-13

The methods for manufacturing an organic electroluminescent device were similar to the method in Example 4-1, except that in step 9), the compound H02 was replaced with the compound H53.

Example 4-14

The methods for manufacturing an organic electroluminescent device were similar to the method in Example 4-1, except that in step 9), the compound H02 was replaced with the compound H01.

Comparative Example 4-1

The method for manufacturing an organic electroluminescent device was similar to that in Example 4-1, except that in step 9), the compound H02 was replaced with the compound C1.

Comparative Example 4-2

The method for manufacturing an organic electroluminescent device was similar to that in Example 4-1, except that in step 9), the compound H02 was replaced with the compound C2.

The methods for testing the performances of the organic electroluminescent devices were the same as those in Examples 3-1 to 3-8, and the results were shown in Table 4.

TABLE 4

| Number | First capping layer material | Second capping layer material | CE (cd/A) | $EQE_{(max)}$ (%) |
|---|---|---|---|---|
| Example 4-1 | H02 | D1 | 7.85 | 19.2 |
| Example 4-2 | H02 | D2 | 7.88 | 19.3 |
| Example 4-3 | H02 | D3 | 7.88 | 19.6 |
| Example 4-4 | H02 | D4 | 7.86 | 19.2 |
| Example 4-5 | H02 | D5 | 7.87 | 19.1 |
| Example 4-6 | H02 | D6 | 7.87 | 19.0 |
| Example 4-7 | H02 | D7 | 7.89 | 19.4 |
| Example 4-8 | H02 | D8 | 7.87 | 19.1 |
| Example 4-9 | H02 | D9 | 7.86 | 19.0 |
| Example 4-10 | H02 | D10 | 7.96 | 19.5 |
| Example 4-11 | H02 | D11 | 8.01 | 20.1 |
| Example 4-12 | H24 | D1 | 7.92 | 19.2 |
| Example 4-13 | H53 | D1 | 7.89 | 18.9 |
| Example 4-14 | H01 | D1 | 7.95 | 18.9 |
| Comparative Example 4-1 | C1 | D1 | 6.94 | 15.2 |

TABLE 4-continued

| Number | First capping layer material | Second capping layer material | CE (cd/A) | $EQE_{(max)}$ (%) |
|---|---|---|---|---|
| Comparative Example 4-2 | C2 | DI | 6.93 | 14.9 |

It can be seen from Table 4 that, the matching of the compounds provided by the present application as the first capping layer material with the second capping layer material containing an organic small molecule material with a low refractive index was more conducive to improving the efficiency, especially the external quantum efficiency of the device than the matching of the compounds C1 and C2 with the second capping layer material containing an organic small molecule material with a low refractive index.

The compound of the present application and the application thereof are described by the above examples, but the present application is not limited to the above examples. In other words, it does not mean that the present application must rely on the above examples for implementation. Those skilled in the art should anticipate any improvements on the present application, equivalent replacements of raw materials used in the present application, addition of auxiliary ingredients, selection of specific methods, etc., all of which fall within the scope of protection and disclosure of the present application.

What is claimed is:

1. A compound having the structure shown in Formula 1,

Formula 1

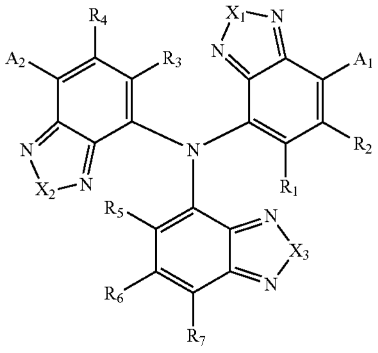

$A_1$ and $A_2$ each independently represent $-(L)_n-R$, where L each independently represents 6-membered to 60-membered divalent aryl unsubstituted or substituted by $R^a$ or 5-membered to 60-membered divalent heteroaryl unsubstituted or substituted by $R^a$, R represents 6-membered to 60-membered monovalent aryl unsubstituted or substituted by $R^a$ or 5-membered to 60-membered monovalent heteroaryl unsubstituted or substituted by $R^a$, and n represents 0, 1 or 2;

$R_1$, $R_2$, $R_3$, $R_4$, $R_5$, $R_6$, and $R_7$ each independently represent hydrogen, deuterium, tritium, a halogen atom or the following group unsubstituted or substituted by $R^a$:

C1-C20 monovalent alkyl, C1-C20 monovalent alkoxy, C1-C20 monovalent alkylthio, C2-C20 monovalent alkenyl, C2-C20 monovalent alkynyl, 3-membered to 20-membered monovalent alcyl, 3-membered to 20-membered monovalent heteroalcyl, 6-membered to 40-membered monovalent aryl, or 5-membered to 40-membered monovalent heteroaryl;

$X_1$, $X_2$, and $X_3$ all represent S or O; and $R^a$ represents deuterium, tritium, a halogen atom, cyano, nitro, carboxyl, carbonyl, amino, C1-C20 monovalent alkyl, C1-C20 monovalent alkoxy, C1-C20 monovalent alkylthio, C2-C20 monovalent alkenyl, C2-C20 monovalent alkynyl, 3-membered to 20-membered monovalent alcyl, 3-membered to 20-membered monovalent heteroalcyl, 6-membered to 40-membered monovalent aryl, or 5-membered to 40-membered monovalent heteroaryl, wherein one or more hydrogens of C1-C20 monovalent alkyl, C1-C20 monovalent alkoxy, C1-C20 monovalent alkylthio, C2-C20 monovalent alkenyl, C2-C20 monovalent alkynyl, 3-membered to 20-membered monovalent alcyl, 3-membered to 20-membered monovalent heteroalcyl, 6-membered to 40-membered monovalent aryl, or 5-membered to 40-membered monovalent heteroaryl each are independently replaced by deuterium, tritium, a halogen atom, cyano, nitro, carboxyl, carbonyl, or amino.

2. The compound according to claim 1, wherein heteroatoms in the heteroaryl or heteroalcyl comprise at least one of N, O, S, Si, or Se.

3. The compound according to claim 1, wherein $A_1$ and $A_2$ are the same.

4. The compound according to claim 1, wherein n represents 0 or 1.

5. The compound according to claim 1, wherein

L each independently represents phenyl, naphthyl, anthryl, phenanthryl, biphenyl, terphenyl, tetraphenyl, triphenylenyl, pyrenyl, chrysenyl, perylenyl, indenyl, triphenylenyl, fluorenyl, 9,9-dimethylfluorenyl, spirobifluorenyl, pyrrolyl, furanyl, thienyl, indolyl, benzofuranyl, benzothienyl, dibenzofuran, dibenzothiophene, carbazolyl, indenocarbazolyl, indolocarbazolyl, pyridyl, pyrimidinyl, pyrazinyl, pyridazinyl, triazinyl, oxazolyl, isooxazolyl, thiazolyl, isothiazolyl, benzoxazolyl, benzoisoxazolyl, benzothiazolyl, or benzoisothiazolyl unsubstituted or substituted by $R^a$, and R represents phenyl, naphthyl, anthryl, phenanthryl, biphenyl, terphenyl, tetraphenyl, triphenylenyl, pyrenyl, chrysenyl, perylenyl, indenyl, triphenylenyl, fluorenyl, 9,9-dimethylfluorenyl, spirobifluorenyl, pyrrolyl, furanyl, thienyl, indolyl, benzofuranyl, benzothienyl, dibenzofuran, dibenzothiophene, carbazolyl, indenocarbazolyl, indolocarbazolyl, pyridyl, pyrimidinyl, pyrazinyl, pyridazinyl, triazinyl, oxazolyl, isooxazolyl, thiazolyl, isothiazolyl, benzoxazolyl, benzoisoxazolyl, benzothiazolyl, or benzoisothiazolyl unsubstituted or substituted by $R^a$.

6. The compound according to claim 1, wherein n represents 0 or 1,

L represents phenyl, and

R represents phenyl, naphthyl, anthryl, phenanthryl, 9,9-dimethylfluorenyl, dibenzofuran, dibenzothiophene, carbazolyl, benzoxazolyl, or benzothiazolyl unsubstituted or substituted by $R^a$.

7. The compound according to claim 1, wherein $A_1$ and $A_2$ each independently represent any one of the following groups,

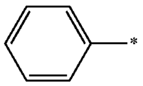
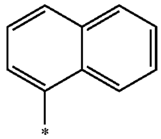
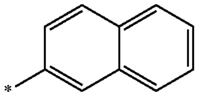
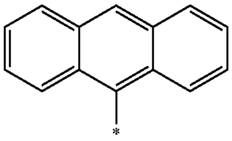
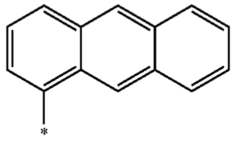
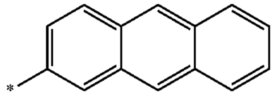
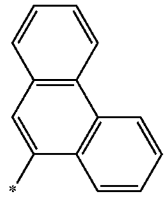
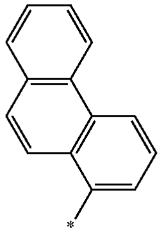
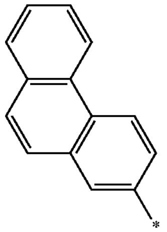
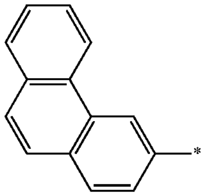
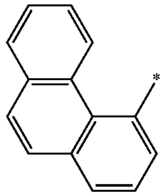
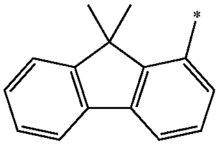
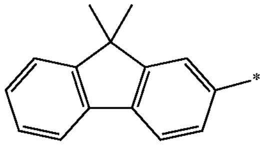
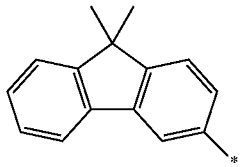
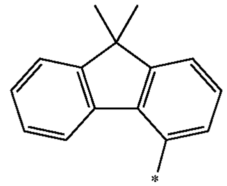
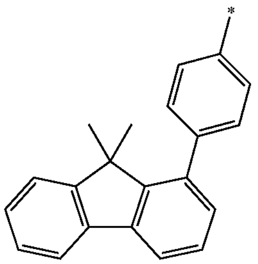
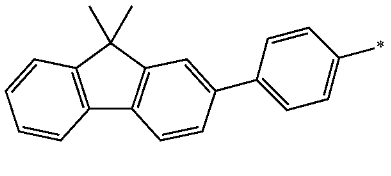

-continued

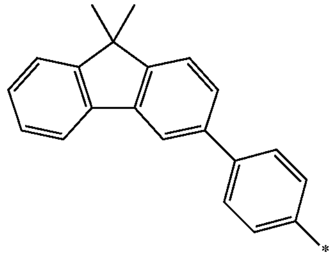

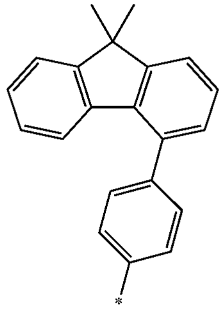

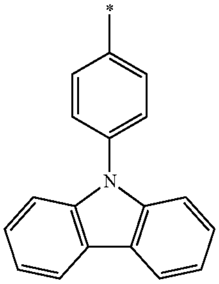

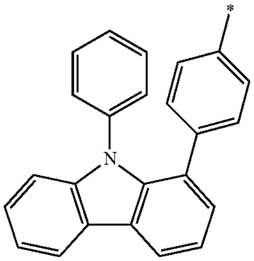

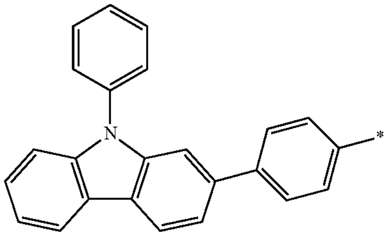

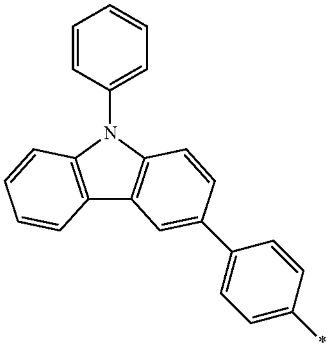

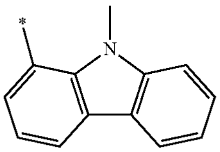

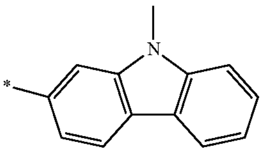

-continued

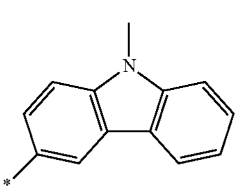

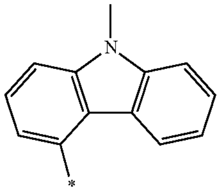

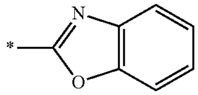

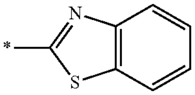

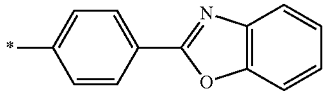

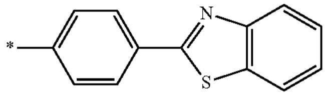

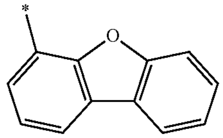

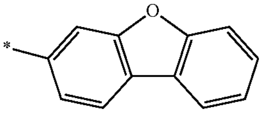

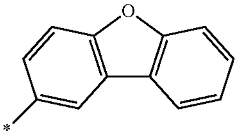

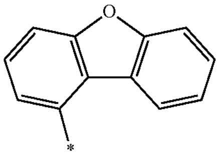

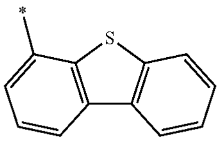

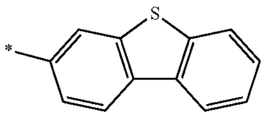

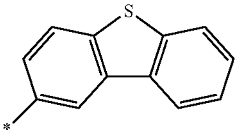

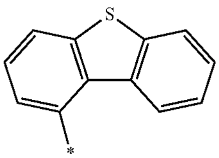

# represents an attachment position.

8. The compound according to claim 1, wherein $R_1$, $R_2$, $R_3$, $R_4$, $R_5$, $R_6$, and $R_7$ each independently represent hydrogen, deuterium, tritium, a halogen atom or the following group unsubstituted or substituted by $R^a$:

methyl, ethyl, propyl, butyl, methoxy, ethoxy, propoxy, cyclopropyl, cyclobutyl, cyclopentyl, cyclohexyl, tetrahydrofuranyl, tetrahydrothienyl, or phenyl.

9. The compound according to claim 1, wherein the compound is selected from any of the following, H01
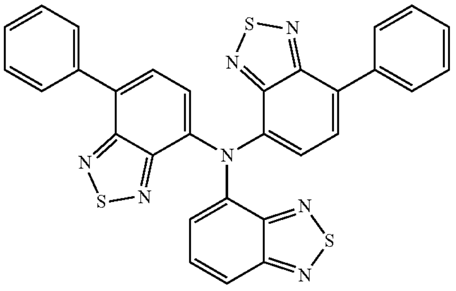
H02
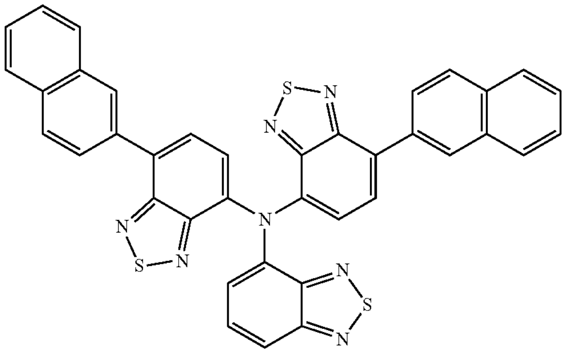
H03
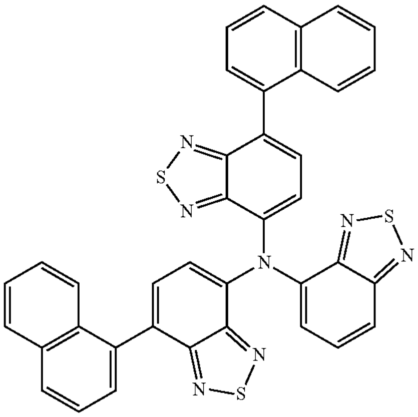
H04
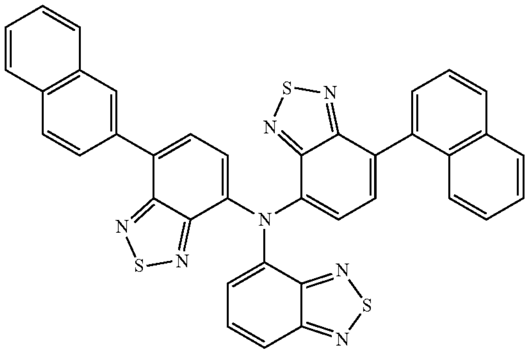
H05
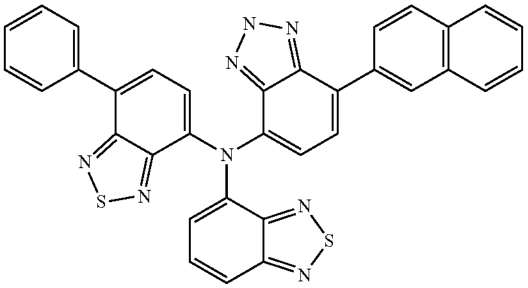
H06
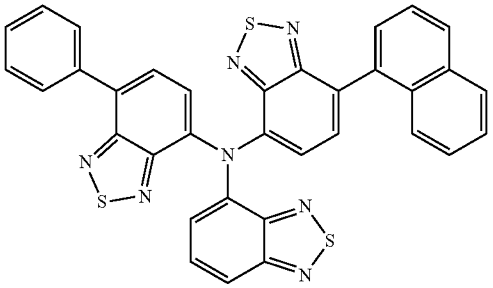
H07
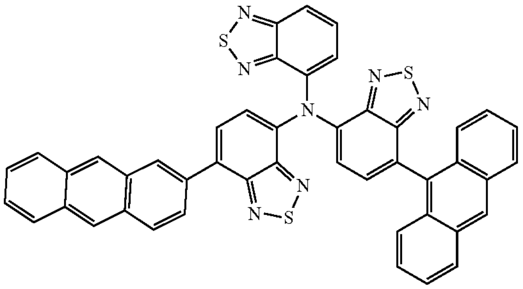
H08
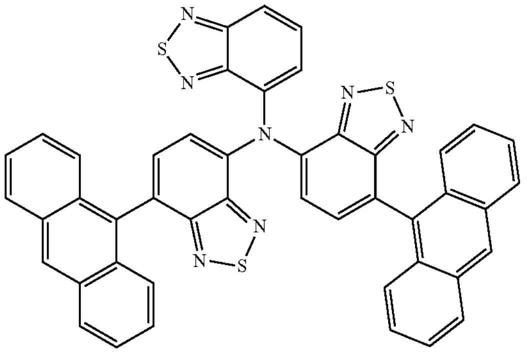

-continued
H09
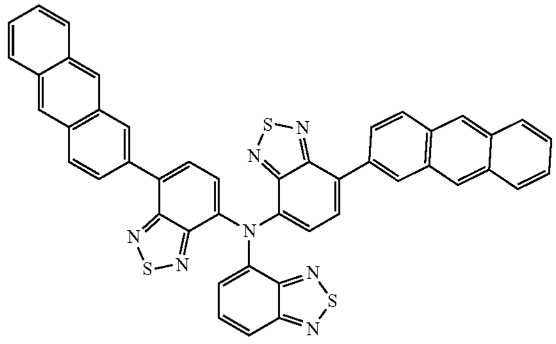
H10
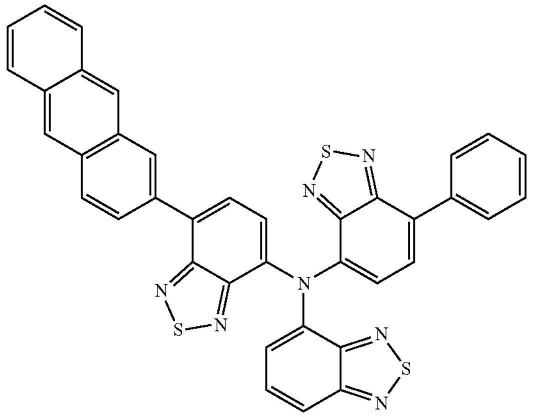
H11
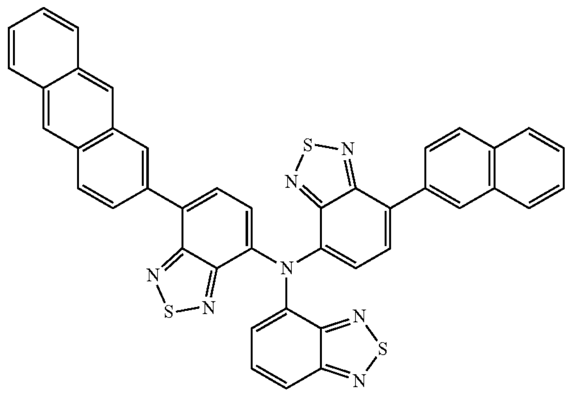
H12
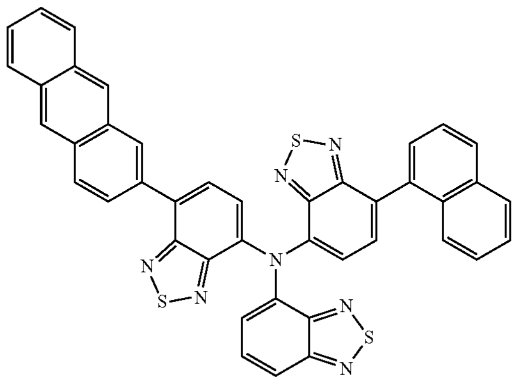
H13
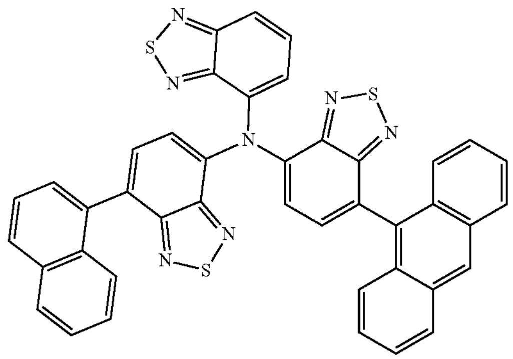
H14
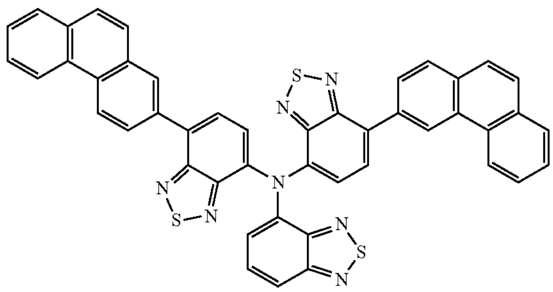
H15
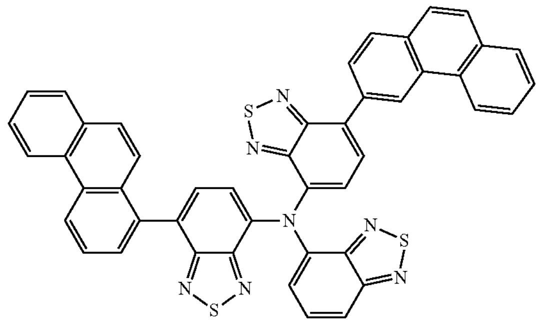
H16
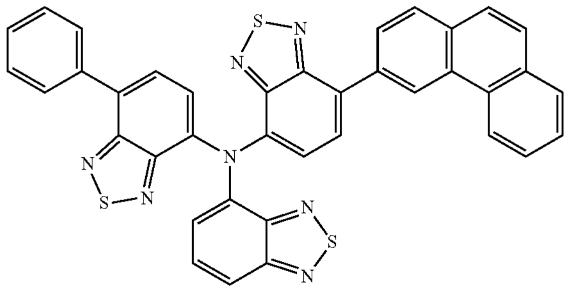

-continued
H17
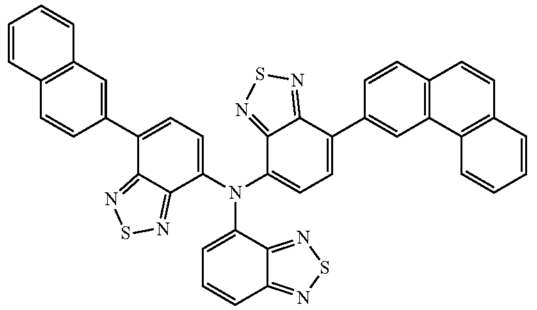
H18
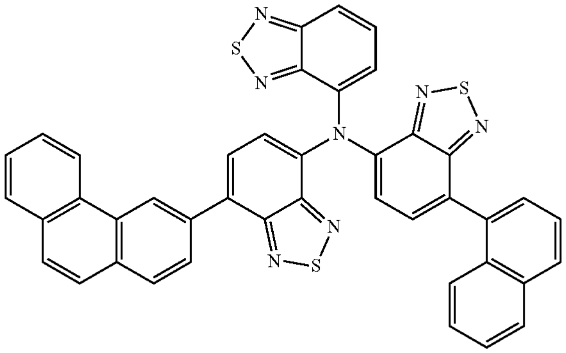
H19
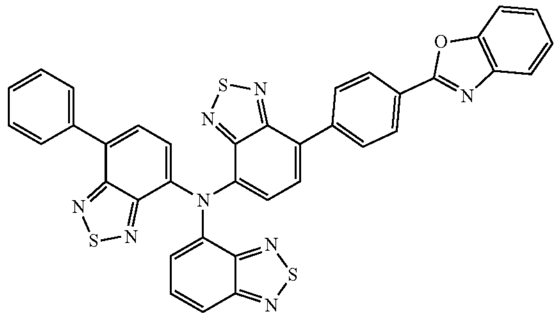
H20
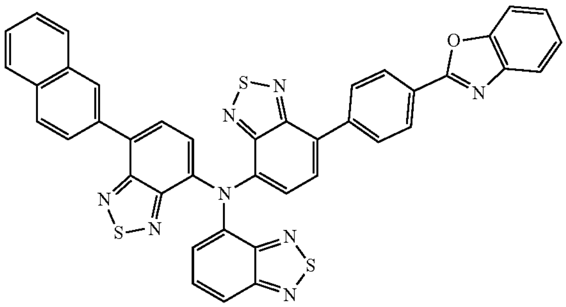
H21
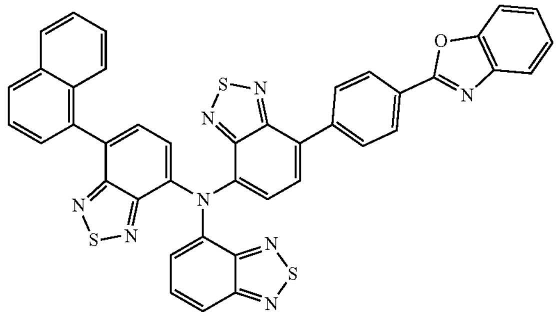
H22
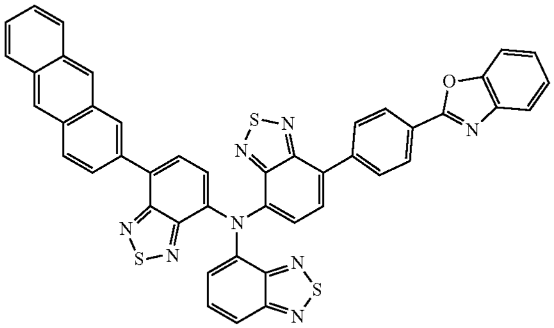
H23
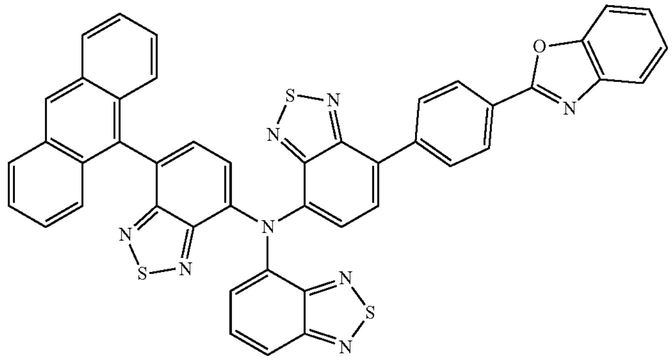

-continued
H24
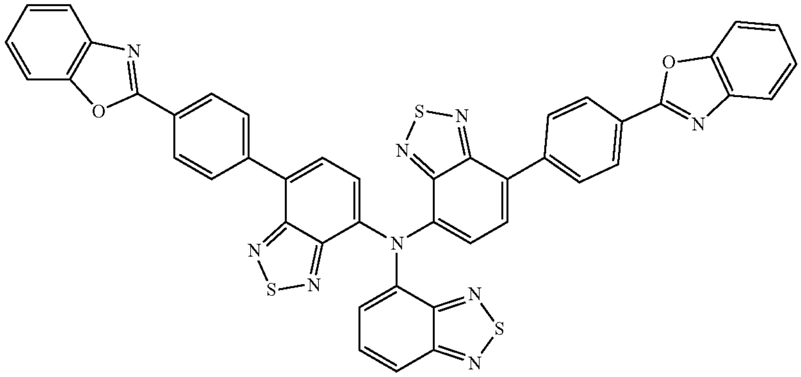
H25
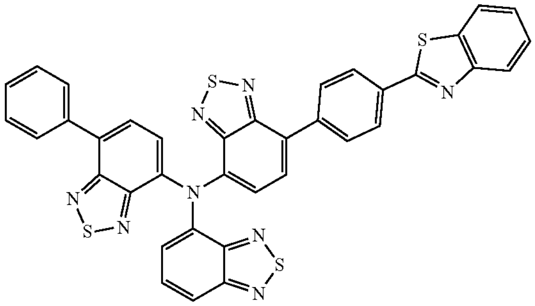
H26
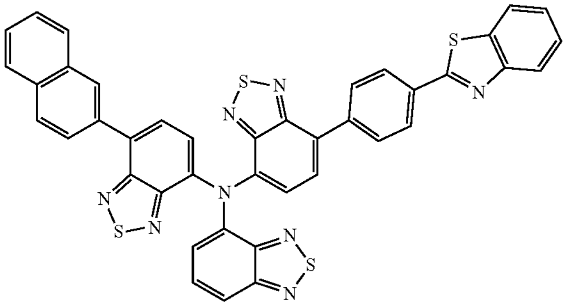
H27
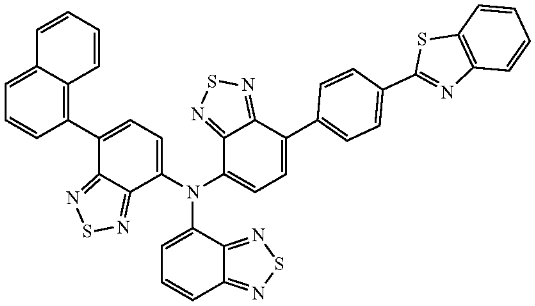
H28
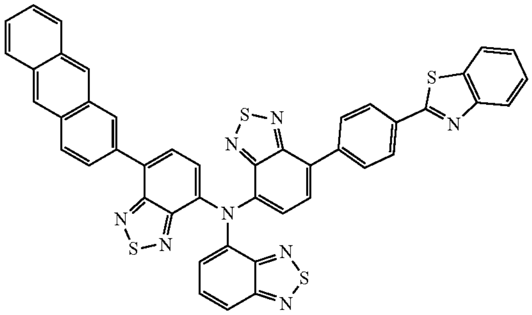
H29
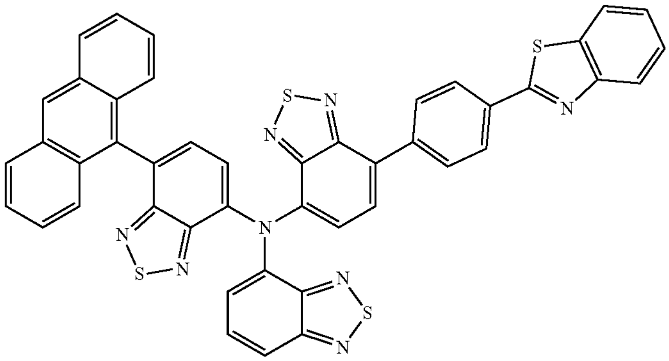

-continued
H30
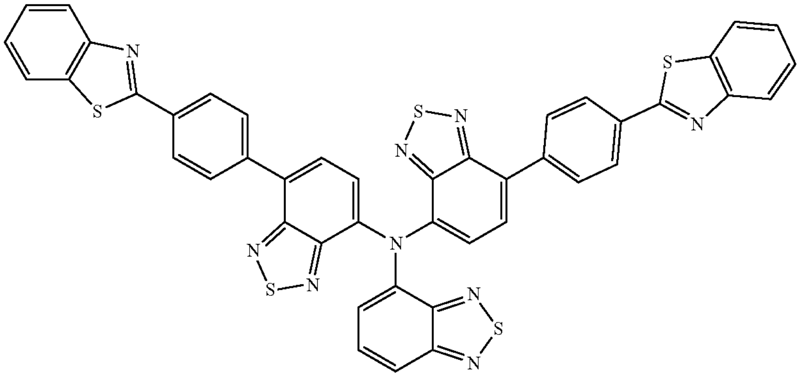
H31
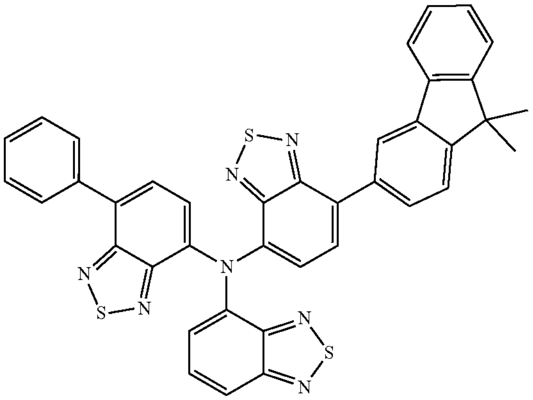
H32
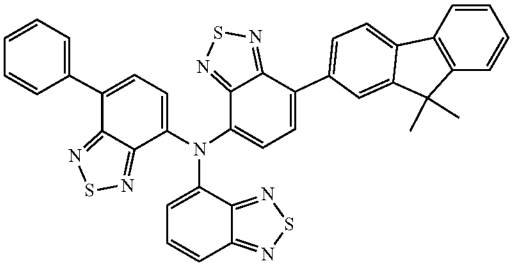
H33
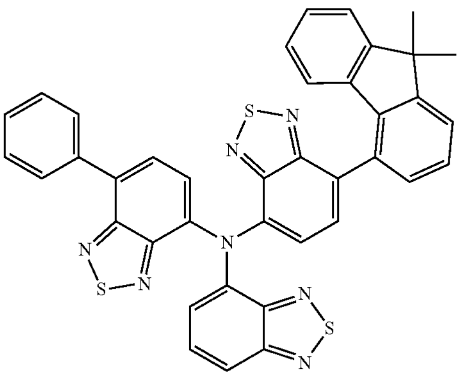
H34
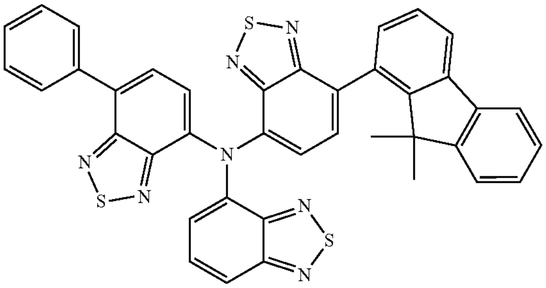
H35
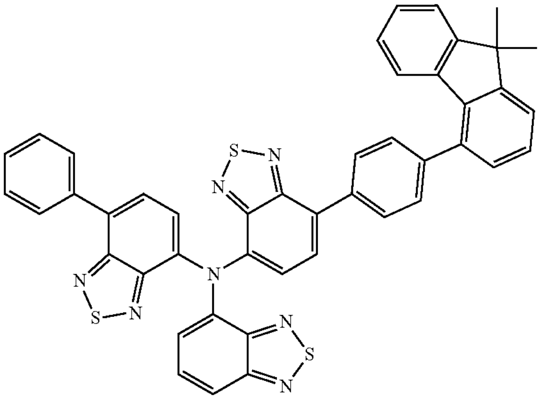
H36
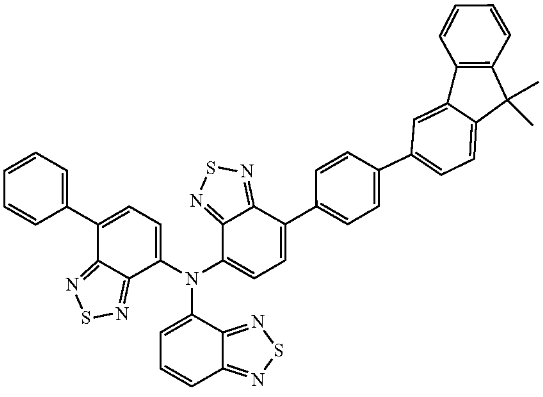

-continued
H37
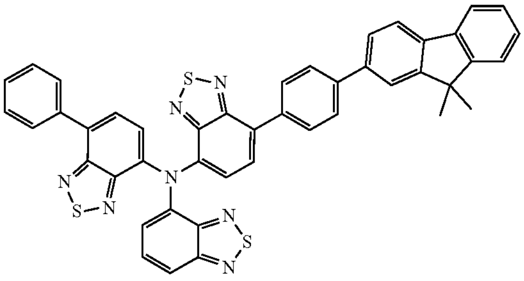
H38
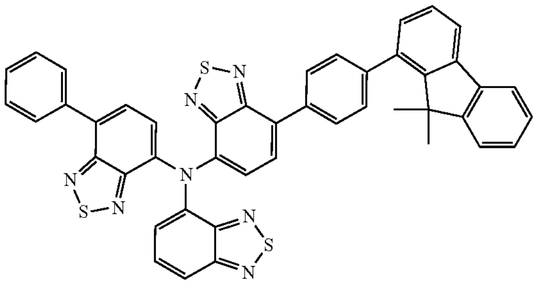
H39
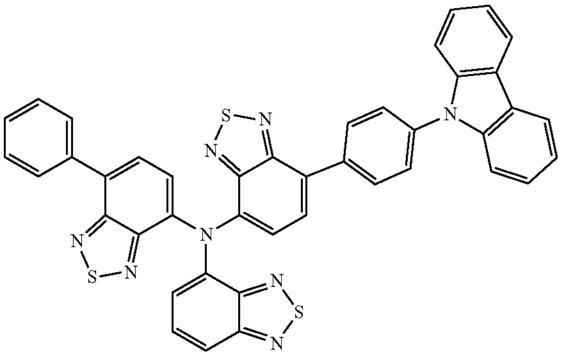
H40
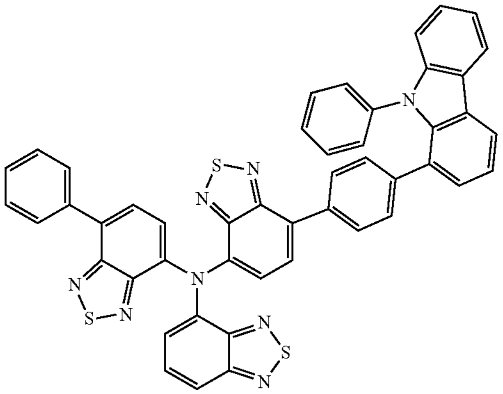
H41
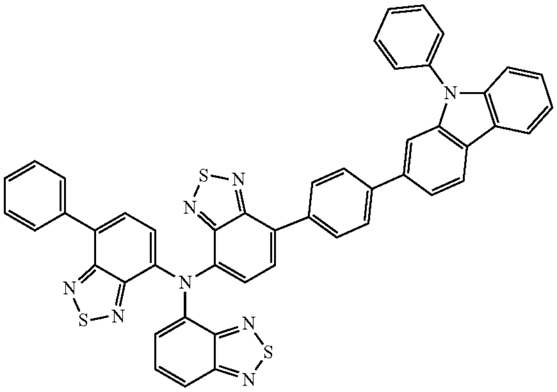
H42
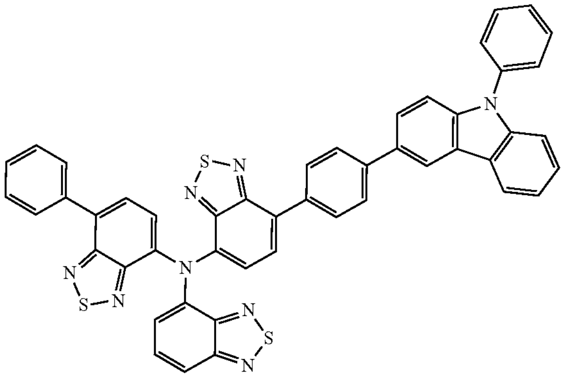
H43
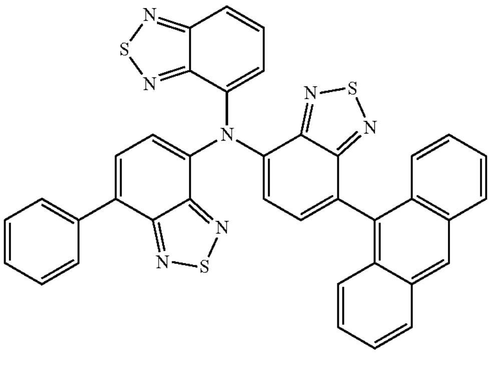
H44
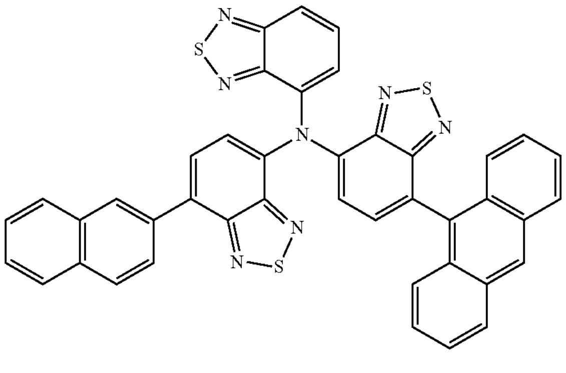

-continued
H45
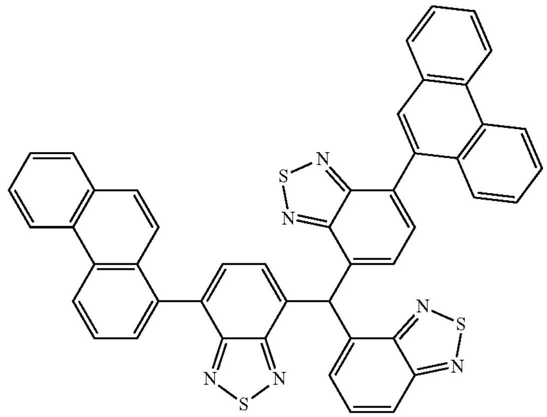
H46
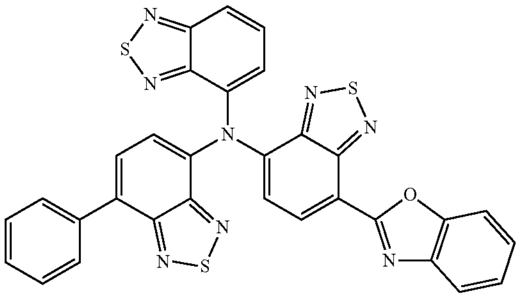
H47
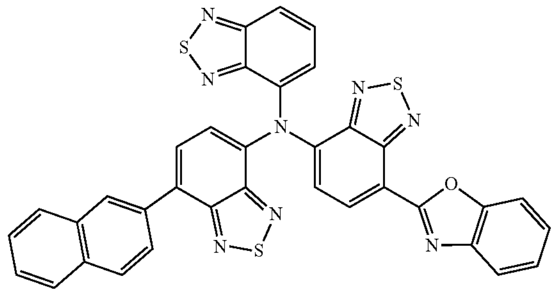
H48
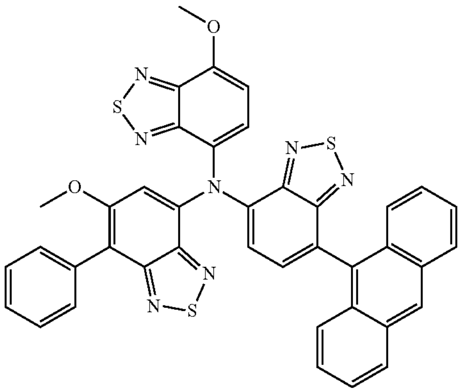
H49
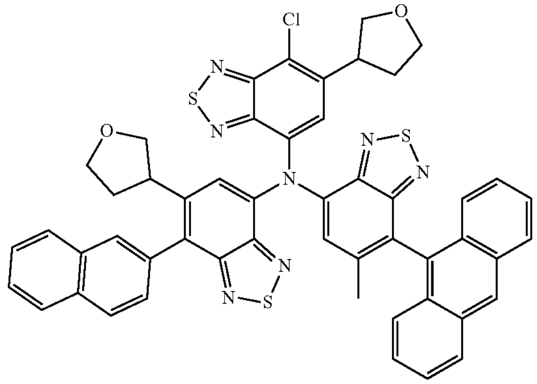
H50
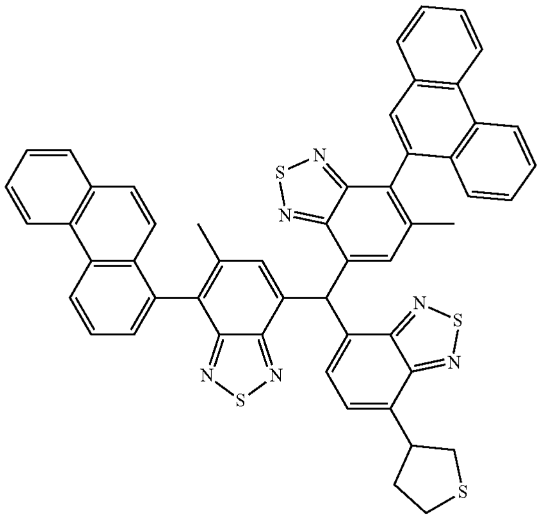

-continued
H51
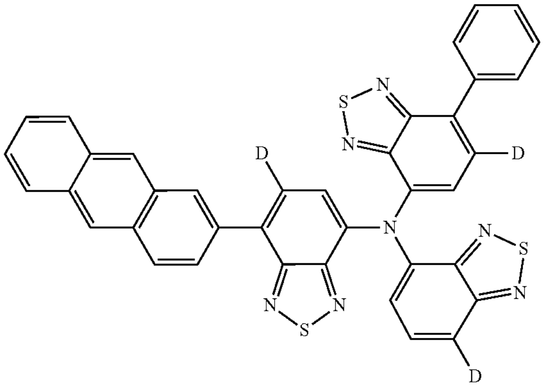
H52
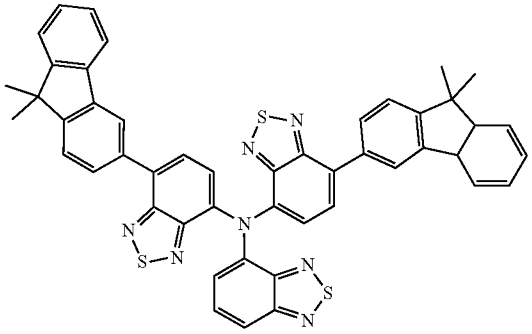
H53
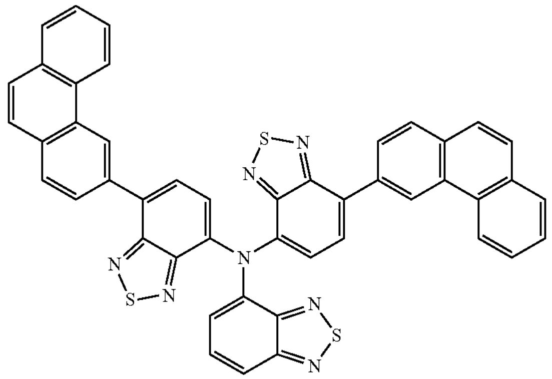
H54
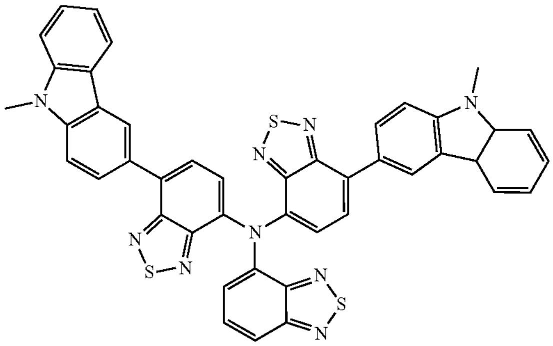
H55
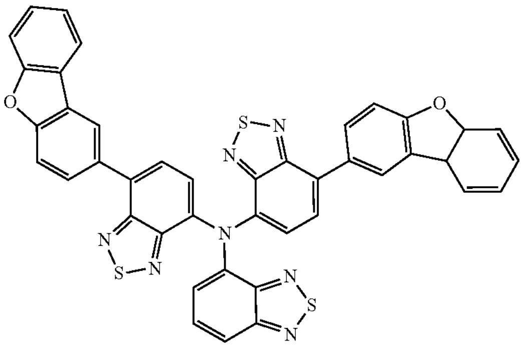
H56
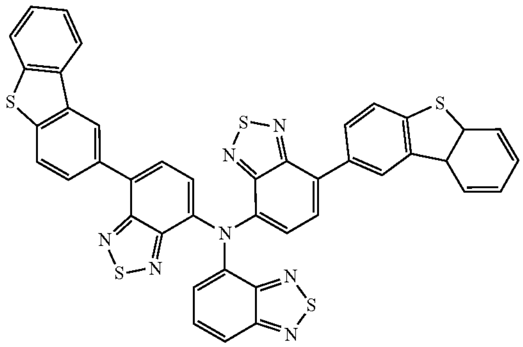
H57
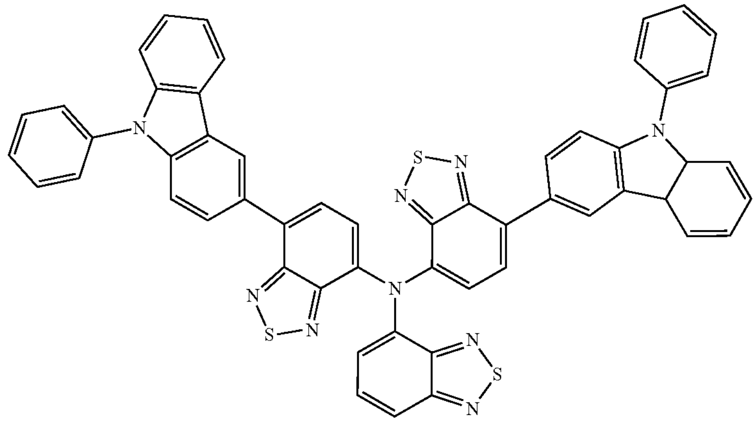

-continued
H58
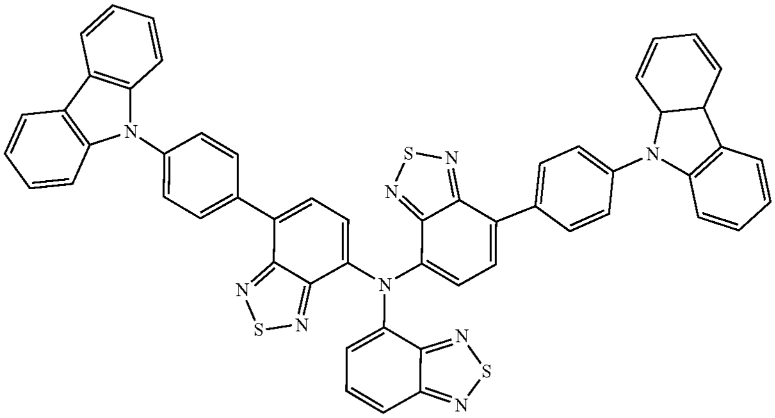
H59
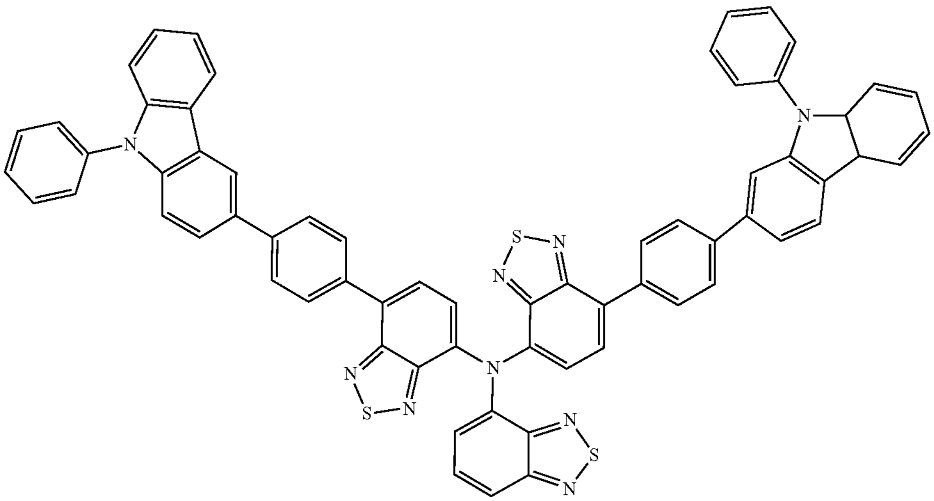
H60
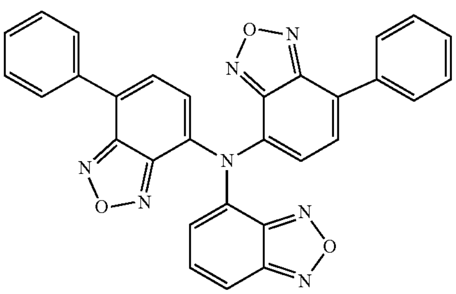
H61
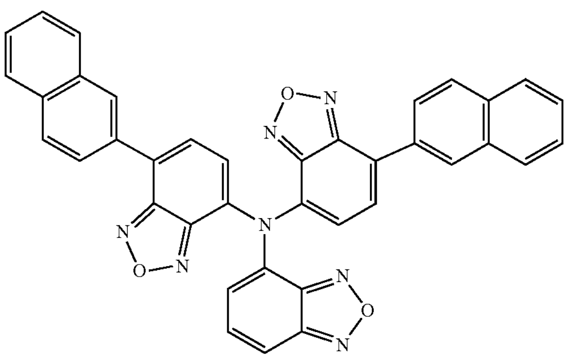

-continued
H62
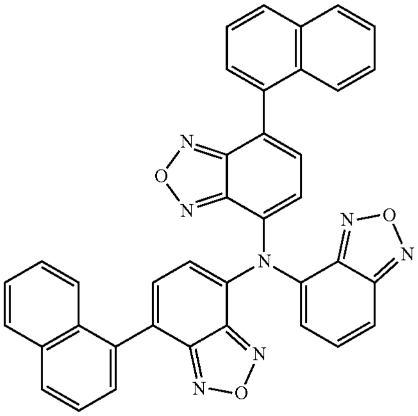
H63
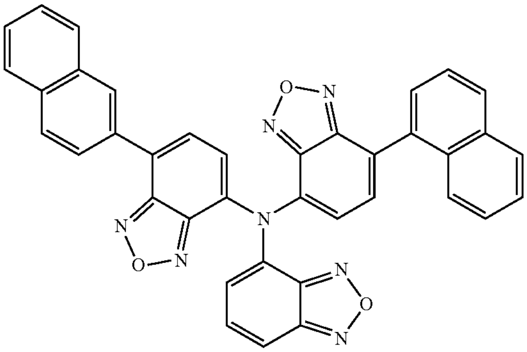
H64
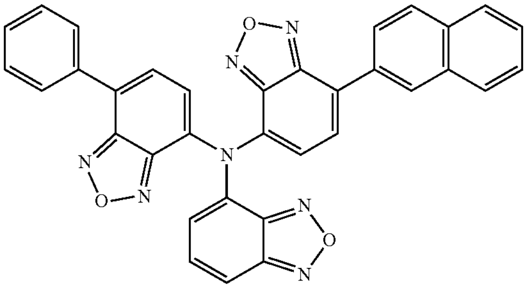
H65
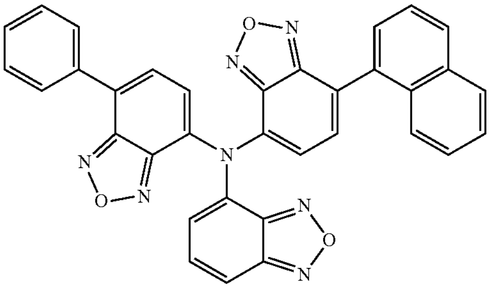
H66
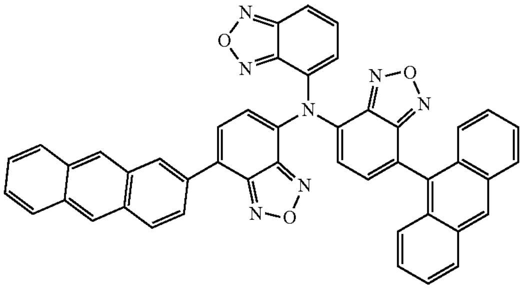
H67
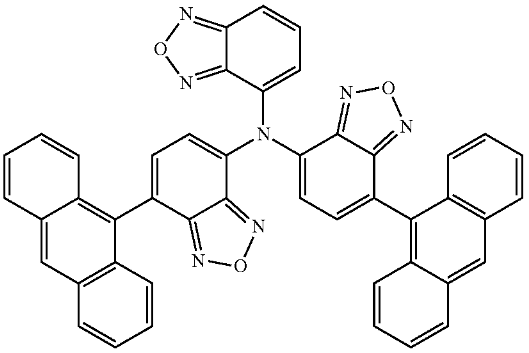
H68
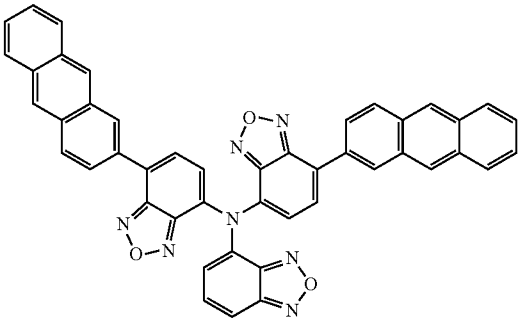
H69
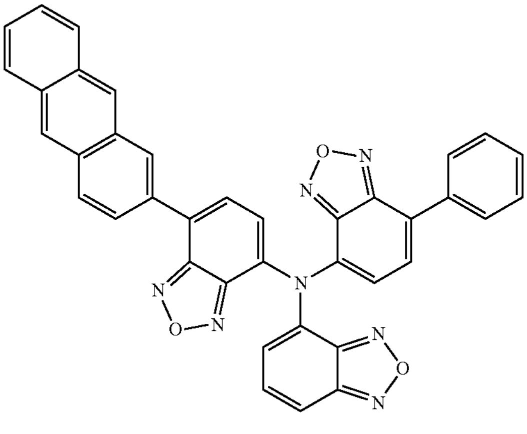

-continued
H70
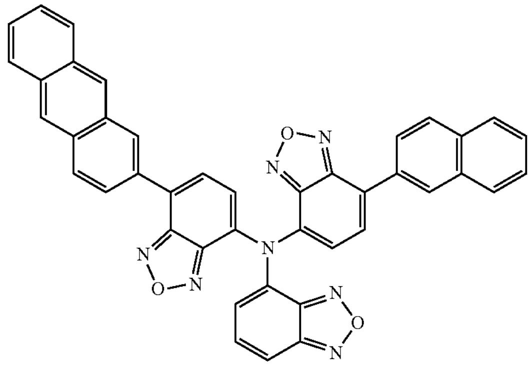
H71
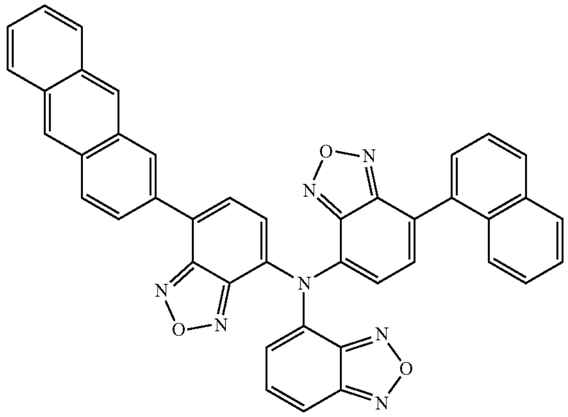
H72
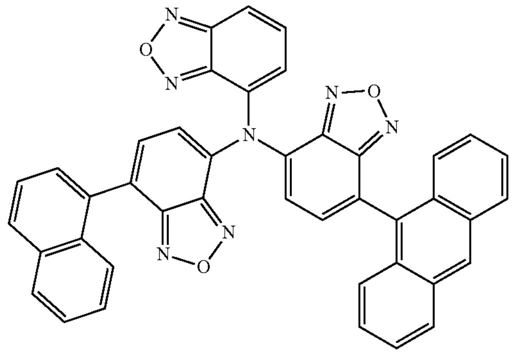
H73
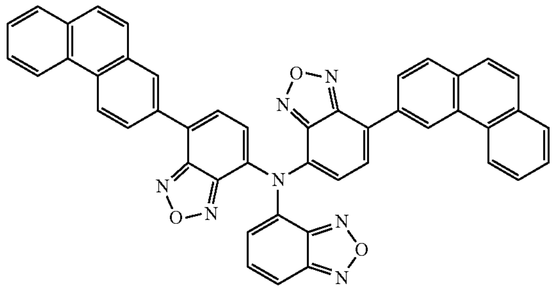
H74
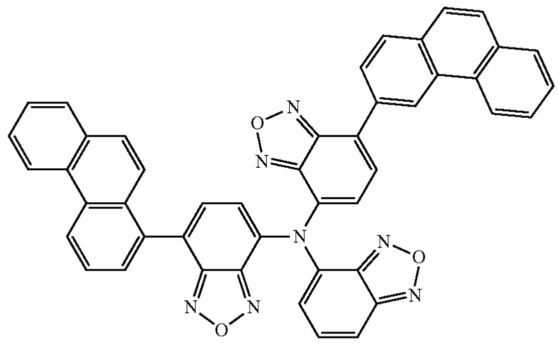
H75
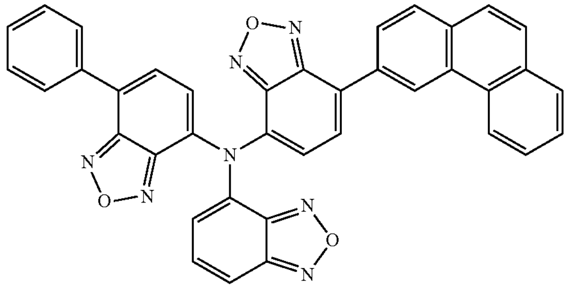
H76
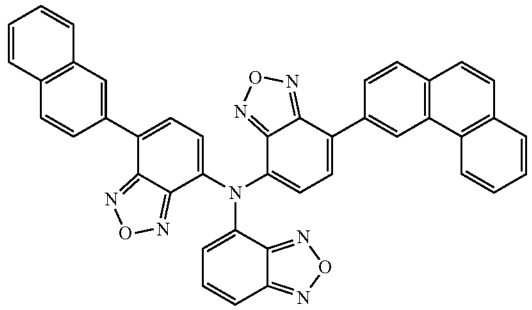
H77
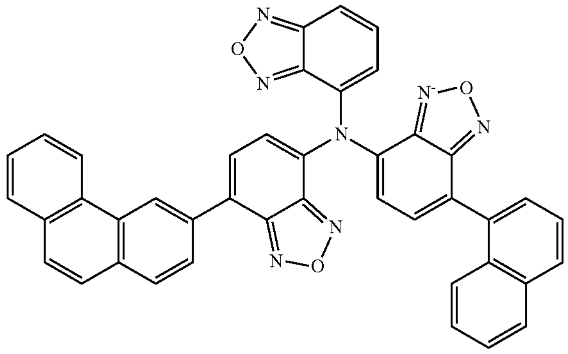

-continued
H78
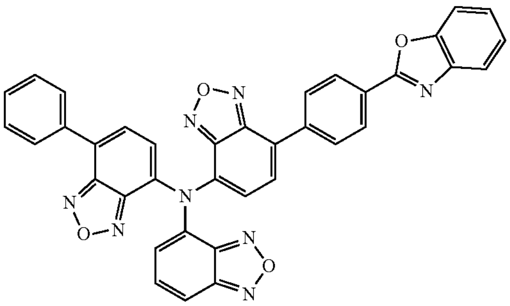
H79
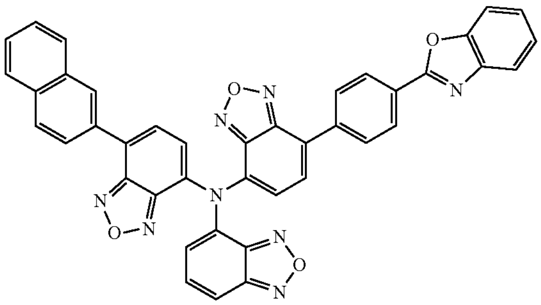
H80
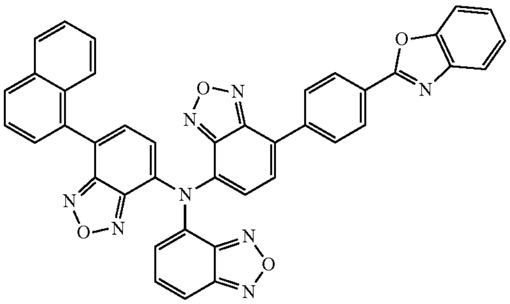
H81
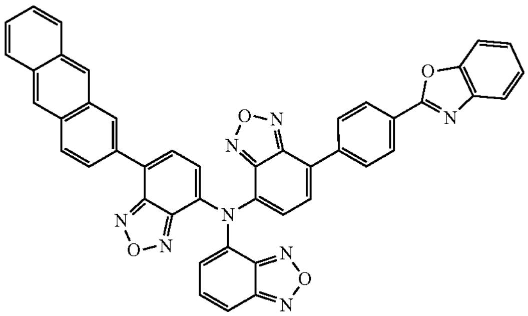
H82
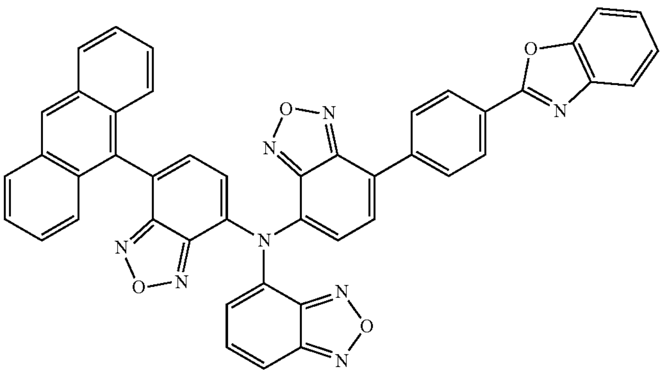
H83
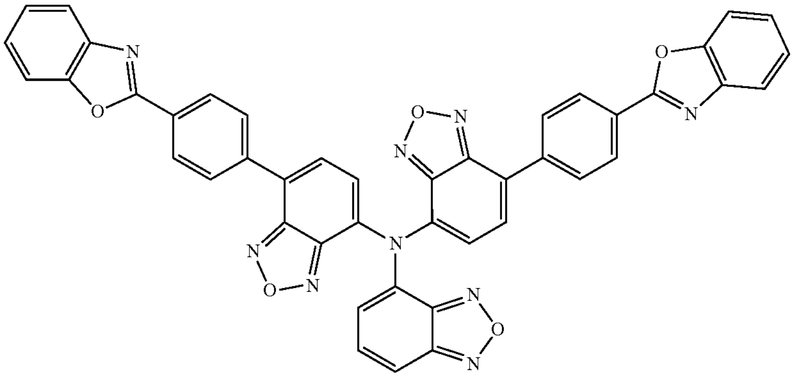

-continued
H84
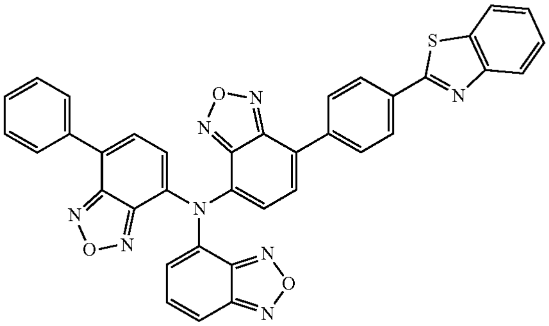
H85
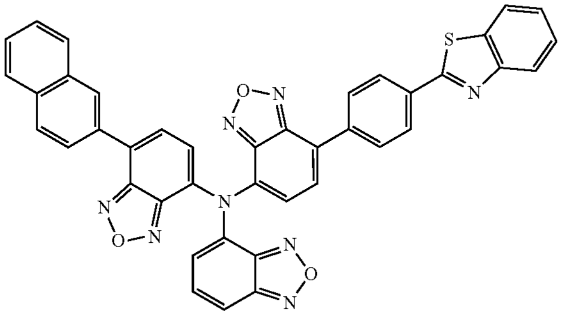
H86
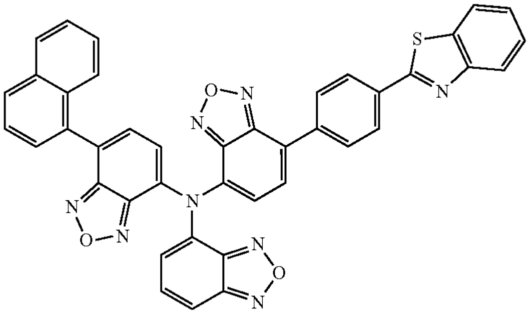
H87
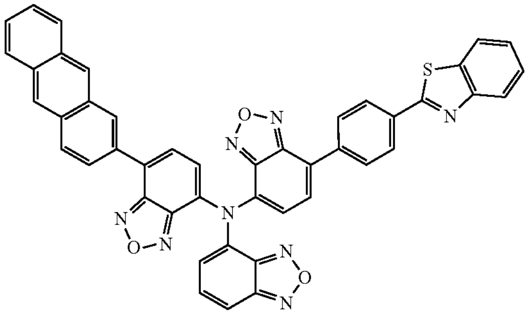
H88
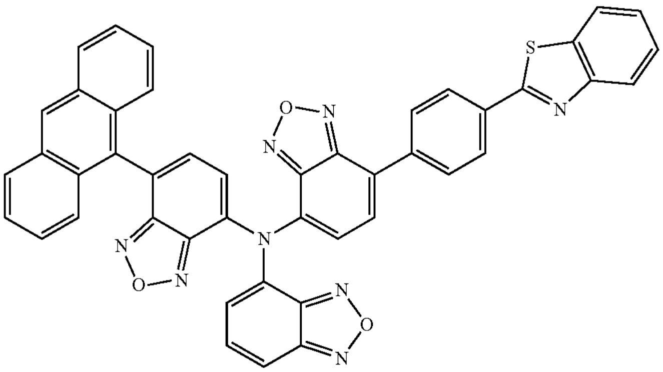
H89
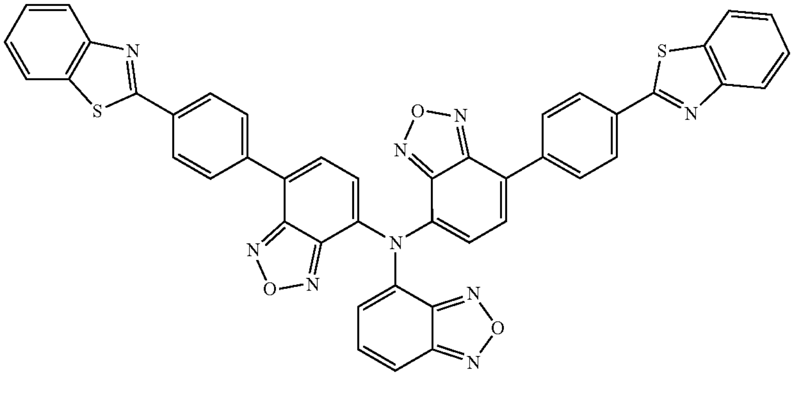

-continued
H90
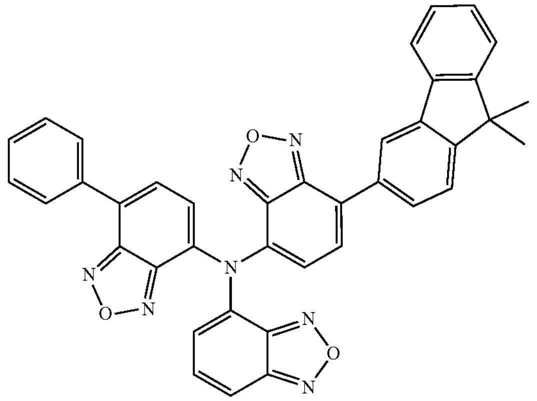
H91
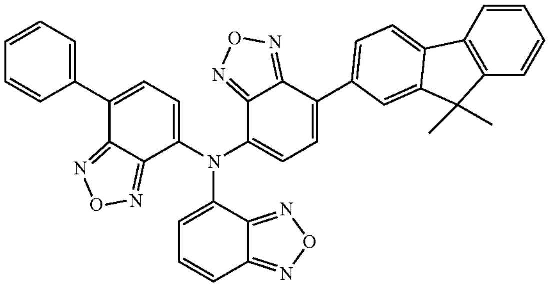
H92
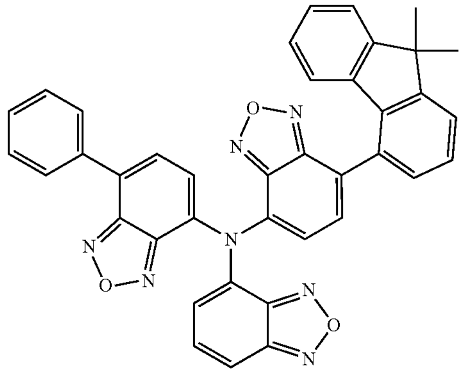
H93
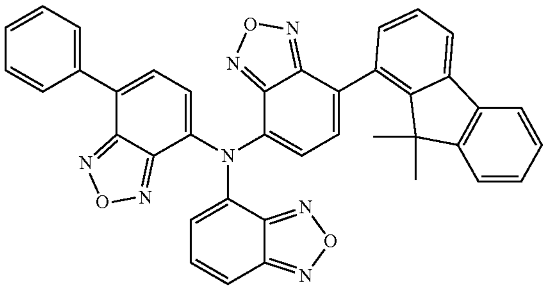
H94
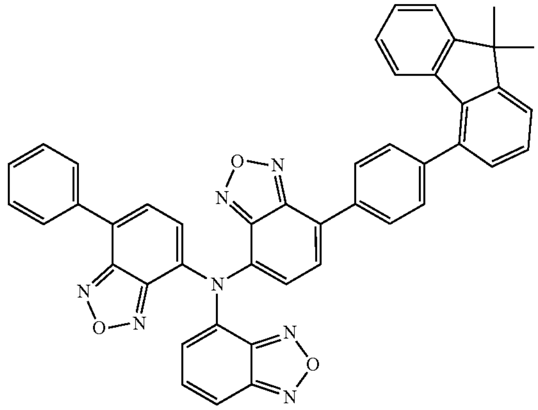
H95
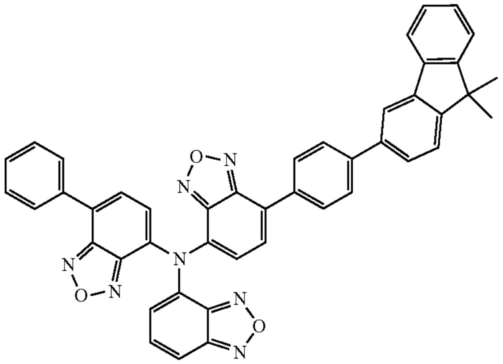
H96
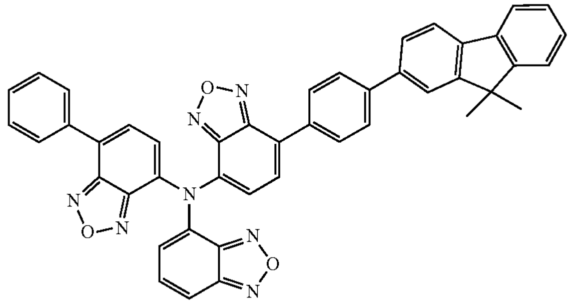
H97
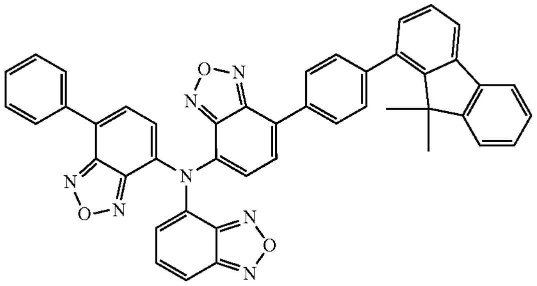

-continued
H98
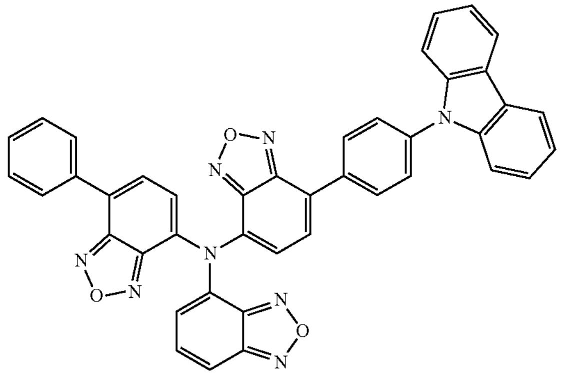
H99
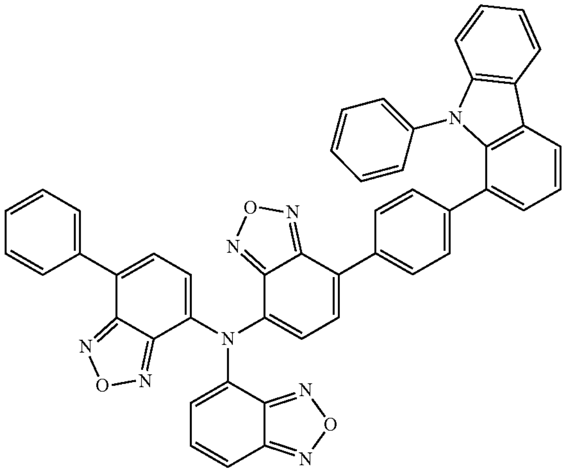
H100
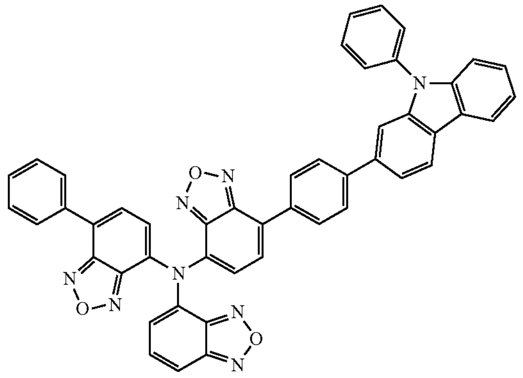
H101
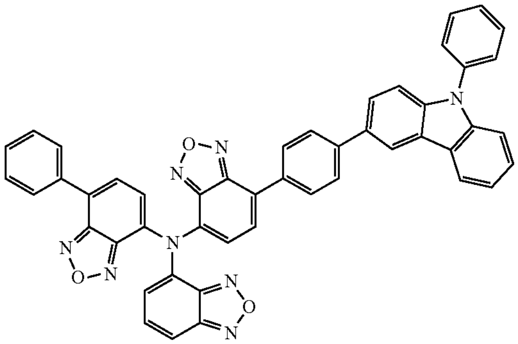
H102
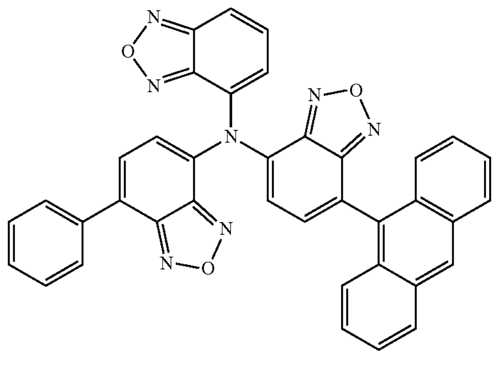
H103
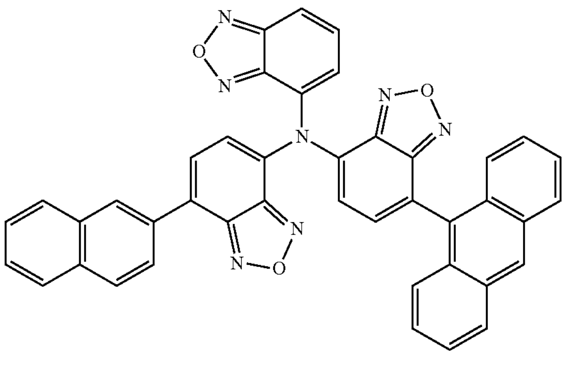

-continued
H104
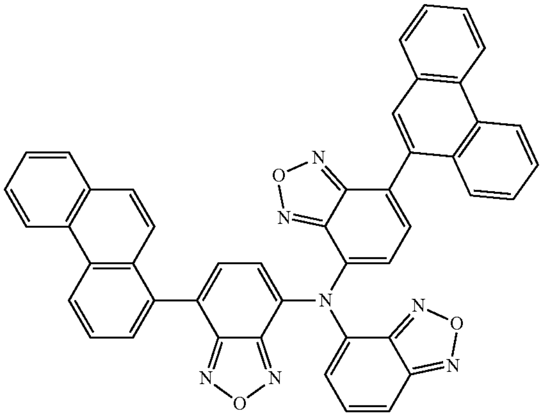
H105
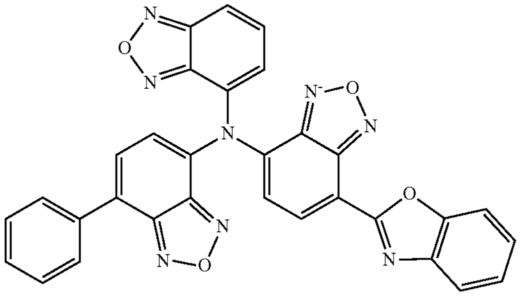
H106
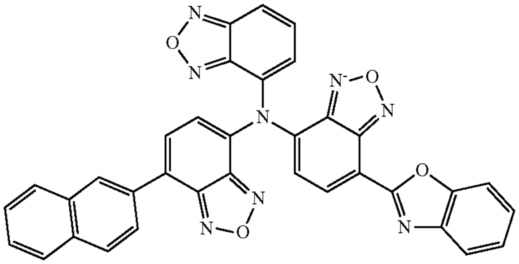
H107
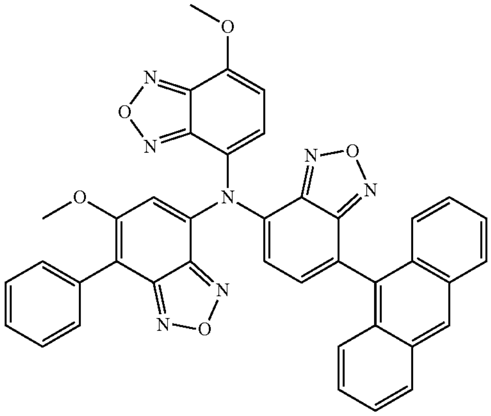
108
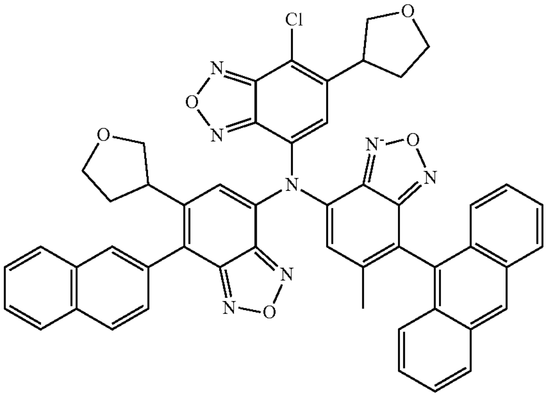
109
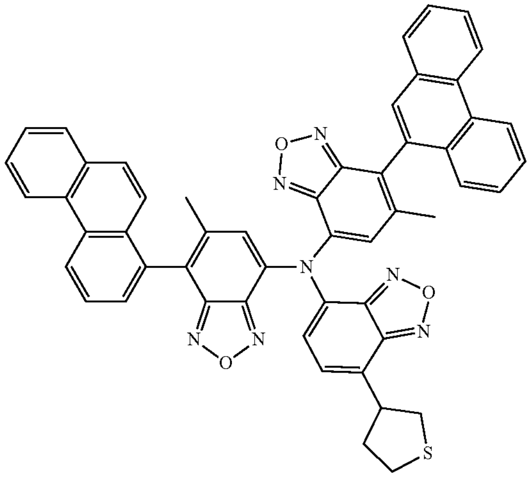

-continued
H110
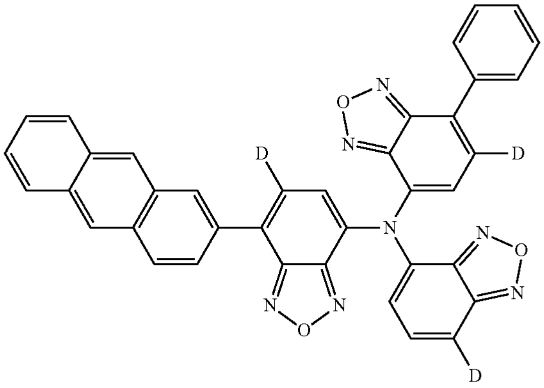
H111
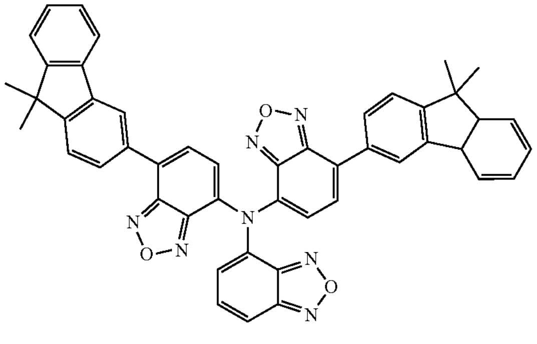
H112
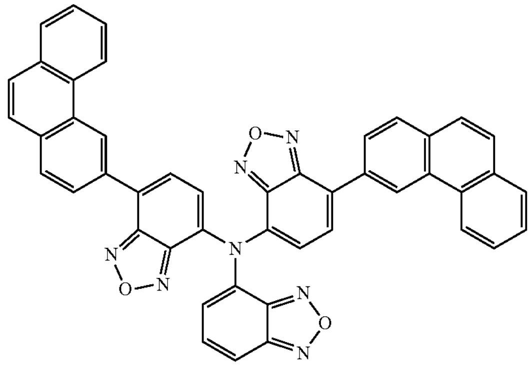
H113
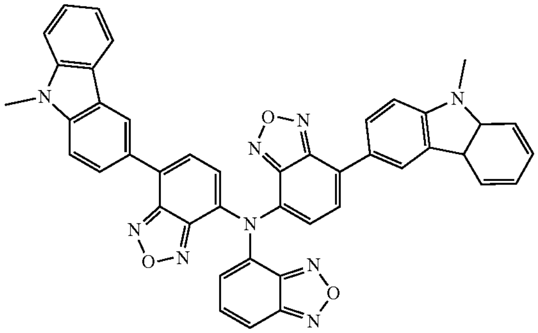
H114
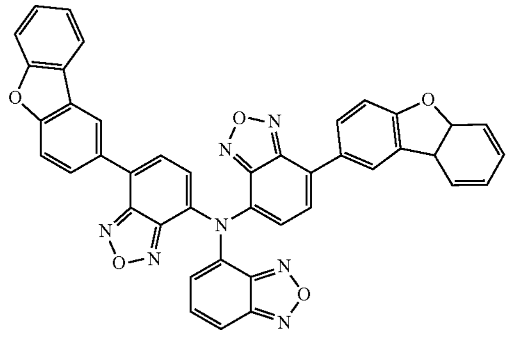
H115
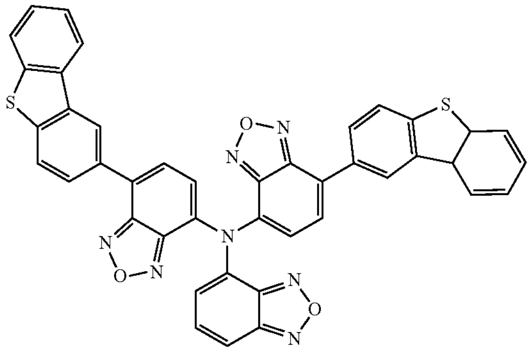
H116
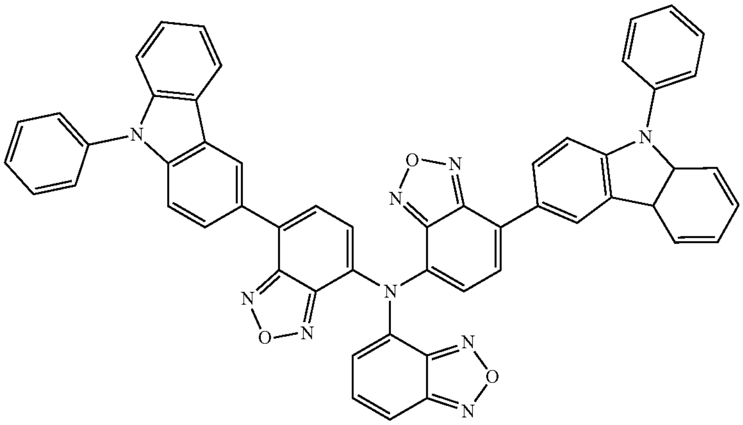

-continued
H117
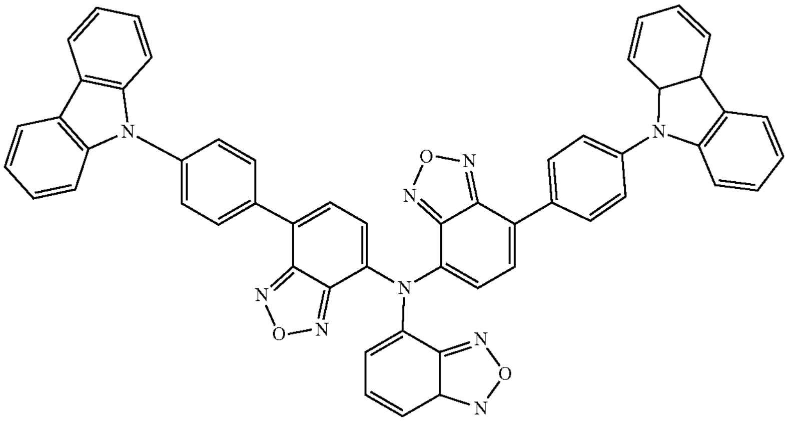
H118
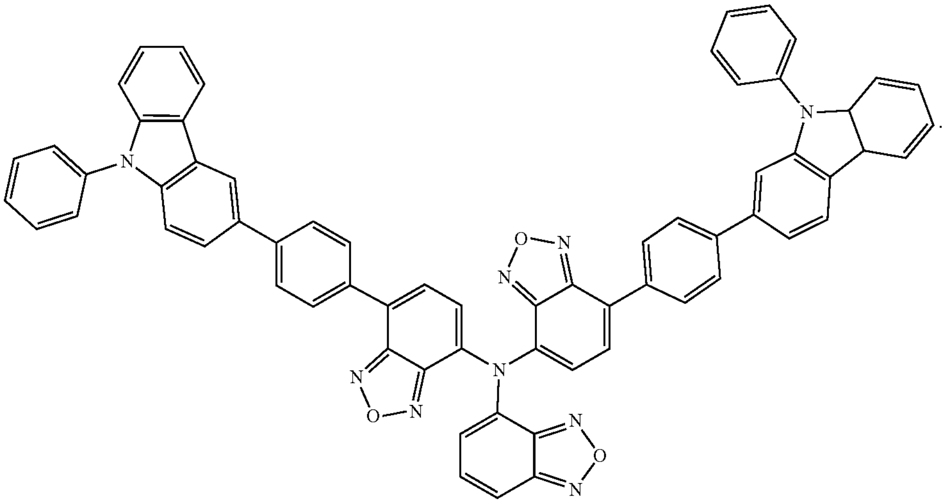
10. A compound, wherein the compound is selected from any of the following:
H119
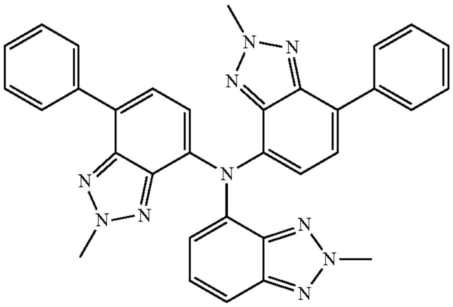
H120
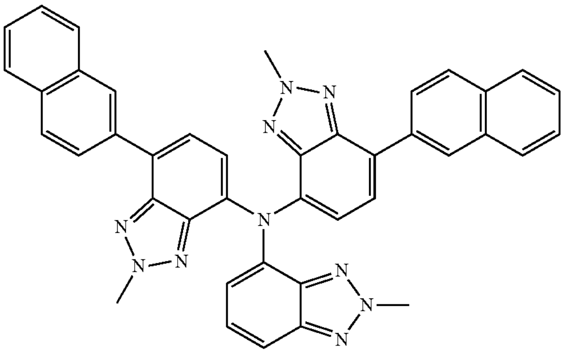

-continued
H121
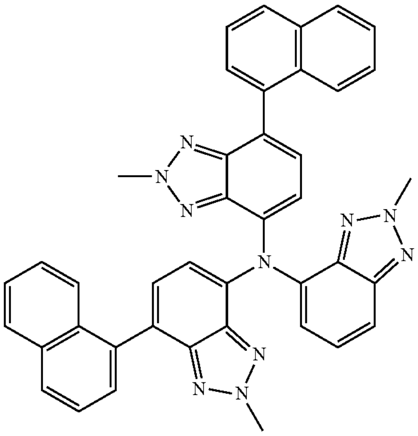
H122
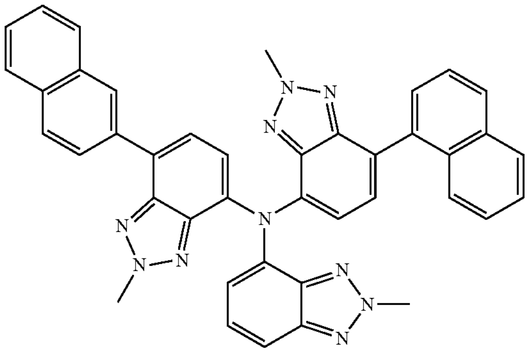
H123
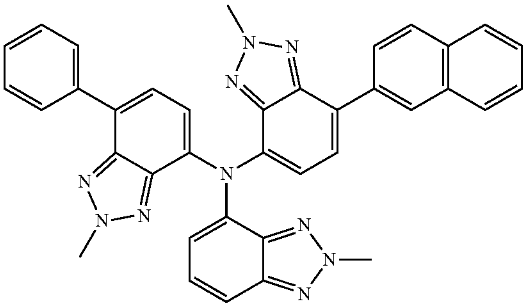
H124
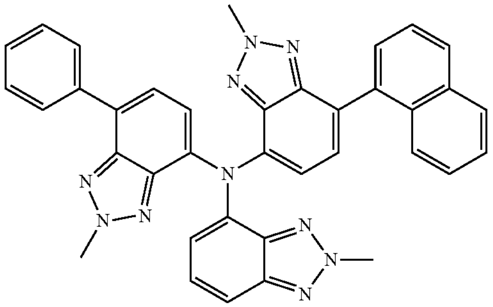
H125
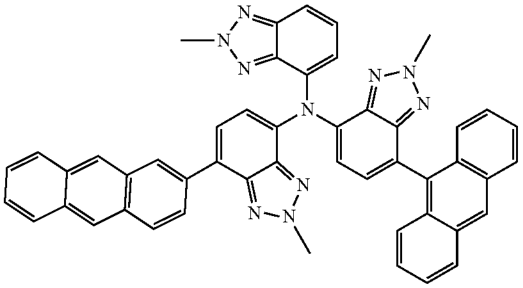
H126
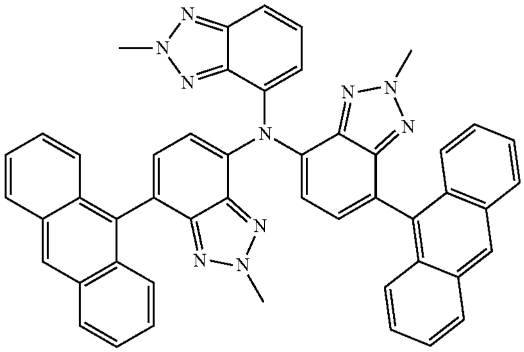
H127
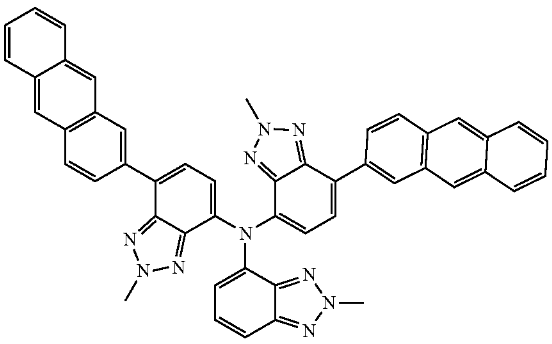
H128
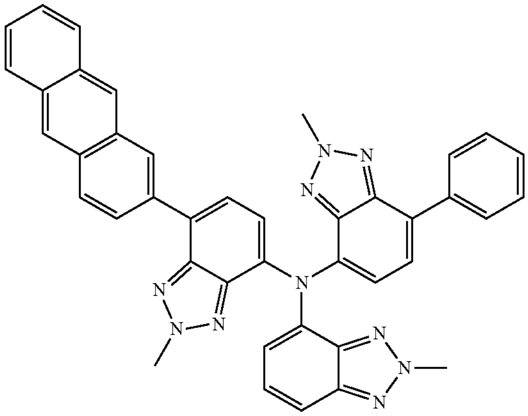

-continued
H129
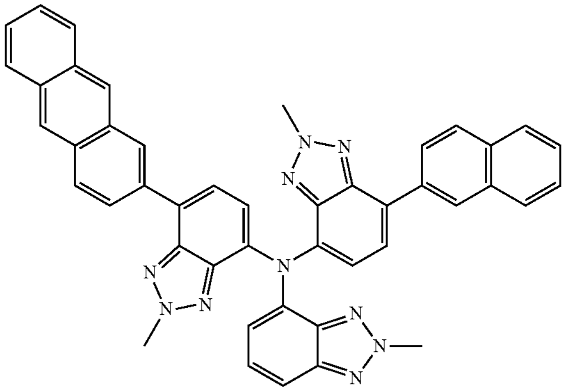
H130
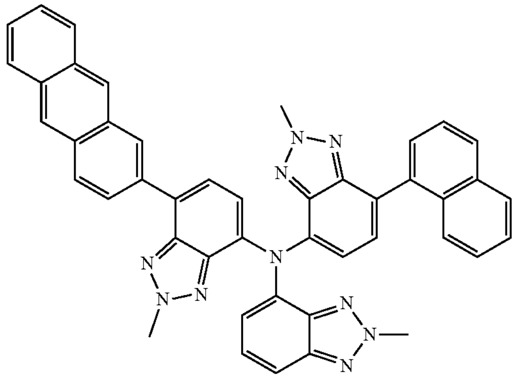
H131
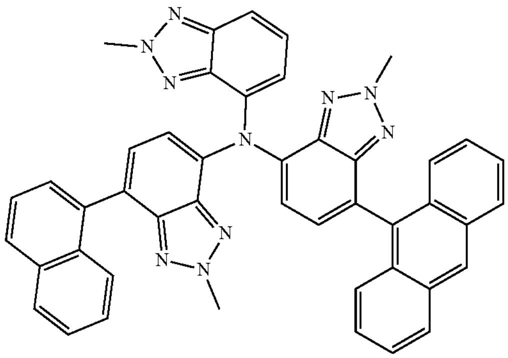
H132
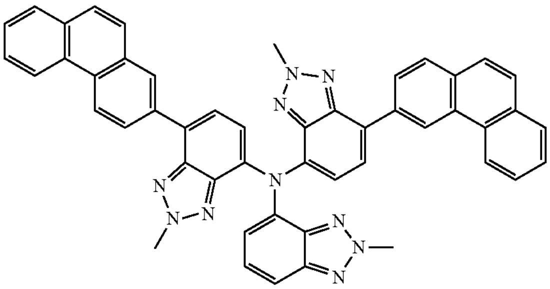
H133
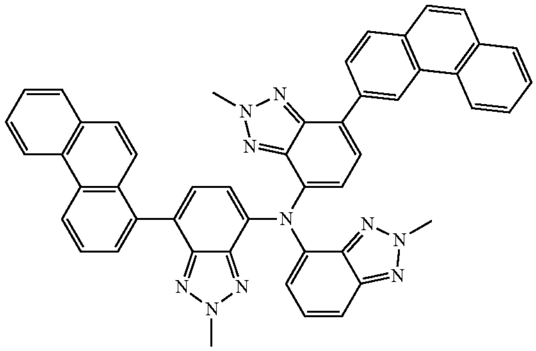
H134
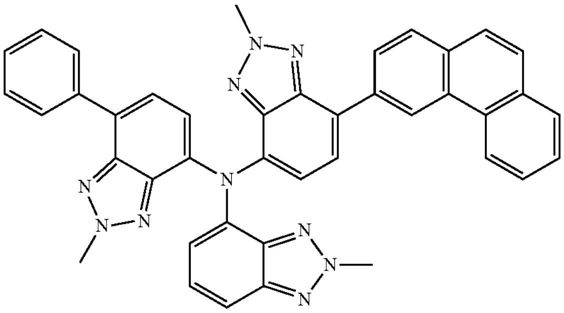
H135
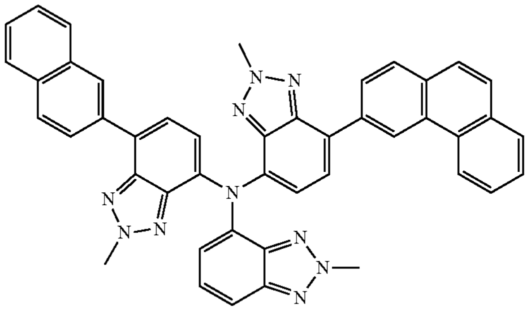
H136
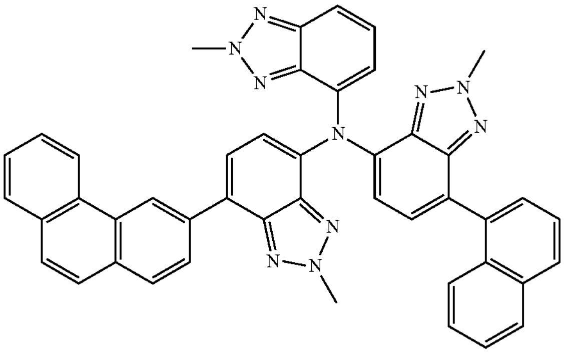

-continued
H137
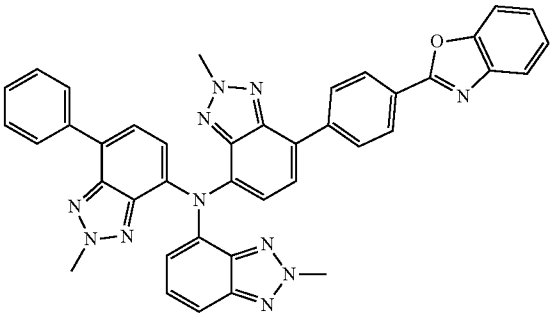
H138
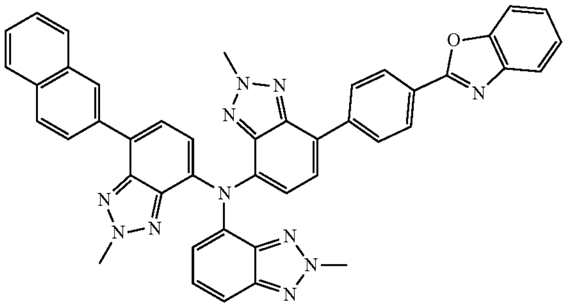
H139
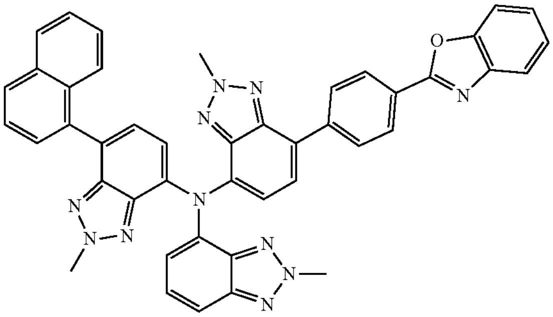
H140
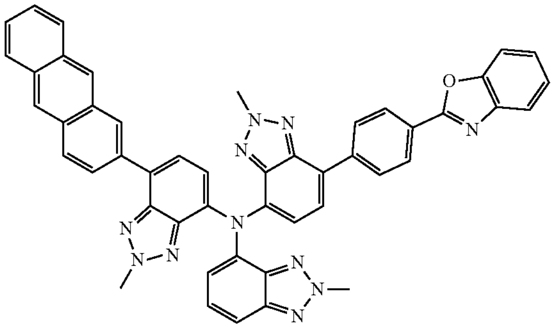
H141
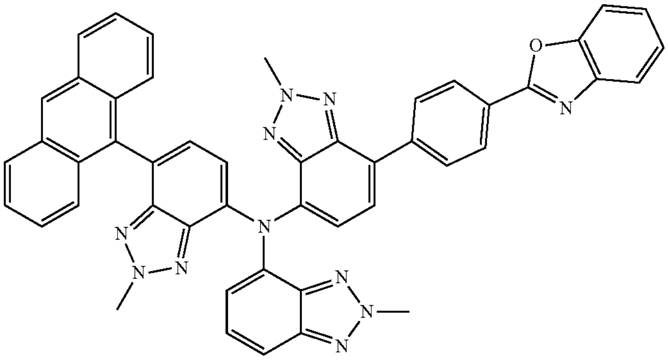
H142
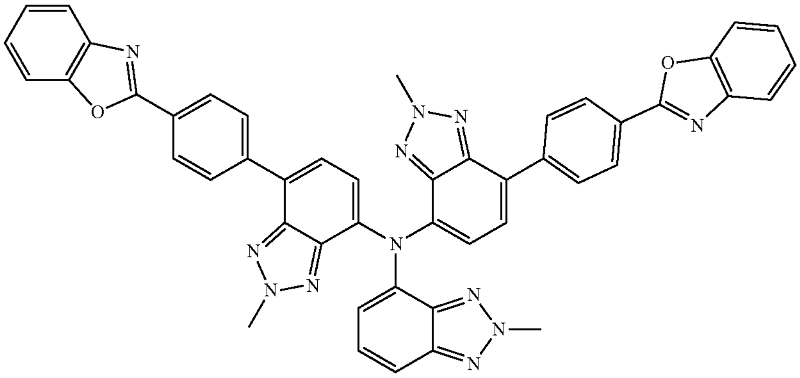

-continued
H143
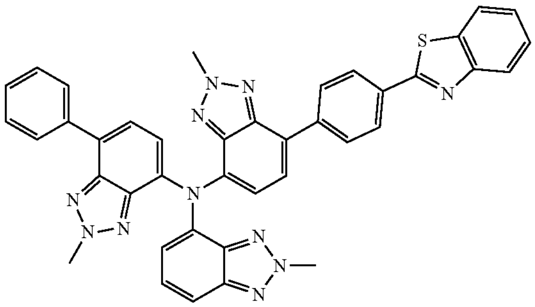
H144
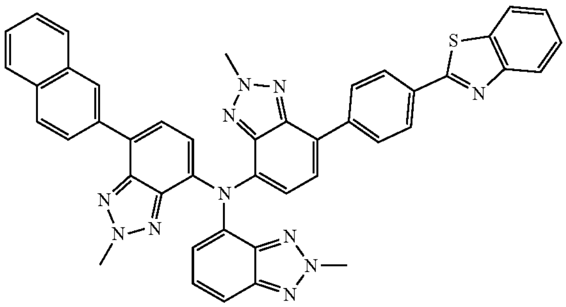
H145
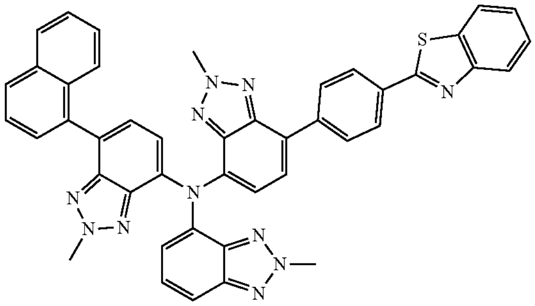
H146
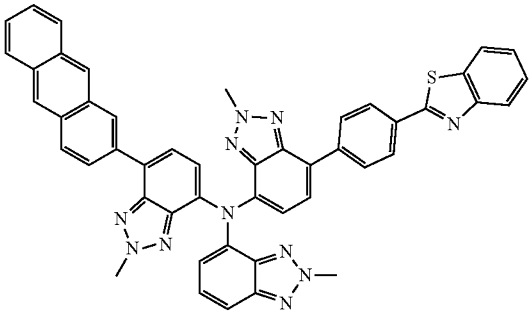
H147
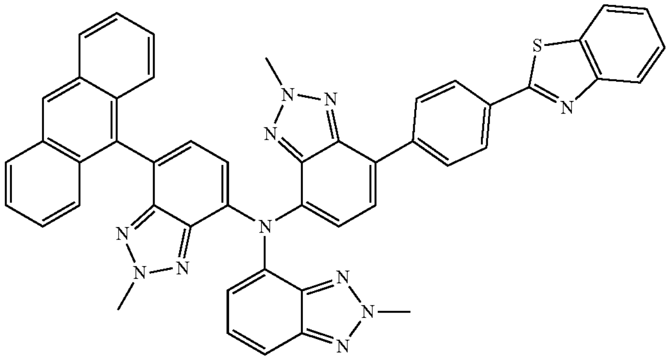
H148
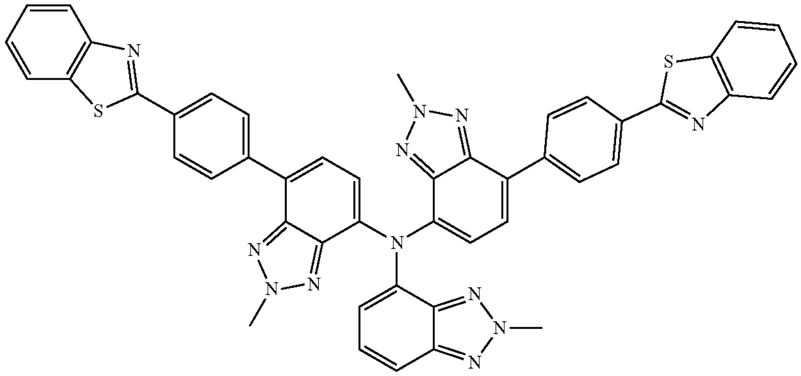

-continued
H149
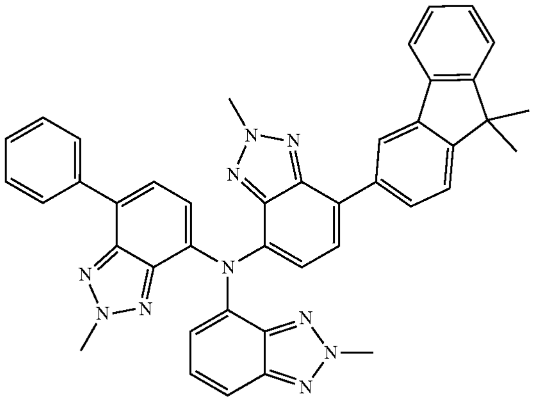
H150
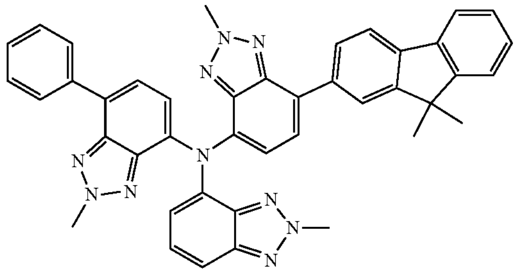
H151
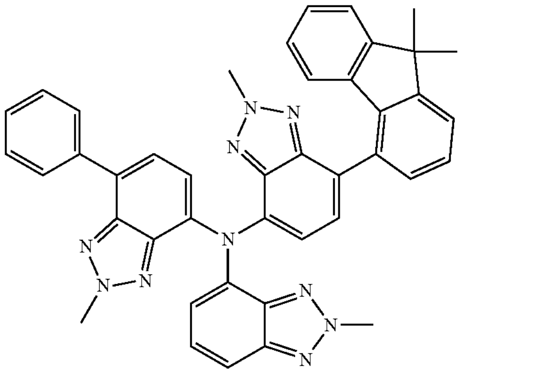
H152
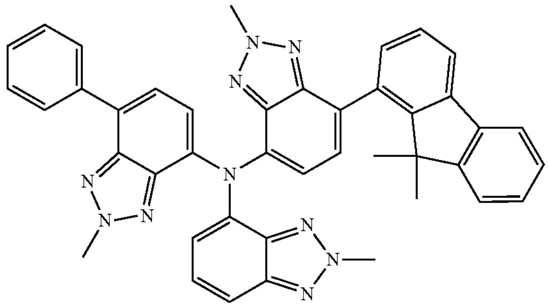
H153
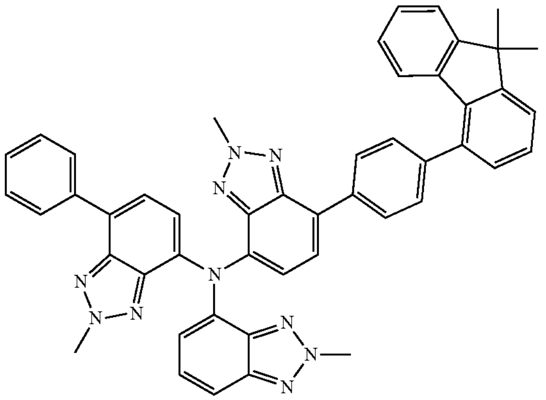
H154
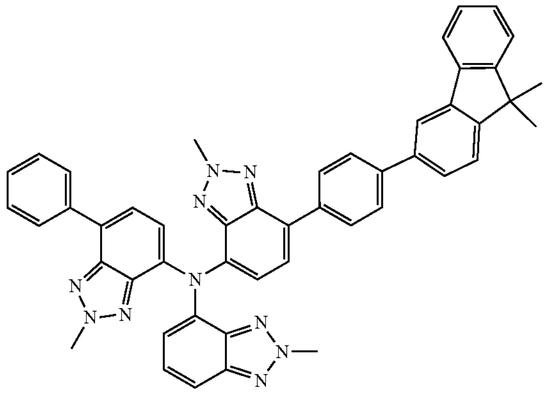
H155
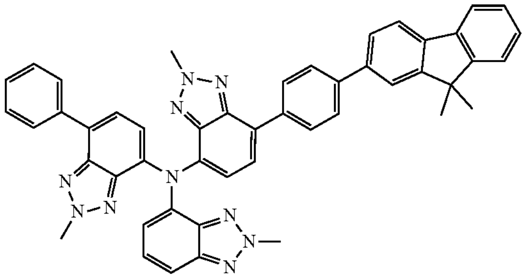
H156
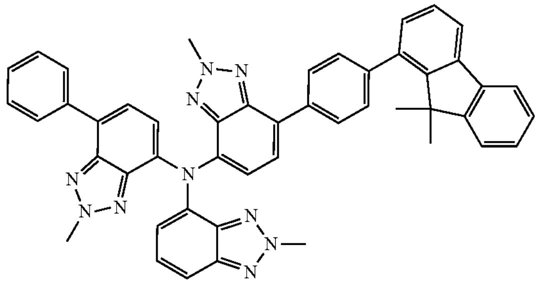

-continued
H157
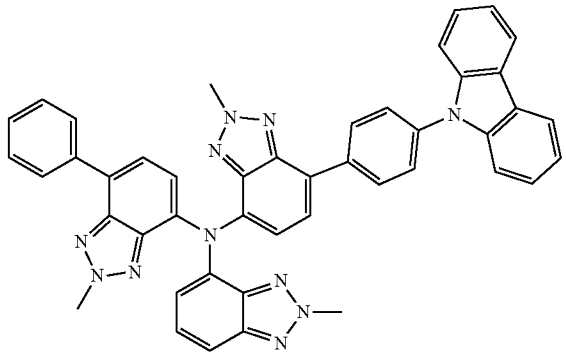
H158
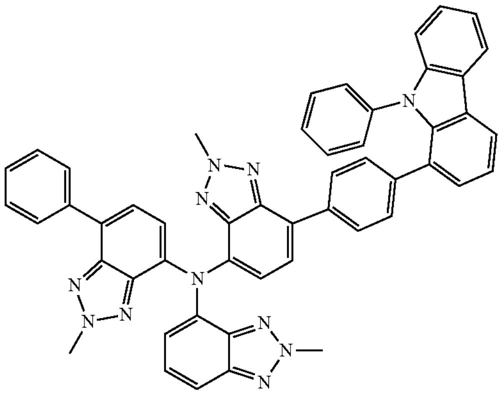
H159
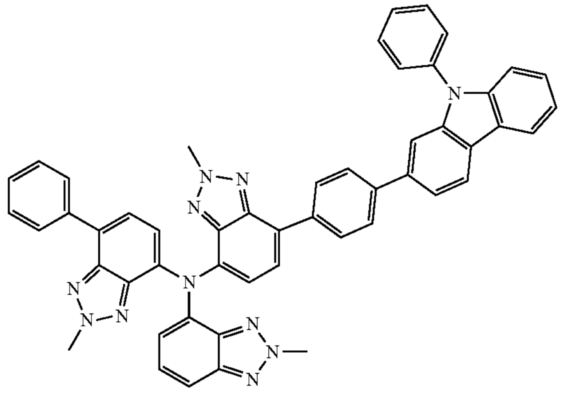
H160
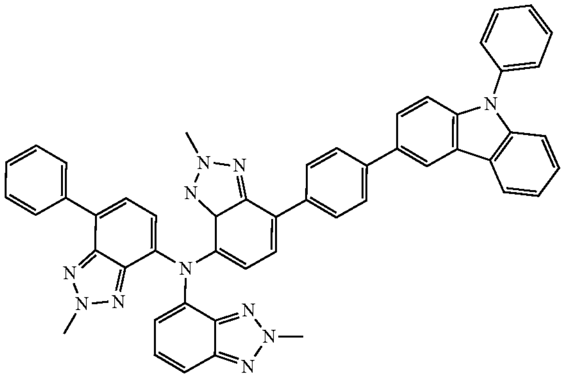
H161
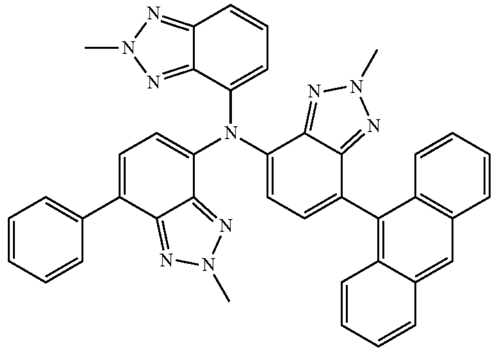
H162
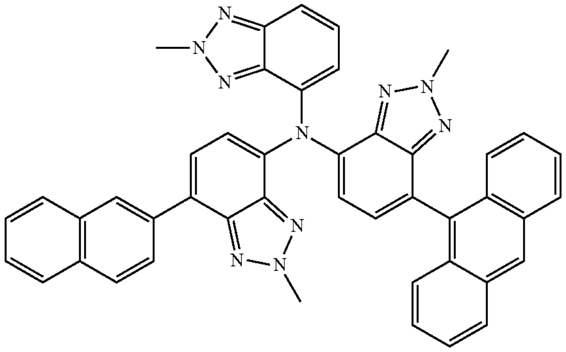

-continued
H163
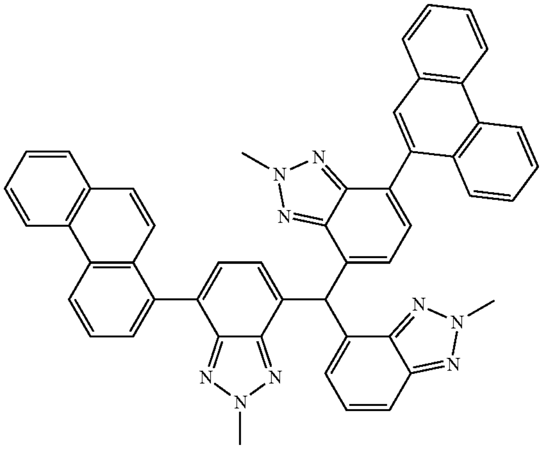
H164
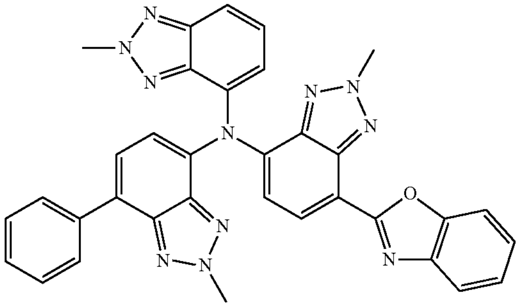
H165
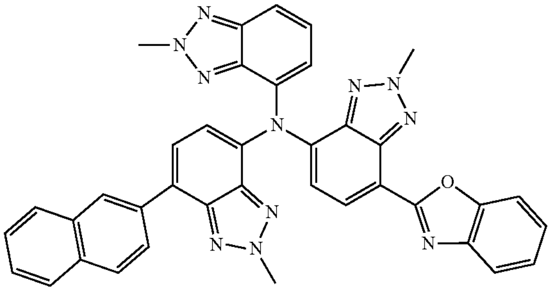
H166
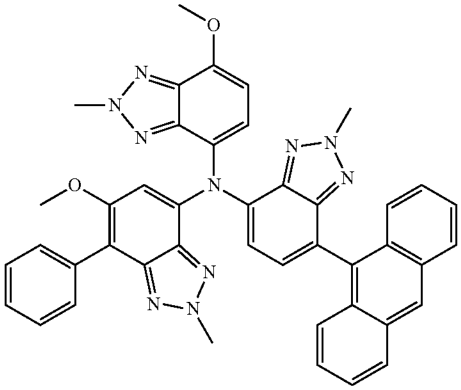
H167
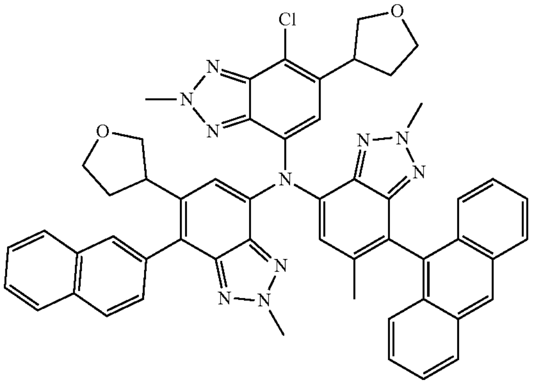
H168
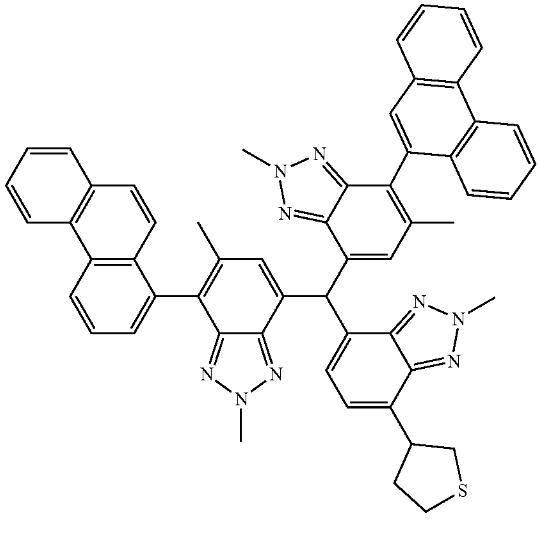

-continued
H169
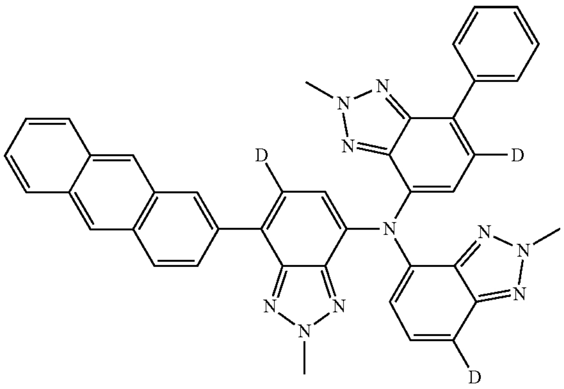
H170
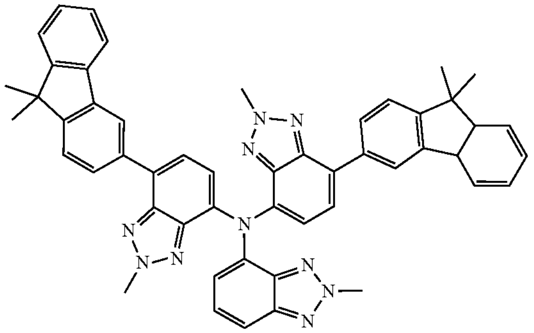
H171
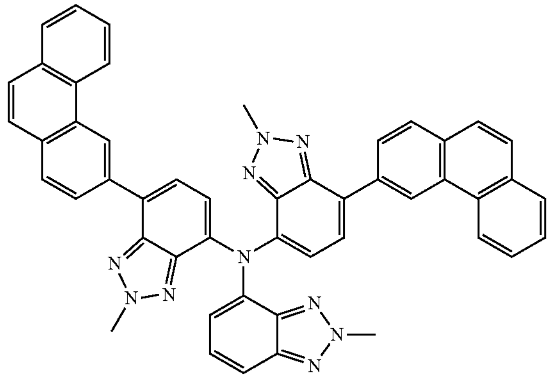
H172
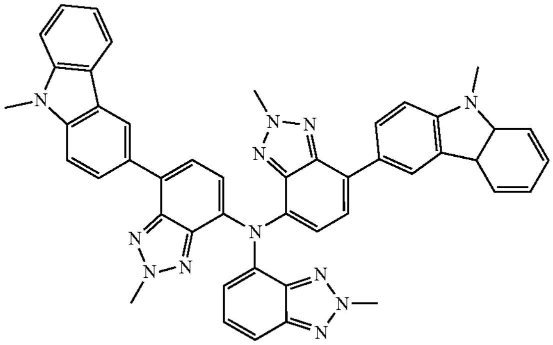
H173
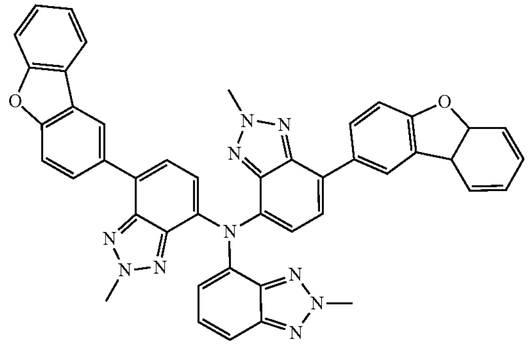
H174
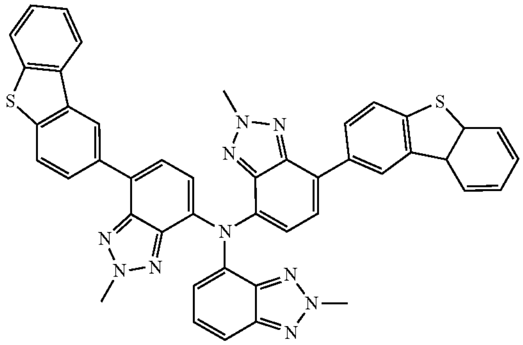
H175
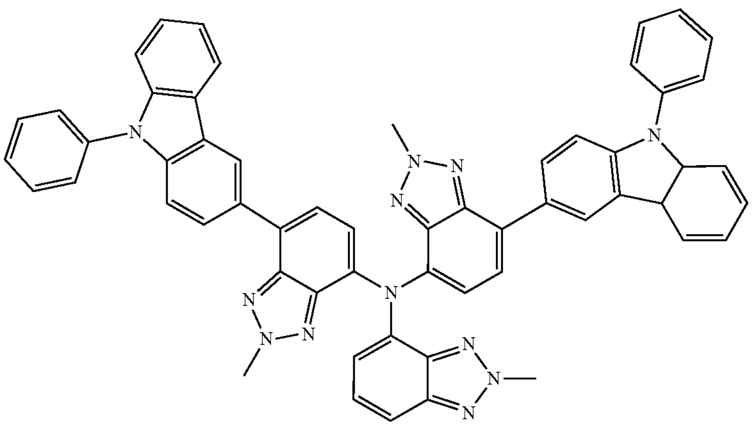

-continued
H176
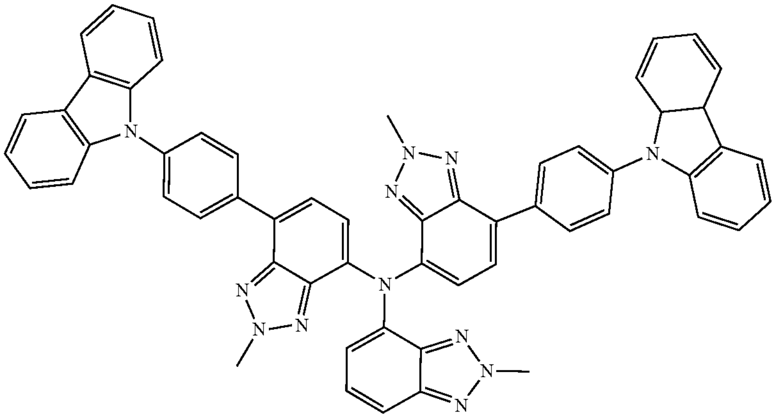
H177
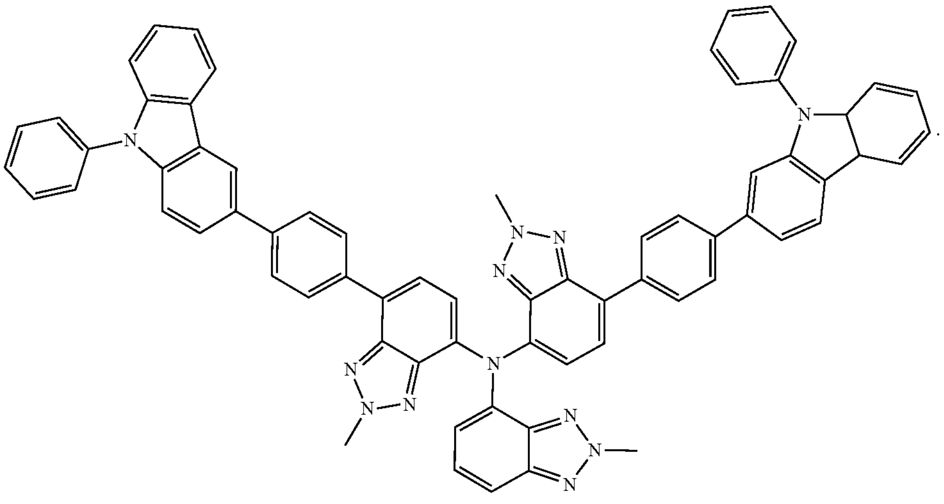
11. A compound, wherein the compound is selected from any of the following:
H178
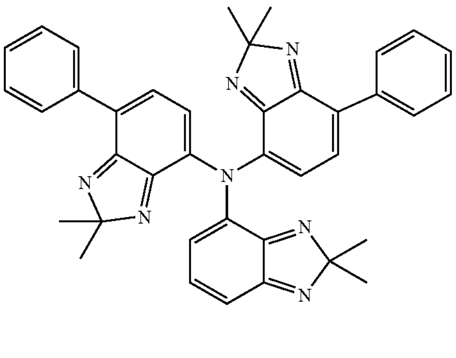
H179
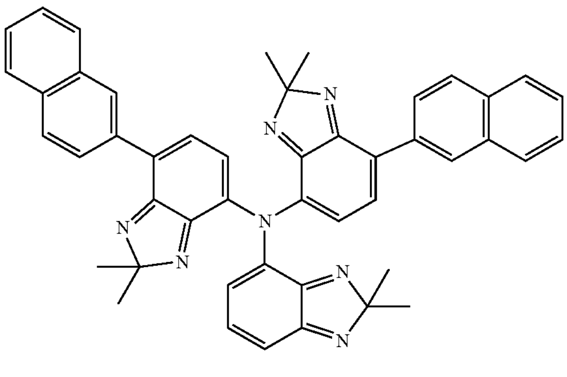

-continued
H180
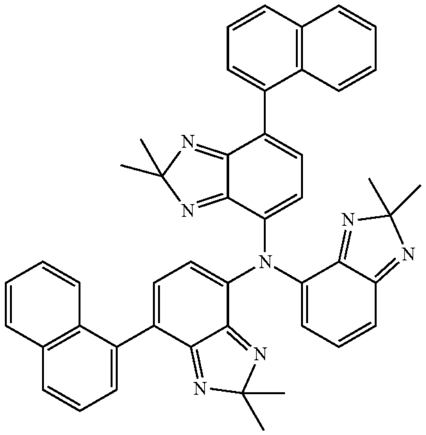
H181
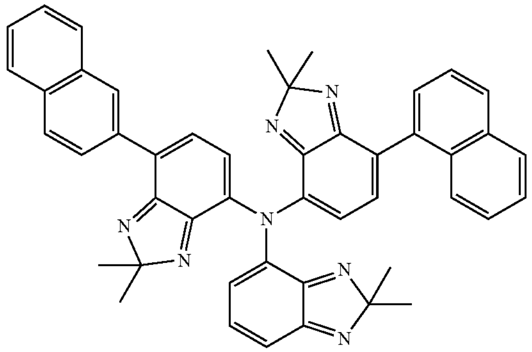
H182
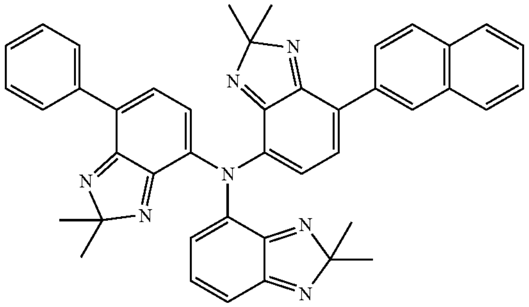
H183
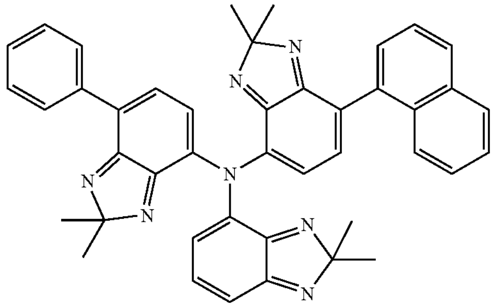
H184
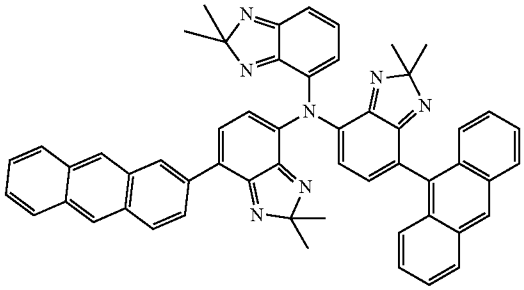
H185
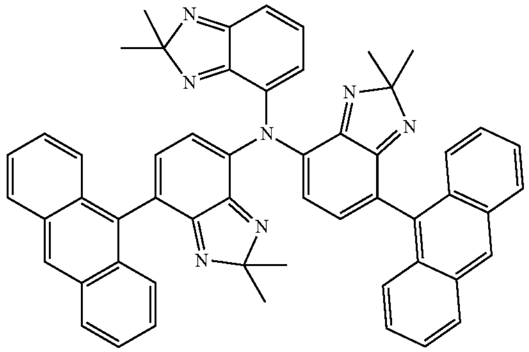
H186
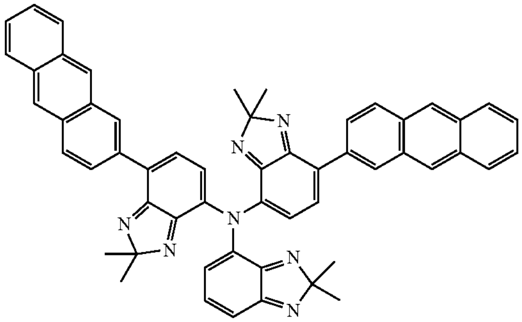
H187
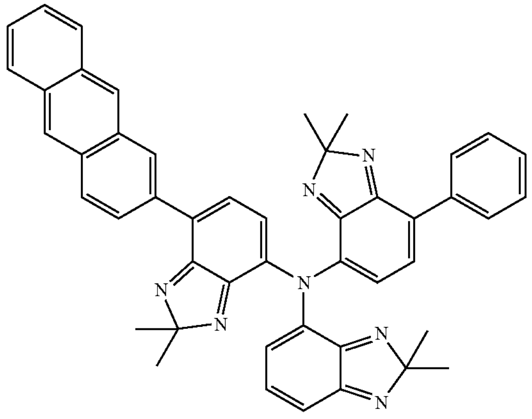

-continued
H188
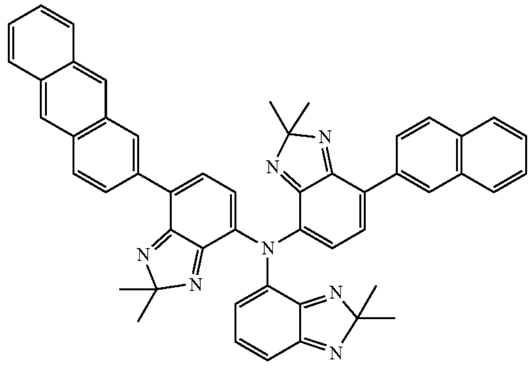
H189
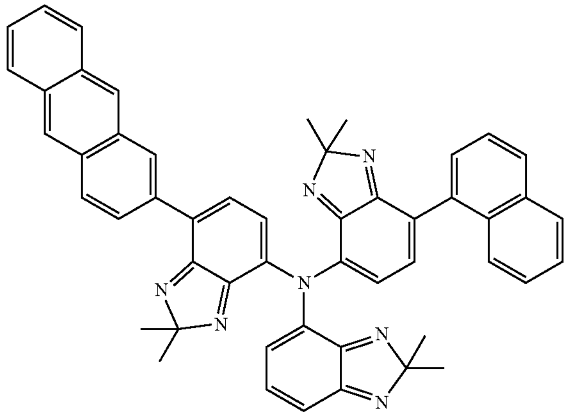
H190
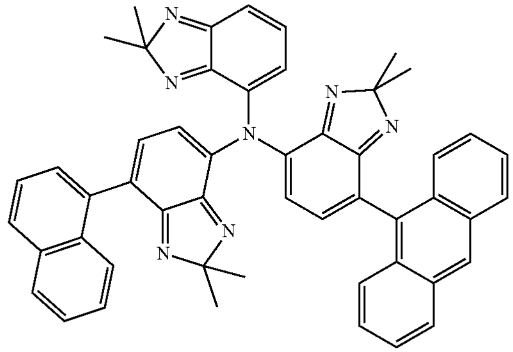
H191
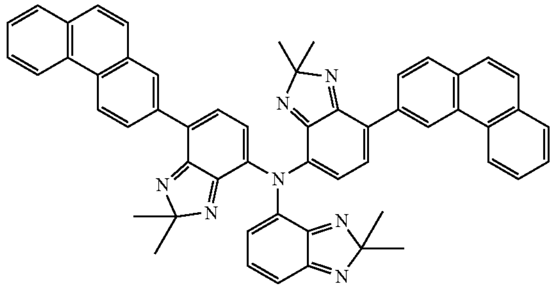
H192
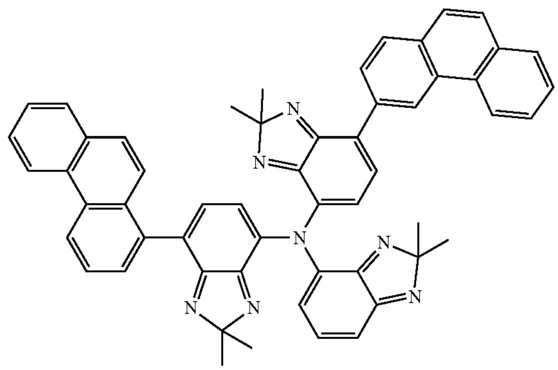
H193
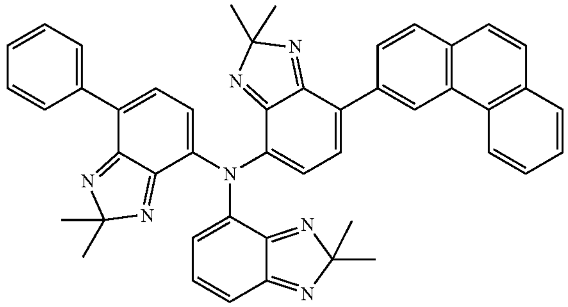
H194
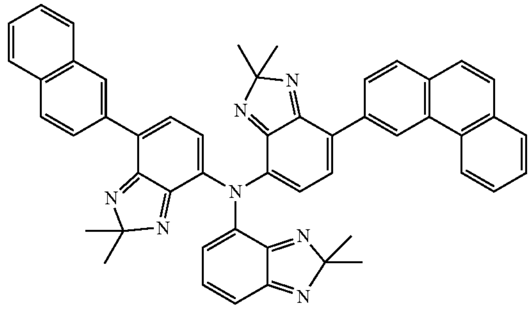
H195
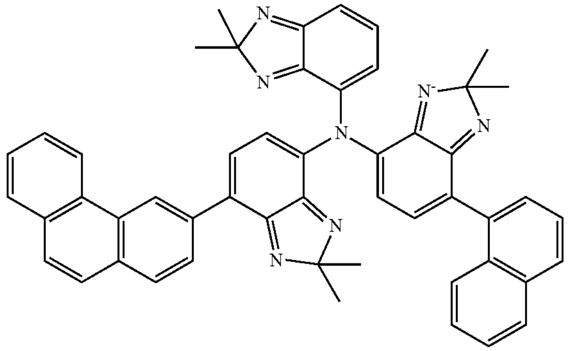

-continued
H196
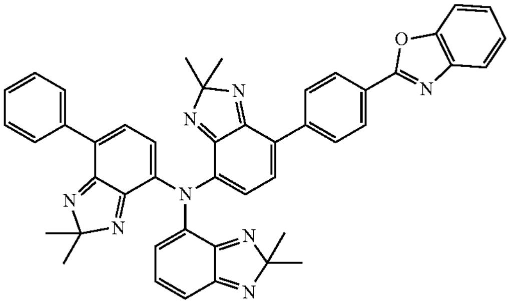
H197
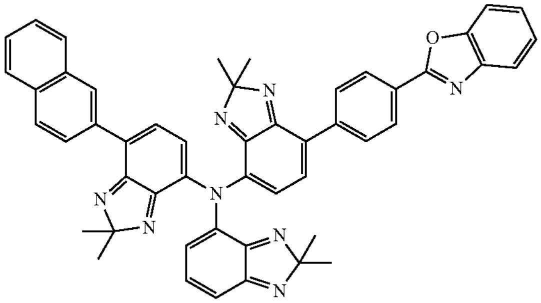
H198
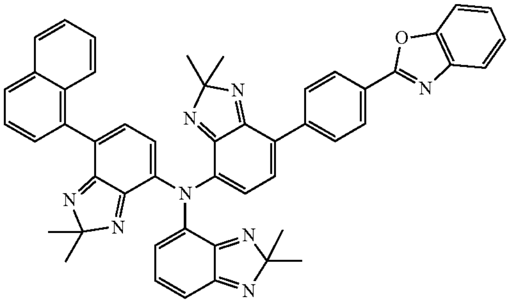
H199
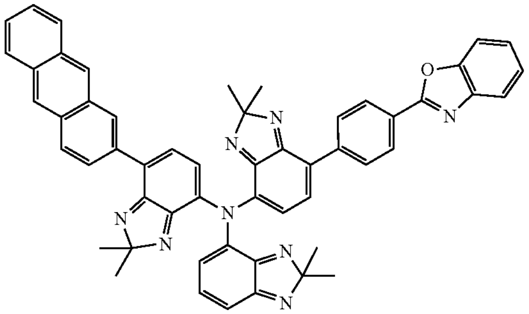
H200
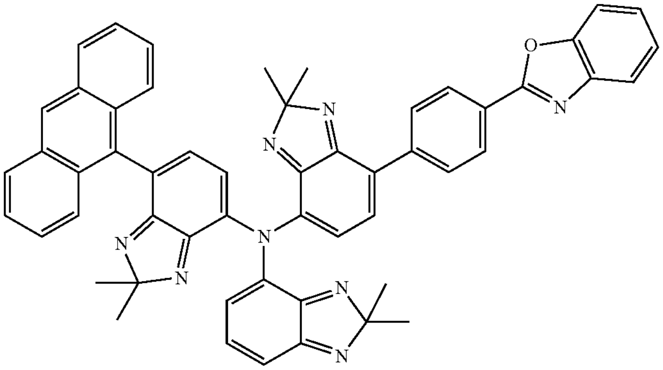
H201
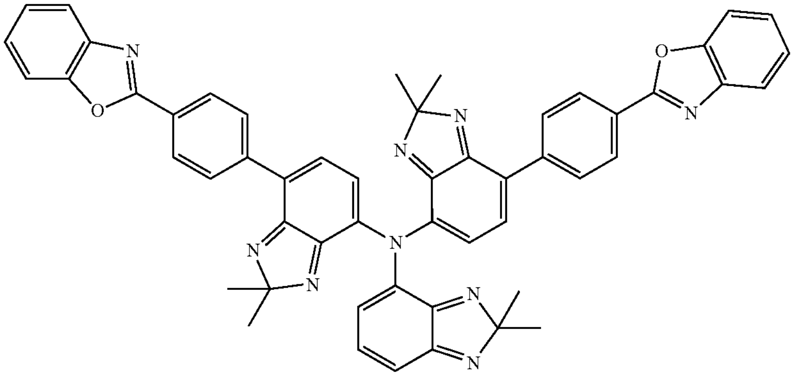

-continued
H202
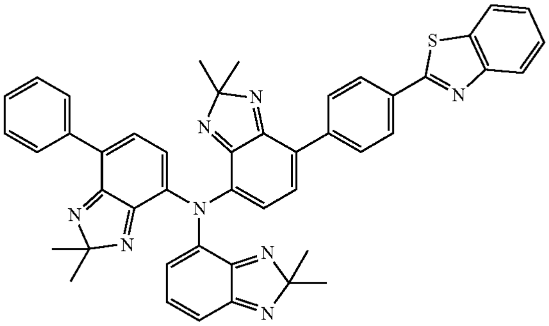
H203
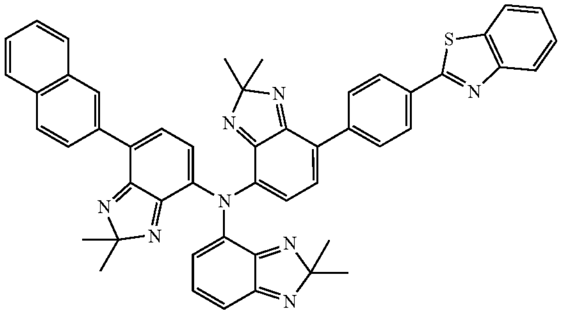
H204
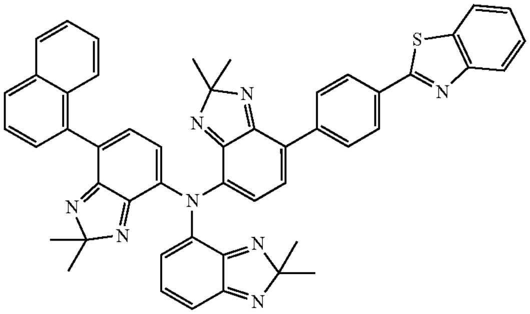
H205
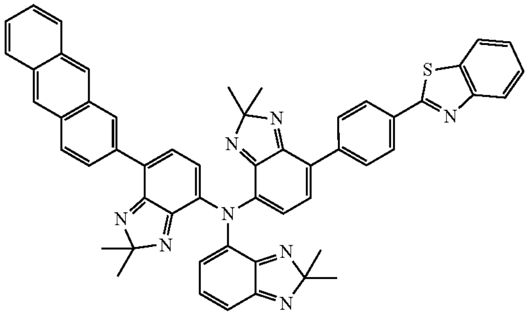
H206
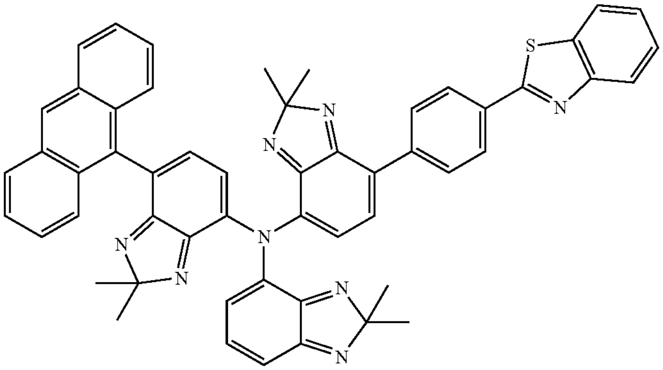
H207
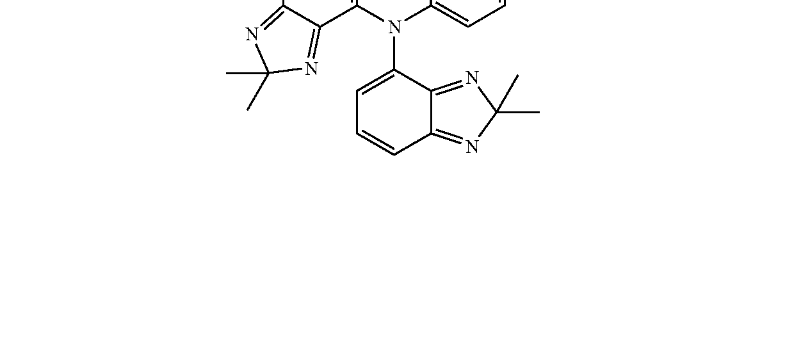

-continued
H208
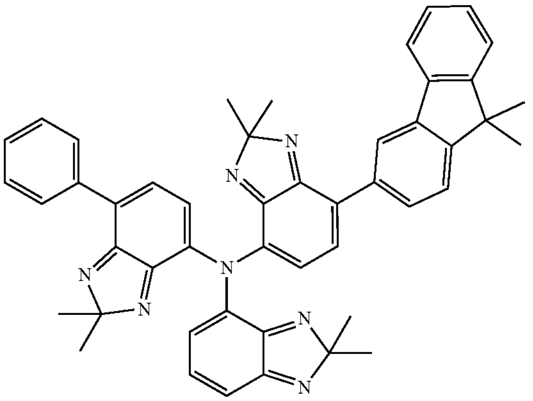
H209
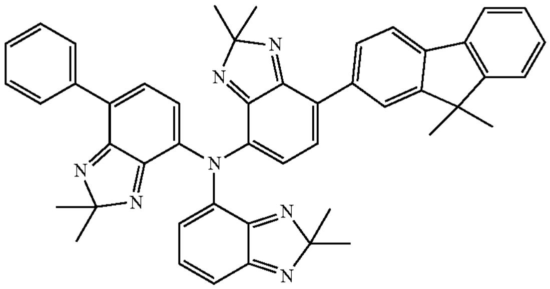
H210
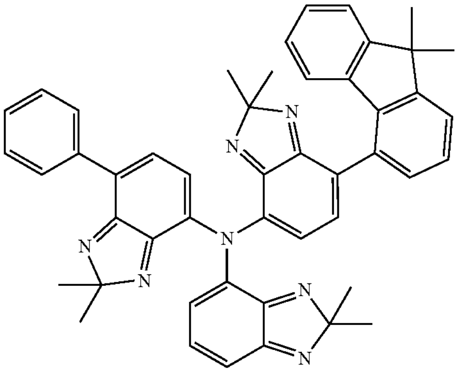
H211
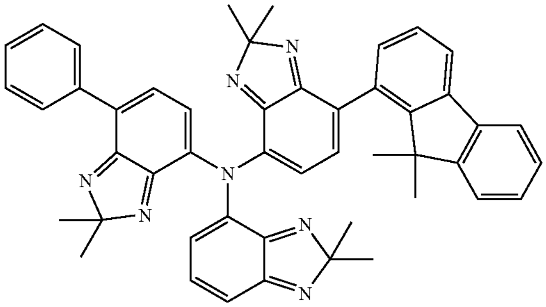
H212
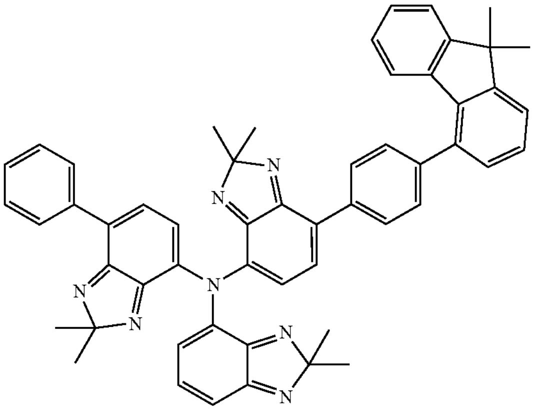
H213
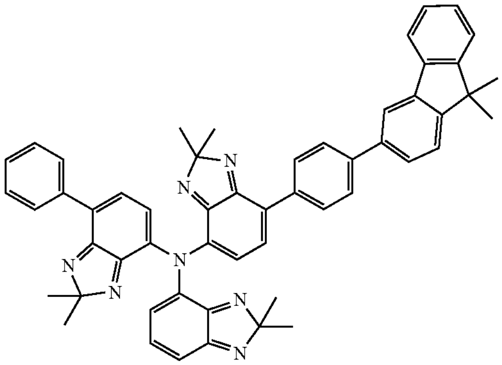
H214
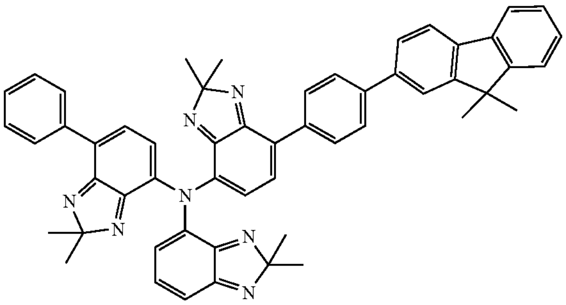
H215
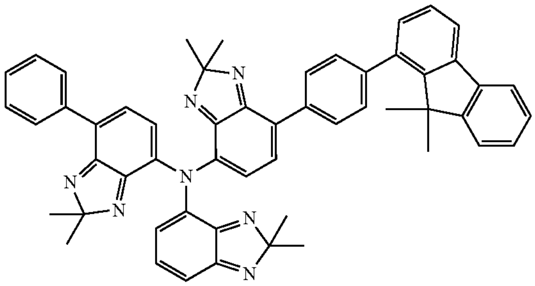

-continued
H216
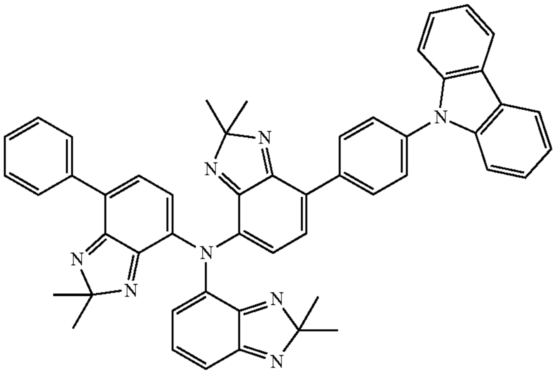
H217
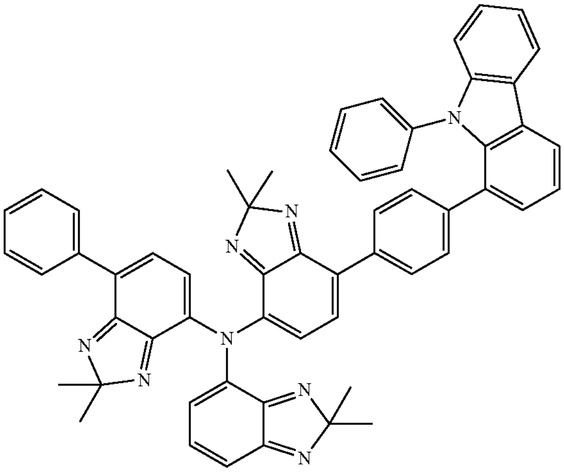
H218
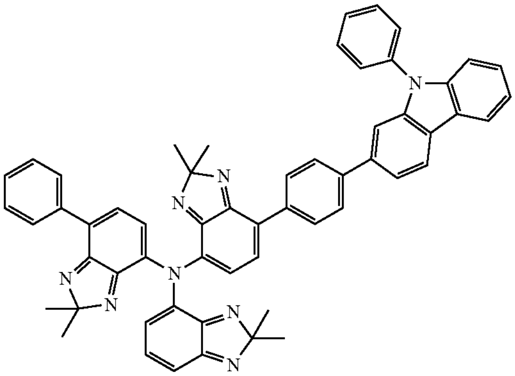
H219
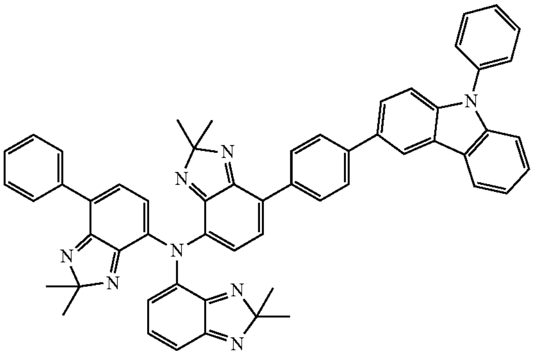
H220
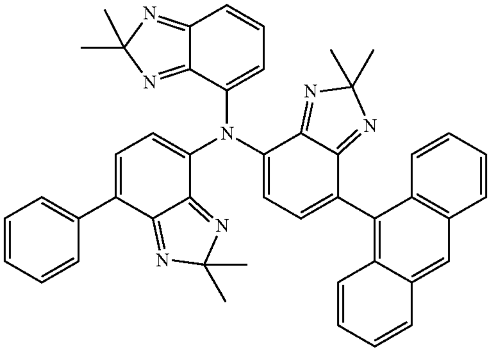
H221
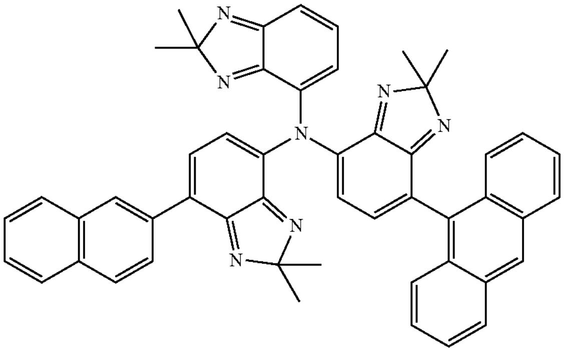
H222
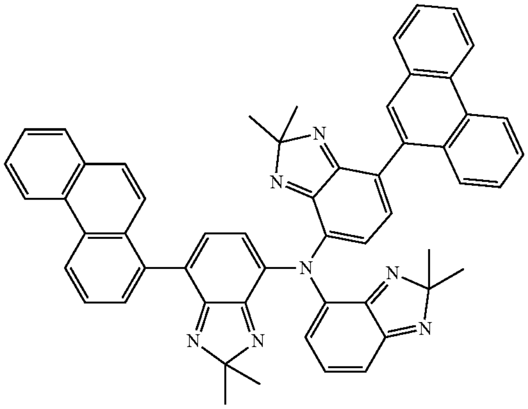
H223
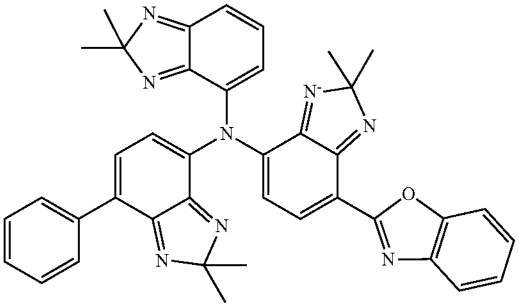

-continued
H224
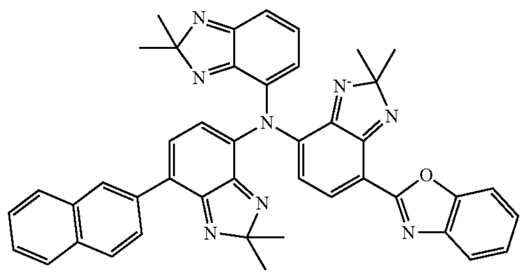
H225
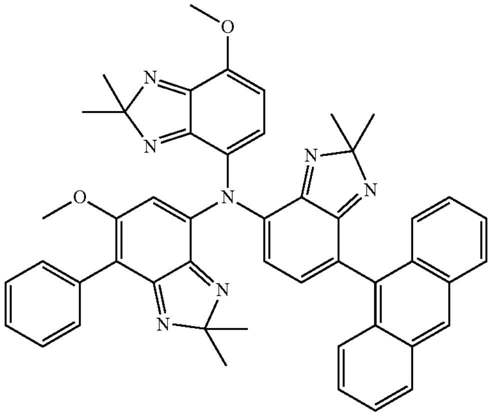
H226
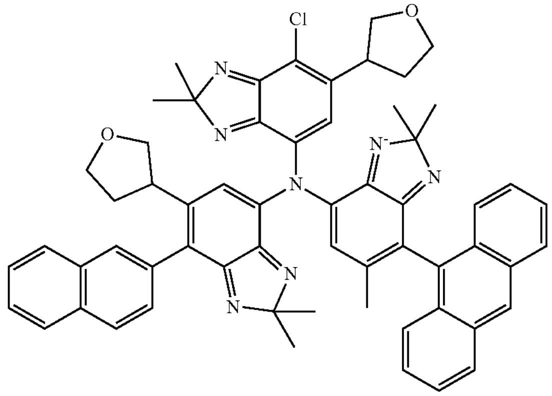
H227
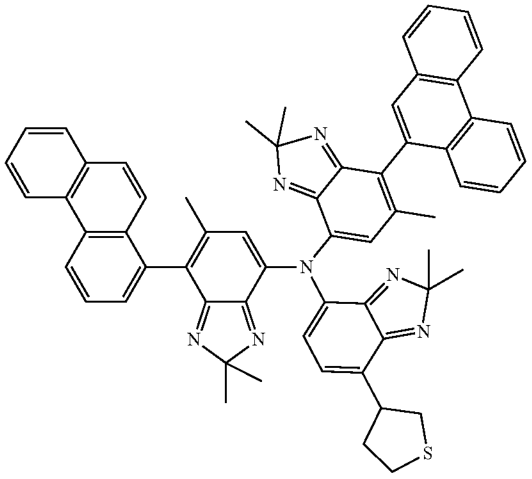
H228
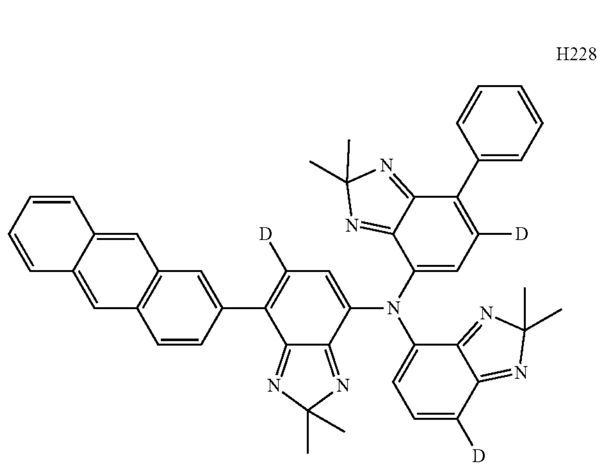
H229
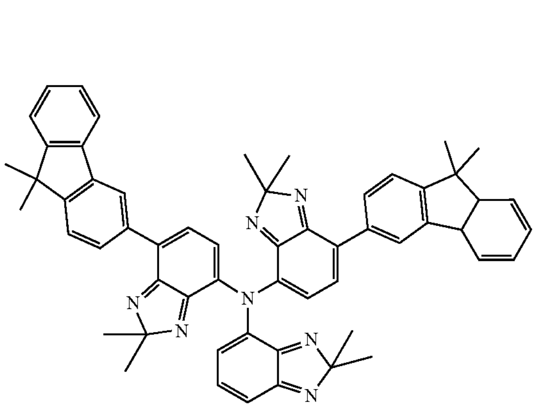

-continued
H230
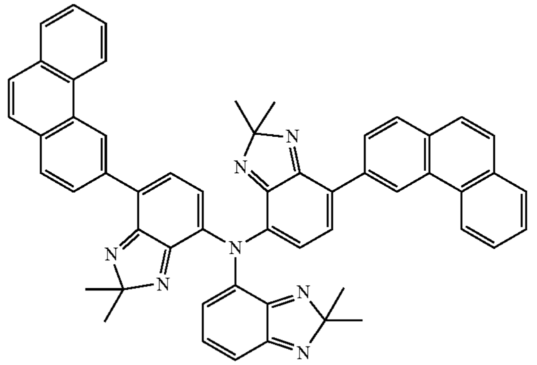
H231
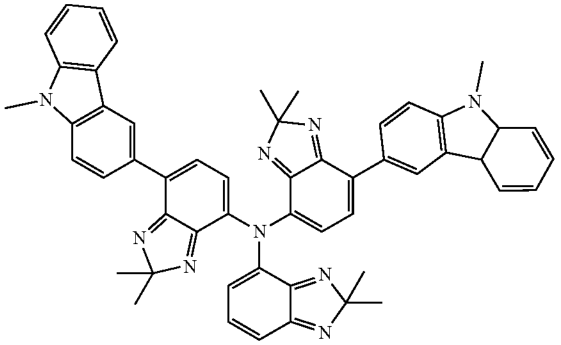
H232
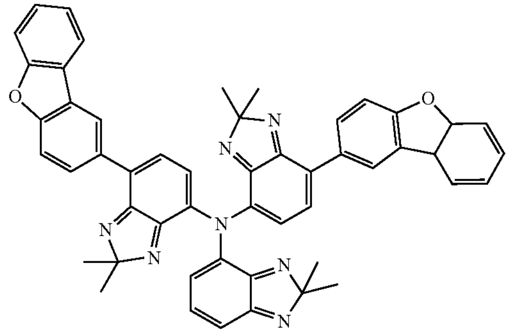
H233
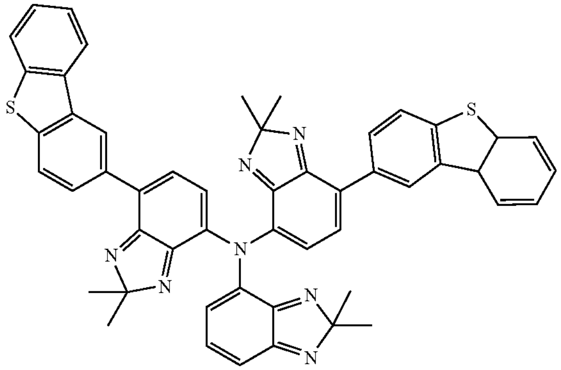
H234
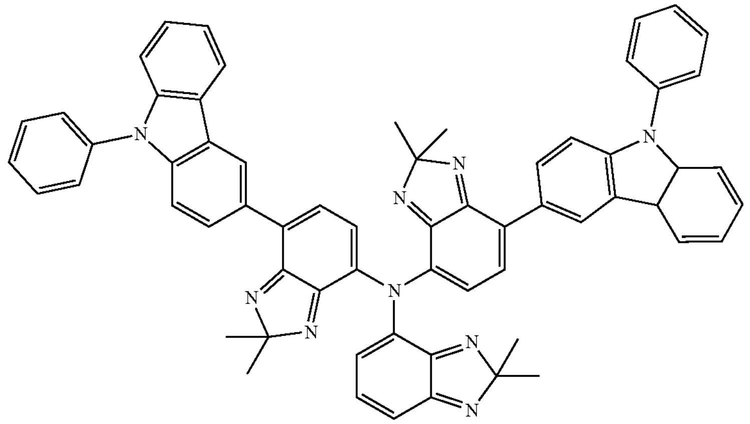
H235
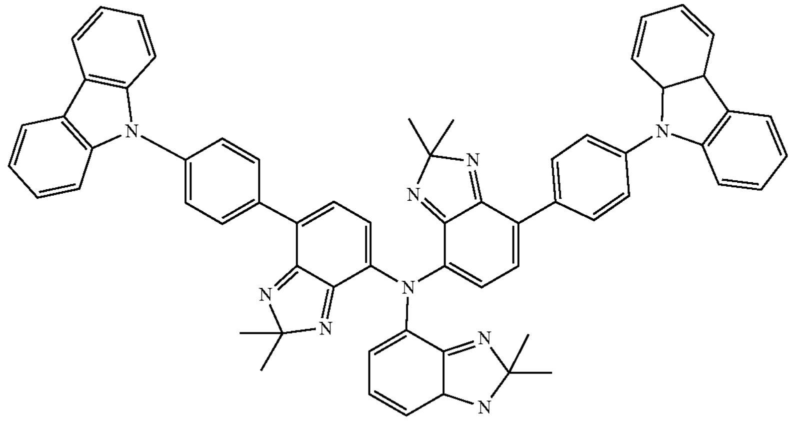

-continued
H236
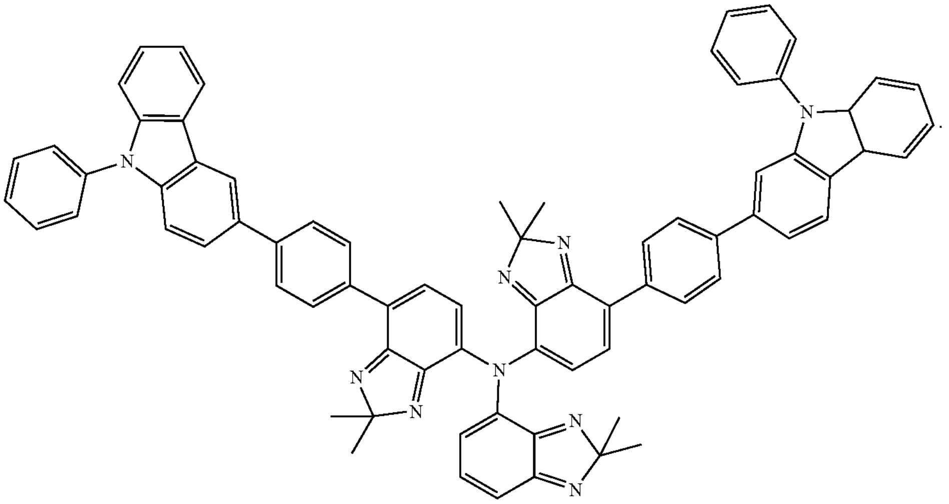
H237
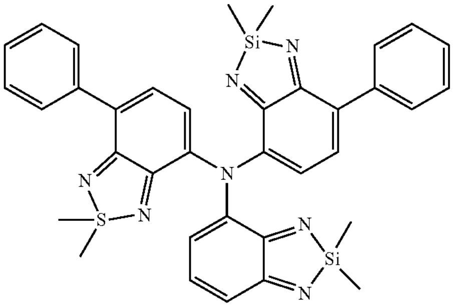
H238
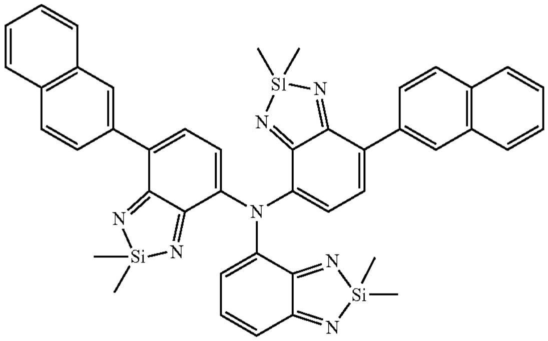
H239
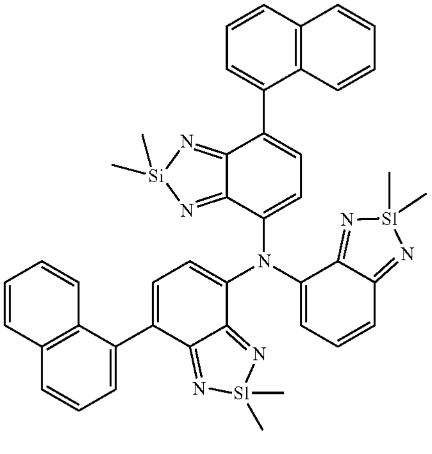
H240
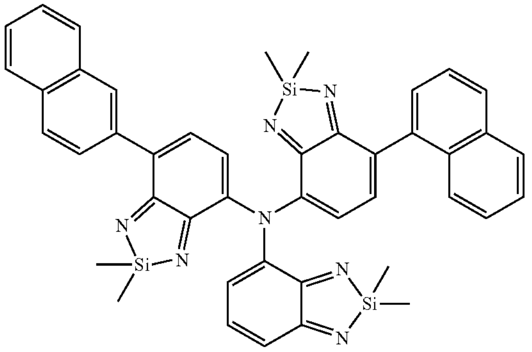
H241
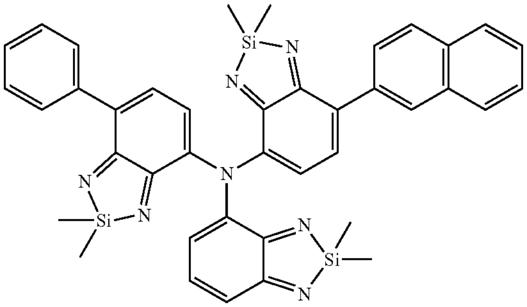
H242
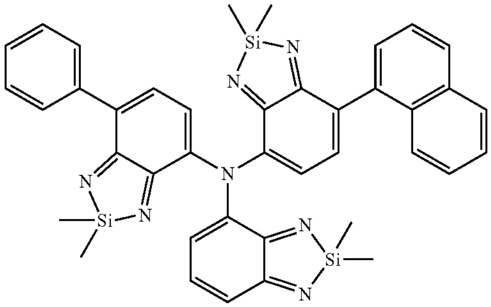

-continued
H243
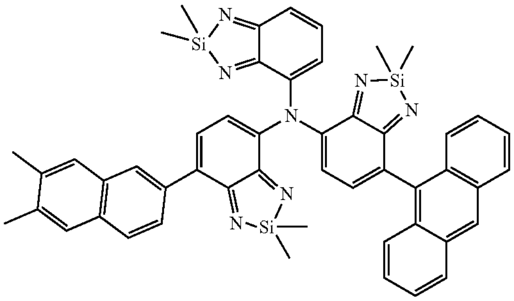
H244
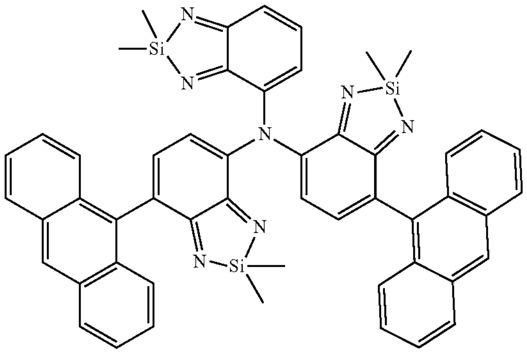
H245
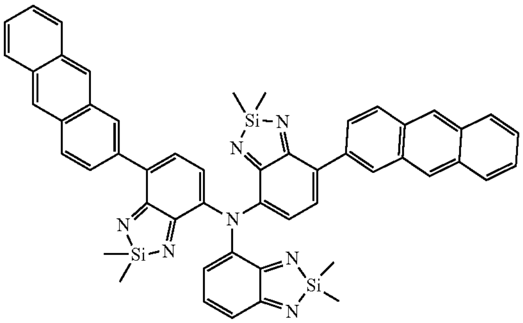
H246
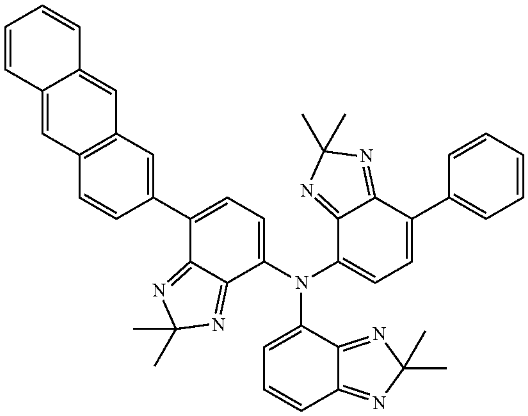
H247
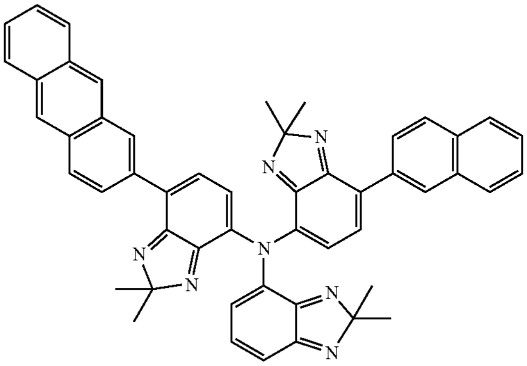
H248
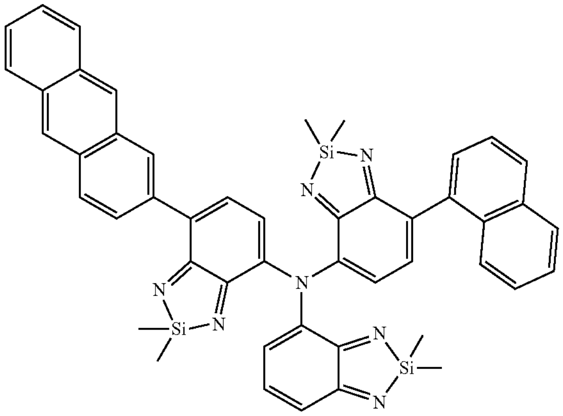
H249
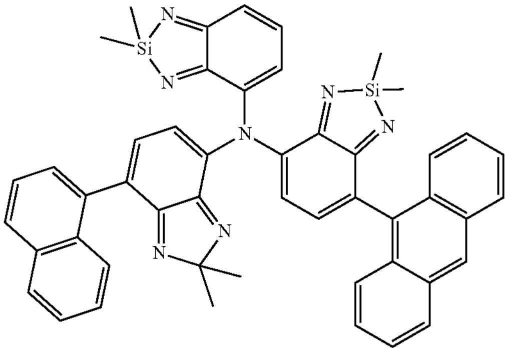
H250
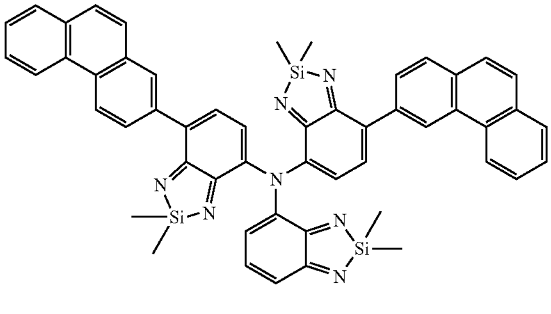

-continued
H251
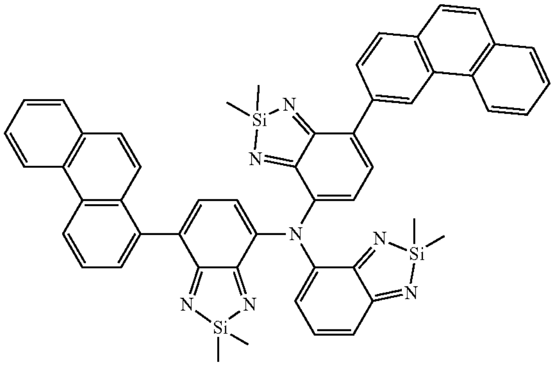
H252
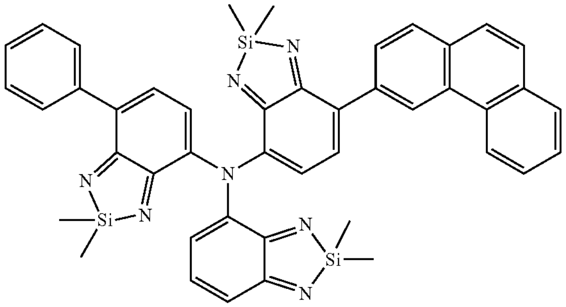
H253
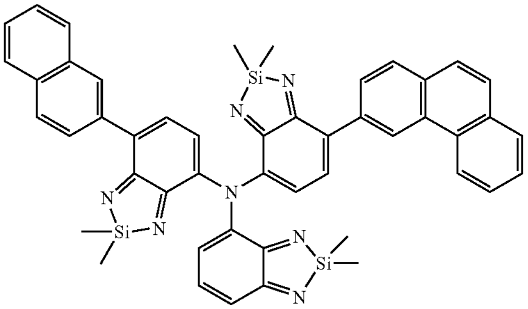
H254
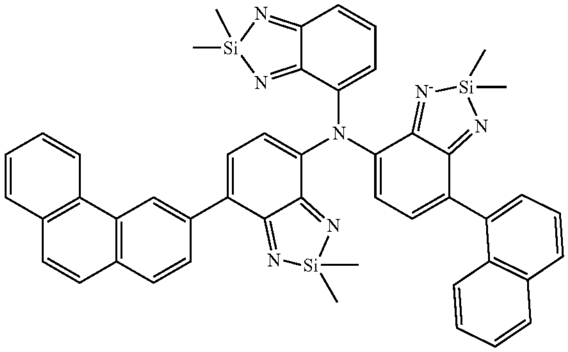
H255
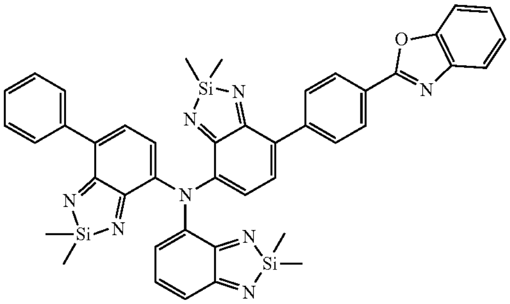
H256
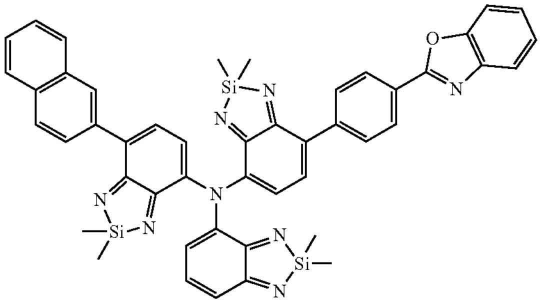
H257
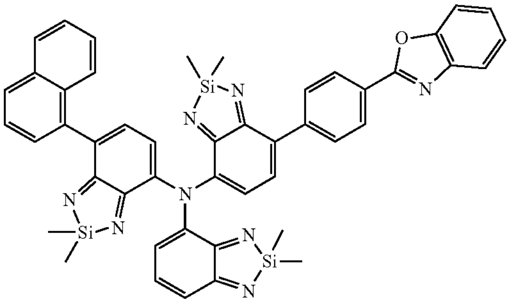
H258
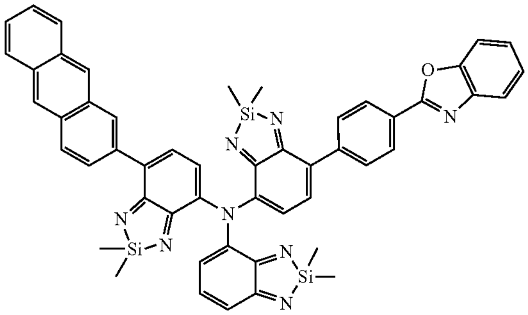

-continued
H259
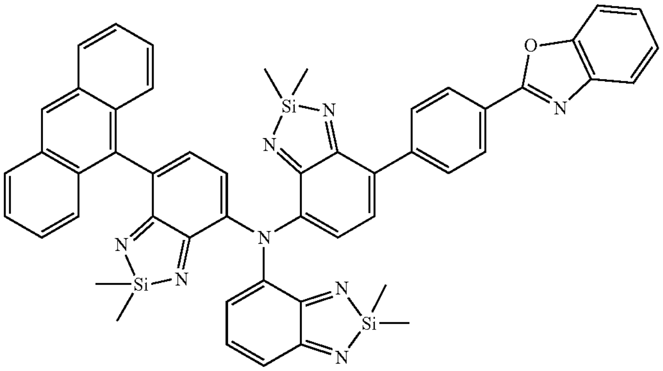
H260
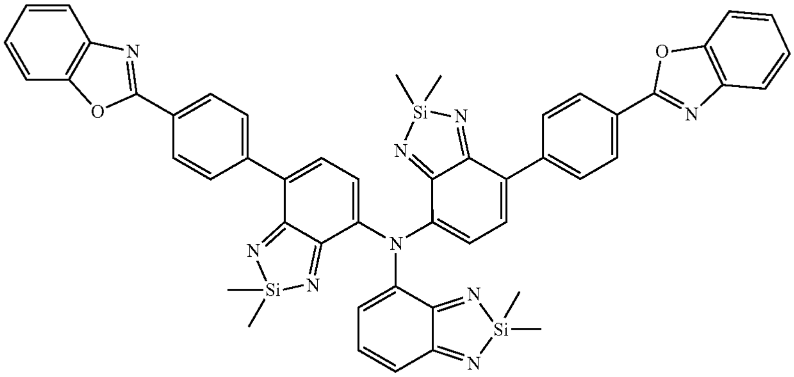
H261
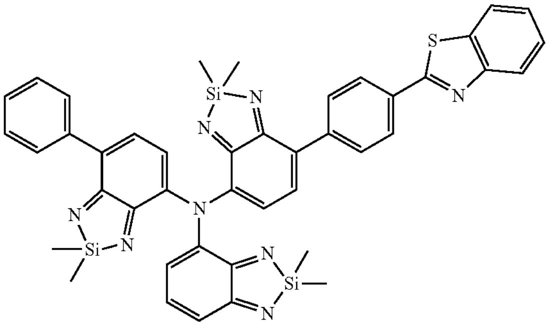
H262
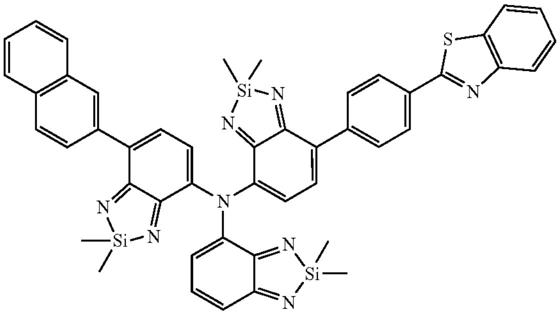
H263
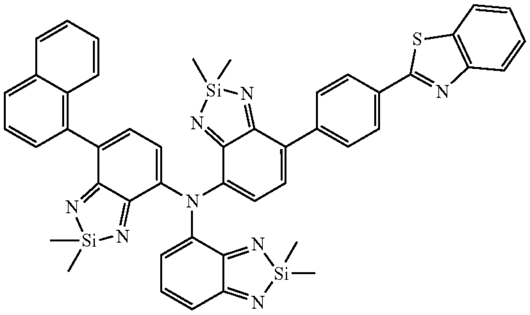
H264
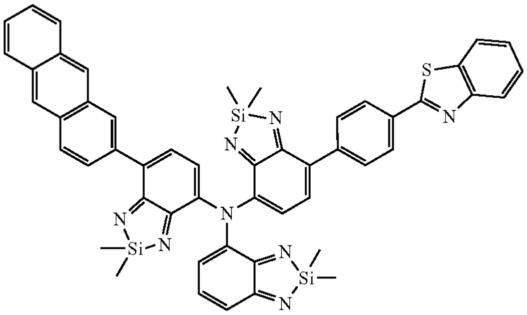

-continued
H265
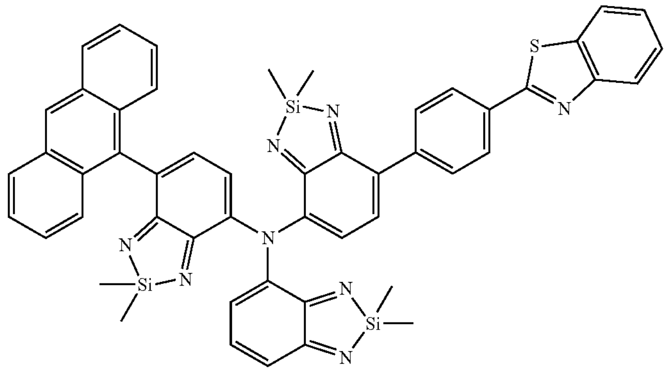
H266
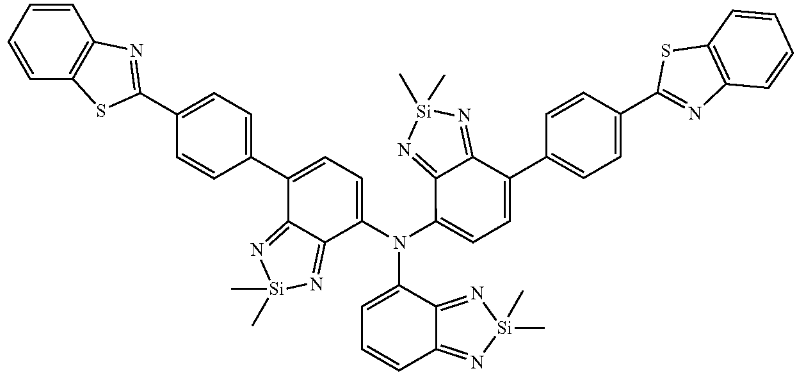
H267
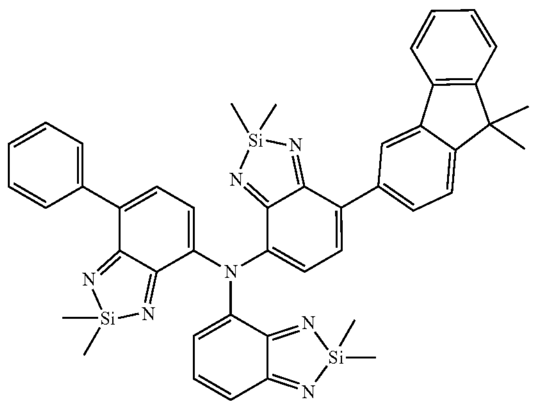
H268
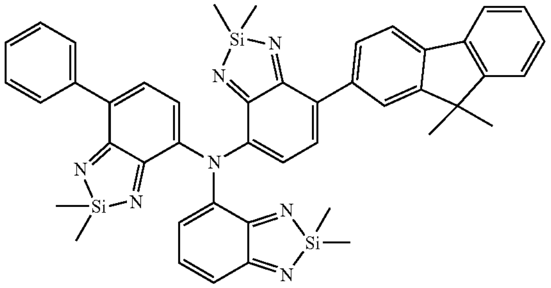
H269
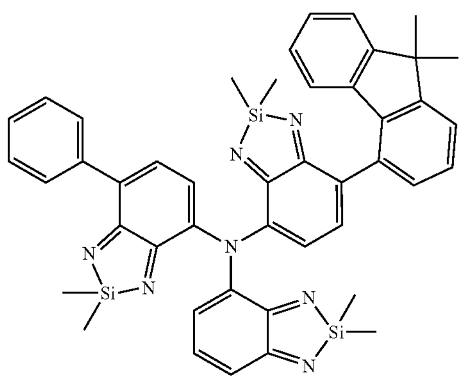
H270
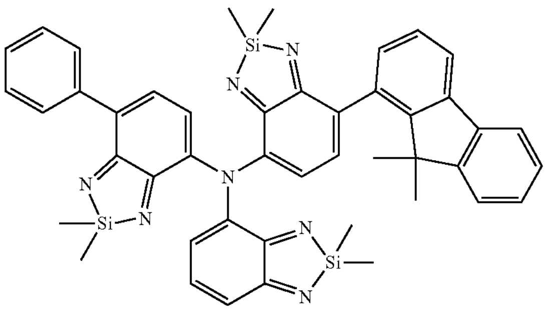

-continued
H271
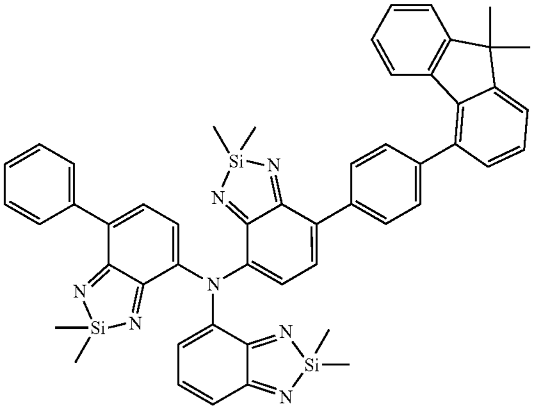
H272
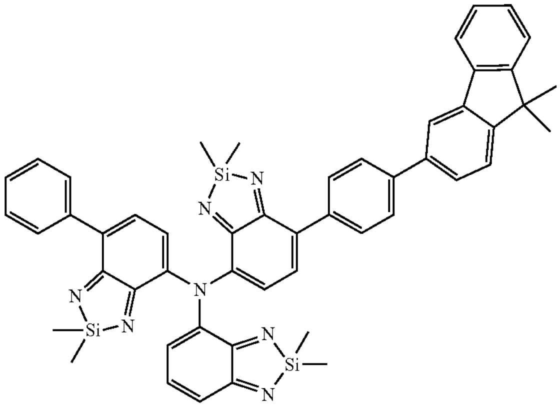
H273
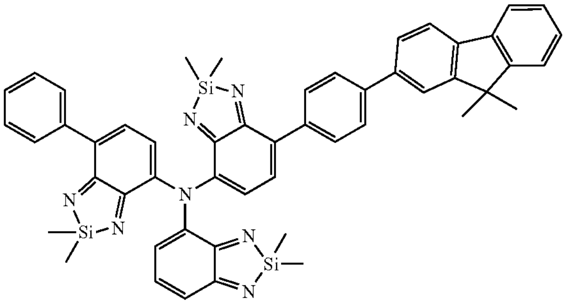
H274
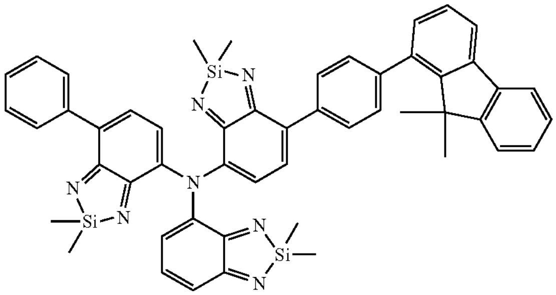
H275
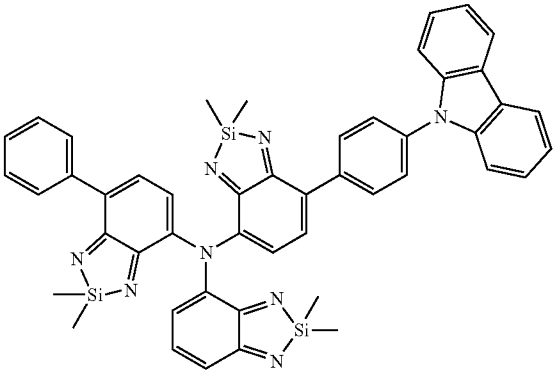
H276
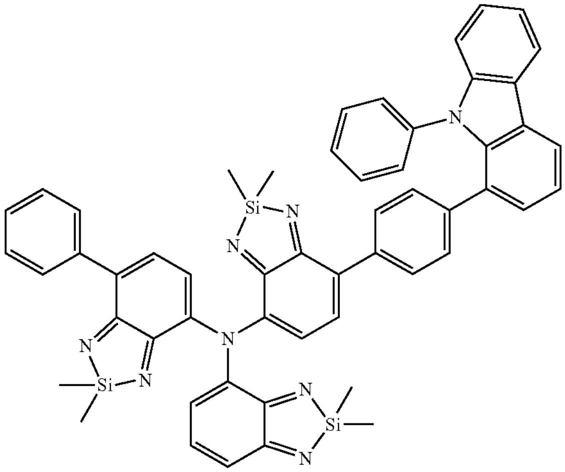
H277
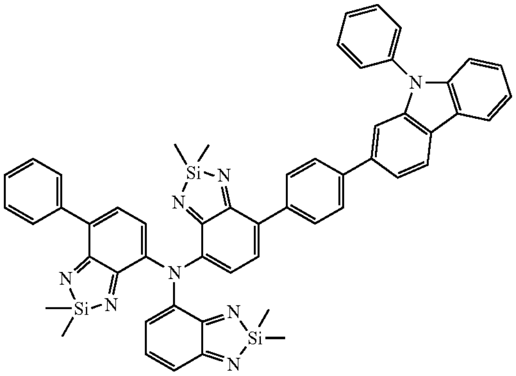
H278
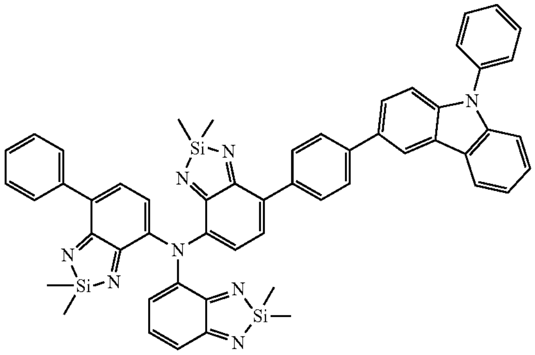

-continued
H279
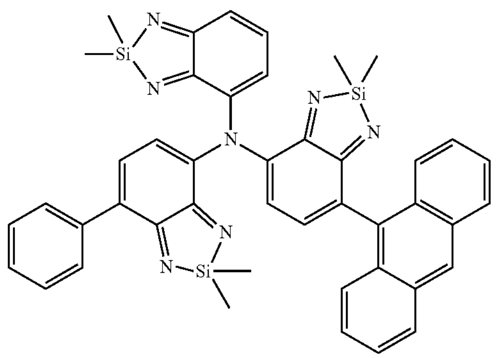
H280
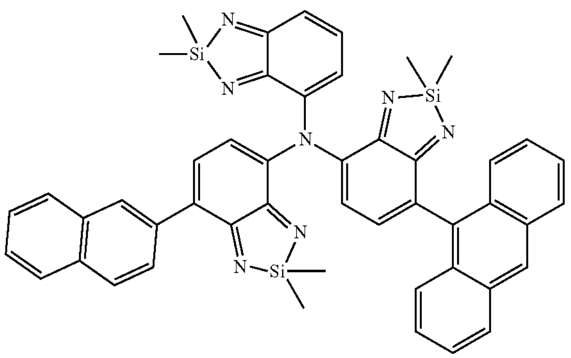
H281
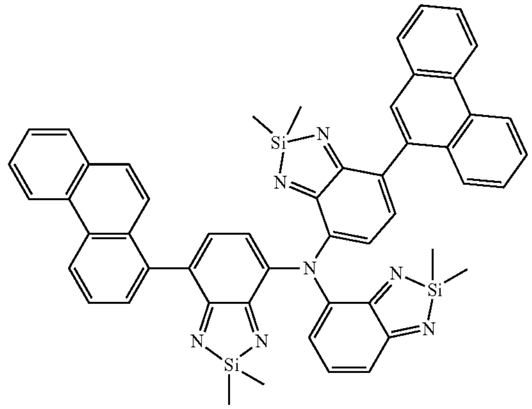
H282
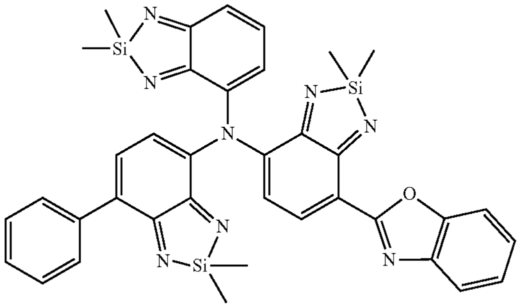
H283
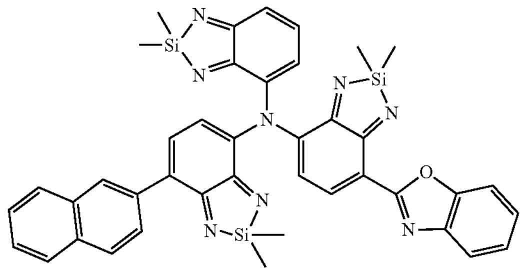
H284
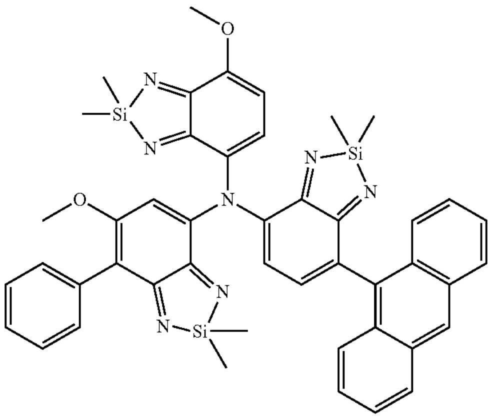

-continued
H285
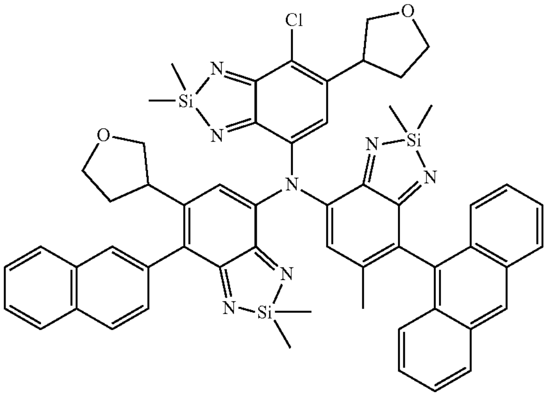
H286
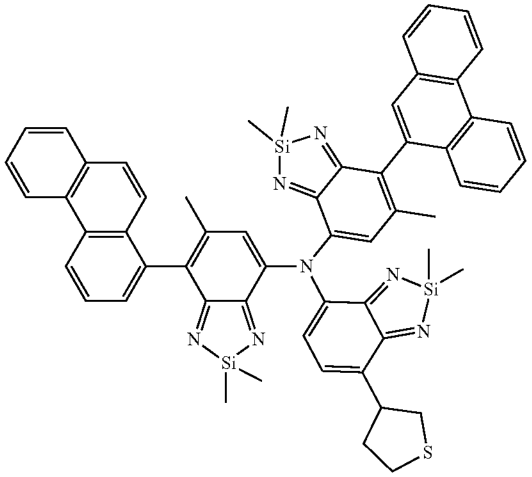
H287
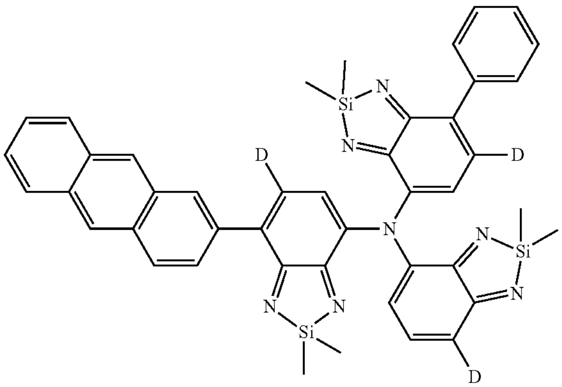
H288
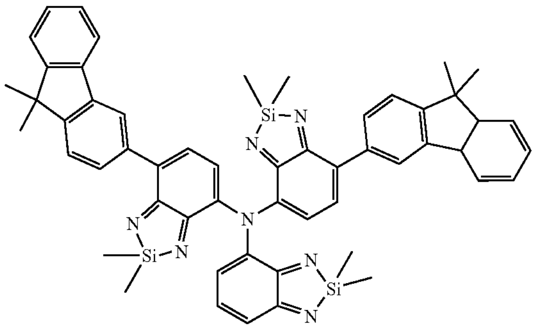
H289
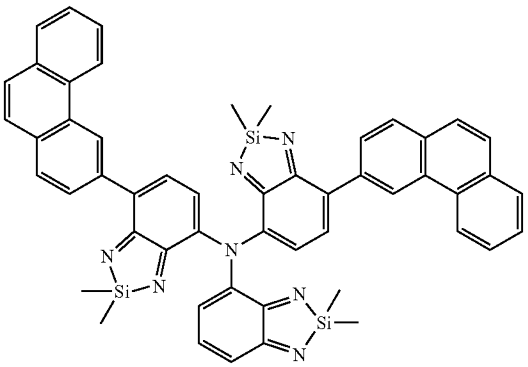
H290
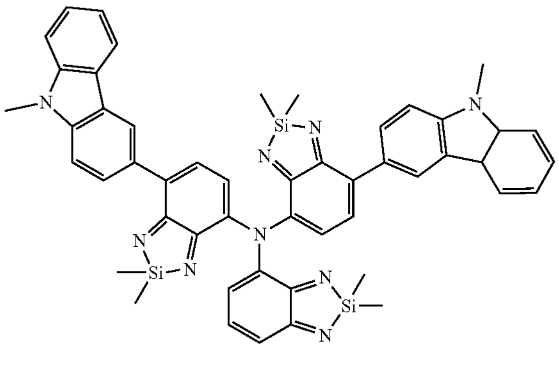

-continued
H291
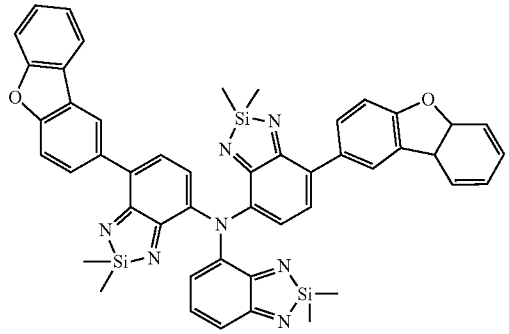
H292
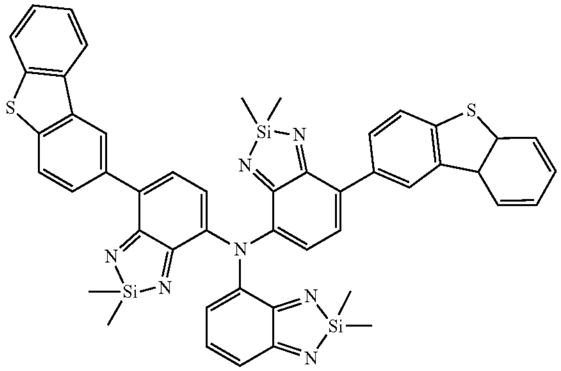
H293
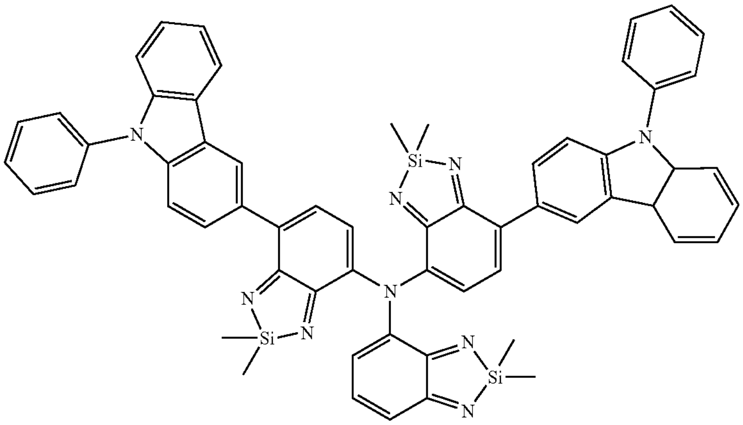
H294
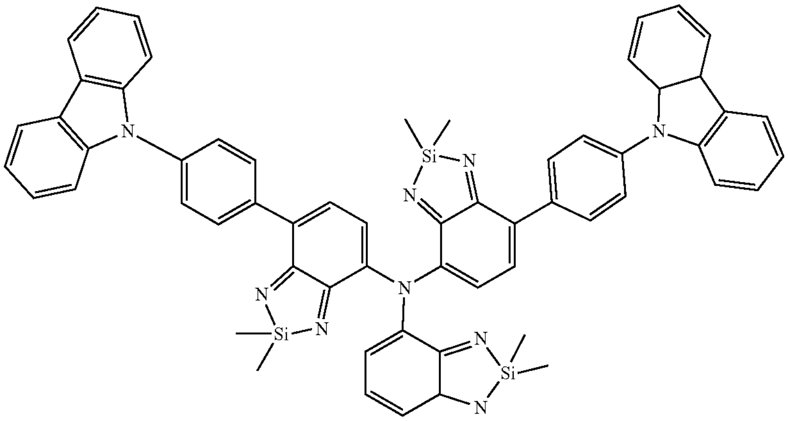

-continued

H295

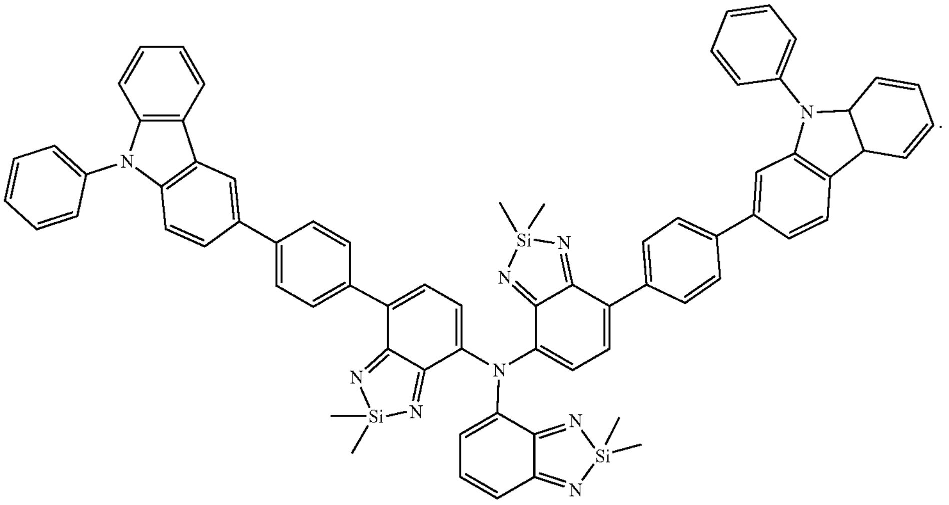

12. The compound according to claim 1, wherein the compound has a refractive index n≥2.1 at a wavelength of 460 nm, the compound has a difference between refractive index at a wavelength of 460 nm and refractive index at a wavelength of 530 nm being 0.09-0.17, the compound has a difference between refractive index at a wavelength of 530 nm and refractive index at a wavelength of 620 nm being 0.03-0.11, and the compound has a difference between refractive index at a wavelength of 460 nm and refractive index at a wavelength of 620 nm being 0.15-0.24.

13. A display panel, comprising an organic electroluminescent device, the organic electroluminescent device comprising a cathode, an anode arranged opposite to the cathode, a capping layer located on the side of the cathode away from the anode, and an organic film layer located between the cathode and the anode, wherein at least one of the capping layer and the organic film layer comprises the compound according to claim 1.

14. A display device, comprising the display panel according to claim 13.

* * * * *